(12) United States Patent
Rose et al.

(10) Patent No.: US 10,898,568 B2
(45) Date of Patent: Jan. 26, 2021

(54) MODULAR ANTIGEN TRANSPORTATION MOLECULES AND USES THEREOF IN ANIMALS

(71) Applicant: Boehringer Ingelheim Vetmedica GmbH, Ingelheim am Rhein (DE)

(72) Inventors: Horst Rose, Burgdorf (DE); Dania Birte Reiche, Bingen am Rhein (DE); Harald Tammen, Hannover (DE)

(*) Notice: Subject to any disclaimer, the term of this patent is extended or adjusted under 35 U.S.C. 154(b) by 167 days.

(21) Appl. No.: 15/276,922

(22) Filed: Sep. 27, 2016

(65) Prior Publication Data

US 2017/0087246 A1 Mar. 30, 2017

(30) Foreign Application Priority Data

Sep. 30, 2015 (EP) ..................................... 15187810

(51) Int. Cl.

| A61K 39/35 | (2006.01) |
|---|---|
| A61K 39/385 | (2006.01) |
| C07K 7/06 | (2006.01) |
| C07K 14/435 | (2006.01) |
| C07K 14/47 | (2006.01) |
| C12N 7/00 | (2006.01) |
| A61K 39/00 | (2006.01) |
| A61K 38/00 | (2006.01) |

(52) U.S. Cl.
CPC ............ *A61K 39/35* (2013.01); *A61K 39/385* (2013.01); *C07K 7/06* (2013.01); *C07K 14/4359* (2013.01); *C07K 14/43531* (2013.01); *C07K 14/47* (2013.01); *C12N 7/00* (2013.01); *A61K 38/00* (2013.01); *A61K 2039/552* (2013.01); *A61K 2039/55505* (2013.01); *A61K 2039/575* (2013.01); *A61K 2039/577* (2013.01); *A61K 2039/622* (2013.01); *C07K 2319/10* (2013.01); *C07K 2319/21* (2013.01); *C07K 2319/33* (2013.01); *C12N 2740/16033* (2013.01); *C12N 2740/16071* (2013.01)

(58) Field of Classification Search
None
See application file for complete search history.

(56) References Cited

U.S. PATENT DOCUMENTS

| 5,633,234 A | 5/1997 | August et al. |
|---|---|---|
| 5,804,604 A | 9/1998 | Frankel et al. |
| 7,563,866 B2 | 7/2009 | Lamping et al. |
| 2005/0281816 A1 | 12/2005 | Lamping et al. |
| 2008/0108561 A1 | 5/2008 | Nandy et al. |
| 2014/0039163 A1 | 2/2014 | Nagamune et al. |
| 2014/0105906 A1 | 4/2014 | Venugopal et al. |
| 2015/0274790 A1 | 10/2015 | Rose et al. |

FOREIGN PATENT DOCUMENTS

| EP | 1541135 | 6/2005 |
|---|---|---|
| EP | 1621615 A1 | 2/2006 |
| JP | 2008504004 A | 2/2008 |
| WO | 199418999 A1 | 9/1994 |
| WO | 2004035793 A1 | 4/2004 |
| WO | 2004094639 A2 | 11/2004 |
| WO | 2007065633 A1 | 6/2007 |
| WO | 2009007418 | 1/2009 |
| WO | 2009022154 A2 | 2/2009 |
| WO | 2012121395 A1 | 9/2012 |
| WO | 2014063704 | 5/2014 |
| WO | 2015150243 A1 | 10/2015 |
| WO | 2017055235 A1 | 4/2017 |

OTHER PUBLICATIONS

Bowie et al. (Science, 1990, 247:1306-1310).*
Greenspan et al. (Nature Biotechnology 7: 936-937, 1999).*
Vad Der Meide et al., "Cloning and expression of candidate allergens from Culicoides obsoletus for diagnosis of insect bite hypersensitivity in horses." Veterinary Immunology and Immunopathology, vol. 153, 2013, pp. 227-239.
Peeters et al., "Evaluation of an IgE ELISA with *Culicoides* spp. extracts and recombinant salivary antigens for diagnosis of insect bite hypersensistivity in Warmblood horses." The Veterinary Journal, vol. 198, 2013, pp. 141-147.
UniProtKB Accession No. Q9MXD5. "MHC class II associated invariant chain." Oct. 1, 2000, pp. 1-4.
International Search Report and Written Opinion for PCT/EP2016/072898 dated Jan. 4, 2017.
Yang et al., "Expression of hypoallergenic Der f2 derivatives with alterned intramolecular disulphide bonds induces the formation of novel ER-derived protein bodies in transgenic rice seeds." Journal of Experimental Botany, vol. 63, No. 8, 2012, pp. 2947-2959.
"Conference: Report of the 3rd Havemeyer workshop on allergic diseases of the Horse, Holar, Iceland, Jun. 2007". Veterinary Immunology and Immunopathology, vol. 126, 2008, pp. 351-361.
Akdis et al., "Mechanisms and treatment of allergic disease in the big picture of regulatory T cells". Clinical Reviews in Allergy and Immunology, vol. 123, 2009, pp. 735-746.
Bonini et al., "Targeting Antigen in Mature Dendritic Cells for Simultaneous Stimulation of CD4+ and CD8+ T Cells".The Journal of Immunology, vol. 166, No. 8, Apr. 2001, pp. 5250-5257.
Durham et al., "Grass pollen immunotherapy inhibits allergen-induced infiltration of CD4+ T lymphocytes and eosinophils in the nasal mucosa and increases the number of cells expressing messenger RNA for interferon-g". Journal of Allergy and Clinical Immunology, vol. 97, No. 6, 1996, pp. 1356-1365.

(Continued)

*Primary Examiner* — Brian Gangle
(74) *Attorney, Agent, or Firm* — Steffan Finnegan

(57) ABSTRACT

The present invention relates to (isolated) recombinant proteins, also referred to as improved MAT (iMAT) molecules, comprising at least one translocation module, at least one targeting module and at least one antigen module, wherein at least one cysteine residue is substituted with a different amino acid residue. Such iMAT molecules are useful specifically as vaccines, e.g. for therapy and/or prevention of allergies and/or infectious diseases and/or prevention of transmission of

(56) References Cited

OTHER PUBLICATIONS

Gadermaier et al., "Targeting the cysteine-stabilized fold of Art v 1 for immunotherapy of Artemisia pollen allergy". Molecular Immunology, vol. 47, No. 6, 2010, pp. 1292-1298.
Ginel et al., "Allergen-specific immunotherapy in horses with insect bite hypersensitivity: a double-blind, randomized, placebo-controlled study". Veterinary Dermatology, vol. 25, 2014, pp. 29-34, e9-10.
Hare et al., "Evaluation of an In Vitro Degranulation Challenge Procedure for Equine Pulmonary Mast Cells". Canadian Journal of Veterinary Research, vol. 62, 1998, pp. 133-139.
Hoffmann-Sommergruber et al., "IgE reactivity to Api g 1, a major celery allergen, in a Central European population is based on primary sensitization by Bet v 1". The Journal of Allergy and Clinical Immunology, vol. 104, No. 2, Part 1, 1999, pp. 478-484.
James et al., "Update on mechanisms of allergen injection immunotherapy". Clinical and Experimental Allergy, vol. 38, 2008, pp. 1074-1088.
Kehrli et al., "Multiple Hypersensitivities Including Recurrent Airway Obstruction, Insect Bit Hypersensitivity, and Urticaria in 2 Warmblood Horse Populations". Journal of Veterinary Internal Medicine, vol. 29, 2015, pp. 320-326.
Klein et al., "Design and characterization of structured protein linkers with differing flexibilities". Protein Engineering, Design & Selection, vol. 27, No. 10, 2014, pp. 325-330.
Landholt et al., "Low-dose DNA vaccination into the submandibular lymph nodes in ponies". Veterinary Record, vol. 167, 2010, pp. 302-304.
Langner et al., "Comparison of cellular and humoral immunoassays for the assessment of summer eczema in horses". Veterinary Immunology and Immunopathology, vol. 122, 2008, pp. 126-137.
Leclere et al., "Heaves, an asthma-like disease of horses". Respirology, vol. 16, 2011, pp. 1027-1046.
Martinez-Gomez et al., "Targeting the MHC class II pathway of antigen presentation enhances immunogenicity and safety of allergen immunotherapy". Allergy, vol. 64, No. 1, 2008, pp. 172-178.
Möbs et al. "Cellular and Humoral Mechanisms of Immune Tolerance in Immediate-Type Allergy Induced by Specific Immunotherapy". International Archives of Allergy and Immunology, vol. 147, 2008, pp. 171-178.
Niederberger et al., "Vaccination with genetically engineered allergens prevents progression of allergic disease". Proceedings of the National Academy of Sciences, vol. 101, Supp. 2, 2004, pp. 14677-14682.
Olsen et al., "Pharmacokinetics and effects of cetirizine in horses with insect bite hypersensitivity". The Veterinary Journal, vol. 187, 2011, pp. 347-351.
Pirie, R.S. "Recurrent airway obstruction: A review". Equine Veterinary Journal, vol. 46, 2014, pp. 276-288.
Platts-Mills et al., "Current reviews of allergy and clinical immunology". The Journal of Allergy and Clinical Immunology, vol. 102, No. 3, 1998, pp. 335-343.
Schaffartzik et al., "Equine insect bit hypersensitivity: What do we know?" Veterinary Immunology and Immunopathology, vol. 147, No. 3, 2012, pp. 113-126.
Senti et al., "Intralymphatic immunotherapy for cat allergy induces tolerance after only 3 injections". Journal of Allergy and Clinical Immunology, vol. 129, No. 5, 2012, pp. 1290-1296.
Tilley et al. "Comparison of Skin Prick Tests with In Vitro Allergy Tests in the Characterization of Horses with Recurrent Airway Obstruction". Journal of Equine Veterinary Science, vol. 32, 2012, pp. 719-727.
Van Der Meide et al., "Evaluation of a diagnostic ELISA for insect bit hypersensitivity in horses using recombinant Obsoletus complex allergens". The Veterinary Journal, vol. 200, 2014, pp. 31-37.
Vazquez-Boland et al., "Rhodococcus equi: The many facets of a pathogenic actinomycete". Veterinary Microbiology, vol. 167, 2013, pp. 9-33.
Von Bargen et al., "Molecular and infection biology of the horse pathogen Rhodococcus equi". FEMS Microbiology Review, vol. 33, 2009, pp. 870-891.
Wachholz et al. "Inhibition of allergen-IgE binding to B cells by IgG antibodies after grass pollen immunotherapy". Journal of Allergy and Clinical Immunology, vol. 112, Nov. 2003, pp. 915-922.

\* cited by examiner

FIG. 9A

| No. | Short name | Entry | Protein names | Organism | Length |
|---|---|---|---|---|---|
| 1 | Der p 1 | P08176 | Peptidase 1(EC 3.4.22.65) | Dermatophagoides pteronyssinus (European house dust mite) | 320 |
| 2 | Der p 2 | P49278 | Mite group 2 allergen (DPX) | Dermatophagoides pteronyssinus (European house dust mite) | 146 |
| 3 | Der p 3 | P39675 | Mite allergen Der p 3 (EC 3.4.21.-) | Dermatophagoides pteronyssinus (European house dust mite) | 261 |
| 4 | Der p 4 | Q9Y197 | Alpha-amylase (EC 3.2.1.1) | Dermatophagoides pteronyssinus (European house dust mite) | 496 |
| 5 | Der p 5 | P14004 | Mite allergen Der p 5 (IgE-binding allergen) | Dermatophagoides pteronyssinus (European house dust mite) | 132 |
| 6 | Der p 6 | P49277 | Mite allergen Der p 6 (EC 3.4.21.-) | Dermatophagoides pteronyssinus (European house dust mite) | 20 |
| 7 | Der p 7 | P49273 | Mite allergen Der p 7 | Dermatophagoides pteronyssinus (European house dust mite) | 215 |
| 8 | Der p 8 | P46419 | Glutathione S-transferase (EC 2.5.1.18) (GST class-mu) | Dermatophagoides pteronyssinus (European house dust mite) | 219 |
| 9 | Der p 9 | Q7Z163 | Trypsin-like serine protease | Dermatophagoides pteronyssinus (European house dust mite) | 273 |
| 10 | Der p 10 | O18416 | Tropomyosin (allergen Der p 10) | Dermatophagoides pteronyssinus (European house dust mite) | 284 |
| 11 | Der p 11 | Q6Y2F9 | HDM allergen | Dermatophagoides pteronyssinus (European house dust mite) | 875 |
| 12 | Der p 13 | E0A8N8 | Der p 13 allergen | Dermatophagoides pteronyssinus (European house dust mite) | 131 |
| 13 | Der p 14 | Q8N0N0 | Group 14 allergen protein | Dermatophagoides pteronyssinus (European house dust mite) | 1662 |
| 14 | Der p 15 | Q4JK69 | Group 15 allergen protein | Dermatophagoides pteronyssinus (European house dust mite) | 532 |
| 15 | Der p 18 | Q4JK71 | Group 18 allergen protein | Dermatophagoides pteronyssinus (European house dust mite) | 462 |
| 16 | Der p 20 | B2ZSY4 | Der p 20 allergen | Dermatophagoides pteronyssinus (European house dust mite) | 356 |
| 17 | Der p 21 | Q2L7C5 | Allergen | Dermatophagoides pteronyssinus (European house dust mite) | 140 |
| 18 | Der p 23 | L7N6F8 | Dust mite allergen | Dermatophagoides pteronyssinus (European house dust mite) | 90 |
| 19 | Der p 30 | Q96I7 | Ferritin (EC 1.16.3.1) | Dermatophagoides pteronyssinus (European house dust mite) | 180 |

FIG. 9B

| No. | Short name | Entry | Protein names | Organism | Length |
|---|---|---|---|---|---|
| 1 | Der f 1 | Q58A71 | Der f 1 allergen preproenzyme | Dermatophagoides farinae (American house dust mite) | 321 |
| 2 | Der f 2 | Q00855 | Mite group 2 allergen Der f 2 | Dermatophagoides farinae (American house dust mite) | 146 |
| 3 | Der f 3 | P49275 | Mite allergen Der f 3 (EC 3.4.21.-) | Dermatophagoides farinae (American house dust mite) | 259 |
| 4 | Der f 5 | B2GM84 | Allergen Der f 21 (Der f 5.02 allergen) | Dermatophagoides farinae (American house dust mite) | 136 |
| 5 | Der f 7 | Q26456 | Mite allergen Der f 7 (Allergen Der f VII) | Dermatophagoides farinae (American house dust mite) | 213 |
| 6 | Der f 8 | L7V2G7 | Glutathione S-transferase (EC 2.5.1.18) | Dermatophagoides farinae (American house dust mite) | 197 |
| 7 | Der f 9 | A1KXG4 | Der f 9 allergen | Dermatophagoides farinae (American house dust mite) | 246 |
| 8 | Der f 10 | Q23939 | Tropomyosin (Mag44) | Dermatophagoides farinae (American house dust mite) | 284 |
| 9 | Der f 11 | Q967Z0 | Paramyosin (Antigen Df642) | Dermatophagoides farinae (American house dust mite) | 692 |
| 10 | Der f 13 | Q1M2P5 | Der f 13 allergen | Dermatophagoides farinae (American house dust mite) | 131 |
| 11 | Der f 14 | Q94507 | Mag3 | Dermatophagoides farinae (American house dust mite) | 349 |
| 12 | Der f 15 | Q9U6R7 | 98kDa HDM allergen (Group 15 allergen Der f 15) | Dermatophagoides farinae (American house dust mite) | 555 |
| 13 | Der f 16 | Q8MVU3 | Der f 16 allergen (Gelsolin-like allergen Der f 16) | Dermatophagoides farinae (American house dust mite) | 480 |
| 14 | Der f 18 | Q86R84 | 60 kDa allergen Der f 18p | Dermatophagoides farinae (American house dust mite) | 462 |
| 15 | Der f 22 | A5X5X4 | Group 22 allergen Der f 22 | Dermatophagoides farinae (American house dust mite) | 155 |
| 16 | Der f 23 | A0A088SAW7 | Der f 23 allergen | Dermatophagoides farinae (American house dust mite) | 91 |
| 17 | Der f 24 | M9RZ95 | Cytochrome b-c1 complex subunit 7 | Dermatophagoides farinae (American house dust mite) | 118 |
| 18 | Der f 25 | L7UZA7 | Triosephosphate isomerase (EC 5.3.1.1) | Dermatophagoides farinae (American house dust mite) | 247 |
| 19 | Der f 28 | L7V065 | Heat shock protein 70 | Dermatophagoides farinae (American house dust mite) | 659 |
| 20 | Der f 29 | A1KXG2 | Peptidyl-prolyl cis-trans isomerase (EC 5.2.1.8) | Dermatophagoides farinae (American house dust mite) | 164 |
| 21 | Der f 30 | L7UZ91 | Ferritin (EC 1.16.3.1) | Dermatophagoides farinae (American house dust mite) | 171 |
| 22 | Der f 31 | A0A088SAY1 | Der f 31 allergen | Dermatophagoides farinae (American house dust mite) | 148 |
| 23 | Der f 32 | A0A088SCP3 | Der f 32 allergen (Protein disulfide isomerase) | Dermatophagoides farinae (American house dust mite) | 296 |
| 24 | Der f 33 | A0A088SV41 | Der f 33 allergen | Dermatophagoides farinae (American house dust mite) | 461 |
| 25 | Der f EF | L7UW58 | Translation elongation factor 2 | Dermatophagoides farinae (American house dust mite) | 429 |
| 26 | Der f Actinin | L7UZ85 | Alpha-actinin | Dermatophagoides farinae (American house dust mite) | 885 |
| 27 | ZEN1 | I7HDR2 | Zen 1 protein | Dermatophagoides farinae (American house dust mite) | 500 |

FIG. 10

```
                                          10         20         30         40         50         60
                                          ....|....|....|....|....|....|....|....|....|....|....|....|
gi|545496088|Canis_lupus_familiaris|XP_005619355.1| MEDQRDLISNHEQLPILGQRPGAPESKCSRGALYTGFSVLVALLLAGQATTAYFLYQQG
gi|410949651|Felis_catus|XP_003981534.1|            ............................................A...............

70         80         90        100        110
                                          ....|....|....|....|....|....|....|....|....|....|....|
gi|545496088|Canis_lupus_familiaris|XP_005619355.1| RLDKLTVTSQNLQLESLRMKLPKPPKPLSKMPVATPMMMQALPIQSLPQG
gi|410949651|Felis_catus|XP_003981534.1|            .......A.......N.........A......N.L...L..IM.VRG.L.A
```

US 10,898,568 B2

MODULAR ANTIGEN TRANSPORTATION MOLECULES AND USES THEREOF IN ANIMALS

SEQUENCE LISTING

This application contains a sequence listing in accordance with 37 C.F.R. 1.821-1.825. The sequence listing accompanying this application is hereby incorporated by reference in its entirety.

FIELD OF THE INVENTION

The present invention relates to (isolated) recombinant proteins, also referred to as improved MAT (iMAT) molecules, comprising at least one translocation module, at least one targeting module and at least one antigen module, wherein at least one cysteine residue is substituted with a different amino acid residue. The iMAT molecules can be produced with substantially reduced manufacturing efforts and are species-specific, safer and immunologically very effective. Such (isolated) recombinant proteins are useful specifically as vaccines, e.g. for therapy and/or prevention of allergies and/or infections and/or prevention of transmission of infections in animals, preferably ruminants, pigs, humans, dogs and/or cats, but excluding equines.

BACKGROUND OF THE INVENTION

Prior art publication from Crameri et al. describes the background in more detail (Crameri R. et al., Allergy 2007, 62: 197-206). Briefly, the processing of antigens by antigen-presenting cells (APCs) takes place by two different routes. Antigens occurring inside the cell are presented by MHC I (major histocompatibility complex class I, MHC class I) molecules on the cell surface, whereas extracellular antigens are presented by MHC II (major histocompatibility complex class II, MHC class II) molecules on the cell surface.

Both mechanisms initiate an immune response by the host to the antigen. Major histocompatibility class-II molecules are cell surface glycoproteins that present peptides to CD4+T cells. In the endoplasmic reticulum (ER), MHC-II molecules become associated with a type II transmembrane protein termed the invariant chain (Ii) preventing peptide binding to MHC-II in the ER. Ii homotrimers associate in the ER with 3 MHC class II Aβ dimers and this prevents the binding of endogenous peptides to class II molecules. The N-terminal cytoplasmic domain of Ii contains targeting motifs which leads to its retention in the ER, or to targeting of class II Aβ dimers into the endosomal-lysosomal pathway via the Golgi. Subsequent proteolytic degradation of Ii leaves a small fragment CLIP (Class II associated Ii peptide) bound to class II Aβ dimers in the peptide-binding groove. The interaction of class II αβ/CLIP complexes with HLA-DM, a class II-related Aβ dimer, in a specialized compartment releases the CLIP and allows the class II molecules to bind peptides derived from exogenous proteins. It has been shown that endogenously synthesized proteins, generally excluded from the MHC-II presentation pathway, can be efficiently presented as peptide-MHC-II complexes when they are expressed as Ii fusion proteins. This property has been exploited to clone genes encoding MHC-II-restricted antigens from cell lines transfected with Ii-cDNA fusion libraries. Efficient allergy vaccines targeting the MHC-II processing and presentation pathway were achieved using translocable Ii-allergen fusions. The concept, termed modular antigen translocation (MAT) technology bases on a fusion protein consisting of a TAT-derived translocation peptide converting extracellular into cytoplasmic proteins, the first 110 amino-acids of Ii for targeting the fusion proteins to endosomal/lysosomal compartments, and an antigen for induction of specific immune responses.

The concept of providing modular antigen transportation (MAT) molecules for modulating immune responses, associated constructs, method and uses thereof is disclosed in WO 2004/035793 (US equivalent US 2005/0281816). This document describes the usefulness of a three-part-molecule, the MAT molecule, for introducing epitopes of antigens into cells, thus, determining the immune response to be modulated by such MAT molecule. Therein, various translocation modules, targeting modules as well as antigen modules are described. This technology and its underlying method make it possible, firstly, to convey antigens efficiently from the extracellular space into the intracellular space of a target cell, and, secondly, make it possible for the antigens, after arrival in the interior of the cell, to reach efficiently cell organelles in order to be subsequently processed for antigen presentation. Generally, the two-stage process can be utilized for the targeted, efficient modulation of the immune response in a subject. The use of MAT molecules is disclosed for example in Martínez-Gómez J M et al. [Allergy 2009, 64(1): 172-178]; Rose H (Arb Paul Ehrlich Inst Bundesinstitut Impfstoffe Biomed Arzneim Langen Hess, 2009, 96, 319-327) as well as recently in Senti G et al. [J Allergy Clin Immunol., 2012, 129(5): 1290-1296]. Based on the MAT technology, the major cat allergen Fel d1 was fused to a TAT-derived protein translocation domain and to a truncated invariant human chain for targeting the MHC class II pathway. Immunogenicity was evaluated in mice, while potential safety issues were assessed by suitable tests based on basophil reactivities from cat-dander-allergic patients. The possible use of this model compound has been demonstrated. It is described therein, that it is expected that MAT molecules are safer and more efficient in inducing the desired immune response, namely hyposensitization, than recombinant allergens or allergen extracts in conventional allergen-specific immunotherapy (SIT). In the recent publication by Senti G. et al. intralymphatic immunotherapy for cat dander allergy in humans inducing tolerance after three injections was described. Therein, a first-in-human clinical study with the MAT-Fel d1 was described, demonstrating safety and induction of allergen tolerance after intralymphatic injection of three injections, only.

Further prior art is as follows:

Gadermaier G et al. (Molecular Immunology 2010, 47: 1292-1298) described the targeting of the cysteine-stabilized fold of Art v for immunotherapy of *Artemisia* pollen allergy. The authors used genetic engineering approaches for targeting Art v1 posttranslational modifications aiming at the creation of hypoallergenic molecules: (i) disulfide bridges of the defensin domain were disrupted by site-directed mutagenesis and (ii) the mutant constructs expressed in *E. coli* for the production of non-glycosylated proteins. However, the objective was clearly only manipulating the three-dimensional fold of the Art v defensin domain to abrogate IgE-binding (i.e. creating a hypoallergenic molecule) by exchanging single cysteine residues for serine—while keeping intact (i.e. unmodified) the recognized T-cell epitopes (even if such contain cysteine residues).

The report of the 3$^{rd}$ Havemeyer workshop on allergenic diseases of the Horse (Hólar, Iceland, June 2007, Veterinary Immunology and Immunotherapy 2008, 126: 351-361) focused on immunological and genetic aspects of insect's bite hypersensitivity (IBH) and recurrent airway obstruction (RAO). At this workshop novel approaches for SIT against IBH were discussed, among others the use of viral vectors or protein vaccination with allergens coupled to modular antigen translocating (MAT) molecules.

In SIAF Annual Reports 2010 and 2011 Crameri R reports the use of MAT technology for vaccination of IBH-affected horses.

Zhao et al. (Int J Clin Exp Med 2015; 8(4):6436-6443) reported results of experiments with mosaic fusion proteins with the MAT structure disclosed in WO 2004/035793 and 3 segments of T cell epitope coding for Der p1 as antigen module. They reassembled these sequences in linear manner to form a fusion gene for protein expression. They describe their construct to exhibit a stronger allergenicity (hyperallergenicity) as compared to the Der p1 protein.

However, major problems arose when producing and manufacturing the MAT molecules described in the prior art. In particular standard methods used in developing a downstream process (DSP) for manufacturing of the MAT molecules under good manufacturing practice (GMP) could not be applied. It was not possible to purify a homogeneous molecular species of the MAT molecules, evidently due to their anomalous physicochemical properties.

Several methods of purification could not be applied (see Example 4 herein) with the MAT molecules described in the prior art although different separation principles (e.g., size exclusion chromatography, RP-HPLC) were tested. Methods applied for determination of purity for recombinant proteins in general include chromatographic separation, e.g. RP-HPLC and electrophoretic separation (e.g. capillary zone electrophoresis, isoelectric focusing, SDS-PAGE under reducing or non-reducing conditions). Also, these analytical methods could not be applied on MAT molecules without molecule-specific adaptations. For the assessment of purity, an adapted specific SDS-PAGE test procedure had to be developed. This test procedure includes sample preparation with reducing agent and lithium dodecyl sulfate (LDS) and heating up to 75° C., resulting in multiple, reproducible sharp bands after electrophoretic separation. Staining with Coomassie blue dye leads to linear quantitative behavior (densitometry) in gels. Using a monoclonal antibody that allows for detection of the allergen module in a MAT molecule exhibited a main band and several minor bands. All bands migrate reproducibly to the same position as in the original gel also after re-loading a second gel with excised bands of the first gel. Surprisingly, in all of these bands with apparent lower and higher molecular weight, the full length MAT molecules were identified by excision of bands out of the gel, their tryptic digestion and subsequent analysis by mass spectrometry (nanoLC/ESI-MS-MS). From these experiments an untypical, anomalous behavior of different folding variants of MAT molecules in the SDS-PAGE can be concluded ("gel shifting"). Furthermore, in all batches of MAT molecules multimeric forms of the protein could be detected which were difficult to separate from monomeric forms.

For e.g. economic aspects, but also for regulatory requirements, it is necessary to improve (i) the manufacturing process of the MAT molecules and (ii) their suitability for standard analytical methods of purity determination. Additionally, for adapting the MAT molecules to specific target species, such as ruminants, pigs, dogs and/or cats, adaption of the immunological targeting within the MAT technology is required. This species specificity is necessary to be represented in said iMAT molecules since differences in homologues Ii amino acid sequences between mammalian species exist (FIG. 10). However, a proper binding of the Ii fusion protein (iMAT) to the Δβ subunits of MHC class II, specifically in the CLIP region is required for an optimal immunological function with respect to the antigen in said iMAT molecules. A proper binding to said MHC class II molecules is achieved if the Ii sequence in iMAT does resemble the original as far as possible.

Additionally, the MAT molecules are readily employed in allergies elicited by a known major allergen (e.g. cat dander allergy in humans by Fel d1). However, it seems difficult to employ the MAT molecules of the prior art in clinical settings, such as allergies, where for instance a variety of non-cross-reactive allergens are known to be involved, but the importance of such allergens in eliciting the allergy is unknown (i.e. the major allergens are unknown).

Furthermore, the prior art does not describe how more than one (e.g. 2, 3, 4 or more) allergen can be embedded into (i) MAT molecules without exceeding a certain size of the fusion protein that hinders protein manufacturing.

The objective underlying the invention is to provide improved MAT molecules useful as active agents in pharmaceutical composition, such as vaccines, and their corresponding therapeutic and/or preventive uses in animals, excluding equines, which overcome the problems of the prior art.

SUMMARY OF THE INVENTION

In one aspect, the objective underlying the invention has surprisingly been solved by providing a(n) (isolated) recombinant protein, preferably an improved MAT (iMAT) molecule, comprising:

(i) at least one first module being an amino acid sequence allowing the translocation of the iMAT molecule from the extracellular space into the interior of cells, (ii) at least one second module being an amino acid sequence allowing species-specific intracellular targeting of the iMAT molecule to the cell organelles which are involved in the processing of antigens and/or the loading of MHC molecules with antigens, preferably processed antigens, and (iii) at least one third module as antigen module being an amino acid sequence derived from at least one full or partial epitope of at least one antigen, preferably at least one allergen, determining the specificity of an immune response modulated by such iMAT molecule, characterized in that at least in the antigen module(s) at least one cysteine residue is substituted with a different amino acid residue, preferably serine, leucine, isoleucine, arginine, methionine, and/or aspartic acid, for use in a method of prevention and/or therapy of one or more allergies in animals excluding equines and/or for use in a method of prevention and/or therapy of one or more infectious diseases in animals excluding equines and/or for use in a method of prevention of transmission of one or more infectious diseases in animals excluding equines and/or for use in a method of prevention of transmission of one or more infectious diseases in animals excluding equines by vectors.

Corresponding methods of prevention and/or treatment of animals excluding equines, in need thereof and uses for the preparation of a pharmaceutical composition/medicament for the prevention and/or treatment of animals excluding equines, are also intended to be within the scope of the present invention.

Preferably, in the at least one antigen module all cysteine residues are substituted with a different amino acid residue, preferably serine, leucine, isoleucine, arginine, methionine, and/or aspartic acid. More preferably in the entire iMAT molecule all cysteine residues are substituted with a different amino acid residue, preferably serine, leucine, isoleucine, arginine, methionine, and/or aspartic acid.

Preferably, if not all cysteine residues are substituted with a different amino acid residue, preferably serine, leucine, isoleucine, arginine, methionine, and/or aspartic acid, an even number of cysteine residues remains in the entire iMAT molecule.

Preferably, all of such modules are covalently linked to each other, optionally by additional spacer module(s) between two or more adjacent, optionally all, of such first, second and/or third modules.

More preferably, all of such modules are covalently linked to each other and no additional spacer module(s) are present between two or more adjacent modules of such first, second and/or third modules at all.

In another aspect, the objective underlying the invention has surprisingly been solved by providing an iMAT molecule relating to one or more of the amino acid sequences according to SEQ ID NOs:2 or 3, preferably comprising one or more of the amino acid sequences according to SEQ ID NOs:4 or 5. In a further aspect, the objective underlying the invention has surprisingly been solved by providing an iMAT molecule comprising one or more of the amino acid sequences according to SEQ ID NOs:14-23. In a preferred aspect, the objective underlying the invention has surprisingly been solved by providing an iMAT molecule comprising, preferably consisting of, one or more of the amino acid sequences according to SEQ ID NOs: 24-83.

In another aspect, the objective underlying the invention has surprisingly been solved by providing a vaccine or immunogenic composition or pharmaceutical composition comprising the (isolated) recombinant protein as herein disclosed and claimed.

In another aspect, the objective underlying the invention has surprisingly been solved by providing the (isolated) recombinant protein as herein disclosed and claimed or the vaccine or immunogenic composition or pharmaceutical composition as herein disclosed and claimed for use in a method of prevention and/or therapy of one or more allergies in animals, preferably dogs and/or cats, but excluding equines; preferably allergies to flea bites preferably in dogs and/or cats; allergies to certain food components preferably in dogs and/or cats; atopic dermatitis preferably in dogs and/or cats; allergic airway inflammation and/or obstruction preferably in cats. Corresponding methods of prevention and/or treatment of animals, preferably dogs and/or cats, but excluding equines, in need thereof and uses for the preparation of a pharmaceutical composition/medicament for the prevention and/or treatment of animals, preferably dogs and/or cats, but excluding equines, are also intended to be within the scope of the present invention.

In another aspect, the objective underlying the invention has surprisingly been solved by providing the (isolated) recombinant protein as herein disclosed and claimed or the vaccine or immunogenic composition or pharmaceutical composition as herein disclosed and claimed for use in a method of prevention and/or therapy of one or more infectious diseases in animals, preferably ruminants, pigs, dogs and/or cats, but excluding equines, and/or prevention of transmission of one or more infectious diseases in animals, preferably ruminants, pigs, dogs and/or cats, but excluding equines, by vectors, preferably by blood feeding bugs, flies, midges, ticks and/or mosquitos. The infectious pathogen and/or infectious disease may be one or more selected from *campylobacter*, heartworm, ehrlichiosis, leishmaniosis, trypanomiasis, borreliosis, Schmallenberg-, blue tongue- and/or west nile virus infection, dermatophytosis and/or infections of the digestive tract and/or other organs by viruses (e.g. rota-, coronavirus) and/or parasites (e.g., helminths) and/or protozoa (e.g., coccidiosis, cryptosporidiosis) and/or their pre-patent stages. Corresponding methods of prevention and/or treatment of animals, preferably ruminants, pigs, humans, dogs and/or cats, but excluding equines, in need thereof and uses for the preparation of a pharmaceutical composition/medicament for the prevention and/or treatment of animals, preferably ruminants, pigs, humans, dogs and/or cats, but excluding equines, are also intended to be within the scope of the present invention.

In a further aspect, the objective underlying the invention has surprisingly been solved by providing a nucleic acid encoding the (isolated) recombinant protein as herein disclosed and claimed.

In a further aspect, the objective underlying the invention has surprisingly been solved by providing a vector comprising at least one nucleic acid as herein disclosed and claimed.

In yet a further aspect, the objective underlying the invention has surprisingly been solved by providing a primary cell or cell line comprising at least one nucleic acid as herein disclosed and claimed and/or at least one vector as herein disclosed and claimed.

Surprisingly, the iMAT molecules according to the present invention, as herein disclosed and claimed, do possess physicochemical and/or immunological characteristics that render them superior to the MAT molecules of the pertinent prior art:

(i) The substitution of at least one cysteine residue, preferably all cysteine residues, with a different amino acid residue in the antigen module(s), preferably entire iMAT molecule, which was selected in silico not to compromise the stability of the final iMAT molecule, renders the iMAT molecule according to the present invention surprisingly suitable for the application of standard purification procedures for biopharmaceuticals as well as for standard analytical methods.

(ii) The preferred direct covalent linkage of the modules of the iMAT molecule, i.e. first translocation module, second targeting module and third antigen module, without any additional spacer modules between such modules, i.e. no additional spacer modules between two or more adjacent modules of such first, second and/or third modules at all, contributes in addition to the superior characteristics of the iMAT molecules according to the present invention: such iMAT molecules which are thought to be more rigid in three-dimensional structure and hence unable to form conformational IgE epitopes, are even more hypoallergenic—virtually to the extent of no allergenicity at all.

(iii) The preferred presence of a(n) (quasi) N-terminal or C-terminal His-tag results in iMAT molecules according to the present invention that can be used as a surrogate marker for monitoring immunity and/or duration of immunity since such tag module, optionally together with one or more adjacent amino acid residues from the translocation module, can be used to induce a specific immunologically detectable signal (e.g. an antibody) in the target subject, that is specific to the structure of the iMAT molecules (see Example 1 herein). Additionally, the presence of such tag module can be used for separating proteins in a sample containing the iMAT molecules according to the present invention, e.g. using zinc- or cobalt-charged solid supports, and hence further improves the possibility to produce iMAT molecules according to the present invention without aggregation during the purification process. A(n) (quasi) N-terminal His-tag is preferred.

(iv) The at least one targeting module in the iMAT molecules according to the present invention is preferably species-specific, i.e. in case of an intended application of such iMAT molecules to canine, feline, bovine, ovine, caprine or porcine a targeting module, e.g. the canine invariant chain, is chosen accordingly. By this species-specific targeting optimized binding characteristics of the iMAT molecules according to the present invention to the MHC Class II molecules can successfully be achieved.

(v) The at least one antigen module in the iMAT molecules according to the present invention is preferably an allergen. This could be derived from food and/or mold (fungi and/or their spores), pollen, house dust or forage mites (and/or their feces) and/or fleas, preferably pollen from tree, grass, herbaceous, ambrosia and/or brassicaceae pollen and/or fungi and/or their spores of the genera *aspergillus, alternaria, botrytis, cercospora, cladosporium, curvularia, drechslera, eurotium, helminthosporium, epicoccum, erysipheloidium, fusarium, lichtheimia, nigrospora, penicillium, periconia, peronospora, polythrincium, saccharopolyspora* (formerly also *faenia* or *micropolyspora*), *thermoactinomyces, stemphylium, torula* and/or mites (or their feces) of the genera *acarus, glycophagus, tyrophagus, dermatophagoides, euroglyphus, lepidoglyphus, blomia* and/or fleas of the genera *Ceratophyllus, Ctenocephalides, Pulex, Archaeopsylla*. The at least one antigen module in the iMAT molecules according to the present invention is more preferably a *Dermatophagoides* allergen. The allergen can be selected according to the following criteria: when major allergens eliciting an allergy in subjects are unknown, the at least one antigen module in the iMAT molecules according to the present invention can be selected by a bioinformatics approach as described exemplarily and in detail in Examples 5 and 6 herein. By this means improved MAT molecules can be achieved which are useful specifically as vaccines, e.g. for therapy and/or prevention of allergies in animals, preferably dogs and/or cats, but excluding equines. The at least one antigen module in the iMAT molecules according to the present invention may also be an antigen of a pathogen involved in one or more infectious disease(s). This could be derived from the genera *Campylobacter, Dirofilaria, Ehrlichia, Leishmania, Trypanosoma, Borrelia*, Orthobunyavirus, Orbivirus, Flavivirus, Rotavirus, Coronavirus, *Trichophyton, Microsporum*; other helminths like *Cooperia, Haemonchus, Ostertagia, Trichostrongylus, Dictyocaulus, Metastrongylus*; and/or protozoa with gastrointestinal infestation like *Eimeria, Isospora, Cryptosporidium, Giardia*—in case of parasites also antigens derived of the pre-patent stages might be employed. The at least one antigen module in the iMAT molecules according to the present invention may also be an antigen (e.g. saliva component) of a vector involved in the transmission of one or more infectious disease(s), e.g., belonging to the families Culicidae, Ceratopogonidae, Phlebotominae Ixodidae and/or Cimicidae. By this means improved MAT molecules can be achieved which are useful specifically as vaccines, e.g. for therapy and/or prevention and/or prevention of transmission of infectious diseases in animals, preferably ruminants, pigs, dogs and/or cats, but excluding equines.

(vi) Production of novel iMAT molecules that comprise sequence motifs of more than one allergen in only one of said iMAT molecule, i.e. mosaic fusion proteins, can be achieved. The selection of the peptide sequences embedded in the allergen module is based on pan allergenic motifs detected in the relevant major allergens by bioinformatics tools. By this approach the size of such iMAT molecules can be kept low enough to allow efficient production in suitable expression systems.

In particular, the present invention provides (isolated) recombinant proteins exhibiting an improved solubility, that are readily applicable to chromatographic separation techniques and that show an improved stability.

In addition, the (isolated) recombinant proteins according to the present invention preferably display high activities and efficacies in inducing the desired immunological effects, namely, advantageously species specific modulating the immune response against allergens in a subject becomes feasible, e.g. in animals, more preferably dogs and/or cats, but excluding equines, allergen specific IgE mediated hypersensitivity reactions may be modulated in different target organs as skin, respiratory and/or the gastrointestinal system. And/or prevention and/or therapy of infectious diseases and/or prevention of transmission of infectious diseases by vectors in animals, preferably ruminants, pigs, humans, dogs and/or cats, but excluding equines, becomes feasible.

The allergenicity of a therapeutic allergen is of utmost importance, it is a measure of the potential to induce adverse events, e.g. provoke anaphylaxis. With regard to prior art MAT molecules conflicting results about their allergenicity in comparison to the corresponding native allergens have been reported in the prior art. Senti G et al. (J Allergy Clin Immunol. 2012, 129(5): 1290-1296) demonstrated hypoallergenicity of a MAT-Fel d1 in the Cellular Antigen Stimulation Test (CAST) assay as well as in the intradermal and in the intracutaneous test. The quantitative difference in sensitivity between the allergen and the MAT molecule comprising the Fel d1 was 100-, 23- and 16-fold, respectively. Though MAT-Fel d1 was clearly hypoallergenic, some allergenicity remained. In contrast Zhao et al. (Int J Clin Exp Med 2015; 8(4): 6436-6443) describe their MAT-Der p1 construct to exhibit an even stronger allergenicity (hyperallergenicity) as compared to the native Der p1 protein.

Surprisingly, the safety of the improved MAT molecules, as disclosed and claimed herein, is superior in this respect. In contrast to native allergens, which usually elicit a strong histamine release, surprisingly the iMAT molecules according to the present invention show virtually no histamine release response at all. Thus, iMAT molecules show superiority in respect to safety as compared with the MAT molecule as described in the prior art (see above).

The consequence of this surprising safety property of iMAT molecules in contrast to prior art MAT molecules is, that iMAT molecules used as desensitizing proteins can be used similar to vaccines against pathogens. No up-dosing as with classical therapeutic allergens is needed, since vaccines comprising iMAT molecules do not show allergen properties with respect to allergic adverse events. Already the dose of the first injection of the iMAT molecule in a treatment course is selected based on efficacy considerations only and one does not have to consider potential allergic adverse reactions. This could not be performed using MAT molecules described in the prior art since the allergenicity of MAT, compared to the native allergen, is only reduced to a certain level. However, MAT molecules described in the prior art are still allergens; iMAT molecules in contrast are not. The advantage of this improved property renders a more efficacious treatment regime possible with e.g. three subcutaneous or intralymphatic injections with a high biopharmaceutical content (e.g. 3 times 1 pig to 100 pig, preferably 3 times 10 pig to 50 pig iMAT protein).

The lack of allergenicity of the iMAT molecules can be explained by the fact that in contrast to the MAT molecules described in the prior art no linker amino acid residues [i.e. spacer module(s) between the first, second and/or third module(s)] are used to separate the different modules in such iMAT molecules.

It is known in the prior art that engineered fusion proteins containing two or more functional polypeptides joined by a peptide or protein linker, such linker is important for the function (e.g. epitope recognition by the immune system) of the proteins [Klein J S et al., Protein Eng Des Sel. 2014, 27(10): 325-330]. The separation distance between functional units can impact epitope access and the ability to bind with avidity.

It is assumed that in iMAT molecules of the present invention, which are missing the amino acid residue linkers between the modules, in particular between the targeting domain and the antigen module, lead to a more rigid structure, conformational epitopes of the allergen module might not be formed due to incorrect folding. A cross linking of antibodies bound on the surface of basophils (e.g. IgE) by its high affinity receptors is necessary to induce activation and histamine release. However, misfolded allergens might not be able to induce such cross linking. Thus, an iMAT molecule without additional spacer modules/linkers between the first, second and third module may not form conformational IgE epitopes, which renders the iMAT molecules according to the present invention non-allergenic. Thus, in a specific embodiment the iMAT molecules of the present invention lack any additional spacer modules or linkers between the first, second and third module.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The terms "isolated recombinant protein", "recombinant protein" and/or "improved MAT (iMAT) molecule" are interchangeably used in the course of the present invention. They all have the identical meaning.

The term "module" in the course of the present invention refers to a specific amino acid sequence, e.g. a part, a unit or a moiety of a polypeptide, usually short amino acid/peptide sequences, having a defined function.

The term "first module being an amino acid sequence allowing the translocation of the (isolated) recombinant protein, preferably improved MAT (iMAT) molecule, from the extracellular space into the interior of cells", herein also interchangeably referred to as "translocation module" or "translocation sequence", in the course of the present invention refers to a specific amino acid sequence that promotes the transport of the cargo molecule, e.g. amino acid sequence, peptide, polypeptide, protein and other classes of substances, such as nucleic acids or pharmaceutically active ingredients (API), to the interior of cells, in particular eukaryotic cells, more particular, cells expressing the MHC class II molecules on the surface and/or the MHC class I molecules on the surface, as known in the literature.

By the presence of the translocation module it is possible to promote the entry of said cargo molecule into the cells.

Amino acid sequences useful as translocation modules are described in the prior art. For example, U.S. Pat. No. 7,653,866 discloses several useful translocation sequences including the HIV-tat molecule or the protein VP22, which is derived from herpes simplex virus. This principal of promoting the entry of a given target molecule into the interior of cells is described numerously in various studies in the pertinent patent and non-patent literature. In addition, suitable translocation sequences include homeoprotein sequences, leucine zipper sequences, arginine-rich and/or lysine-rich sequences, and various other sequences of proteins or polypeptides which are secreted despite the absence of a secretion signal sequence. Particularly useful are viral peptide sequences, e.g. the protein HIV transcriptional activator protein (HIV tat). The Tat sequence or Tat peptide has been described in the prior art including various modifications. All the variations described in the prior art for peptide sequences of Tat are generally suitable as translocation modules. Other examples include the VP22 peptide as well as antennapedia peptides derived from the *drosophila* homeotic protein antennapedia. In addition, other homeoproteins may be used. Various examples of suitable homeoproteins are described in the prior art. In addition, leucine zipper proteins, like human cFos-(139-164), or human cJun-(252-279) can be used. Moreover, arginine-rich and/or lysine-rich peptides are suitable as translocation modules including sequences like HIV-1 rev (34-50) or other peptides derived from virus or yeast. Of course, the polyarginine-rich and/or polylysine-rich peptides can be produced synthetically. Said polyarginine-rich and/or polylysine-rich peptides may comprise further amino acids. Suitable examples are described in the pertinent prior art.

In a preferred embodiment, the at least one translocation module comprises, preferably consists of, an amino acid sequence which does not consist of a complete protein sequence, as illustrated above, but instead of a minimal sequence still being functional, i.e. capable of effectively promoting cell entry. A suitable minimal sequence is for instance the amino acid sequence YGRKKRRQRRR (SEQ ID NO: 1).

In another preferred embodiment, the at least one translocation module comprises, preferably consists of, HIV-tat, VP22 and/or Antennapedia or a partial sequence thereof, provided that such at least one translocation module is functional as a module for translocation from the extracellular space into the interior of cells.

The term "second module being an amino acid sequence allowing species-specific intracellular targeting of the (isolated) recombinant protein, preferably improved MAT (iMAT) molecule, to the cell organelles which are involved in the processing of antigens and/or the loading of MHC molecules with antigens, preferably processed antigens", herein also interchangeably referred to as "targeting module" or "targeting sequence", in the course of the present invention refers to a specific amino acid sequence that allows/promotes the intracellular transport of the (isolated) recombinant proteins, as disclosed and claimed herein, to such cell organelles that are involved in the processing of antigens and/or the loading of MHC molecules with antigens.

In particular, such cell organelles include the endoplasmic reticulum, the Golgi apparatus, the trans-Golgi network, lysosomes, endosomes and MHC II compartments. These intracellular organelles are involved in processes such as, for example, the transport and/or processing of antigens, the preparation and/or loading of MHC II molecules with antigens or processed antigens, and/or the transport of the MHC II molecules loaded with such antigens to the cell surface.

A number of sequences are known in the prior art. A prominent example of useful targeting sequences includes the invariant chain of MHC class II molecules also known as Ii invariant chain or MHC II gamma chain. Various variants of the invariant chain are described in the patent and non-patent literature.

In a preferred embodiment of the present invention, the invariant chain is chosen from the species in which the immune response should be modulated and/or from the species in which the iMAT molecule should be intracellularly targeted. This species specificity is necessary to be represented in said iMAT molecules since differences in homologues Ii amino acid sequences between mammalian species exist (FIG. 10). However, a proper binding of the Ii fusion protein (iMAT) to the Aβ subunits of MHC class II, specifically in the CLIP region is required for an optimal immunological function with respect to the antigen in said iMAT molecules. A proper binding to said MHC class II molecules is achieved if the Ii sequence in iMAT does resemble the original as much as possible.

For example, for dogs, cats, cattle, sheep, goats or pigs the preferred invariant chain chosen is the canine, feline, bovine, ovine, caprine or porcine invariant chain. For dogs and cats, the preferred invariant chain is the amino acid sequence according to SEQ ID NO: 2 (canine) and SEQ ID NO: 3 (feline) or fragments thereof, provided such fragments maintain their intracellular transport function (e.g. the first 110 amino acids as shown in FIG. 10).

Other suitable examples for targeting sequences include lysosomal membrane proteins, comprising sequences suitable as targeting modules. That are, a number of membrane proteins occurring in lysosomes which have sequence motifs that allow targeting the lysosome. These groups of proteins include inter alia lamp 1, lamp 2, lamp 3, limp II and lap. In addition, tetraspan proteins are known in the prior art as targeting modules. Additional proteins can be found in the endosomal/lysomal compartments that show targeting properties. A skilled person is aware how to determine suitable targeting sequences accordingly.

In another embodiment, the at least one targeting module comprises, preferably consists of, the canine, feline, bovine, ovine, caprine or porcine invariant chain or fragments thereof provided such fragments maintain their intracellular transport function.

In a preferred embodiment, the at least one targeting module is the canine invariant chain, comprising, preferably consisting of SEQ ID NO: 4 (canine).

In a further preferred embodiment, the at least one targeting module is the feline invariant chain, comprising, preferably consisting of SEQ ID NO: 5 (feline).

The term "third module as antigen module being an amino acid sequence derived from at least one full or partial epitope of at least one antigen, preferably at least one allergen, determining the specificity of an immune response modulated by such (isolated) recombinant protein, preferably improved MAT (iMAT) molecule (in a subject, preferably an animal, more preferably a ruminant, pig, dog and/or cat, but excluding an equine)", herein also interchangeably referred to as "antigen module" or "antigen sequence", in the course of the present invention refers to a specific amino acid sequence that allows modulating the immune response against the epitope/antigen and determining the specificity of the immune response in a subject, preferably an animal, more preferably a ruminant, pig, dog and/or cat, but excluding an equine.

In this context, such antigen module(s) comprise(s) at least one cysteine residue that is substituted with a different amino acid residue, preferably serine, leucine, isoleucine, arginine, methionine, and/or aspartic acid. Thus, the immune response is different compared to the immune response of a subject, preferably an animal, more preferably a ruminant, pig, dog and/or cat, but excluding an equine, exposed to the unchanged amino acid sequence of the antigen.

There are no restrictions relating to the antigens on the basis of the method. The method can be used for example for activating the immune system of a subject against pathogens such as, for example, against viruses, bacteria, fungi, parasites, protozoa etc., i.e. very generally as vaccine. Additionally, the method can be used not only directly against such pathogens, but also to activate the host immune system to prevent the transmission in vector-borne diseases involving viruses, bacteria, fungi, parasites, protozoa, etc. In addition, the method can be used to activate the immune system against degenerated cells such as, for example, tumor cells, etc. However, it can also be used on the other hand for desensitization of the immune system of a subject against allergens such as, for example derived from food and/or aeroallergens, e.g. mold (fungi and/or their spores), pollen, animal hair, house dust or forage mites (and/or their feces), insect toxins, etc. or for targeted suppression of the immune system, e.g. if autoimmune reactions are present, such as, for example, arthritis, rheumatism, diabetes, SLE (systemic lupus erythematosus), etc., and for suppressing transplant rejection reactions. Further disorders which are not expressly mentioned and which are associated with an immune reaction which is too strong or too weak can likewise be treated with the iMAT molecules, as disclosed and claimed herein.

It is possible to employ as antigen modules for the purposes of the invention in principle all types of antigens able to modulate an immune response. Both, antigens currently already known and antigens to be discovered in future are suitable. In some circumstances, the antigens may also be those which do not lead to an immune response with conventional immunization methods known in the art at present, but which lead on application of the novel method described in the present invention to an immune response by the subject. Further, the term antigen encompasses antigenic fragments comprising the antigenic determinant/the antigenic determinants which are also known as epitope(s). Thus, the antigen module may be the whole molecule, e.g. the protein, or is a part of the molecule, i.e. a fragment thereof, like a peptide, encompassing at least one antigenic determinant or epitope. The at least one antigenic determinant or epitope is able to elicit an immune response against the antigen. The epitope can comprise one or more than one amino acid or peptide or other structure capable of eliciting an immune response such as sugar structures, phosphorylated amino acids, etc. or combinations thereof. The antigen can be a continuous epitope (i.e. not dependent on conformation, e.g. present in for example native and denatured proteins) or a discontinuous epitope (i.e. dependent on conformation, e.g. only present in native, folded, but not present in denatured proteins). It is possible to use not only proteins and peptides, but also sugar structures, lipids, e.g. lipopolysaccharides, lipoteichoic acids and other constituents of bacterial membranes (CD1b binds, for example, sugar structures and lipids), nucleic acids such as, for example, DNA comprising CpG motifs, organic substances such as, for example, latex or pharmaceutically active substances as antigen for the purposes of the present invention. The antigen may be derived from all possible life forms, such as e.g. animals, plants, fungi, parasites, unicellular or multicellular microorganisms, viruses and other life forms. The antigens may have been isolated from biological material, have been prepared as recombinant antigens or have been prepared by synthesis, e.g. by peptide synthesis. Synthetically prepared antigens may be substances which occur in nature or which do not occur in nature but are obtainable by chemical synthesis. Examples of non-naturally occurring substances which are, however, suitable as antigen in some circumstances are, for example, synthetically prepared substances which are present in medicaments, or synthetic peptides having amino acid sequences which do not occur in nature, or peptidomimetics, etc. Naturally occurring or synthetic or recombinant antigens can be modified by molecular biology, enzymatic, chemical and/or other methods in order to confer on them properties which are more advantageous for the particular application. These advantageous properties may be, inter alia, a higher or lower activity as antigen, a broader or a more specific action as antigen, a better solubility in hydrophilic or hydrophobic solvents, a greater permeability of the antigen modules for cell membranes, for membranes of organelles, for the blood-brain barrier, for the blood-CSF barrier etc., a higher or lower half-life in vivo or in vitro, a lower or higher toxicity, a better detectability of the antigen in vivo or in vitro after application of the antigen in the form of an iMAT molecule etc. It is additionally possible for the purposes of the present invention to combine a plurality of antigens in one antigen module. For this it is possible for identical antigens to be present in more than one copy in the antigen module, or it is possible for example for different variants of the same antigen to be combined in an antigen module. Combination of antigens, e.g. of antigen 1, and other antigens, e.g. of antigen 2, in an antigen module is also possible, etc. Further combinations, such as, for example, antigen 1 in more than one copy and antigen 2 in a single copy may also be combined in an antigen module, etc. It is additionally possible also for one or more different and/or one or more identical antigen modules to be present in an iMAT molecule. In principle, it is conceivable that for all possible combinations of single or multiple, identical or altered, copies of antigens derived from one or more different antigens can be combined for the purposes of the invention.

In a preferred embodiment, the antigen module comprises at least one full or partial epitope derived from at least one antigen, wherein such antigen is an allergen. At least one epitope is able to elicit an immune response against the allergen whereby the epitope can comprise one or more than one structure, e.g. a peptide, capable of eliciting an immune response. The epitope may be a continuous epitope or a discontinuous epitope of the allergen. Epitopes are preferably at least eight amino acids in length preferably are at least ten amino acids in length, more preferably are at least 13 amino acids in length. The antigen module comprises at least one full or partial epitope, but may also comprise two or more full or partial epitopes which may be identical or different from each other. Furthermore, the antigen module may comprise additional amino acid sequences adjacent to the at least one full or partial epitope. The epitope may be the natural occurring epitope or may be a modified epitope, either modified in its amino acid sequence and/or by one or more post-translational modifications.

In an embodiment, the at least one (third) antigen module comprises at least one full or partial epitope derived from at least one antigen of a pathogen involved in one or more infectious disease(s) of animals, more preferably ruminants, pigs, dogs and/or cats, but excluding equines. This could be derived from the genera *Campylobacter, Dirofilaria, Ehrlichia, Leishmania, Trypanosoma, Borrelia, Orthobunyavirus, Orbivirus, Flavivirus, Rotavirus, Coronavirus, Trichophyton, Microsporum*; other helminths like *Cooperia, Haemonchus, Ostertagia, Trichostrongylus, Dictyocaulus, Metastrongylus*; and/or protozoa with gastrointestinal infestation like *Eimeria, Isospora, Cryptosporidium, Giardia*—in case of parasites also antigens derived of the pre-patent stages might be employed. The at least one antigen module in the iMAT molecules according to the present invention may also be an antigen (e.g. saliva component) of a vector involved in the transmission of one or more infectious disease(s), e.g. belonging to the families Culicidae, Ceratopogonidae, Phlebotominae, Ixodidae and/or Cimicidae.

In a further preferred embodiment, the at least one (third) antigen module comprises at least one full or partial epitope derived from at least one allergen eliciting one or more allergies in animals, more preferably dogs and/or cats, but excluding equines. This could be at least one full or partial epitope of at least one allergen derived from food and/or mold (fungi and/or their spores), pollen, house dust or forage mites (and/or their feces), preferably pollen from tree, grass, herbaceous, ambrosia and/or brassicaceae pollen and/or fungi and/or there spores of the genera *aspergillus, alternaria, botrytis, cercospora, cladosporium, curvularia, drechslera, eurotium, helminthosporium, epicoccum, erysipheloidium, fusarium, lichtheimia, nigrospora, penicillium, periconia, peronospora, polythrincium, saccharopolyspora* (formerly also *faenia* or *micropolyspora*), *thermoactinomyces, stemphylium, torula* and/or mites (or their feces) of the genera *acarus, glycophagus, tyrophagus, dermatophagoides, euroglyphus, lepidoglyphus, blomia* and/or fleas of the genera *Ceratophyllus, Ctenocephalides, Pulex, Archaeopsylla*.

In a preferred embodiment this is, preferably at least one full or partial epitope of at least one allergen derived from mites more preferably from the genus *dermatophagoides*.

Examples of allergens of the genus *dermatophagoides* are shown in FIG. 9 (9A and 9B) identifying the species, the allergen and the UNIPROT accession number.

In a further preferred embodiment, such at least one allergen is Der f 15 according to SEQ ID NO: 11 (full) and SEQ ID NO: 18 (iMAT form). Preferred specific sequences of the antigen modules are the amino acid sequences according to SEQ ID NOS: 7-23, preferably SEQ ID NOs: 14-23 (iMAT forms).

The term "immune response modulated by" or interchangeably "immunomodulatory immune response", in connection with "(isolated) recombinant protein" and/or "iMAT molecule" in the course of the present invention refers to immunogenic and/or tolerogenic immune responses.

The term "hybrid iMAT" or "iMAT hybrid" or "mosaic-like iMAT" are used interchangeably. These terms refer to an iMAT molecule, which comprises in its third module more than one full or partial epitope sequence from two or more antigens. Preferably said antigens are two or more allergens, more preferably two or more short peptide sequences from different allergens, determining the specificity of an immune response modulated by such iMAT molecule (in a subject, preferably an animal).

The term "allergen" in the course of the present invention refers to a type of antigen that in the native form produces an abnormally vigorous immune response in which the immune system fights off all perceived threats that would otherwise be harmless to the subject. Typically, these kinds of reactions result in the phenotype known as allergy. Various types of allergens are described in the prior art, including foods, drugs, animal products or natural or synthetic materials. Preferably, a protein is considered to be an allergen, when it elicits in its native form a specific IgE response in at least five subjects, preferably animals, more preferably dogs and/or cats, but excluding equines. For the avoidance of doubt, an "allergen" in connection with the "at least one (third) antigen module comprising at least one full or partial epitope derived from at least one allergen" does not need to be in the native form any longer, which is also preferred—in other words, the term "allergen" in the course of the present invention also explicitly refers to non-native amino acid sequences as part of the iMAT molecules, as described and claimed herein, that do not elicit a specific IgE response in at least five subjects, preferably animals, more preferably dogs and/or cats, but excluding equines, any longer.

The term "allergenicity" of a therapeutic allergen is a measure of the potential to induce adverse events, e.g. provoke anaphylaxis. Exemplarily for an allergy in mammals, an assay to measure allergenicity in dogs is described in Griffin et al. [Griffin C E. Diagnosis of canine atopic dermatitis DOI: 10.1002/9781118738818.ch10]. This document describes measurement of allergen specific IgE mediated hypersensitivity in procedures as the allergen provocation tests, in particular such tests targeting the skin. Intradermal skin tests are used for the biological evaluation of recombinant allergens and for validation of genetically engineered hypoallergenic derivatives. Intradermal testing in a dog is performed by administering injections of small amounts of allergen solutions directly into the dog's dermis. This is done with small-gauge (27 gauge) needles and injections of 0.05 to 0.1 mL at each site. The positive reactions are arbitrarily interpreted by the presence of erythema, turgidity, height, and size of the wheal. The advantage of the intradermal test is a high sensitivity. This is of particular importance if the test shall deliver a quantitative measure for allergenicity. Performing said test by Griffin et al. with the iMAT molecules according to the present invention, those iMAT molecules show a 10-, 100- to 1000-times or even higher molar concentration of the allergenic component as compared to the corresponding natural, native allergen applied in the same test to reach a positive reaction in sensitized individuals, as for example cats and dogs.

The term "epitope", herein also interchangeably referred to as "antigenic determinant", in the course of the present invention refers to the part of an antigen that is recognized by the immune system, either by B-cells or T-cells. Epitopes are presented on the surface of antigen presenting cells by means of MHC molecules to which they are bound.

The term "subject", herein also interchangeably referred to as "individual" and/or "organism" and/or "host", in the course of the present invention preferably refers to animals and/or humans, e.g. ruminants, pigs, more preferably dogs and/or cats, but excluding equines. The term "ruminant", in the course of the present invention encompasses ruminating mammals including cattle, goats, and sheep. Thus, members of the genus *Bos, Capra* and/or *Ovis*, are interchangeably referred to as "bovine", "caprine" and/or "ovine" species. The term "animal" as used herein includes mammals. The animal may be selected from the group consisting of ruminants or members of the genus *Canis* or interchangeably referred to as "canine" species (e.g. dogs, wolves, foxes, coyotes, jackals), or members of the genus *Felis* or interchangeably referred to as "feline" species (e.g. lions, tigers, domestic cats, wild cats, other big cats, and other felines including cheetahs and lynx) or pigs, i.e. members of the genus *Sus* interchangeably referred to as "porcine" species.

The terms "peptide" and "protein" are used side by side as equivalent in the course of the present invention. A peptide or a protein means for the purposes of the present invention a covalent bond of at least two amino acids via a peptide linkage. The term "amino acid" and the term "amino acid residue" are used as equivalents in the present application, i.e. the meaning of the two terms is identical. The terms amino acid/amino acid residue and peptide/protein are used in the present application in the form of the widest possible definition.

In this connection, the term "recombinant protein" refers to a polypeptide which may be obtained by genetic engineering and expression in eukaryotic or prokaryotic systems. In addition, said term encompasses polypeptides obtained by artificial (e.g. solid-phase) synthesis.

As used herein, the term "different amino acid residue" refers to a known amino acid residue other than cysteine unless otherwise indicated. For example, said amino acid residue may be a naturally occurring amino acid residue, such as serine or isoleucine.

As used herein, the term "linear form" refers to proteins according to the present invention that lack secondary structure. Such proteins are often assumed to exhibit a random-coil conformation in which the only fixed relationship is the joining of adjacent amino acid residues by a peptide bond.

In a preferred embodiment, the (isolated) recombinant protein as herein disclosed and claimed is present in monomeric form and/or linear form.

As used herein, the term "treatment" refers to the administration of the (isolated) recombinant protein, as disclosed and claimed herein, and/or the corresponding vaccines and/or immunogenic compositions and/or pharmaceutical compositions in order to obtain the desired clinical results including prophylactic and/or therapeutic treatment.

As used herein, the term "immunotherapy" refers to a therapeutic and/or prophylactic treatment of a subject, e.g. by prophylactic and/or therapeutic vaccination.

As used herein, the term "vector" in connection with "transmission of one or more infectious disease(s)" refers to an alive organism and is herein interchangeably used with terms "biological vector", "biological carrier" and/or "disease carrier", such as blood feeding bugs, flies, midges, ticks and/or mosquitos.

Furthermore, it is possible, and preferred, that the (isolated) recombinant protein, as disclosed and claimed herein, contains in addition at least one tag module. That is, it is possible, and preferred, that one or more different and/or identical tag modules are part of the (isolated) recombinant protein, as disclosed and claimed herein. Tag modules may be short peptides, frequently consisting of up to 20 amino acids or functional groups which are not composed of amino acids, such as for example biotin or digoxigenin. Suitable tag modules include the well-known and preferred His-tag containing a histidine sequence of 4 to 12 or more, preferably directly consecutive histidine residues, preferably 5, 6 or 7 consecutive histidine residues. Other suitable tag modules include HA-tag, FLAG-tag, GST-tag or Strep-tag. Although the tag can be present anywhere in the (isolated) recombinant protein, as disclosed and claimed herein, in a preferred embodiment, the tag module is present at the (quasi) N-terminus and/or at the C-terminus of the (isolated) recombinant protein.

The tag modules are useful for isolating the (isolated) recombinant proteins, as disclosed and claimed herein, and in addition allow detecting the presence of such (isolated) recombinant proteins in vitro or in vivo. Furthermore, the tag module optionally together with one or more adjacent amino acid residues from an adjacent module or a linker spacing apart the different modules can be used in order to induce a specific immunologically detectable signal, (e.g. an antibody) in the target subject that can be used as a surrogate marker for immunity and/or duration of immunity. Immunotherapies with the (isolated) recombinant proteins, as disclosed and claimed herein, elicit an antigen-specific, preferably allergen-specific immune response in the target subjects that is qualitatively indistinguishable from the natural immune response after exposure to naturally existing antigens, preferably allergens. Thus, antibodies binding to the antigen module are not suitable for the purpose of being a surrogate marker for the efficiency of the iMAT induced immune modulatory effect. This obstacle can be eliminated by determining the unique, antigen-specific immunological signal obtained by the C-terminal and/or (quasi) N-terminal tag module—optionally together with the adjacent amino acid residues. Hence, it is possible to provide suitable surrogate markers accordingly.

In a preferred embodiment, the (isolated) recombinant protein, as disclosed and claimed herein, further comprises at least one tag module, preferably at least one His-tag, wherein such at least one tag module preferably is present N-terminally and/or C-terminally of the (isolated) recombinant protein, more preferably N-terminally after one methionine residue.

Moreover, the modules of the (isolated) recombinant protein, as disclosed and claimed herein, namely, the at least one translocation module, the at least one targeting module and the at least one antigen module may optionally be spaced apart by one or more spacer modules located between at least two of such modules.

The spacer modules may be, in particular, peptide sequences or organic molecules. Numerous spacer molecules which can be used for the purposes of the invention are known in the art. In addition, it is also possible to use spacer molecules which will be developed or discovered in future for the purposes of the invention. Suitable spacer modules are, inter alia, peptide spacers, crosslinkers, natural or synthetic polymers such as, for example, nucleic acids, substituted or unsubstituted hydrocarbons, etc.

The coupling can take place both by covalent (preferred) and by non-covalent linkages. The spacer modules have the task inter alia of separating the various modules of the (isolated) recombinant protein, as disclosed and claimed herein, from each other in space so that they do not have adverse effects on each other with regard to their functionality. Modules of the (isolated) recombinant protein for the purposes of the invention can be coupled by one or more spacer modules which can be cleaved by chemical and/or enzymatic reactions, e.g. by proteases. It is thus possible to separate the modules of the (isolated) recombinant protein, as disclosed and claimed herein, which are connected by the spacer modules, from each other as required.

In a preferred embodiment, however, in particular if the antigen module is an amino acid sequence derived from at least one full or partial epitope of at least one antigen being at least one allergen, no any such additional spacer modules, i.e. no additional spacer modules between two or more adjacent modules of such first, second and/or third modules at all are present.

Any desired arrangement of the individual modules of the (isolated) recombinant protein, as disclosed and claimed herein, is in general possible. Each module may be present one or more times in the (isolated) recombinant protein. The minimum requirement is the presence of at least one translocation module, at least one targeting module and at least one antigen module. Additional modules, such as tag modules, spacer modules, etc. may optionally be present but do not need to be present. All modules may be present one or more times in the (isolated) recombinant protein, as disclosed and claimed herein. If modules are present more than once, they may be present in the form of identical copies, or different versions of a module may be present in each case in a single copy or in more than one copy. It is also possible for entirely different modules of the same class of modules, e.g. a His-tag module and a biotin-tag module, to be present in the (isolated) recombinant protein, as disclosed and claimed herein. Both modules undertake functionally the same task (tag module) in the (isolated) recombinant protein, but do not need to have anything in common in terms of their molecular structure.

In a preferred embodiment, it is possible that two or more copies of one of the modules are present in the (isolated) recombinant protein, as disclosed and claimed herein. That is, two or more copies of identical or different antigen modules may be present. Alternatively, the (isolated) recombinant protein may contain two different antigen modules, for modulating the immune response in a subject.

Two or more identical copies of an antigen module in a recombinant protein may for example cause an enhanced immune response to such relevant antigen. Two or more different antigen modules may for example be combined in one (isolated) recombinant protein in order to modulate simultaneously the immune response towards two or more different antigens. Two or more different translocation modules can be used in the (isolated) recombinant protein, as disclosed and claimed herein. For example, a Tat sequence and a VP22 sequence can serve to make translocation more efficient since the translocation of the (isolated) recombinant protein then takes place efficiently in a broader spectrum of different cell types or tissue types. It is also possible for example to use two or more tag modules in one (isolated) recombinant protein, e.g. a His-tag and a FLAG-tag, in which case for example the His-tag is used to isolate the recombinant protein and for example the FLAG-tag serves to detect the (isolated) recombinant protein. It is possible to use two or more different targeting modules in one (isolated) recombinant protein, e.g. a sequence from the invariant chain of the MHC II molecule and as a further targeting module a mannose 6-phosphate group. For example, the invariant chain acts as targeting module into the MIICs, and the mannose 6-phosphate group mediates targeting into the lysosome, thus it being possible to increase the efficiency of antigen presentation or the number of different epitopes of the antigen presented by the antigen-presenting cells overall. In addition, the iMAT molecule of the present invention may encompass two or more different invariant chains stemming from identical or different species, thus, allowing using the proteins according to the present invention in different species.

The position of the individual modules within the (isolated) recombinant proteins, as disclosed and claimed herein, can also be varied as desired, as long as at least one translocation module, at least one targeting module and at least one antigen module are present. It is also possible for all or some of the modules of the (isolated) recombinant protein for example to be present not in the form of a linear sequential arrangement of modules, but as circular or as branched module structure or else in the form of dendrimers, or as a combination of linear and/or branched and/or circular and/or dendrimeric molecule portions. There are commercial suppliers of expression vectors which supply specific vectors which make it possible to prepare circular fusion proteins by these mechanisms, such as, for example, the IMPACT-TWIN system from New England Biolabs, Beverly, Mass., USA. Branched modules might be prepared for example by synthesizing peptides in which, starting from poly L-lysine, a new lysine residue is attached to both free amino groups of each of the subsequent lysine residues. In this way it is possible to create a peptide structure with virtually any extent of branching. It is then possible to synthesize, for example, translocation modules and/or targeting modules subsequently onto the branched peptide basic structure. Further modules can also be coupled onto a linear, circular or branched peptide basic structure by protein ligation. It is also possible to introduce for example biotin groups into the peptide basic structure during the peptide synthesis, and modules can then be attached to these biotin groups via, for example, streptavidin, the Strep tag system or via the PINPOINT™ system (respectively IBA GmbH, Gottingen, Germany and Promega Biosciences Inc., San Louis Obispo, Calif., USA). Modules attached in this way are then coupled via non-covalent linkages to the peptide's basic structure.

The antigen module of iMAT molecules according to the present invention can be selected by a bioinformatics approach as described exemplarily and in detail in Examples 5 and 6 herein. By this means iMAT molecules can be rendered useful specifically as vaccines, e.g. for therapy and/or prevention of allergic diseases on the bases of the participation of allergen specific IgE mediated hypersensitivity reactions in different target organs as skin, respiratory—as well as gastrointestinal system, like atopic dermatitis (AD), food allergies and/or allergic asthma in subjects, preferably animals, more preferably dogs and/or cats, but excluding equines.

In a preferred embodiment, the (isolated) recombinant protein relates to, comprises, preferably consists of one or more of the amino acid sequences according to SEQ ID NOs:24 to 83.

The (isolated) recombinant proteins, as disclosed and claimed herein, are in particular useful in a method for specifically addressing the therapy and/or prophylaxis in subjects, such animals, more preferably dogs and/or cats, but excluding equines, suffering from allergic diseases on the bases of the participation of allergen specific IgE mediated hypersensitivity reactions in different target organs, e.g. skin, respiratory—as well as gastrointestinal system.

In veterinary medicine allergies are of major importance in particular in the field of companion animals.

Dogs and cats suffer from such diseases, as e.g. canine atopic dermatitis or feline atopic dermatitis or feline asthma.

Canine or feline atopic dermatitis (AD) has been defined as a genetically predisposed inflammatory and pruritic allergic skin disease with characteristic clinical features. It is most commonly associated with IgE antibodies to environmental allergens. The atopic phenotype can be seen in animals with IgE-mediated skin disease, food allergy, or a condition called "atopic-like dermatitis" (ALD). ALD is defined as a pruritic skin disease in dogs with characteristic features of AD but negative tests for IgE antibodies. Feline atopic dermatitis has many similarities to canine atopic dermatitis. Common clinical signs in canine atopic dermatitis include a history of seasonal or non-seasonal pruritus, otitis externa, recurrent and chronic inflammatory dermatitis especially in the axillary, inguinal, and flexor skin surfaces, recurrent bacterial infections, face rubbing and/or foot licking and chewing.

The etiology and pathogenesis of AD is complex and involves a genetic predisposition, impairment of the normal barrier function of the skin, and immunologic aberrations. Animals with AD are thought to be genetically predisposed to become sensitized to allergens in the environment. Allergens are proteins that, when inhaled or absorbed through the skin, respiratory tract, or GI tract, evoke allergen-specific IgE production. These allergen-specific IgE molecules affix themselves to tissue mast cells or basophils via the Fee receptors on such cells. When these primed cells come in contact with the specific allergen again, mast cell degranulation results in the release of proteolytic enzymes, histamine, bradykinins, and other vasoactive amines, leading to inflammation (erythema, edema, and pruritus). The skin is the primary target organ in dogs and cats, but rhinitis and asthma can also occur in ~15% of affected animals.

Mites are known as major causes of allergic diseases such as atopic dermatitis and asthma in e.g. dogs and cats. Conventionally, desensitization therapy that uses causative substances of allergies as therapeutic agents for allergic diseases is regarded as the most important basic remedy. In particular, the desensitization therapy is broadly conducted for diseases such as pollinosis, house dust allergies, and fungal allergies, which are induced by antigens such as inhalant allergens that are difficult to avoid. However, the desensitization therapy involves the risk of adverse events in particular anaphylaxis due to the action of sensitizing antigens, so that administration of safe therapeutic antigens like iMAT molecules is required.

Regarding mite allergic diseases, several species have been described to be of relevance *Dermatophagoides pteronyssinus, Dermatophagoides farinae, Euroglyphus maynei, Dermatophagoides siboney, Dermatophagoides microceras, Lepidoglyphus destructor, Blomia tropicalis, Tyrophagus putrescentiae, Glycophagus domesticus, Acarus siro*. However, two types of mites, *Dermatophagoides pteronyssinus* and *Dermatophagoides farinae*, have been reported as main allergen sources in house dust (Thomas, W R. et al., Chang Gung Med J 2004; 27:563-569). Major mite allergens have been fractionated from these mites.

The group 1 and 2 allergens of *Dermatophagoides* sp. induce high titers of IgE and Th2 cytokines in 80% of allergic patients. The allergens Der p 3, 5, 6, 7 and 8 induce IgE in about 50% of subjects usually at lower titers. The 92/98 kDa paramyosin (group 11) allergens binds IgE in 80% of allergic subjects and the 98 and 60 kDa chitinase enzymes (Der f 15 and 18) bind IgE from about 70% and 54% of allergic subjects and are important allergens for allergic dogs (McCall C et al., Vet Immunol Immunopath 2001; 78: 231-247).

In general, a variety of environmental allergens as pollens of grasses, trees, weeds, house dust, dust and storage mites and mold and/or mold spores, but also epidermal and insect antigens have been described to contribute to the sensitization of dogs in canine atopic dermatitis (Hill et al. Vet Immunol Immunopathol, 2001; 81(3-4):169-186).

As described above—the atopic phenotype may also be induced by food allergies, a hypersensitivity with a number of clinical manifestations. Besides gastrointestinal alterations (e.g. gastroenteritis, diarrhea or vomiting), food hypersensitivity often manifests in animals as a pruritic dermatitis and/or dermatosis of the face and neck, miliary dermatitis, generalized scaling or symmetrical alopecia. Especially in cats all the entities of the eosinophilic granuloma may be a consequence of hypersensitivity to certain food allergens.

The most common food allergens derive from meat, milk, fish, but also soybeans and/or more in general tinned food and dried food. Especially in the latter also involvement of allergies to additives and/or storage mites are reported (Guaguere E et al. EJCAP, 2009, 19 (3), 234-241; Jackson H A, EJCAP, 2009, 19 (3), 230-233).

Currently veterinary therapeutic options are restricted to symptomatic (e.g. corticoid) treatments and/or eliminating the foodstuff(s) responsible. However, care must be taken to not adversely affect the nutritional balance of the diet. More recently diets containing hydrolyzed proteins are available. Proteins are broken down—thus being less allergenic, which is effective and well-tolerated. However, these diets tend to be costly and little palatable, which can be a mayor limitation for compliance of the animals.

Allergen specific immunotherapy to treat food allergic animals, preferably dogs and/or cats has not yet been applied.

In a further embodiment the (isolated) recombinant proteins, as disclosed and claimed herein, are in particular useful as a method for specifically addressing the therapy and/or prophylaxis in cats suffering from allergic airway inflammation and/or obstruction (allergic asthma).

Cats spontaneously develop eosinophilic airway inflammation and airway hyper-reactivity that is very similar to human allergic asthma, i.e. feline allergic asthma is a chronic inflammatory disorder of the lower airways that may manifest with acute, life-threatening clinical signs.

Typical treatment involves palliative treatment only (e.g. bronchodilators and/or corticosteroids), but currently no causative treatment is available. Some pilot studies of the university group around Carol Reinero have addressed allergen specific immunotherapy in an animal model of induced Bermuda grass allergic asthma in cats.

Feline allergic asthma is a complex disease, but clearly exposure to airborne allergens plays a pivotal role in the etiology. Clinical remission can be achieved by eliminating the exposure to the aeroallergens. Though, the major antigens involved in triggering feline allergic asthma have not been clearly identified so far. Numerous potential agents are present in the cat's habitual environment e.g. pollen, molds, dust from cat litter, perfumes, room fresheners, carpet deodorizers, hairspray, aerosol cleaners or cigarette smoke. When screened using serum or intradermal skin tests, naturally allergic cats kept in-house had IgE reactivity to many of the same allergens implicated in human allergic asthma, i.e. mainly to house dust and storage mites and/or pollen (Prost C, Rev Fr Allergol Immunol Clin, 2008, 48 (5), 409-413).

In a further embodiment the (isolated) recombinant proteins, as disclosed and claimed herein, are in particular useful in a method for specifically addressing the therapy and/or prophylaxis in cats and/or dogs suffering from AD caused by flea bites (FAD).

FAD is one of the most severe skin allergies caused by flea infestations in dogs and cats. FAD can have manifestations of both immediate and delayed-type hypersensitivity. Typically, an immediate hypersensitive response in an animal susceptible to FAD includes wheal formation at the site of a fleabite. Such wheals can develop into a papule with a crust, representative of delayed-type hypersensitivity. Hypersensitive reactions to fleabites can occur in genetically predisposed animals as well as in animals sensitized by previous exposure to fleabites. Furthermore, flea bites can cause scratch-related secondary infections as a consequence of the inflammatory irritation of host's erythema, papules, crusts, and alopecia. Previous work found that pets rarely became desensitized to bites of flea once they have been made allergic to them. So besides the elimination of the flea, the alleviation of the animal's distress becomes the challenging problem. Current therapies for this disease include desensitization therapy or using some types of pharmacological intervention. However, each of these therapeutic approaches has some disadvantages. For example, anti-histamine medications could increase drowsiness, dry mouth, difficulty in urination, and constipation; whereas, classical desensitization therapy may cause life-threatening anaphylactic shock. Other disadvantages of these therapies are the high possibility of recrudescence and requirement for long-term treatments. Therefore, novel, effective therapeutic approaches are needed and should be developed in order to overcome unwanted adverse reactions. Effective treatment of FAD has been difficult if not impossible to achieve. FAD afflicts about 15% of cats and dogs in flea endemic areas and the frequency is increasing each year. In a geographical area, effective flea control requires treatment of all animals. One treatment investigators have proposed includes desensitization of animals using flea allergens. However, reliable, defined preparations of flea allergens are needed for such treatments. Whole flea antigen preparations have been used to diagnose and desensitize animals with FAD. Available commercial whole flea extracts, however, comprise only as a minor part saliva proteins and thus are unpredictable in their specific allergen content and, therefore, have limited usefulness. Prior art U.S. Pat. No. 7,629,446 as well as McDermott M J et al. (Molecular Immunology 2000, 37: 361-375) describe the discovery of the allergen Cte f 1 as major allergen in FAD. In this publication, they describe the cloning of the cDNA and characterization of a flea saliva protein, Cte f 1, a major allergen for flea allergic dogs and cats. Native Cte f 1 has a calculated molecular weight of 18 kDa and pI of 9.3. Mass spectrometry analysis indicates that the native molecule has no post-translational modifications and that all of the 16 cysteines are involved in intramolecular disulfide bonds. However, in the same publication the authors show several isoforms of the recombinant protein. The 16 cysteines in the secreted protein lead to the occurrence of these isoforms which renders purification and thus manufacturing of such a product difficult or even impossible under GMP conditions.

In research dogs experimentally sensitized to flea bite, Cte f 1 is a major allergen. Using *E. coli* produced rCte f 1 as the antigen in intradermal skin test and in solid phase ELISA, IgE can be detected in 100% of these experimentally sensitized FAD dogs. In addition, competition ELISA performed using sera from 14 sensitized dogs demonstrated that ICte f 1 produced in three different expression systems (*E. coli, P. pastoris* and baculovirus infected insect cells) could inhibit approximately 95% of the binding of antigen specific IgE to native Cte f 1.

The therapeutic potential of immunotherapeutic approaches comprising the Cte f 1 have been demonstrated by J. Jin et al. (Jin J. et al. Vaccine 28 (2010) 1997-2004). They reported that the simultaneous co-immunization with a DNA vaccine and its cognate coded protein antigen (Cte f 1) exhibit the potential to protect animals from FAD in a murine model. Furthermore, in their study they clinically tested this protocol to treat established FAD in cats following flea infestations. They presented data showing therapeutic improvement of dermatitis in these FAD cats following two co-immunizations.

iMAT molecules comprising the modified Cte f 1 sequence substituting the cysteines with other amino acid residues can be included into the iMAT molecule as allergen module together with either the cat or the dog invariant chain in order to achieve an optimized species specific immunemodulatory effect. Surprisingly these molecules (i) allow efficient recombinant protein production in suitable expression systems, (ii) have a substantially reduced safety risk since effector cells as mast cells are activated at much higher concentrations as compared to the unmodified Cte f 1 and (iii) induce a sustained immunological effect and a long lasting clinical improvement after only three injections.

In a further embodiment the (isolated) recombinant proteins, as disclosed and claimed herein, are in particular useful in a method for specifically addressing the therapy and/or prophylaxis in animals, more preferably ruminants, pigs, dogs and/or cats, but excluding equines, suffering from infectious diseases caused by bacteria.

The Gram-negative bacterium *Campylobacter* is the most common bacterial cause of gastroenteritis in domesticated animals, e.g. dogs, cats, pigs, ruminants. Clinical signs are mostly more severe in young mammals. Besides enteritis also abortions and infertility in various species has been reported. The infection is primarily through ingestion—on entry the bacterium needs to overcome the host defense with the expression of a variety of colonization and virulence determinants. A number of those are antigenic surface or outer membrane proteins, their interaction with e.g. epithelial cells of the gastrointestinal tract is essential for colonization, i.e. infection of the host.

In order to solve this medical problem, the at least one antigen module in a campylobacteriosis dedicated (isolated) recombinant protein, as disclosed and claimed herein, may be selected from antigens derived from *campylobacter* spp. e.g. flagellin, surface-exposed proteins (CadF and PEB 1), or other surface proteins. Improved MAT molecules may be useful specifically as vaccines, e.g. for therapy and/or prevention of campylobacteriosis. The treatment according to the present invention can involve the administration of the iMAT molecule to the offspring and/or can also comprise a treatment of the pregnant mother.

In a further embodiment the (isolated) recombinant proteins, as disclosed and claimed herein, are in particular useful in a method for specifically addressing the therapy and/or prophylaxis in animals more preferably ruminants, pigs, dogs and/or cats, but excluding equines, suffering from infectious diseases caused by viruses.

For example, West Nile virus (WNV) is a mosquito-transmitted positive-stranded RNA virus grouped within the Japanese encephalitis virus serocomplex of the genus Flavivirus in the family Flaviviridae. The WNV is the causative agent of the disease syndrome also named West Nile Fever. Birds are the natural reservoir hosts, and WNV is maintained in nature in a mosquito-bird-mosquito transmission cycle. However, man, horses, dogs, cats, but also ruminants have been described to be susceptible. Though most WNV infections remain clinically latent—WNV being a potentially neuroinvasive virus, it may cause meningitis or encephalitis. In animals WNV remains frequently unrecognized, but animals might be euthanatized due to severe neurologic signs caused by WNV—including paresis, ataxia, recumbency, and muscle fasciculation, whereas others exhibit mild to severe polioencephalomyelitis.

In a further embodiment the (isolated) recombinant proteins, as disclosed and claimed herein, are in particular useful in a method for specifically addressing the prevention of transmission of infectious diseases in animals, more preferably ruminants, pigs, dogs and/or cats, but excluding equines, by vectors, e.g. blood feeding bugs, flies, midges, ticks and/or mosquitos.

The pathogens are delivered into the skin of the mammalian host along with arthropod saliva, which contains a wide variety of bioactive molecules. These saliva components are capable of altering hemostasis and immune responses and may contribute to the ability of the pathogen to induce an infection. The presence of infectious microorganisms in the salivary glands of blood-feeding arthropods itself alters saliva composition, such as changes in the concentration of e.g. apyrase or anti-thrombinase in infected mosquitoes. Vector-associated or saliva components can e.g. alter vasoactivity and/or modulate the immune response of a host and be of crucial importance for transmission of infectious diseases. Vaccination of the host against arthropod saliva components can interfere with viral transmission, as shown for sandfly salivary proteins and transmission of *leishmania* spp. These vaccines have however not passed preclinical research up to date (WHO PD-VAC 2014—Status of Vaccine Research and Development of Vaccines for Leishmaniasis).

Arthropod saliva antigens are well suited to be employed in the antigen module of iMAT molecules according to the present invention and may be useful specifically as vaccines to activate the host immune system to prevent the transmission of infectious pathogens by vectors e.g. viruses, fungi and/or parasites and/or their pre-patent stages in animals, more preferably ruminants, pigs, dogs and/or cats, but excluding equines.

In a further embodiment the (isolated) recombinant proteins, as disclosed and claimed herein, are in particular useful in a method for specifically addressing the therapy and/or prophylaxis in animals, more preferably ruminants, pigs, dogs and/or cats, but excluding equines, suffering from infectious diseases caused by fungi.

Dermatophytosis or ringworm is a fungal infection of the hair and of the superficial keratinized cell layers of the skin occurring in animals and man. Several species of genus *Microsporum* or genus *Trichophyton* belonging to the groups of zoophilic or geophilic dermatophytes can cause clinical infections in mammals. A variety of surface antigens of the fungi and/or their spores are well suited to be employed in the antigen module of iMAT molecules according to the present invention and may be useful specifically as vaccines, e.g. for therapy and/or prevention of dermatophytosis in animals, more preferably ruminants, pigs, dogs and/or cats, but excluding equines.

In a further embodiment the (isolated) recombinant proteins, as disclosed and claimed herein, are in particular useful in a method for specifically addressing the therapy and/or prophylaxis in animals more preferably ruminants, pigs, dogs and/or cats, but excluding equines, suffering from infectious diseases caused by parasites.

Parasites infecting mammals are ubiquitous and clinically important across the world. The major parasitic threats to ruminants, pigs, dogs and/or cats are e.g. *Cooperia, Haemonchus, Ostertagia, Trichostrongylus, Dictyocaulus, Metastrongylus*. Increasing levels of anthelmintic resistance is reported worldwide in parasites. For protozoa, e.g. *Cryptosporidium* few drugs consistently inhibit parasite infestation and/or reproduction in the host. Mainly neonatal or young mammals are affected and outcome relies on innate and adaptive immune responses.

Antigens deriving from adult parasites as well as prepatent stages are another example to be employed in the antigen module of iMAT molecules according to the present invention and may be useful specifically as vaccines, e.g. for therapy and/or prevention of parasite infection in animals, more preferably ruminants, pigs, dogs and/or cats, but excluding equines.

The treatment according to the present invention can involve the administration of the iMAT molecule to the offspring and/or can also comprise a treatment of the pregnant mother.

In particular, in case of modulating the immune response in canine, feline, bovine, ovine, caprine or porcine species the at least one targeting module preferably is the respective invariant chain.

In a preferred embodiment the at least one targeting module is the canine invariant chain according to SEQ ID NO: 2 or 4. In another preferred embodiment the at least one targeting module is the feline invariant chain according to SEQ ID NO: 3 or 5.

In an advantageous embodiment, the (isolated) recombinant protein, as disclosed and claimed herein, is present in a monomeric form since, for instance, recombinant allergens tend to aggregate formation, particularly, if produced via inclusion bodies. By substituting at least one, preferably all cysteine residues in the entire sequence of the (isolated) recombinant protein, preferably by substituting for serine, leucine, isoleucine, arginine, methionine and/or aspartic acid, it is possible to prevent intermolecular disulfide bond formation, thus, avoiding any aggregation, in particular, any non-native formation of inter- and/or intramolecular bonds. That is, the (isolated) recombinant protein being entire devoid of cysteine residues does not aggregate. Consequently, the protein is easily to express and demonstrates improved targeting and MHC presentation.

Furthermore, such cysteine-free variants of, for instance, allergens, in which the cysteine residues in the amino acid sequence of wild-type allergens have been mutated solely or in combinations, show a reduced IgE reactivity compared to the corresponding wild-type allergens and at the same time have substantially retained reactivity towards T-lymphocytes and are thus hypoallergenic.

The invention accordingly relates to such hypoallergenic variants of allergens eliciting for example allergies to flea bites; to certain food components and/or atopic dermatitis and/or allergic airway inflammation and/or obstruction in animals, more preferably ruminants, pigs, dogs and/or cats, but excluding equines, wherein in the variants the cysteine residues of wild-type allergens have been mutated solely or in combination.

Furthermore, the presence of a tag module for separating proteins in a sample, comprising the iMAT molecules according to the present invention, e.g. using zinc- or cobalt-charged solid support further improve the possibility to produce fusion proteins without aggregates during the purification process. Typically, the tag module includes a polyhistidine tag of five to six consecutive histidine residues.

The (isolated) recombinant proteins, as disclosed and claimed herein, are useful in a pharmaceutical composition. For example, the (isolated) recombinant proteins are for use in a vaccine. Hence, the present invention provides vaccine compositions containing one or more (isolated) recombinant proteins, as disclosed and claimed herein. Such vaccine composition can be used therapeutically and/or prophylactically in animals, more preferably dogs and/or cats, but excluding equines, suffering from allergic diseases on the basis of participation of allergen specific IgE mediated hypersensitivity reactions in different target organs such as skins, respiratory and gastrointestinal systems; or such vaccine composition can be used therapeutically and/or prophylactically in animals, more preferably ruminants, pigs, dogs and/or cats, but excluding equines, suffering from infectious diseases induced by pathogens, e.g. viruses, fungi and/or parasites and/or their prepatent stages. Additionally, the method is not only directed against such pathogens, but also capable to activate the host immune system to prevent the transmission of a disease by vectors, e.g. blood feeding bugs, flies, midges, ticks and/or mosquitos.

Thus, in a preferred embodiment of the present invention a vaccine for subjects, such as animals, more preferably dogs and/or cats, but excluding equines, is provided in order to treat and/or prevent atopic dermatitis and/or allergic asthma caused by a response of e.g. exposure to *dermatophagoides* mites.

In a further embodiment of the present invention a vaccine for subjects, such as animals, more preferably cats, but excluding equines, is provided in order to treat and/or prevent allergic asthma caused by a response to e.g. mold (fungi and/or their spores), pollen, house dust or forage mites (and/or their feces).

In a further embodiment of the present invention a vaccine for subjects, such as animals, more preferably ruminants, pigs, dogs and/or cats, but excluding equines, is provided in order to treat and/or prevent infectious diseases involving e.g. the genera *Campylobacter, Dirofilaria, Ehrlichia, Leishmania, Trypanosoma, Borrelia*, Orthobunyavirus, Orbivirus, Flavivirus, Rotavirus, Coronavirus, *Trichophyton, Microsporum*; other helminths like *Cooperia, Haemonchus, Ostertagia, Trichostrongylus, Dictyocaulus, Metastrongylus*; and/or protozoa with gastrointestinal infestation like *Eimeria, Isospora, Cryptosporidium, Giardia*—in case of parasites also antigens derived from the prepatent stages might be employed. Additionally, the vaccine can be provided to activate the host immune system to prevent transmission of diseases by vectors, e.g. belonging to the families Culicidae, Ceratopogonidae, Phlebotominae Ixodidae and/or Cimicidae and/or other blood feeding insects.

The pharmaceutical composition, e.g. in form of a vaccine, of the (isolated) recombinant proteins is preferably designed for sublingual administration, subcutaneous and/or intradermal injection, injection into a lymph node and/or for administration via the mucous membranes, in particular, via the mucous membranes of the gastrointestinal tract or of the respiratory system.

In a preferred embodiment of the present invention, the pharmaceutical compositions are parenterally administered.

The iMAT molecules according to the present invention can be used as a pharmaceutical or as a vaccine to modify, for instance, allergic disorders. For example, atopic dermatitis and/or allergic asthma can be treated by such iMAT molecules.

Low amounts (1 to 1000 pjg referring to the weight of solely the one or more antigen modules) of recombinant iMAT molecules comprising allergens of atopic dermatitis and/or allergic asthma eliciting from mites of the genus *dermatophagoides* e.g. injected 1 to 5 times subcutaneously, intradermally or directly into the lymph node, induce a strong and long lasting immune response in cat and/or dog leading to prevention of the disease and/or an amelioration of clinical symptoms.

In one preferred embodiment, the iMAT molecules of the present invention are administered in combination with at least one adjuvant. The adjuvant includes, but is not limited to, one or more of the following: alum, BCG, aluminium hydroxide, aluminium phosphate, calcium phosphate, lipid emulsions, lipid or polymeric nano- or microspheres, micelles, liposomes, saponin, lipid A, or muramyl dipeptide, bacterial products, chemokines, cytokines and hormones, chitosan, starch, alginate, cellulose derivatives (e.g., ethyl cellulose, hydroxypropylmethyl cellulose), nucleic acids, or a nucleic acid construct. One or more of these components may be added to enhance or modify the immune response. Alternatively, the iMAT molecule may be administered without an adjuvant or in an aqueous form.

The iMAT molecules may be administered in a dose of about 1 jpg to 1000 jpg (this and the subsequent doses referring to the weight of solely the one or more antigen modules) and more preferably in a dose from about 10 jpg to about 100 jpg and even more preferably in a dose from about 20 jpg to about 50 jpg, although the optimal dose may vary depending on the antigen, preferably allergen, being injected, the weight of the subject, the immune system of the subject, and alike. Effective treatment in many cases may be accomplished with one administration. In some embodiments, treatment includes 1 to 15 administrations. In preferred embodiments, treatment includes 1 to 5 administrations and more preferably 1 to 3 administrations. For initial treatment administrations may be periodically, e.g. over a course of days, once or twice per month or year, or several times a year. For maintenance of immune response, administrations may be done in intervals of several months to several years.

In a preferred embodiment of the present invention, the (isolated) recombinant proteins, as disclosed and claimed herein, are designed for lymphatic intranodal administration. In the course of direct injection into a lymph node, the respective lymph node may be visualized during the injection procedure e.g. by ultrasound, in order to monitor the location of the needle and changes in the lymph node, such as swelling. Injection into the mandibular, axillary, inguinal and/or popliteus lymph nodes is preferred due to ease of ultrasound guided location and injection.

It is known in the art that several of the identified proteins from mites in feces and from whole mite bodies induce IgE reactivity and pathological dermal and respiratory reactions in dogs and/or cats [Allergome (www.allergome.org)]. Thus, it is expected that a treatment can only be successful, if most of the relevant allergens are included in a medicine for specific immunotherapy. However, surprisingly only 1, 2, 3 or 4 of such iMAT molecules according to the present invention each comprising different antigen modules e.g. of mites or a mosaic-like construct of epitopes are sufficient to induce an immunomodulation and/or clinical improvement of the diseased subjects if such iMAT molecules are injected 1 to 5 times subcutaneously, intradermally and/or directly into the lymph node.

In a preferred embodiment, a single iMAT molecule is employed and is sufficient for the induction of a therapeutic effect and/or prevention of development of allergen specific IgE mediated hypersensitivity reactions in different target organs as skin, respiratory and/or the gastrointestinal system e.g. in animals, more preferably dogs and/or cats, but excluding equines. Prevention and/or therapy of infectious diseases and/or prevention of transmission of infectious diseases by vectors can be achieved in animals, preferably ruminants, pigs, dogs and/or cats, but excluding equines.

In another preferred embodiment, a combination of 2, 3 or 4 iMAT molecules is employed by means of simultaneous, sequential and/or a chronologically staggered co-administrations.

In a preferred embodiment, a single iMAT molecule is employed and is sufficient for the induction of a therapeutic effect and/or prevention and/or prevention of transmission of infectious diseases in animals, more preferably ruminants, pigs, dogs and/or cats, but excluding equines, e.g. induced by viruses, fungi and/or parasites and/or their prepatent stages and/or the transmission of such infectious diseases by e.g. blood feeding bugs, flies, midges, ticks and/or mosquitos.

In another preferred embodiment, a combination of 2, 3 or 4 iMAT molecules is employed by means of simultaneous, sequential and/or a chronologically staggered co-administrations.

Depending on the thermodynamic evaluation of the (isolated) recombinant protein, as herein disclosed and claimed, stability is influenced by the cysteine mutation, namely the substituting different amino acid residue(s). For example, the substitution may be a Cys to Ser substitution. However, the stability may be higher using a different amino acid residue than the Ser amino acid to achieve the desired stability and solubility. That is, while a first choice may be substitution of Cys with Ser, in case of instability other amino acid residues than Ser should replace Cys.

In order to select stabilizing amino acid residues as replacements for cysteine residues in targeted sequences a three step approach is chosen:

1. Modeling the tertiary structure of the targeted protein including terminal Hexa-Histidine tags, iMAT sequence and the primary amino acid sequence of the protein of interest. Modeling can be conducted with the native sequence and with cysteine substitutions.
2. Iterative determination of protein stabilities based on single point substitutions, such as substitution of a cysteine residue with a different amino acid residue, e.g. Ser and/or Ile, and scoring to determine stabilizing replacements by analyzing all available three dimensional structures.
3. Re-Modeling of the stabilized structure and validation of the stability by repeating step 1 and 2.

Three-dimensional protein structures are crucial for understanding protein function on a molecular level and are of great interest for the rational design of many different types of biological experiments, such as site-directed mutagenesis. However, the number of structurally characterized proteins is small compared to the number of known protein sequences. It is possible to identify a homologous protein with a known structure (template) for a given protein sequence (target). In these cases, homology modeling has proven to be the method of choice to generate a reliable 3D model of a protein from its primary amino acid sequence. Building a homology model comprises four main steps: (1) identification of structural template(s), (2) alignment of target sequence and template structure(s), (3) model building and (4) model quality evaluation. These steps can be repeated until a satisfying modeling result is achieved. In cases where no accurate homologue model can be determined, computational approaches to determine a protein structure from the primary structure (amino acid sequences) are used. "De novo" or "ab initio" methods are based on physical principles and try to imitate the folding process. Such methods have to sample a large number of conformations and require very accurate energy functions to identify structures in the global minima of free energy. Many methods use a combination of these described principles.

The availability of computational tools yielding reasonably accurate estimations of the impact of amino acid substitutions on the stability of proteins is of crucial importance in a wide range of applications. In particular, such tools have the potential of stimulating and supporting protein engineering and design projects dedicated to the creation of modified proteins.

Protein stability can be regarded in terms of the thermodynamic stability of a protein that unfolds and refolds rapidly, reversibly. In these cases, the stability of the protein is the difference in Gibbs free energy between the folded and the unfolded states. The only factors affecting stability are the relative free energies of the folded and the unfolded states. The larger and more positive the folding free energy difference is, the more stable the protein is to denaturation. The folding free energy difference is typically small, of the order of 5-15 kcal/mol for a globular protein. However, on the other hand, protein stability can be regarded as a protein property to withstand harsh temperature or solvent conditions. This is related to the thermodynamic stability but also to reversibility or irreversibly of folding/unfolding (kinetic stability).

To predict the thermodynamic stability changes caused by single site substitutions in proteins, several different approaches can be applied to study the impacts of such substitutions on protein structure and function [Pires D E et al., Bioinformatics 2014, 30(3):335-342]. Such approaches can be broadly classified into those that seek to understand the effects of substitutions from the amino acid sequence of a protein alone, and those that exploit the extensive structural information. Structure-based approaches typically attempt to predict either the direction of change in protein stability on substitutions or the actual free energy value ($\Delta\Delta G$).

The results for each specific protein and its corresponding models are statistically analyzed in terms of the number of appearances of specific substitutions using a scoring system, that grades the replacement based on occurrences in used models and the protein stability free energy change ($\Delta\Delta G$) thereby determining most destabilizing residues (if any) within the input structure and possible replacements. The score is calculated by determination of the lowest $\Delta\Delta G$ ($\Delta\Delta G<0$) at each position of interest in each model and assigning corresponding linear values and cumulative $\Delta\Delta G$'s values for each potential replacement position and results are than evaluated to determine consistency among models. Since calculated protein models possess different qualities (the probability of predicting the correct three-dimensional structure) a weighting factor can be implemented to prioritize results from more accurate models. A significant (based on the $\Delta\Delta G$) destabilizing residue (if any) is substituted; new models are generated and re-analyzed iteratively until a steady state is reached. Additionally, generated models are evaluated by analyzing the xyz coordinates via principal component analysis to determine potential structural misfoldings due to replacement of amino acids at specific positions.

In yet a further aspect, the objective underlying the invention has surprisingly been solved by providing a method of identifying amino acid substitutions in a predetermined amino acid sequence allowing the stabilization of such predetermined amino acid sequence comprising the steps of:
  i. modeling of the three-dimensional/tertiary structure of the targeted predetermined amino acid sequence,
  ii. iterative determination of protein stabilities based on single point substitutions, such as substitutions of cysteine residues with different amino acid residues, preferably serine and/or isoleucine residues, and a scoring system based on the protein stability free energy changes ($\Delta\Delta G$) to determine stabilizing substitutions by analyzing all available three-dimensional/tertiary amino acid sequence structures,
  iii. re-modeling of the substituted three-dimensional/tertiary amino acid sequence structure and calculation of its stability by repeating steps (ii) and (iii) until a steady state is reached;

In yet a further aspect, the objective underlying the invention has surprisingly been solved by providing an (isolated) recombinant protein as herein disclosed and claimed, wherein its full or partial amino acid sequence was stabilized by the method of identifying amino acid substitutions in a predetermined amino acid sequence as herein disclosed and claimed (see Example 5 as well as Example 6 herein).

SEQUENCES

The following protein sequences are detailed and disclosed hereby in the present invention (aa or AA being short for amino acids):

SEQ ID NO: 1 relates to a suitable minimal amino acid sequence for one translocation module according to the present invention which is still being functional, i.e. capable of effectively promoting cell entry→TAT sequence;

SEQ ID NOs: 2-5 Invariant Chains (Full Sequences and 110aa):

SEQ ID NO: 2 relates to the full canine invariant chain amino acid sequence;
>gi|545496086|Canis_lupus_familiaris|XP_536468.5|PREDICTED: HLA class II histocompatibility antigen gamma chain isoform X1 [Canis lupus familiaris]

SEQ ID NO: 3 relates to the full feline invariant chain amino acid sequence;
>gi|410949651|Felis_catus|XP_003981534.11  PREDICTED: HLA class II histocompatibility antigen gamma chain isoform X1 [Felis catus]

SEQ ID NO: 4 relates to the first 110 aa of the canine invariant chain amino acid sequence;

SEQ ID NO: 5 relates to the first 110 aa of the feline invariant chain amino acid sequence;

SEQ ID NO: 6 relates to the N-Terminal Marker of 22 aa

SEQ ID NOs: 7-13 Allergens, Full Sequences:

SEQ ID NO: 7 relates to the full Der f 1 allergen amino acid sequence;
>Q58A71 Der f 1 allergen preproenzyme Dermatophagoides farinae (American house dust mite)

SEQ ID NO: 8 relates to the full Der f 2 allergen amino acid sequence;
>Q00855 Mite group 2 allergen Der f 2 (Allergen Der f II) (allergen Der f 2) Dermatophagoides farinae (American house dust mite)

SEQ ID NO: 9 relates to the full Der f 23 allergen amino acid sequence;

>A0A088SAW7 Der f 23 allergen *Dermatophagoides farinae* (American house dust mite)
SEQ ID NO: 10 relates to the full Der f 18p allergen amino acid sequence; >Q86R84 60 kDa allergen
Der f 18p *Dermatophagoides farinae* (American house dust mite)
SEQ ID NO: 11 relates to the full Der f 15 allergen amino acid sequence;
>Q9U6R7 98 kDa HDM allergen (Der f 15 allergen) (Group 15 allergen Der f 15) *Dermatophagoides farinae* (American house dust mite)
SEQ ID NO: 12 relates to the full Zen 1 protein allergen amino acid sequence;
>I7HDR2 Zen 1 protein *Dermatophagoides farinae* (American house dust mite)
SEQ ID NO: 13 relates to the full Cte f 1 allergen amino acid sequence;
>Q94424 Salivary antigen 1 (FS-I) (allergen Cte f 1) *Ctenocephalides felis* (Cat flea)
SEQ ID NOs: 14-20 Allergens, IMAT Forms (Short):
SEQ ID NO: 14 relates to the iMAT Form (short) of Der f 1 allergen amino acid sequence;
SEQ ID NO: 15 relates to the iMAT Form (short) Der f 2 allergen amino acid sequence;
SEQ ID NO: 16 relates to the iMAT Form (short) Der f 23 allergen amino acid sequence;
SEQ ID NO: 17 relates to the iMAT Form (short) Der f 18p allergen amino acid sequence;
SEQ ID NO: 18 relates to the iMAT Form (short) Der f 15 allergen amino acid sequence;
SEQ ID NO: 19 relates to the iMAT Form (short) Zen 1 protein allergen amino acid sequence;
SEQ ID NO: 20 relates to the iMAT Form (short) Cte f 1 allergen amino acid sequence;
SEQ ID NOs: 21-23 Allergens from Hybrids 1, 2, and 3—IMAT Forms (Short):
SEQ ID NO: 21 relates to the iMAT Form (short) Hybrid 1 allergen
SEQ ID NO: 22 relates to the iMAT Form (short) Hybrid 2 allergen
SEQ ID NO: 23 relates to the iMAT Form (short) Hybrid 3 allergen
SEQ ID NOs: 24-44 iMATs for Cat (with N-Terminal or C-Terminal Hexa-Histidine or without Hexa-Histidine/Methionine (IMAT_Pure)):
SEQ ID NO: 24 relates to a Der f 1 iMAT molecule (cat) with N-terminal Hexa-Histidine tag;
SEQ ID NO: 25 relates to a Der f 1 iMAT molecule (cat) with C-terminal Hexa-Histidine tag;
SEQ ID NO: 26 relates to a Der f 1 iMAT molecule (cat) without tag;
SEQ ID NO: 27 relates to a Der f 2 iMAT molecule (cat) with N-terminal Hexa-Histidine tag;
SEQ ID NO: 28 relates to a Der f 2 iMAT molecule (cat) with C-terminal Hexa-Histidine tag;
SEQ ID NO: 29 relates to a Der f 2 iMAT molecule (cat) without tag;
SEQ ID NO: 30 relates to a Der f 23 iMAT molecule (cat) with N-terminal Hexa-Histidine tag;
SEQ ID NO: 31 relates to a Der f 23 iMAT molecule (cat) with C-terminal Hexa-Histidine tag;
SEQ ID NO: 32 relates to a Der f 23 iMAT molecule (cat) without tag;
SEQ ID NO: 33 relates to a Der f 18p iMAT molecule (cat) with N-terminal Hexa-Histidine tag;
SEQ ID NO: 34 relates to a Der f 18p iMAT molecule (cat) with C-terminal Hexa-Histidine tag;
SEQ ID NO: 35 relates to a Der f 18p iMAT molecule (cat) without tag;
SEQ ID NO: 36 relates to a Der f 15 iMAT molecule (cat) with N-terminal Hexa-Histidine tag;
SEQ ID NO: 37 relates to a Der f 15 iMAT molecule (cat) with C-terminal Hexa-Histidine tag;
SEQ ID NO: 38 relates to a Der f 15 iMAT molecule (cat) without tag;
SEQ ID NO: 39 relates to a Zen 1 protein iMAT molecule (cat) with N-terminal Hexa-Histidine tag;
SEQ ID NO: 40 relates to a Zen 1 protein iMAT molecule (cat) with C-terminal Hexa-Histidine tag;
SEQ ID NO: 41 relates to a Zen 1 protein iMAT molecule (cat) without tag;
SEQ ID NO: 42 relates to a Cte f 1 protein iMAT molecule (cat) with N-terminal Hexa-Histidine tag;
SEQ ID NO: 43 relates to a Cte f 1 protein iMAT molecule (cat) with C-terminal Hexa-Histidine tag;
SEQ ID NO: 44 relates to a Cte f 1 protein iMAT molecule (cat) without tag;
SEQ ID NOs: 45-65 MATs for Dog (with N-Terminal or C-Terminal Hexa-Histidine or without Hexa-Histidine/Methionine (IMAT_Pure)):
SEQ ID NO: 45 relates to a Der f 1 iMAT molecule (dog) with N-terminal Hexa-Histidine tag;
SEQ ID NO: 46 relates to a Der f 1 iMAT molecule (dog) with C-terminal Hexa-Histidine tag;
SEQ ID NO: 47 relates to a Der f 1 iMAT molecule (dog) without tag;
SEQ ID NO: 48 relates to a Der f 2 iMAT molecule (dog) with N-terminal Hexa-Histidine tag;
SEQ ID NO: 49 relates to a Der f 2 iMAT molecule (dog) with C-terminal Hexa-Histidine tag;
SEQ ID NO: 50 relates to a Der f 2 iMAT molecule (dog) without tag;
SEQ ID NO: 51 relates to a Der f 23 iMAT molecule (dog) with N-terminal Hexa-Histidine tag;
SEQ ID NO: 52 relates to a Der f 23 iMAT molecule (dog) with C-terminal Hexa-Histidine tag;
SEQ ID NO: 53 relates to a Der f 23 iMAT molecule (dog) without tag;
SEQ ID NO: 54 relates to a Der f 18p iMAT molecule (dog) with N-terminal Hexa-Histidine tag;
SEQ ID NO: 55 relates to a Der f 18p iMAT molecule (dog) with C-terminal Hexa-Histidine tag;
SEQ ID NO: 56 relates to a Der f 18p iMAT molecule (dog) without tag;
SEQ ID NO: 57 relates to a Der f 15 iMAT molecule (dog) with N-terminal Hexa-Histidine tag;
SEQ ID NO: 58 relates to a Der f 15 iMAT molecule (dog) with C-terminal Hexa-Histidine tag;
SEQ ID NO: 59 relates to a Der f 15 iMAT molecule (dog) without tag;
SEQ ID NO: 60 relates to a Zen 1 protein iMAT molecule (dog) with N-terminal Hexa-Histidine tag;
SEQ ID NO: 61 relates to a Zen 1 protein iMAT molecule (dog) with C-terminal Hexa-Histidine tag;
SEQ ID NO: 62 relates to a Zen 1 protein iMAT molecule (dog) without tag;
SEQ ID NO: 63 relates to a Cte f 1 protein iMAT molecule (dog) with N-terminal Hexa-Histidine tag;
SEQ ID NO: 64 relates to a Cte f 1 protein iMAT molecule (dog) with C-terminal Hexa-Histidine tag;
SEQ ID NO: 65 relates to a Cte f 1 protein iMAT molecule (dog) without tag;

SEQ ID NOs: 66-74 Hybrid/Mosaic-Like MATs for Cat (N-Terminal or C-Terminal Hexa-Histidine or without Hexa-Histidine/Methionine (IMAT_Pure)):
SEQ ID NO: 66 relates to a Hybrid 1 iMAT molecule (cat) with N-terminal Hexa-Histidine tag;
SEQ ID NO: 67 relates to a Hybrid 1 iMAT molecule (cat) with C-terminal Hexa-Histidine tag;
SEQ ID NO: 68 relates to a Hybrid 1 iMAT molecule (cat) without tag (consisting of SEQ ID NO: 1, SEQ ID NO: 5 and SEQ ID NO: 21);
SEQ ID NO: 69 relates to a Hybrid 2 iMAT molecule (cat) with N-terminal Hexa-Histidine tag;
SEQ ID NO: 70 relates to a Hybrid 2 iMAT molecule (cat) with C-terminal Hexa-Histidine tag;
SEQ ID NO: 71 relates to a Hybrid 2 iMAT molecule (cat) without tag (consisting of SEQ ID NO: 1, SEQ ID NO: 5 and SEQ ID NO: 22);
SEQ ID NO: 72 relates to a Hybrid 3 iMAT molecule (cat) with N-terminal Hexa-Histidine tag;
SEQ ID NO: 73 relates to a Hybrid 3 iMAT molecule (cat) with C-terminal Hexa-Histidine tag;
SEQ ID NO: 74 relates to a Hybrid 3 iMAT molecule (cat) without tag (consisting of SEQ ID NO: 1, SEQ ID NO: 5 and SEQ ID NO: 23);
SEQ ID NOs: 75-83 Hybrid/Mosaic-Like MATs for Dog (N-Terminal or C-Terminal Hexa-Histidine or without Hexa-Histidine/Methionine (IMAT_Pure)):
SEQ ID NO: 75 relates to a Hybrid 1 iMAT molecule (dog) with N-terminal Hexa-Histidine tag;
SEQ ID NO: 76 relates to a Hybrid 1 iMAT molecule (dog) with C-terminal Hexa-Histidine tag;
SEQ ID NO: 77 relates to a Hybrid 1 iMAT molecule (dog) without tag (consisting of SEQ ID NO: 1, SEQ ID NO: 4 and SEQ ID NO: 21);
SEQ ID NO: 78 relates to a Hybrid 2 iMAT molecule (dog) with N-terminal Hexa-Histidine tag;
SEQ ID NO: 79 relates to a Hybrid 2 iMAT molecule (dog) with C-terminal Hexa-Histidine tag;
SEQ ID NO: 80 relates to a Hybrid 2 iMAT molecule (dog) without tag (consisting of SEQ ID NO: 1, SEQ ID NO: 4 and SEQ ID NO: 22);
SEQ ID NO: 81 relates to a Hybrid 3 iMAT molecule (dog) with N-terminal Hexa-Histidine tag;
SEQ ID NO: 82 relates to a Hybrid 3 iMAT molecule (dog) with C-terminal Hexa-Histidine tag;
SEQ ID NO: 83 relates to a Hybrid 3 iMAT molecule (dog) without tag (consisting of SEQ ID NO: 1, SEQ ID NO: 4 and SEQ ID NO: 23);
SEQ ID NOs: 84-88 Non-Redundant Hybrid Allergens:
SEQ ID NO: 84 relates to A1KXC1_DERFA DFP1 (UNIPROT database);
SEQ ID NO: 85 relates to A0A088SAS1_DERFA Der f 28 allergen (UNIPROT database);
SEQ ID NO: 86 relates to B7U5T1_DERFA Der f 6 allergen (UNIPROT database);
SEQ ID NO: 87 relates to T2B4F3_DERPT LytFM (UNIPROT database);
SEQ ID NO: 88 relates to A7XXV2_DERFA Der f 2 allergen (UNIPROT database);
SEQ ID NOs: 89-90 Miscellaneous Sequences:
SEQ ID NO: 89 relates to a Cul o2 iMAT molecule with N-terminal HEXA-HISTIDINE;
SEQ ID NO: 90 relates to a Cul o3 iMAT molecule with N-terminal HEXA-HISTIDINE.
SEQ ID NOs: 91-102 Peptide Components of Hybrids:
SEQ ID NO: 91 relates to a peptide part of a hybrid derived from SEQ ID NO: 10, SEQ ID NO: 92 relates to a peptide part of a hybrid derived from SEQ ID NO: 85, SEQ ID NO: 93 relates to a peptide part of a hybrid derived from SEQ ID NO: 88, SEQ ID NO: 94 relates to a peptide part of a hybrid derived from SEQ ID NO: 86, SEQ ID NO: 95 relates to a peptide part of a hybrid derived from SEQ ID NO: 87, SEQ ID NO: 96 relates to a peptide part of a hybrid derived from SEQ ID NO: 11, SEQ ID NO: 97 relates to a peptide part of a hybrid derived from SEQ ID NO: 7, SEQ ID NO: 98 relates to a peptide part of a hybrid derived from SEQ ID NO: 10, SEQ ID NO: 99 relates to a peptide part of a hybrid derived from SEQ ID NO: 12, SEQ ID NO: 100 relates to a peptide part of a hybrid derived from SEQ ID NO: 9, SEQ ID NO: 101 relates to a peptide part of a hybrid derived from SEQ ID NO: 11, SEQ ID NO: 102 relates to a peptide part of a hybrid derived from SEQ ID NO: 8.

Hybrid/Mosaic-Like iMAT Molecules:

In a specific aspect of the present invention the iMAT molecules are further improved if components (amino acid sequences/epitopes) of more than one allergen are included into the antigen module. For this purpose it is possible to apply the basic principle of the described bioinformatics selection approach (Example 5) in a different way. Instead of selecting complete allergens based on the hit count of allergen peptides found in the allergen database, only the most abundant peptides of several of such allergens are used to engineer an iMAT antigen module (see e.g. Example 6). Thus, such an iMAT molecule consists of an antigen module of peptides that stem from several allergens. This allows broadening of the spectrum of a single iMAT molecule with respect to its targeted immunological profile and is thus beneficial for pharmacological drug development.

As a further step in engineering hybrid iMAT molecules the TAT and the targeting domain, and optionally a His-Tag, are added. Finally cysteine residues are replaced by most stabilizing residues as described in examples 5 and 6.

Hybrid I

A protein precursor is chosen from the list of precursor proteins corresponding to top ranking peptides and used as a scaffold protein (SEQ ID NO: 84) for embedding other top ranking peptides from other antigens (SEQ ID NOS: 10, 11, 85, 86, 87, 88). The signal peptide sequence is removed from the scaffold protein. Optionally additional adjacent N- or C-terminal amino acids are inserted within the original sequence of the scaffold protein and replace parts of the original sequence of the scaffold protein as described below.

Components of the following proteins are employed to construct hybrid 1:
SEQ ID NO: 84 (A1KXC1_DERFA DFP1 OS=Dermatophagoides farina)
SEQ ID NO: 10 (Q86R84_DERFA 60 kDa allergen Der f 18p OS=Dermatophagoides farinae GN=Der f 18 PE=2 SV=1)
SEQ ID NO: 85 (A0A088SAS1_DERFA Der f 28 allergen OS=Dermatophagoides farinae PE=2 SV=1)
SEQ ID NO: 88: (A7XXV2_DERFA Der f 2 allergen OS=Dermatophagoides farinae PE=4 SV=1)
SEQ ID NO: 86 (B7U5T1_DERFA Der f 6 allergen OS=Dermatophagoides farinae PE=2 SV=1)
SEQ ID NO: 87 (T2B4F3_DERPT LytFM OS=Dermatophagoides pteronyssinus GN=lytFM PE=4 SV=1)
SEQ ID NO: 11 (Q9U6R7_DERFA 98 kDa HDM allergen OS=Dermatophagoides farinae PE=2 SV=1)

Backbone of Hybrid 1:
SEQ ID NO: 84 (A1KXC1 18-400, without replacement parts below)

[Replacement 1 for: SEQ ID NO: 84 AA 39-52]:
SEQ ID NO: 10 (Q86R84_AA 97-110) i.e. GNAKAMIAVGGS™ (SEQ ID NO: 91)

[Replacement 2 for: SEQ ID NO: 84 AA 261-274]:
SEQ ID NO: 85 (A0A088SAS1_AA 611-624) i.e. MMKIYQQQQQQHHP (SEQ ID NO: 92)

[Replacement 3 for: SEQ ID NO: 84 AA 234-246]:
SEQ ID NO: 88 (A7XXV2_AA 48-61) i.e. FLVYIHIANNEIKK (SEQ ID NO: 93)

[Replacement 4 for: SEQ ID NO: 84 AA 53-65]:
SEQ ID NO: 86 (B7U5T1_AA 166-178) i.e. IVDGDKVTIYGWG (SEQ ID NO: 94)

[Replacement 5 for: SEQ ID NO: 84 AA 276-289]:
SEQ ID 87: (T2B4F3_AA 134-147) i.e. REENIWS-DHIANVA (SEQ ID NO: 95)

[Replacement 6 for: SEQ ID NO: 84 AA 203-216]: SEQ ID NO: 11 (Q9U6R7_AA 469-482) i.e. TPTTPTPAPTTSTP (SEQ ID NO: 96)

After cysteine residues are replaced by most stabilizing residues applying the bioengineering process described in Examples 5 and 6, this results in SEQ ID NO: 21.

The backbone of hybrid 1 is formed by the amino acid sequence SEQ ID NO: 84. The further peptide components of hybrid 1 antigen module SEQ ID NOs: 91-96 are embedded into the backbone sequence derived from SEQ ID NO: 84. These further peptide components of hybrid 1 antigen module SEQ ID NOs: 91-96 can be arranged in any order/in a different order (if compared to the order of replacement described above). Any such re-arranged peptide order based on the above described antigens/allergens is envisaged by the present invention.

Hybrid 2

Complete allergens and/or top ranking peptides are chosen and spliced together to obtain the allergen module for a given IMAT molecule described below.

Components of the following proteins are employed to construct hybrid 2 in the depicted particular order, whereby part 1 is the N-terminus. The further parts are added according to the below order to the C-terminus of the previous part. In case of hybrid 2 these are 5 further parts. There are 6 parts in total.

Part 1: SEQ ID NO 7 (Q58A71 Der f 1 allergen preproenzyme *Dermatophagoides farinae* (American house dust mite) AA 99-321) i.e. TSACRINSVNVPSELDLRSLRTVT-PIRMQGGCGSCWAFSGVAATESAYLAYRNTSLDLSE QELVDCASQHGCHGDTIPRGIEYIQQNGVVEERSYP-YVAREQQCRRPNSQHYGISNYCQIYPPDVKQIREAL-TQTHTAIAVIIGIKDLRAFQHYDGRTIIQHDNGYQPN-YHAVNIVGYGSTQGVDYWIVRNSWDTTWGDSGYG-YFQAGNNLMMIEQYPYVVIM (SEQ ID NO: 97)

Part 2: SEQ ID NO 10 (Q86R84 60 kDa allergen Der f 18p *Dermatophagoides farinae* (American house dust mite) AA 277-304) i.e. FTQTDGFLSYNELCVQIQAETNAF-TITR (SEQ ID NO: 98)

Part 3: SEQ ID NO 12 (I7HDR2 Zen 1 protein *Dermatophagoides farinae* (American house dust mite) AA 181-220) i.e. EPTTPTPEPTTKTPEPTKTPEPSTPTPEPTFKT-PEPTTK (SEQ ID NO: 99)

Part 4: SEQ ID NO 9 (A0A088SAW7 Der f 23 allergen *Dermatophagoides farinae* (American house dust mite) AA 22-91) i.e. DIDHDDDPTMIDVQTTTVQPSDEFECP-TRFGYFADPKDPCKFYICSNWEAIHKSCPGNT RWNE-KELTCT (SEQ ID NO: 100)

Part 5: SEQ ID NO 11 (Q9U6R7 98 kDa HDM allergen (Der f 15 allergen) (Group 15 allergen Der f 15) *Dermatophagoides farinae* (American house dust mite) AA 437-463) i.e. SPTFPTTPSPTFPTTPSPTFTPITTP(SEQ ID NO: 101)

Part 6: SEQ ID NO 8 (Q00855 Mite group 2 allergen Der f 2 (Allergen Der f II) (allergen Der f 2) *Dermatophagoides farinae* (American house dust mite) AA 18-146) i.e. DQVDVKDCANNEIKKVMVDGCHGSDPCIIHRGKPF-TLEALFDANQNTKTAKIEIKASLDGLEIDVPGIDT NA-CHFMKCPLVKGQQYDIKYTWNVPKIAPKSENV VVT-VKLIGDNGVLA CAIATHGKIRD (SEQ ID NO: 102)

After cysteine residues are replaced by most stabilizing residues applying the bioengineering process described in Examples 5 and 6, this results in SEQ ID NO: 22.

However, the above peptide components of hybrid 2 antigen module can be arranged in any order/in a different order (if compared to the order of replacement described above). Any such re-arranged peptide order based on the above described antigens/allergens is envisaged by the present invention.

Hybrid 3

Components of the following proteins are employed to construct hybrid 3 in the depicted particular order, whereby part 1 is the N-terminus. The further parts are added according to the below order to the C-terminus of the previous part. In case of hybrid 3 these are 4 further parts. There are 5 parts in total.

Part 1: SEQ ID NO 7 (Q58A71 Der f 1 allergen preproenzyme *Dermatophagoides farinae* (American house dust mite) AA 99-321) i.e. TSACRINSVNVPSELDLRSLRTVT-PIRMQGGCGSCWAFSGVAATESAYLAYRNTSLDLSE QELVDCASQHGCHGDTIPRGIEYIQQNGVVEERSY-PYVAREQQCRRPNSQHYGISNYCQI YPPDVKQIREA-LTQTHTAIAVIIGIKDLRAFQHYDGRTIIQHDNGYQPN-YHAVNIVGYGS TQGVDYWIVRNSWDTTWGDSGY-GYFQAGNNLMMIEQYPYVVIM (SEQ ID NO: 97)

Part 2: SEQ ID NO 10 (Q86R84 60 kDa allergen Der f 18p *Dermatophagoides farinae* (American house dust mite) AA 277-304) i.e. FTQTDGFLSYNELCVQIQAETNAF-TITR (SEQ ID NO: 98)

Part 3: SEQ ID NO 11 (Q9U6R7 98 kDa HDM allergen (Der f 15 allergen) (Group 15 allergen Der f 15) *Dermatophagoides farinae* (American house dust mite) AA 437-463) i.e. SPTFITTPPSPTITPSPTFPITTP (SEQ ID NO: 101)

Part 4: SEQ ID NO 8 (Q00855 Mite group 2 allergen Der f 2 (Allergen Der f II) (allergen Der f 2) *Dermatophagoides farinae* (American house dust mite) AA 18-146) i.e. DQVDVKDCANNEIKKVMVDGCHGSDPCIIHRGKP-FTLEALFDANQNTKTAKIEIKASLDGLEIDVPGI DTN-ACHFMKCPLVKGQQYDIKYTWNVPKIAPKSENVV-VTVKLIGDNGVLA CAIATHGKIRD (SEQ ID NO: 102)

After cysteine residues are replaced by most stabilizing residues applying the bioengineering process described in Examples 5 and 6, this results in SEQ ID NO: 23.

However, the above peptide components of hybrid 3 antigen module can be arranged in any order/in a different order (if compared to the order of the parts described above).

Any such re-arranged peptide order based on the above described antigens/allergens is envisaged by the present invention.

Further specific aspects of the present invention:

The invention concerns an amino acid sequence/improved MAT (iMAT) molecule, comprising:

(i) at least one first module being an amino acid sequence allowing the translocation of the iMAT molecule from the extracellular space into the interior of cells, (ii) at least one second module being an amino acid sequence allowing species-specific intracellular targeting of the iMAT molecule to the cell organelles which are involved in the processing of antigens and/or the loading of MHC molecules with antigens, preferably processed antigens, and (iii) at least one third module as antigen module being an amino acid sequence derived from at least one full or partial amino acid sequence, preferably an epitope, of at least one antigen, preferably at least one allergen, determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid, for use in a method of prevention and/or therapy of one or more allergies in animals excluding equines and/or for use in a method of prevention and/or therapy of one or more infectious diseases in animals excluding equines and/or for use in a method of prevention of transmission of one or more infectious diseases in animals excluding equines and/or for use in a method of prevention of transmission of one or more infectious diseases in animals excluding equines by vectors.

The invention further concerns a method of prevention and/or therapy of one or more allergies in animals excluding equines and/or a method of prevention and/or therapy of one or more infectious diseases in animals excluding equines and/or a method of prevention of transmission of one or more infectious diseases in animals excluding equines, preferably by vectors, comprising administering a therapeutic effective amount of an amino acid sequence/improved MAT (iMAT) molecule, comprising:

(i) at least one first module being an amino acid sequence allowing the translocation of the iMAT molecule from the extracellular space into the interior of cells, (ii) at least one second module being an amino acid sequence allowing species-specific intracellular targeting of the iMAT molecule to the cell organelles which are involved in the processing of antigens and/or the loading of MHC molecules with antigens, preferably processed antigens, and (iii) at least one third module as antigen module being an amino acid sequence derived from at least one full or partial amino acid sequence, preferably an epitope, of at least one antigen, preferably at least one allergen, determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid.

In a specific aspect the at least one antigen module all cysteine residues are substituted with a different amino acid residue, preferably serine, leucine, isoleucine, arginine, methionine, and/or aspartic acid. Preferably all cysteine residues in the entire iMAT molecule are substituted with a different amino acid residue, preferably serine, leucine, isoleucine, arginine, methionine, and/or aspartic acid.

In a further aspect all of such modules are covalently linked to each other, optionally by additional spacer module(s) between two or more adjacent modules, optionally between all of such first, second and/or third modules.

In a preferred aspect all of such modules are covalently linked to each other, and no additional spacer module(s) between two or more adjacent modules of such first, second and/or third modules are present at all.

In another aspect the at least one second module comprises the invariant chain selected from the canine, feline, bovine, ovine, caprine and/or porcine species' or a partial sequence thereof, provided that such at least one second module is functional as a module allowing species-specific intracellular targeting of the iMAT molecule to the cell organelles which are involved in the processing of antigens and/or loading of MHC molecules with antigens, preferably processed antigens. A preferred canine invariant chain sequence is SEQ ID NO: 2. A preferred feline invariant chain sequence is SEQ ID NO: 3.

In a preferred aspect the at least one second module comprises, preferably consisting of, the amino acid sequence according to SEQ ID NO: 4 (canine) or SEQ ID NO: 5 (feline). SEQ ID NOs: 4 and 5 represent 110 amino acid residues of the invariant chains of SEQ ID NOs: 2 and 3, respectively.

In another preferred aspect the at least one second module comprises, preferably consisting of, the amino acid sequence according to SEQ ID NO: 4 (canine) or SEQ ID NO: 5 (feline) or fragments thereof, provided such fragments maintain their intracellular transport function.

In a further aspect the at least one antigen module comprises at least one full or partial amino acid sequence, preferably an epitope, derived from at least one allergen eliciting an allergy in animals excluding equines, preferably at least one full or partial amino acid sequence, preferably an epitope, of at least one allergen derived from preferably allergies to flea bites, preferably in dogs and/or cats; allergies to certain food components, preferably in dogs and/or cats; atopic dermatitis, preferably in dogs and/or cats; allergic airway inflammation and/or obstruction, preferably in cats.

In a preferred aspect such at least one antigen, preferably at least one allergen, is Der f 15 allergen according to SEQ ID NO: 11 or 18. In a preferred aspect such at least one antigen module comprises, preferably consists of, SEQ ID NO: 18.

In a specific aspect such at least one antigen, preferably at least one allergen, is derived from food and/or mold (fungi and/or their spores), pollen, house dust or forage mites (and/or their feces) and/or fleas, preferably from pollen from tree, grass, herbaceous, ambrosia and/or brassicaceae pollen and/or fungi and/or their spores of the genera *aspergillus, alternaria, botrytis, cercospora, cladosporium, curvularia, drechslera, eurotium, helminthosporium, epicoccum, erysipheloidium, fusarium, lichtheimia, nigrospora, penicillium, periconia, peronospora, polythrincium, saccharopolyspora* (formerly also *faenia* or *micropolyspora*), *thermoactinomyces, stemphylium, torula* and/or mites (or their feces) of the genera *acarus, glycophagus, tyrophagus, dermatophagoides, euroglyphus, lepidoglyphus, blomia* and/or fleas of the genera *Ceratophyllus, Ctenocephalides, Pulex, Archaeopsylla*., and more preferably is a *Dermatophagoides* allergen.

In yet another specific aspect the at least one antigen module comprises at least one full or partial amino acid sequence, preferably an epitope, derived from at least one antigen of a pathogen eliciting one or more infectious diseases in animals excluding equines, preferably at least one full or partial amino acid sequence, preferably an epitope, of at least one antigen of a pathogen eliciting one or more infectious diseases in animals excluding equines selected from the genera *Campylobacter, Dirofilaria, Ehrlichia, Leishmania, Trypanosoma, Borrelia*, Orthobunyavirus, Orbivirus, Flavivirus, Rotavirus, Coronavirus, *Trichophyton, Microsporum; Cooperia, Haemonchus, Ostertagia, Trichostrongylus, Dictyocaulus, Metastrongylus; Eimeria, Isospora, Cryptosporidium, Giardia*, wherein preferably the at least one antigen module may also be an antigen of a vector involved in the transmission of one or more infectious diseases in animals excluding equines, preferably an antigen selected from saliva components of vectors selected from blood feeding bugs, flies, midges, ticks and/or mosquitos.

In a preferred aspect the iMAT molecule further comprises at least one tag module, preferably at least one His-tag. Preferably such at least one tag module is present N-terminally. In another preferred specific aspect such at least one tag module is present C-terminally. In another preferred specific aspect such at least one tag module is present N-terminally and C-terminally.

In a specific preferred aspect the iMAT molecule comprises one tag module, preferably one His-tag, N-terminally after one methionine residue.

In another specific preferred aspect there is no tag module present in the iMAT molecules.

In a further aspect the at least one first module comprises, preferably consists of, the amino acid sequence of HIV-tat, VP22 and/or Antennapedia or a partial sequence thereof, provided that such at least one first module is functional as a module for translocation of the iMAT molecule from the extracellular space into the interior of cells, most preferably is amino acid sequence YGRKKRRQRRR (SEQ ID NO: 1).

In another aspect the iMAT molecule is present in monomeric form and/or in linear form.

In a further aspect at least one third module comprises, preferably consists of, any one of SEQ ID NOs: 14 to 23.

In a preferred aspect the iMAT molecule comprises, preferably consists of, one or more of the amino acid sequences according to SEQ ID NOS: 24 to 83.

A specifically preferred iMAT molecule comprises, preferably consists of, SEQ ID NO: 36 (Der f15 iMAT molecule cat) or SEQ ID NO: 57 (Der f15 iMAT molecule dog). Further preferred iMAT molecules (comprising an N-terminal His-tag) are selected from the group consisting of: SEQ ID NOs: 24, 27, 30, 33, 36, 39, 42, 45, 48, 51, 54, 57, 60, 63, 66, 69, 72, 75, 78, 81. Further preferred iMAT molecules (comprising a C-terminal His-tag) are selected from the group consisting of: SEQ ID NOs: 25, 28, 31, 34, 37, 40, 43, 46, 49, 52, 55, 58, 61, 64, 67, 70, 73, 76, 79, 82. Further preferred iMAT molecules (without His-tag) are selected from the group consisting of: SEQ ID NOs: 26, 29, 32, 35, 38, 41, 44, 47, 50, 53, 56, 59, 62, 65, 68, 71, 74, 77, 80, 83.

Further preferred iMAT molecules (hybrid/mosaic-like iMATs) are selected from the group consisting of: SEQ ID NOs: 66-83. Further preferred hybrid iMAT molecules are 66, 69, 72, 75, 78, 81 (with N-terminal His-tag). Especially preferred is SEQ ID NO: 66 and/or 75. Further preferred specific hybrid iMAT molecules are 67, 70, 73, 76, 79, 82 (with C-terminal His-tag). Especially preferred is SEQ ID NO: 67 and/or 76. Further preferred specific hybrid iMAT molecules are 68, 71, 74, 77, 80, 83 (without His-tag). Especially preferred is SEQ ID NO: 68 and/or 77.

In a further aspect the animal is selected from ruminants, including cattle, goats, sheep, such as members of the genus *Bos, Capra* and/or *Ovis*, members of the genus *Canis*, such as dogs, wolves, foxes, coyotes, jackals, members of the genus *Felis*, such as lions, tigers, domestic cats, wild cats, other big cats, and other felines including cheetahs and lynx, and/or members of the genus *Sus*, such as pigs, wherein preferably the animal is selected from cats and/or dogs.

The invention concerns an amino acid sequence, comprising:
(i) at least one first module being an amino acid sequence allowing the translocation of the iMAT molecule from the extracellular space into the interior of cells, preferably said first module comprises, more preferably consists of SEQ ID NO: 1,
(ii) at least one second module being an amino acid sequence allowing species-specific intracellular targeting of the iMAT molecule to the cell organelles which are involved in the processing of antigens and/or the loading of MHC molecules with antigens, preferably processed antigens, preferably said second module comprises, more preferably consists of, SEQ ID NO: 4 or 5
(iii) at least one third module as antigen module being an amino acid sequence derived from at least one full or partial amino acid sequence, preferably an epitope, of at least one antigen, preferably at least one allergen, determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid. The third module preferably comprises, more preferably consists of any one of SEQ ID NOs: 14 to 23.

The invention concerns an improved MAT (iMAT) molecule, comprising:
(i) at least one first module being an amino acid sequence allowing the translocation of the iMAT molecule from the extracellular space into the interior of cells, preferably said first module comprises, more preferably consists of SEQ ID NO: 1,
(ii) at least one second module being an amino acid sequence allowing species-specific intracellular targeting of the iMAT molecule to the cell organelles which are involved in the processing of antigens and/or the loading of MHC molecules with antigens, preferably processed antigens, preferably said second module comprises, more preferably consists of, SEQ ID NO: 4 or 5
(iii) at least one third module as antigen module being an amino acid sequence derived from at least one full or partial amino acid sequence, preferably an epitope, of at least one antigen, preferably at least one allergen, determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid. The third module preferably comprises, more preferably consists of any one of SEQ ID NOs: 14 to 23.

In a specific aspect the at least one antigen module all cysteine residues are substituted with a different amino acid residue, preferably serine, leucine, isoleucine, arginine, methionine, and/or aspartic acid, Preferably all cysteine residues in the entire iMAT molecule are substituted with a different amino acid residue, preferably serine, leucine, isoleucine, arginine, methionine, and/or aspartic acid.

In a further aspect all of such modules are covalently linked to each other, optionally by additional spacer module(s) between two or more adjacent modules, optionally between all of such first, second and/or third modules.

In a preferred aspect all of such modules are covalently linked to each other, and no additional spacer module(s) between two or more adjacent modules of such first, second and/or third modules are present at all.

In another preferred aspect the at least one second module comprises, preferably consisting of, the amino acid sequence according to SEQ ID NO: 4 (canine) or SEQ ID NO: 5 (feline) or fragments thereof, provided such fragments maintain their intracellular transport function. SEQ ID NOs: 4 and 5 represent 110 amino acid residues of the invariant chains of SEQ ID NOs: 2 and 3, respectively. In a more preferred aspect the at least one second module comprises, preferably consists of, the amino acid sequence according to SEQ ID NO: 4 (canine) or SEQ ID NO: 5 (feline).

In a further aspect the at least one antigen module comprises at least one full or partial amino acid sequence, preferably an epitope, derived from at least one allergen eliciting an allergy in animals excluding equines, preferably at least one full or partial amino acid sequence, preferably an epitope, of at least one allergen derived from preferably allergies to flea bites, preferably in dogs and/or cats; allergies to certain food components, preferably in dogs and/or cats; atopic dermatitis, preferably in dogs and/or cats; allergic airway inflammation and/or obstruction, preferably in cats.

In a specific aspect such at least one antigen comprises the amino acid sequence according to SEQ ID NO: 11 or 18. In a preferred aspect such at least one antigen, preferably at least one allergen, is Der f 15 allergen according to SEQ ID NO: 11 or 18. In another preferred aspect such at least one antigen module comprises, preferably consists of, SEQ ID NO: 18.

In a further preferred aspect the iMAT molecule comprises, preferably consists of, an (one) amino acid sequence according to SEQ ID NOs: 24 to 83 (one of those alternatives). In a further preferred aspect the iMAT molecule comprises, preferably consists of, any one of SEQ ID NOs: 36-38 (Der f15 iMAT molecule cat), most preferably SEQ ID NO: 36, or the iMAT molecule comprises, preferably consists of, any one of SEQ ID NOs: 57-59 (Der f15 iMAT molecule dog), most preferably SEQ ID NO: 57.

In a preferred aspect the iMAT molecule further comprises at least one tag module, preferably at least one His-tag. Preferably such at least one tag module is present N-terminally. In a specific preferred aspect the iMAT molecule comprises one tag module, preferably one His-tag, N-terminally after one methionine residue.

Preferred iMAT molecules with N-terminal His-tag comprise, preferably consist of, any one of SEQ ID NOs: 24, 27, 30, 33, 36, 39, 42, 45, 48, 51, 54, 57, 60, 63, 66, 69, 72, 75, 78, 81.

In another specific preferred aspect such at least one tag module is present C-terminally. In another specific preferred aspect such at least one tag module is present N-terminally and C-terminally. Preferred iMAT molecules with C-terminal His-tag comprise, preferably consist of, any one of SEQ ID NOs: 25, 28, 31, 34, 37, 40, 43, 46, 49, 52, 55, 58, 61, 64, 67, 70, 73, 76, 79, 82.

In another specific preferred aspect there is no tag module present. Preferred iMAT molecules without any tag at all comprise, preferably consist of, any one of SEQ ID NOs: 26, 29, 32, 35, 38, 41, 44, 47, 50, 53, 56, 59, 62, 65, 68, 71, 74, 77, 80, 83.

In a further aspect the at least one first module comprises, preferably consists of, the amino acid sequence of HIV-tat, VP22 and/or Antennapedia or a partial sequence thereof, provided that such at least one first module is functional as a module for translocation of the iMAT molecule from the extracellular space into the interior of cells, most preferably is amino acid sequence YGRKKRRQRRR (SEQ ID NO: 1).

In another aspect the iMAT molecule is present in monomeric form and/or in linear form.

In a further specific aspect the iMAT molecule is a hybrid iMAT molecule (mosaic-like iMAT molecule). Preferably such hybrid iMAT molecule comprises an amino acid sequence according to any one of SEQ ID NOs: 21-23. More specifically such hybrid iMAT molecule comprises, preferably consists of, an amino acid sequence according to any one of SEQ ID NOs: 66-83.

The invention furthermore concerns an amino acid sequence comprising, preferably consisting of, one or more of the amino acid sequences according to SEQ ID NOs: 24 to 83.

The invention further concerns an iMAT molecule comprising, preferably consisting of, one or more of the amino acid sequences according to SEQ ID NOs: 24 to 83.

The invention further concerns an amino acid sequence/iMAT molecule comprising, preferably consisting of, one or more amino acid sequences selected from the group consisting of: SEQ ID NOs: 24 to 83.

A specifically preferred amino acid sequence/iMAT molecule comprises, preferably consists of, SEQ ID NO: 36 (Der f15 iMAT molecule cat) or SEQ ID NO: 57 (Der f15 iMAT molecule dog). Further preferred amino acid sequences/iMAT molecules (comprising an N-terminal His-tag) are selected from the group consisting of: SEQ ID NOs: 24, 27, 30, 33, 36, 39, 42, 45, 48, 51, 54, 57, 60, 63, 66, 69, 72, 75, 78, 81. Further preferred amino acid sequences/ iMAT molecules (comprising a C-terminal His-tag) are selected from the group consisting of: SEQ ID NOs: 25, 28, 31, 34, 37, 40, 43, 46, 49, 52, 55, 58, 61, 64, 67, 70, 73, 76, 79, 82. Further preferred amino acid sequences/iMAT molecules (without His-tag) are selected from the group consisting of: SEQ ID NOs: 26, 29, 32, 35, 38, 41, 44, 47, 50, 53, 56, 59, 62, 65, 68, 71, 74, 77, 80, 83.

Further preferred amino acid sequences/iMAT molecules (hybrid/mosaic-like iMATs) are selected from the group consisting of: SEQ ID NOs: 66-83. Further preferred hybrid iMAT molecules are 66, 69, 72, 75, 78, 81 (with N-terminal His-tag). Further preferred hybrid iMAT molecules are 67, 70, 73, 76, 79, 82 (with C-terminal His-tag). Further preferred hybrid iMAT molecules are 68, 71, 74, 77, 80, 83 (without His-tag).

The invention concerns an amino acid sequence/improved MAT (iMAT) molecule, comprising:

(i) at least one first module being an amino acid sequence allowing the translocation of the iMAT molecule from the extracellular space into the interior of cells, preferably said first module comprises, more preferably consists of SEQ ID NO: 1, (ii) at least one second module being an amino acid sequence allowing species-specific intracellular targeting of the iMAT molecule to the cell organelles which are involved in the processing of antigens and/or the loading of MHC molecules with antigens, preferably processed antigens, preferably said second module comprises, more preferably consists of, SEQ ID NO: 4 or 5

(iii) at least one third module as antigen module being an amino acid sequence derived from at least one full or partial amino acid sequence, preferably an epitope sequence, of any combination of two or more antigens selected from the group consisting of: SEQ ID NO: 7, 8, 9, 10, 11, 12, 84, 85, 86, 87, and 88 determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid.

In a preferred aspect the antigen module is an amino acid sequence derived from at least one full or partial amino acid sequence, preferably an epitope sequence, of any combination of two or more antigens selected from the group consisting of: SEQ ID NO: 10, 11, 84, 85, 86, 87, and 88 (Hybrid 1).

In a specific aspect the antigen module is an amino acid sequence derived from at least one full or partial amino acid sequence, preferably an epitope sequence, of any combination of two or more antigens selected from the group consisting of: SEQ ID NO: 7, 8, 9, 10, 11, and 12 (Hybrid 2).

In a specific aspect the antigen module is an amino acid sequence derived from at least one full or partial amino acid sequence, preferably an epitope sequence, of any combination of two or more antigens selected from the group consisting of: SEQ ID NO: 7, 8, 10, and 11 (Hybrid 3).

Thus, the invention specifically concerns an amino acid sequence/improved MAT (iMAT) molecule, comprising:
(i) at least one first module being an amino acid sequence allowing the translocation of the iMAT molecule from the extracellular space into the interior of cells, preferably said first module comprises, more preferably consists of SEQ ID NO: 1,
(ii) at least one second module being an amino acid sequence allowing species-specific intracellular targeting of the iMAT molecule to the cell organelles which are involved in the processing of antigens and/or the loading of MHC molecules with antigens, preferably processed antigens, preferably said second module comprises, more preferably consists of, SEQ ID NO: 4 or 5
(iii) at least one third module as antigen module being an amino acid sequence based on a backbone derived from SEQ ID NO: 84 comprising any combination of one or more of the peptides according to SEQ ID NOs: 91-96 (in any order) embedded into said backbone sequence, determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid.

In a preferred aspect the order of peptide sequences within the backbone derived from SEQ ID NO: 84 in the third module is SEQ ID NO: 91, followed by SEQ ID NO: 92, followed by SEQ ID NO: 93, followed by SEQ ID NO: 94, followed by SEQ ID NO: 95, followed by SEQ ID NO: 96 starting from the N-terminus. In a most preferred aspect the third module comprises, preferably consist of, SEQ ID NO: 21.

In a further specific aspect the order of peptide sequences within the backbone derived from SEQ ID NO: 84 in the third module is SEQ ID NO: 93, followed by SEQ ID NO: 91, followed by SEQ ID NO: 92, followed by SEQ ID NO: 94, followed by SEQ ID NO: 96, followed by SEQ ID NO: 95 starting from the N-terminus. Further aspects of the present invention relate to any further combination and order of the peptides according to SEQ ID NOs: 91-96 embedded into the backbone sequence derived from SEQ ID NO: 84.

Thus, the invention further concerns an amino acid sequence/improved MAT (iMAT) molecule, comprising:
(i) at least one first module being an amino acid sequence allowing the translocation of the iMAT molecule from the extracellular space into the interior of cells, preferably said first module comprises, more preferably consists of SEQ ID NO: 1,
(ii) at least one second module being an amino acid sequence allowing species-specific intracellular targeting of the iMAT molecule to the cell organelles which are involved in the processing of antigens and/or the loading of MHC molecules with antigens, preferably processed antigens, preferably said second module comprises, more preferably consists of, SEQ ID NO: 4 or 5
(iii) at least one third module as antigen module being an amino acid sequence derived from any combination of two or more of the peptides according to SEQ ID NOs: 97-102 (in any order), determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid. In a preferred aspect the order of peptide sequences within the third module is SEQ ID NO: 97, followed by SEQ ID NO: 98, followed by SEQ ID NO: 99, followed by SEQ ID NO: 100, followed by SEQ ID NO: 101, followed by SEQ ID NO: 102 starting from the N-terminus. In a most preferred aspect the third module comprises, preferably consist of, SEQ ID NO: 22.

In a further specific aspect the order of peptide sequences within the third module is SEQ ID NO: 99, followed by SEQ ID NO: 98, followed by SEQ ID NO: 102, followed by SEQ ID NO: 100, followed by SEQ ID NO: 101, followed by SEQ ID NO: 97 starting from the N-terminus. Further aspects of the present invention relate to any further combination and order of the peptides according to SEQ ID NOs: 97-102.

Thus, the invention additionally concerns an amino acid sequence/improved MAT (iMAT) molecule, comprising:
(i) at least one first module being an amino acid sequence allowing the translocation of the iMAT molecule from the extracellular space into the interior of cells, preferably said first module comprises, more preferably consists of SEQ ID NO: 1,
(ii) at least one second module being an amino acid sequence allowing species-specific intracellular targeting of the iMAT molecule to the cell organelles which are involved in the processing of antigens and/or the loading of MHC molecules with antigens, preferably processed antigens, preferably said second module comprises, more preferably consists of, SEQ ID NO: 4 or 5
(iii) at least one third module as antigen module being an amino acid sequence derived from any combination of two or more of the peptides according to SEQ ID NO: 97, SEQ ID NO: 98, SEQ ID NO: 101, and SEQ ID NO: 102 (in any order), determining the specificity of an immune response modulated by such iMAT molecule, characterized in that at least in the antigen modules at least one cysteine residue is substituted with a different amino acid residue, preferably serine, leucine, isoleucine, arginine, methionine, and/or aspartic acid. In a preferred aspect the order of peptide sequences within the third module is SEQ ID NO: 97, followed by SEQ ID NO: 98, followed by SEQ ID NO: 101, followed by SEQ ID NO: 102 starting from the N-terminus. In a most preferred aspect the third module comprises, preferably consist of, SEQ ID NO: 23.

In a further specific aspect the order of peptide sequences within the third module is SEQ ID NO: 102, followed by SEQ ID NO: 98, followed by SEQ ID NO: 101, followed by SEQ ID NO: 97 starting from the N-terminus. Further aspects of the present invention relate to any further combination and order of the peptides according to SEQ ID NOs: 97, 98, 101, and 102.

The invention further concerns a vaccine or immunogenic composition or a pharmaceutical composition comprising the amino acid sequence/iMAT molecule according to the present invention.

The invention furthermore concerns a nucleic acid encoding the amino acid/iMAT molecule according to the present invention.

Additionally, the invention concerns a vector comprising at least one nucleic acid according to the present invention.

Furthermore, the invention concerns a primary cell or cell line comprising at least one nucleic acid according to the present invention and/or at least one vector according to the present invention.

The invention additionally concerns a method of identifying improved MAT molecules comprising the steps of:
a) selecting a protein as allergen module in iMAT molecules, and
b) constructing an iMAT molecule with said allergens that is thermodynamically stable and can be produced efficiently by protein engineering.

The invention specifically concerns a method of identifying improved MAT molecules comprising the steps of:
a) selecting a protein as allergen module in iMAT molecules that is an allergen and thus has a high potential to cause hypersensitivity in affected subjects and thus can also be the target for tolerance induction, and
b) constructing an iMAT molecule with said allergens that is thermodynamically stable and can be produced efficiently by protein engineering and can additionally be analyzed with standard methods to ensure sufficient enough quality (i.e. identity, purity and potency).

In a specific aspect of the method step a) comprises:
selecting (an) allergen(s) based on local homology searches of peptides derived from given proteins to known allergenic proteins,
exporting amino acid sequences of proteins suspected to have allergenic properties from publicly available databases (e.g. UNIPROT),
determining redundancies by analysis of sequences homologies within the exported dataset,
eliminating highly homologue sequence counterparts (remaining sequences serve as the canonical sequence database of probable valid antigens for subsequent analyses),
in silico cleaving proteins into peptides with lengths of 6 to 15 amino acids (with a one amino acid shifting)
performing local-pairwise alignments of proteins and the corresponding peptides,
scaling of obtained alignment hits by setting the self-alignment score of a given protein to one and aligning hits of the corresponding peptides accordingly,
counting the number of alignment hits exceeding a given threshold for each peptide,
compared the local-pairwise alignment to a randomly generated database of protein sequences with no known allergenic properties,
scaling and counting of hits,
subtracting the "non-allergic protein" counts from those of the allergen results,
calculating cumulative hit scores for each protein based on the number of hits for all corresponding peptides,
selecting proteins with highest counts as iMAT antigen module candidates.

In a specific aspect of the method step b) comprises identifying amino acid substitutions in a predetermined amino acid sequence allowing the stabilization of such predetermined amino acid sequence, preferably comprising the steps of:
(i) modeling of the three-dimensional/tertiary structure of the targeted predetermined amino acid sequence,
(ii) iterative determination of protein stabilities based on single point substitutions, such as substitutions of cysteine residues with different amino acid residues, preferably serine and/or isoleucine residues, and a scoring system based on the protein stability free energy changes ($\Delta\Delta G$) to determine stabilizing substitutions by analyzing all available three-dimensional/tertiary amino acid sequence structures,
(iii) re-modeling of the substituted three-dimensional/tertiary amino acid sequence structure and calculation of its stability by repeating steps (ii) and (iii) until a steady state is reached.

BRIEF DESCRIPTION OF THE FIGURES

FIG. 1A shows the Original SDS-PAGE (10 μg protein per lane, Coomassie staining).

FIG. 9A: shows examples of *D. pteronyssinus* allergens of the genus *dermatophagoides* identifying the species, the allergen and the uniprot accession number.

FIG. 9B: shows examples of *D. farinae* allergens of the genus *dermatophagoides* identifying the species, the allergen and the uniprot accession number.

FIG. 10: shows the N-terminus sequence alignment of invariant chains from dog ((gi|545496088| canis_lupus_familiaris|XP_005619355.1|), SEQ ID NO: 4) and cat ((gi|410949651|felis_catus|XP_003981534.1|), SEQ ID NO: 5). The CLIP sequence is shaded in grey.

EXAMPLES

Figure 1A:
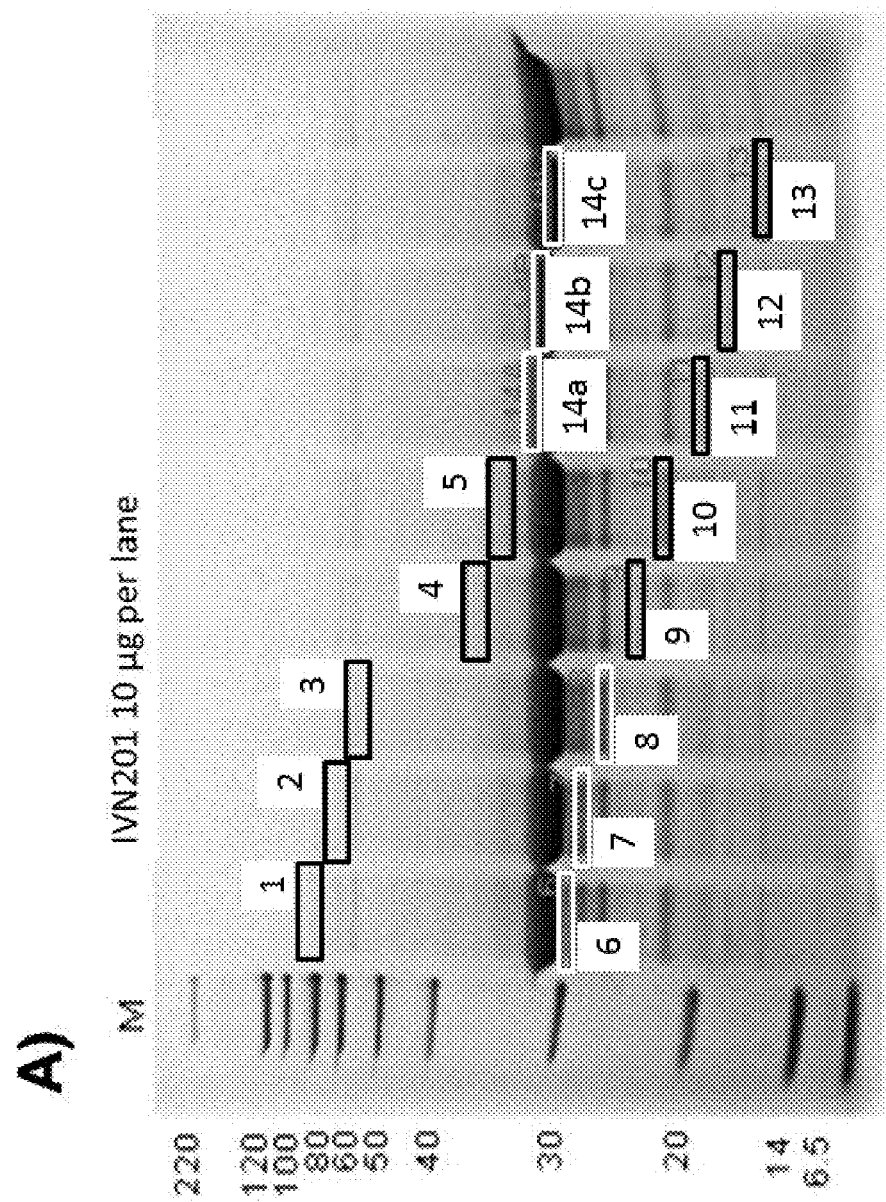
FIG. 1A: shows an SDS-PAGE of MAT-Fel d1 (IVN201) under reducing conditions.

The following examples serve to further illustrate the present invention; but the same should not be construed as a limitation of the scope of the invention disclosed herein.

Example 1—Surrogate Marker for Immunity/Duration of Immunity

Administration of an (isolated) recombinant protein, as disclosed and claimed herein, to an animal, e.g. ruminants, pigs, more preferably a dog and/or a cat, but excluding an equine, produces an immunological response to the allergen and/or epitope present in the antigen module. Additionally, the C- or N-terminal tag, e.g. a HIS-tag, the TAT module together with the adjacent amino acid residues from the adjacent module is used in order to detect a unique product-specific immunological signal (e.g. an antibody—or a T-cell response) in a target subject that is used as a surrogate marker for immunity or duration of immunity. This surrogate marker, as a treatment-specific immunological parameter, enables the assessment of immunity or immune modulation or the duration of immunity or the duration of immune modulation after the administration. Thus, a specific indicator for an immune response triggered by the (isolated) recombinant protein according to the invention is the induction of terminal-tag (optionally with the adjacent amino acid residues) specific antibodies, such as IgG antibodies. Alternatively or additionally, the indicator is the induction of antibodies specific to the junction of a spacer and a module as described and claimed herein or the junction between two modules.

A single iMAT molecule such as SEQ ID NO: 57 (Der f 15 iMAT molecule (dog) with N-terminal Hexa-Histidine tag) or a combination of one or several iMAT molecules selected from SEQ ID NOs: 45, 51, 54, 57, 60, 63, 66, 69, 72 containing different antigen modules according to the present invention are employed for treating prophylactically or therapeutically a dog suffering from or being at risk of allergic diseases, especially atopic dermatitis. In such dogs the above iMAT molecules are administered as described in Example 3. In serum samples derived from a blood draw from these iMAT treated dogs, the immunological reaction upon iMAT treatment against the N-terminus of the iMAT proteins with respect to antibody production more specifically the specific IgG can be measured. The measurement employs standard ELISA (Enzyme Linked Immunosorbent Assay) techniques whereby sufficient amounts of a synthetized peptide comprising SEQ ID NO: 6 is coated on the surface of ELISA plates. Serum samples of treated animals are then incubated on such plates and the specific binding of IgG to the said peptide is detected by a secondary biotinylated antibody, specific for IgG in cats or dogs respectively, followed by application of the corresponding detection system e.g. streptavidin-peroxidase and 3,3',5,5'-tetramethylbenzidine (TMB) as substrate.

With such ELISA test the onset of immunity elicited by iMAT immunotherapy as well as the duration of immunity is determined and observed over time. The therapeutic vaccination regime, i.e. number and schedule of booster injections, is determined by this surrogate parameter during clinical development.

Example 2—Hypoallergenicity

The allergenicity of a therapeutic allergen is of utmost importance, it is a measure of the potential to induce adverse events, e.g. provoke anaphylaxis. Exemplarily for an allergy in mammals, allergen specific IgE mediated hypersensitivity is studied in procedures as the allergen provocation tests, in particular such tests targeting the skin [Griffin C E. Diagnosis of canine atopic dermatitis DOI: 10.1002/978-1118738818.ch10].

Intradermal skin tests have been used for the biological evaluation of recombinant allergens and for validation of genetically engineered hypoallergenic derivatives.

Intradermal testing in a dog is performed by administering injections of small amounts of allergen solutions directly into the dog's dermis. This is usually done with small-gauge (27 gauge) needles and injections of 0.05 to 0.1 mL at each site. The positive reactions are arbitrarily interpreted by the presence of erythema, turgidity, height, and size of the wheal.

The advantages of the intradermal tests are high sensitivities. This is of particular importance if the test shall deliver a quantitative measure for hypoallergenicity. In said tests the MAT molecules show a 10-, 100- to 1000-times or even higher molar concentration of the allergenic component as compared to the natural, native allergen applied in the same test to reach a positive reaction in sensitized individuals, as cats and dogs.

With regard to MAT molecules conflicting results about their allergenicity in comparison to the corresponding native allergens have been reported in the prior art. Senti G et al. (J Allergy Clin Immunol. 2012, 129(5): 1290-1296) demonstrated hypoallergenicity of a MAT-Fel d1 in the Cellular Antigen Stimulation Test (CAST) assay as well as in the intradermal and in the intracutaneous test. The quantitative difference in sensitivity between the allergen and the MAT molecule comprising the Fel d1 was 100-, 23- and 16-fold, respectively. Though MAT-Fel d1 was clearly hypoallergenic, some allergenicity remained. In contrast Zhao et al. Int J Clin Exp Med 2015; 8(4):6436-6443 describe their MAT-Der p1 construct to exhibit an even stronger allergenicity (hyperallergenicity) as compared to the native Der p1 protein.

Surprisingly the improved MAT molecules, as disclosed and claimed herein show clear superiority in this respect. The safety of 2 iMAT molecules manufactured according to the present invention comprising Cul o2 and Cul o3 in the antigen module, respectively, is tested. Freshly withdrawn blood of a horse sensitized to these allergens and suffering from insect bite hypersensitivity (IBH) is employed in the histamine release test (HRT) as described below.

Figure 11A:
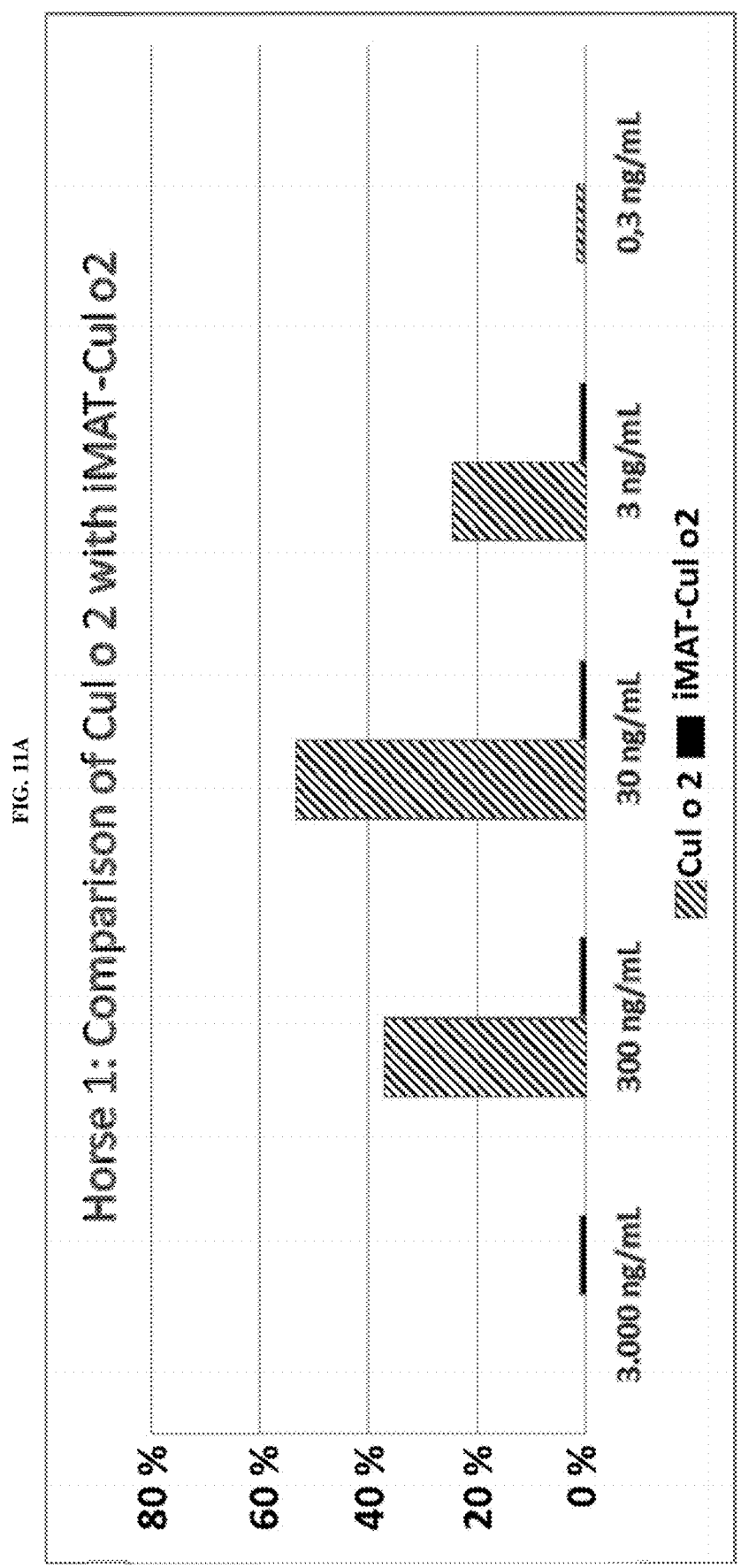
FIG. 11A: shows Histamine Release Test (Details of assay in Example 2) of 5 concentrations of iMAT-Cul o2 and the respective allergens in a polysensitized horse (Horse 1).
Figure 11B:
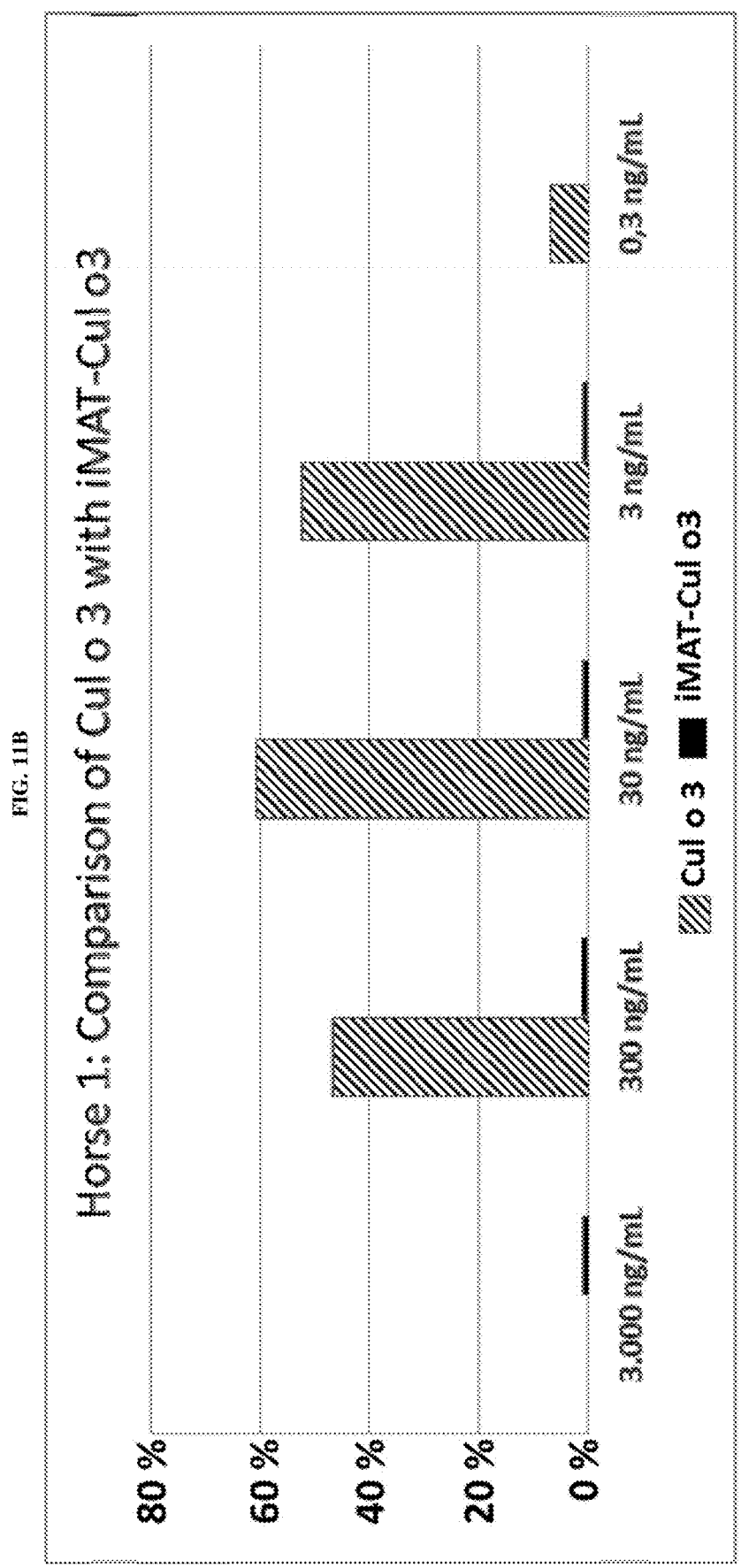
FIG. 11B: shows Histamine Release Test (Details of assay in Example 2) of 5 concentrations of iMAT-Cul o3 and the respective allergens in a polysensitized horse (Horse 1).

As shown in FIG. 11B and FIG. 11A, respectively, the native allergens elicit a strong histamine release whereas surprisingly the two different iMAT molecules (iMAT-Cul o3 and iMAT-Cul o2) show virtually no response at all.

Thus, iMAT molecules show clear superiority in respect to safety as compared with the MAT molecule as described in the prior art (see above).

Histamine release test (HRT): Freshly withdrawn blood of subjects is prepared to test the basophil reactivity to (isolated) recombinant proteins/iMAT molecules, as disclosed and claimed herein. Briefly, a 10-fold dilution series (e.g. ranging from 10 nM to 0.001 nM final allergen concentration) of iMAT molecules and/or recombinant allergens is prepared in PIPES buffer (AppliChem, Darmstadt, Germany), pH 7.4. Washed red and white blood cells obtained from Na-EDTA coagulation-inhibited blood are incubated with individual dilutions for 1 h at 37° C. The reaction is stopped by incubation on ice for 20 min and the supernatant containing the released histamine is collected from each sample after centrifugation. Maximal histamine content is obtained by boiling the blood cells for 10 min in a water bath (maximal release). The incubation of releasing buffer with washed blood cells serves as a negative control (spontaneous release). Histamine concentrations are determined using a competitive RIA (LDN Nordhorn, Germany) as per the manufacturer's instructions.

Alternatively, another basophil activation test is the Cellular Antigen Stimulation Test CAST® ELISA which can also be considered as an in vitro allergy provocation test. This assay is done according to the manufacturer's instructions (Bühlmann Laboratories AG, Allschwil, Switzerland). In the CAST®, sedimented leukocytes from allergic subjects' blood are simultaneously primed with the cytokine IL-3 and stimulated with iMAT molecules and/or recombinant allergens. Basophilic cells among others generate the allergic mediator, sulfidoleukotriene LTC4, and its metabolites LTD4 and LTE4. These freshly synthesized sulfidoleukotrienes (sLT) are subsequently measured in an ELISA test (Enzyme Linked Immunosorbent Assay).

The potential of iMAT molecules to induce adverse events, e.g. provoke anaphylaxis as a side effect of administration can be evaluated in vitro with these assays by comparing the effects of the iMAT molecules (containing an allergen) to the respective recombinant allergen alone.

A reduced basophil degranulation, e.g. histamine and/or sulfidoleukotriene release by iMAT molecules as compared to the recombinant allergen indicates a lower potential for adverse effects, i.e. a better safety profile of the iMAT molecules.

Said HRT (or CAST®) can be used as an in-vitro provocation test for type 1 allergic reactions in a subject. Allergen specific histamine release indicates the relevance of the respective allergen for the basophilic cell activation and thus can be used as a quantitative parameter for the allergen specific sensitization of a subject.

It can be expected that no allergen related adverse reactions occur if subjects suffering from allergen specific IgE mediated hypersensitivity are treated with the corresponding iMAT molecules comprising relevant allergens in the iMAT-antigen module. This makes a desensitization therapy applying iMAT proteins specifically appropriate for treatment of life threatening diseases.

The consequence of this surprising safety property of iMAT molecules in contrast to MAT molecules is, that iMAT molecules used as desensitizing proteins can be used similar to vaccines against pathogens. No up-dosing as with classical therapeutic allergens is needed, since vaccines comprising iMAT molecules do not show allergen properties with respect to allergic adverse events. Already the dose of the first injection of the iMAT molecule in a treatment course is selected based on efficacy considerations only and one does not have to consider potential allergic adverse reactions. This could not be performed using MAT molecules described in the prior art since the allergenicity of MAT, compared to the native allergen, was only reduced to a certain level. However, MAT molecules still are allergens; iMAT molecules in contrast are not. The advantage of this improved property renders a more efficacious treatment regime possible with e.g. three subcutaneous or intralymphatic injections with a high biopharmaceutical content (e.g. 3 times 1 µg to 100 µg, preferably 3 times 10 µg to 50 µg iMAT protein).

The lack of allergenicity of the iMAT molecules can be explained by the fact that in contrast to the MAT molecules described in the prior art no linker amino acid residues [i.e. spacer module(s) between the first, second and/or third module(s)] are used to separate the different modules in such iMAT molecules. It is known in the prior art that engineered fusion proteins containing two or more functional polypeptides joined by a peptide or protein linker are important for the function (e.g. epitope recognition by the immune system) of the proteins [Klein J S et al., Protein Eng Des Sel. 2014, 27(10): 325-330]. The separation distance between functional units can impact epitope access and the ability to bind with avidity. If the missing amino acid residue linkers between the modules, in particular between the targeting domain and the antigen module, lead to a more rigid structure, conformational epitopes of the allergen module might not be formed due to incorrect folding. A cross linking of antibodies bound on the surface of basophils (e.g. IgE) by its high affinity receptors is necessary to induce activation and histamine release. However, misfolded allergens might not be able to induce such cross linking. Thus, an iMAT molecule without linker may not form conformational IgE epitopes which renders the iMAT molecules non-allergenic.

Example 3—Therapeutic Vaccine/Prophylaxis of Atopic Dermatitis in Dogs and/or Cats A single iMAT molecule or a combination of iMAT molecules containing different antigen modules according to the present invention is employed for treating prophylactically or therapeutically a dog and/or a cat suffering from or to be at risk of atopic dermatitis (AD).

In first example the iMAT molecule according to SEQ ID NO: 36 (Der f 15) is administered into the popliteal lymph node of cats suffering from atopic dermatitis.

In a second example the iMAT molecule according to SEQ ID NO: 66 (Hybrid 1) is administered into the popliteal lymph node of cats suffering from atopic dermatitis.

In a third example the iMAT molecule according to SEQ ID NO: 57 (Der f 15) is administered into the popliteal lymph node of dogs suffering from atopic dermatitis.

In a fourth example the iMAT molecule according to SEQ ID NO: 81 (Hybrid 3) is administered into the popliteal lymph node of dogs suffering from atopic dermatitis.

In each case, the hair over the lymph node of the affected animal is clipped and surgically prepared. Using palpation and/or ultrasound for guidance a 25 G needle is inserted into the lymph node. The injected iMAT molecule is adsorbed to an adjuvant. The adjuvant consists e.g. of aluminum phosphate (ADJU-PHOS®, Brenntag Biosector, Denmark). The iMAT molecule stock is a frozen solution of e.g. 375 µg/mL protein concentration in vials, each containing 500 µL to be thawed before use.

After thawing the iMAT molecule solution, 400 µL of the solution are mixed with e.g. 200 µL of the adjuvant. This final formulation is left at room temperature e.g. for 60 minutes prior to the intralymphatic injection to allow for absorption of the iMAT molecule to e.g. ADJU-PHOS®, e.g. 50 µL of the mixture containing 12.5 µg iMAT molecule is removed into a 500 µL syringe for lymph node injection. This preparation is first administered typically on day 0, day 28 and day 56 in a dose between 10 μg and 50 μg (referring to the weight of solely the one or more antigen modules) per injection and iMAT molecule.

Throughout the treatment period and/or thereafter the efficacy of a therapy or the prevention of AD is investigated clinically by quantitative, semi-quantitative or qualitative assessment of pruritus, skin lesions and a medication score (Hobi S, Mueller R S; Tierarztliche Praxis. Ausgabe K, Kleintiere/Heimtiere 2014, 42(3):167-173).

These clinical parameters are compared to clinical signs of the individual dog and/or cat prior to the start of a therapeutic intervention. Alternatively, a comparison to AD affected dogs and/or cats that are not treated or treated with placebo can demonstrate the efficacy of the iMAT molecule-mediated treatment and/or prevention of clinical signs of AD.

Alternatively or in addition an intradermal provocation test with certain *dermatophagoides* allergens can be employed in said dogs and/or cats. A reduced response (immediate and/or late phase reactivity) indicates a therapy and/or prevention effect of the iMAT molecule administration.

Furthermore, the modulation of the different components of the immune system are monitored, e.g. changes in allergen specific IgE and IgG antibody titers indicate therapy and/or prevention effects.

Apart from changes in IgE levels, an increase in allergen-specific IgG is surprisingly found when treating a dog and/or cat for AD with such iMAT molecules. These antibodies block IgE-mediated anaphylaxis in vivo and seem to inhibit not only the allergen-induced release of inflammatory mediators from basophils and mast cells, but also IgE-mediated allergen presentation to T cells. Among the iMAT-induced IgG antibodies specifically binding to the allergen, some allergen-specific subtypes have been suggested to play an important "protective" role, as they compete with allergen-specific IgE antibodies and can prevent the activation of CD4+ T cells, by inhibiting the IgE-mediated antigen presentation. Furthermore, the IgG subset which is secreted promotes a significant reduction in mast cells and eosinophils, accompanied by a diminished release of inflammatory mediators.

Allergen-specific immunotherapy can modulate different components of the immune system. Cellular modifications consist of a reduction in allergen-induced T-cell proliferation, indicating the induction of peripheral tolerance in allergen-specific T cells and a decrease in antigen-specific Th2-dominated immune response in favor of a Th1 reaction with increased IFN-γ production. The key cell type responsible for coordinating this immunological switch is a heterogeneous T-cell population, called regulatory T cells ($T_r$). At the cellular level, the crucial factor for successful allergen immunotherapy is the peripheral induction of type 1 $T_r$ cells. Functional studies on type 1 $T_r$ cells, specific in recognizing antigens, revealed that the modulation of Th1 and Th2 responses by type 1 $T_r$ cells mostly depends on the secretion of the cytokine IL-10, which has immunosuppressive properties. In fact, IL-10 inhibits the proliferative response of peripheral T cells against specific allergens and plays a central role in the induction of T-cell anergy. In vitro, IL-10 enhances the expression of the regulatory factor FoxP3, modulates eosinophilic function and reduces pro-inflammatory mediators released by mast cells.

Another possible marker of the outstanding clinical efficacy of said iMAT molecules-mediated immunotherapy is the detection of changes in the number or the nature of allergen-specific T cells. On the basis of, for example, Bet v tetramer staining studies, the levels and characteristics of circulating birch pollen-specific $CD4^+$ T cells can potentially be compared before and after SIT. Recently, transforming growth factor (TGF)-β has also been identified as a key cytokine in successful SIT. Many actions may account for its relevance, such as the suppression of specific Th1, Th2 and Th17 cells, the induction of FoxP3 and the suppressive function of Tregs. In addition, TGF-3 downregulates FceRI expression on Langerhans cells and suppresses IgE synthesis. These immunological relevant T cell mediated immunological responses can be measured in ex vivo experiments applying peripheral blood mononuclear cell (PBMC) cultures and cytokine detection thereof as described by Nuttall et al. (T. J. Nuttall et al., Veterinary immunology and Immunopathology 84 (2002) 143-150).

Example 4—Comparison of iMAT Molecules According to the Present Invention with Prior Art MAT Molecules According to WO 2004/035793 (US Equivalent US 2005/0281816)

For assessment of purity of a MAT protein, a sodium dodecyl sulfate-polyacrylamide gel electrophoresis (SDS-PAGE) test procedure has been established (Thompson J et al., J Biol Chem 2002, 277: 34310-34331). The method, including sample preparation with a reducing agent, Lithium Dodecylsulphate (LDS) and heating at 75° C., resulted in reproducible multiple sharp bands after electrophoretic separation. Staining with Coomassie blue gives linear quantitative (densitometry) features in gels loaded with 200 to 1000 ng protein. Using a monoclonal antibody, detecting the allergen module in a MAT molecule with Fel d 1 as allergen module (MAT-Fel d1) it has been shown, that the main band and 13 minor bands all contain the MAT-Fel d1 protein. The small bands migrate at the same position as on the original gel also after re-loading on the gel (FIG. 1A and FIG. 1B). Several different methods, such as different temperature and buffer composition protocols, for sample preparation prior to PAGE generated the same band pattern.

In all of these bands the presence of the full length (complete) MAT-Fel d1 protein and only traces of host cell proteins could be demonstrated after each band was cut out of the gel, digested by trypsin and subsequently analyzed by mass spectrometry (nanoLC/ESI-MS). From these experiments an anomalous feature (gel shifting), e.g. of different folding variants, of MAT-Fel d1 in the SDS-PAGE can be concluded. This means that MAT-Fel d1 in the analyzed preparation is not suitable as biopharmaceutical molecule, in particular for clinical and/or commercial biopharmaceutical manufacturing, since its purity could not be determined with standard methods (e.g. SDS-PAGE), but only with the modified procedure explained above.

Figure 2:
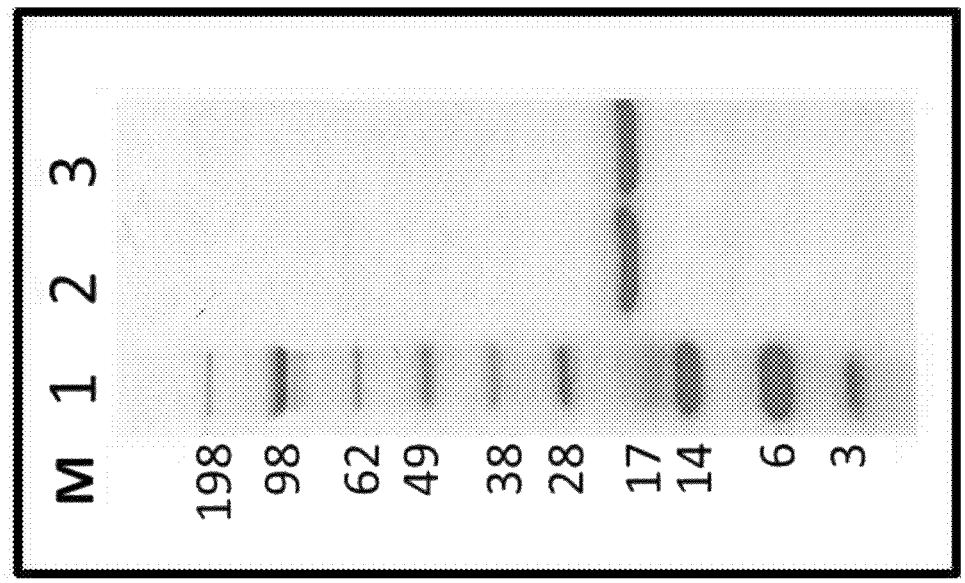
FIG. 2: shows an SDS-PAGE of Fel d1 under reducing conditions; NUPAGE® 4-12% Bis-Tris Gel. Lanes: 1) Marker: SeeBlue Plus2 Pre-Stained Standard 2) 5 μg Fel d1; 3) 5 μg Fel d1.

In contrast to this gel shifting phenomenon of the MAT-Fel d1 molecule, the Fel d1 as such does not show such anomalous feature in SDS PAGE (FIG. 2, lanes 2 and 3). The Fel d1 displays a single sharp band at the expected molecular weight (19.6 kD).

Figure 3A:
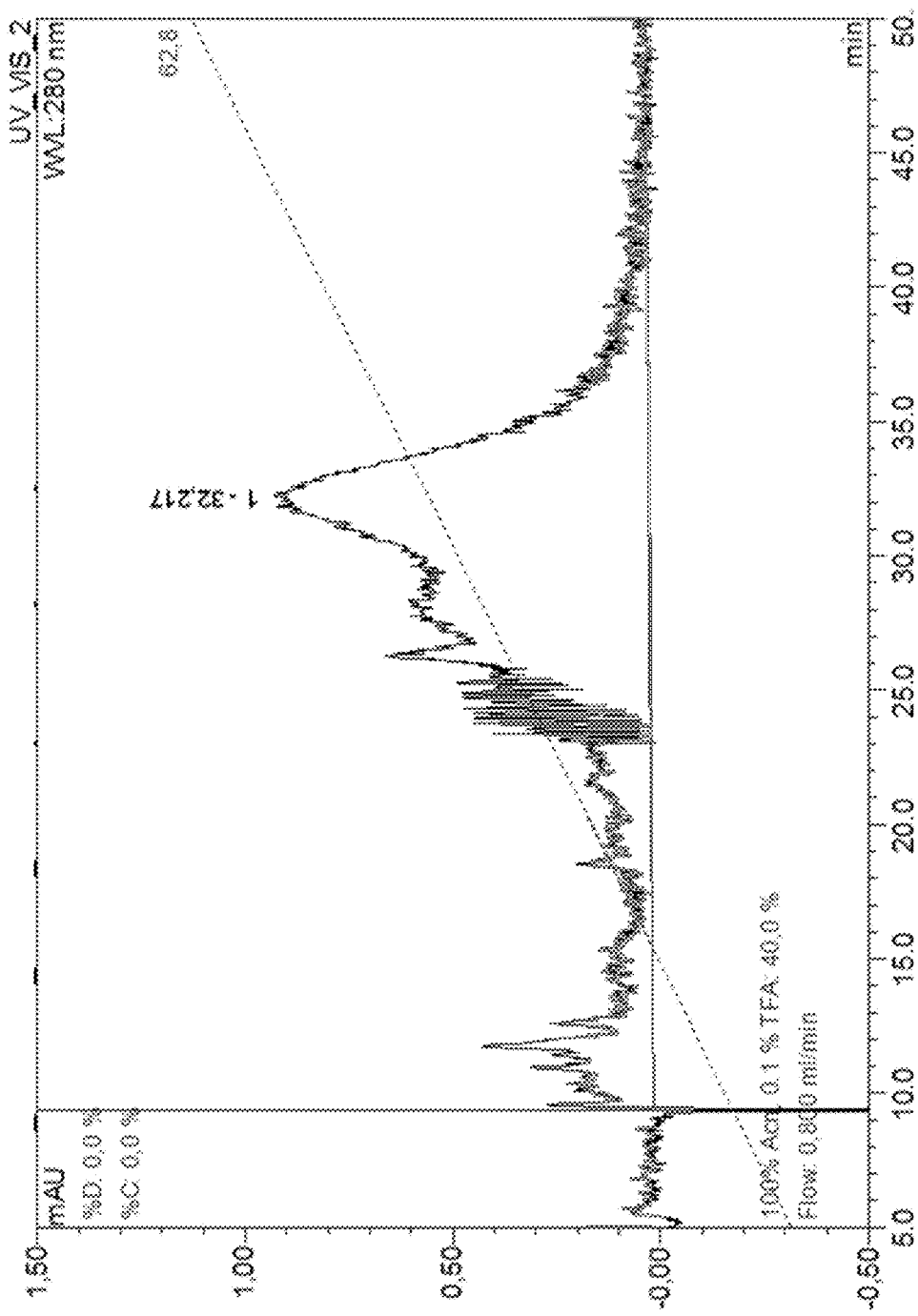
FIG. 3A: shows an RP-HPLC chromatogram 0.1% TFA/Acetonitrile gradient of native protein (MAT-Fel d1) without additives.
Figure 3B:
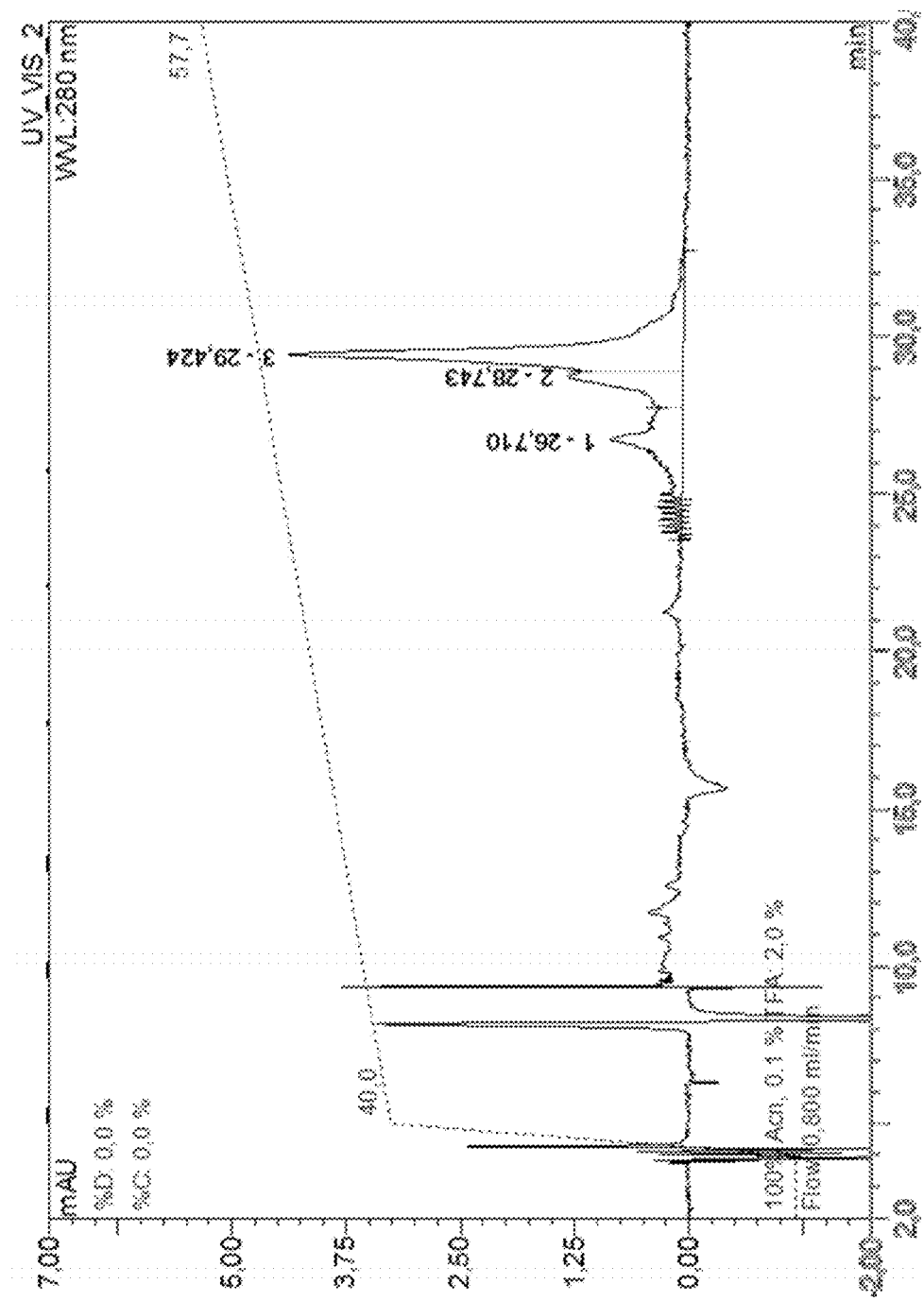
FIG. 3B: shows an RP-HPLC chromatogram 0.1% TFA/Acetonitrile gradient of MAT-Fel d1 denaturated by addition of guanidinium chloride plus DTT.

A further anomalous feature could be observed in RP-HPLC analysis. No single peak of the MAT-Fel d1 was seen in this analytical method (FIG. 3A and FIG. 3B), neither in the native conformation of the protein (FIG. 3A) nor in the denatured form (FIG. 3B) induced by chaotropic and reducing conditions. However, for GMP certified biopharmaceutical manufacturing a single isoform of the biomolecule in marketed pharmaceutical preparations is mandatory.

Figure 4:
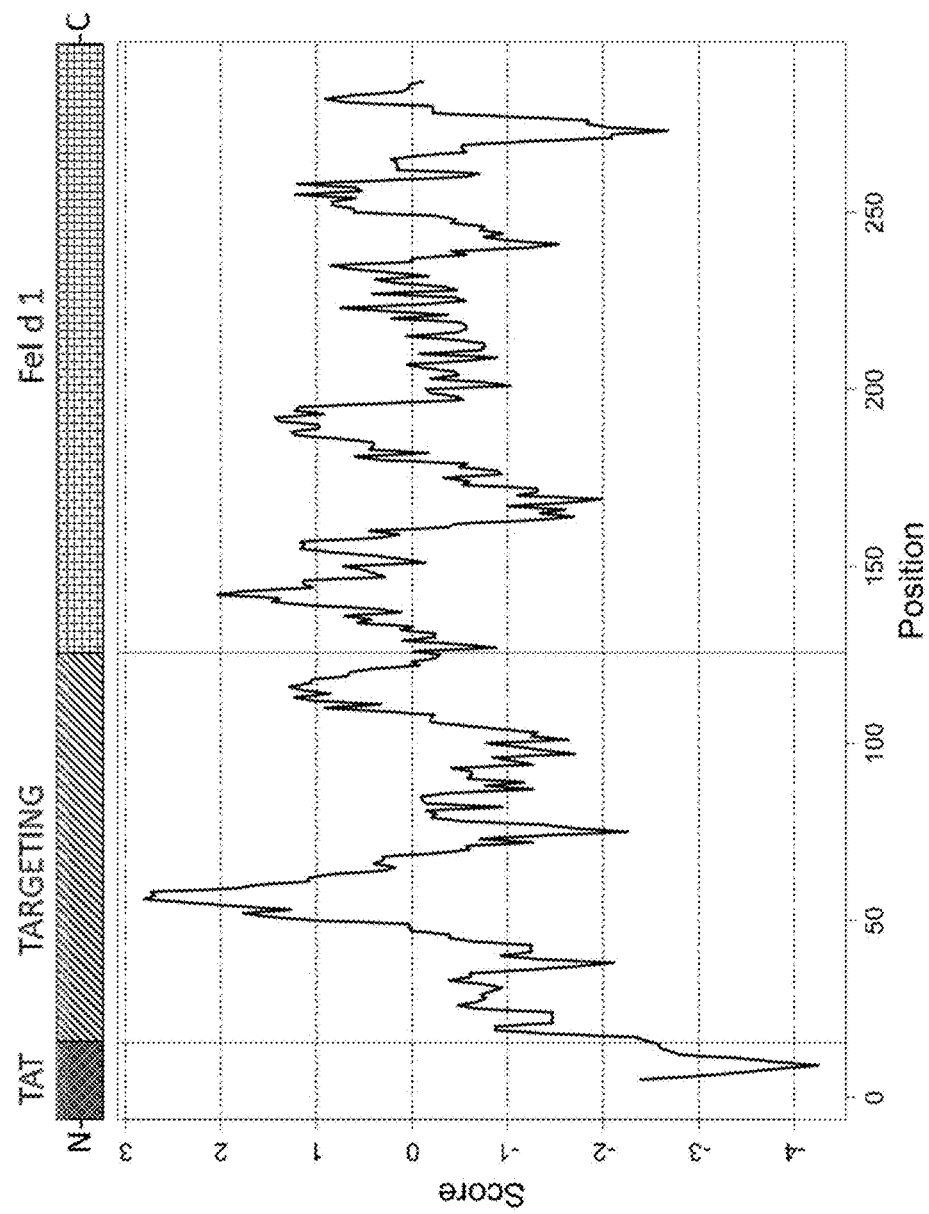
FIG. 4: depicts MAT-Fel d1 molecule and its Kyte Doolittle hydrophobicity plot.

These observations in SDS-PAGE and RP-HPLC analysis may be explained by the physicochemical properties based on the amino acid sequence. Analysis in the Kyte & Doolittle hydrophobicity plot [Kyte J, Doolittle R F, Journal of Molecular Biology 1982, 157(1), 105-132] revealed adjacent extreme hydrophobic and hydrophilic domains (FIG. 4) which may be responsible for this anomalous behavior.

In particular, the hydrophobic region of the targeting domain of the fusion protein is similar to the transmembrane segments of membrane proteins which are known in the art to cause such anomalous feature [Rath A et al., Proc Natl Acad Sci USA. 2009, 106(6): 1760-1765].

Migration on SDS-PAGE, which does not correlate with formula's molecular weights, termed "gel shifting" appears to be common for membrane proteins. This means, that the prerequisite of the SDS-PAGE method, which is a separation of molecules solely according to their molecular weight, independent on their native 2D- or 3D-structure does not apply in these cases. In the above cited work (PNAS article), the authors investigate the anomalous gel mobility of helical membrane proteins using a library of wild-type and mutant helix-loop-helix ("hairpin") sequences derived from transmembrane segments 3 and 4 of the human cystic fibrosis transmembrane conductance regulator (CFTR), including disease-phenotypic residue substitutions. They found that these hairpins migrate at rates of minus 10% to plus 30% vs. their actual formula's molecular weights on SDS-PAGE and load detergent at ratios ranging from 3.4-10 g SDS/g protein. They additionally demonstrated that mutant gel shifts strongly correlate with changes in hairpin SDS loading capacity, and with hairpin helicity, indicating that gel shift behavior originates in altered detergent binding. In some cases, this differential solvation by SDS may result from replacing protein-detergent contacts with protein-protein contacts, implying that detergent binding and folding are intimately linked.

The SDS PAGE (FIG. 5) as well as the RP-HPLC analysis (FIGS. 3A, 3B, and 6) of MAT and iMAT proteins reveal substantial differences in the migration pattern or elution, respectively. The oxidized form of MAT-Fel d1 does not show a single sharp band on the SDS-PAGE gel (Lane 3) but several diffuse bands with larger and smaller apparent molecular weights than the actual 32.2 kD of MAT-Fel d1. In contrast, as an example an iMAT molecule with an antigen module of a *culicoides obsoletus* allergen (iMAT-Cul o4) exhibits a single sharp band (M=41.6 kD) under oxidized conditions. Also the RP-HPLC chromatogram shows a single peak (FIG. 6).

Figure 1B:
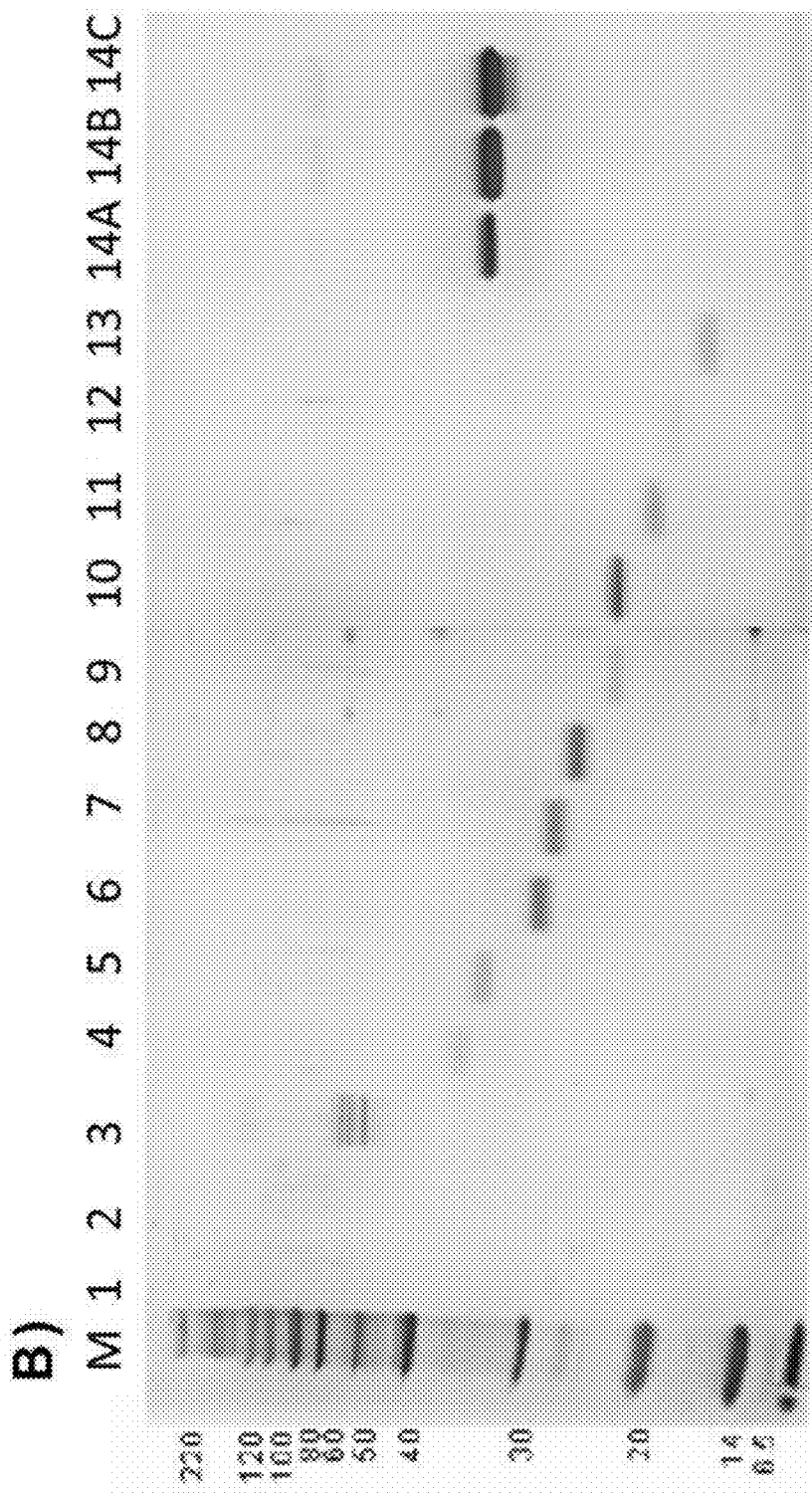
FIG. 1B: shows an SDS-PAGE of MAT-Fel d1 (IVN201) under reducing conditions with bands that have been cut out of the SDS-PAGE gel shown in FIG. 1A and reloaded on SDS-PAGE (silver staining).
Figure 5:
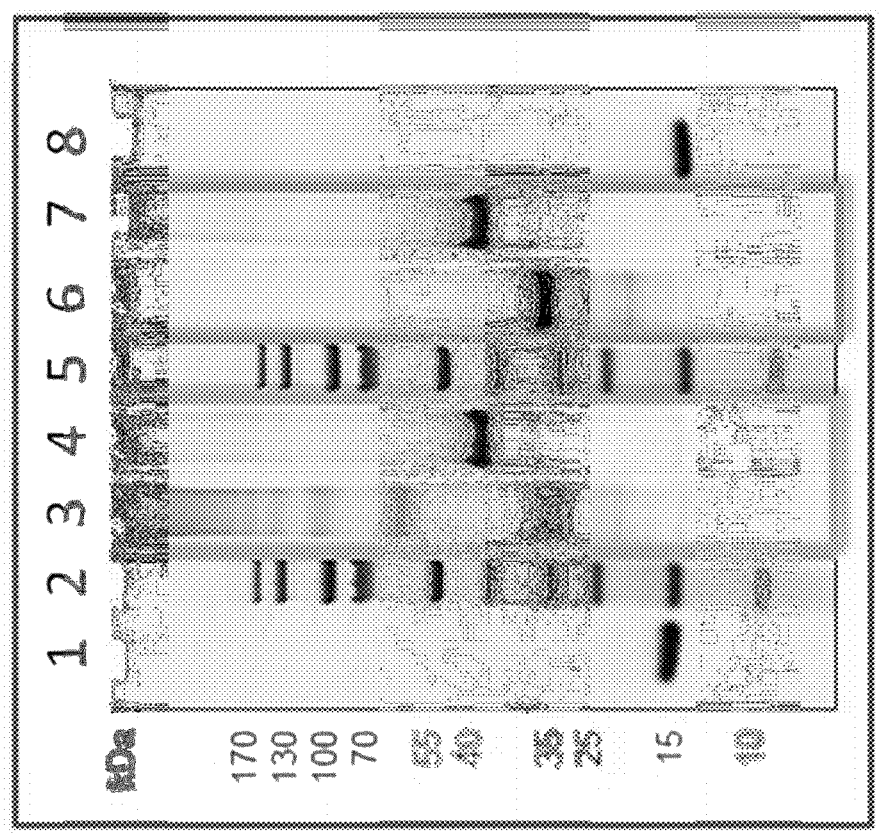
FIG. 5: shows a NUPAGE® SDS-PAGE-System (4-12% Bis-Tris Gels, 1×MES-Running buffer, 35 min, 200 V). Lanes: 1) Lysozyme, 1 μg Protein ox. 2) PageRuler Prestained Protein Ladder; 3) MAT-Fel d1 (5 μg) oxidized with Iodacetamide (ox.); 4) iMAT-Cul o4 (ox.); 5) PageRuler Prestained Protein Ladder; 6) MAT-Fel d1 (5 μg) reduced; 7) iMAT-Cul o4 reduced; 8) Lysozyme reduced.
Figure 6:
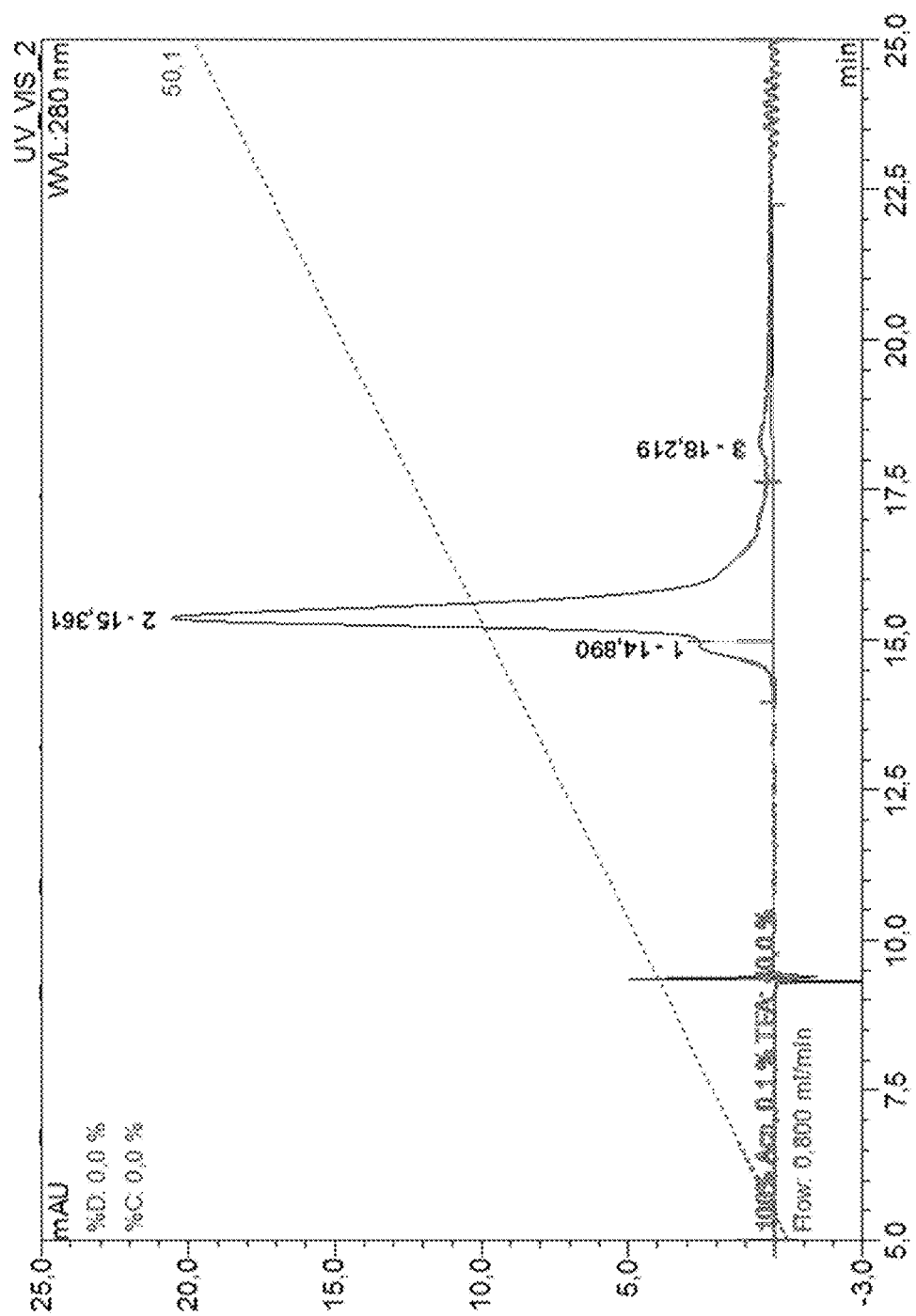
FIG. 6: shows an RP-HPLC chromatogram 0.1% TFA/Acetonitrile gradient. The peak reflects native (oxidized) protein (iMAT-Cul o4) without additives.

Under reducing conditions, the MAT-Fel d1 in the SDS-PAGE reveals a main band migrating approximately at the known molecular weight but in addition some of the minor bands described in FIG. 1A and FIG. 1B known to contain the complete sequence of MAT-Fel d1 emerge again (FIG. 5, lane 6). This is an attribute, which is characteristic for the anomalous feature of MAT-Fel d1. Additionally, the RP-HPLC chromatogram of MAT-Fel d1 under reducing conditions (FIG. 3B) exhibits at least 3 different isoforms of the MAT-Fel d1. In contrast the iMAT molecules reveal characteristics evidently indicative for a single isoform in the SDS-PAGE (FIG. 5, lane 7) as well as in the RP-HPLC (FIG. 6).

The reducing conditions lead to a cleavage of the disulfide bridges in the MAT molecule, thus the MAT and the iMAT molecules should behave alike under reducing conditions if the disulphide bridges are solely responsible for the anomalous feature of MAT. However, this is not the case, since the anomalous gel shifting and the occurrence of isoforms in RP-HPLC of MAT molecules is still present under reducing conditions.

Figure 7:
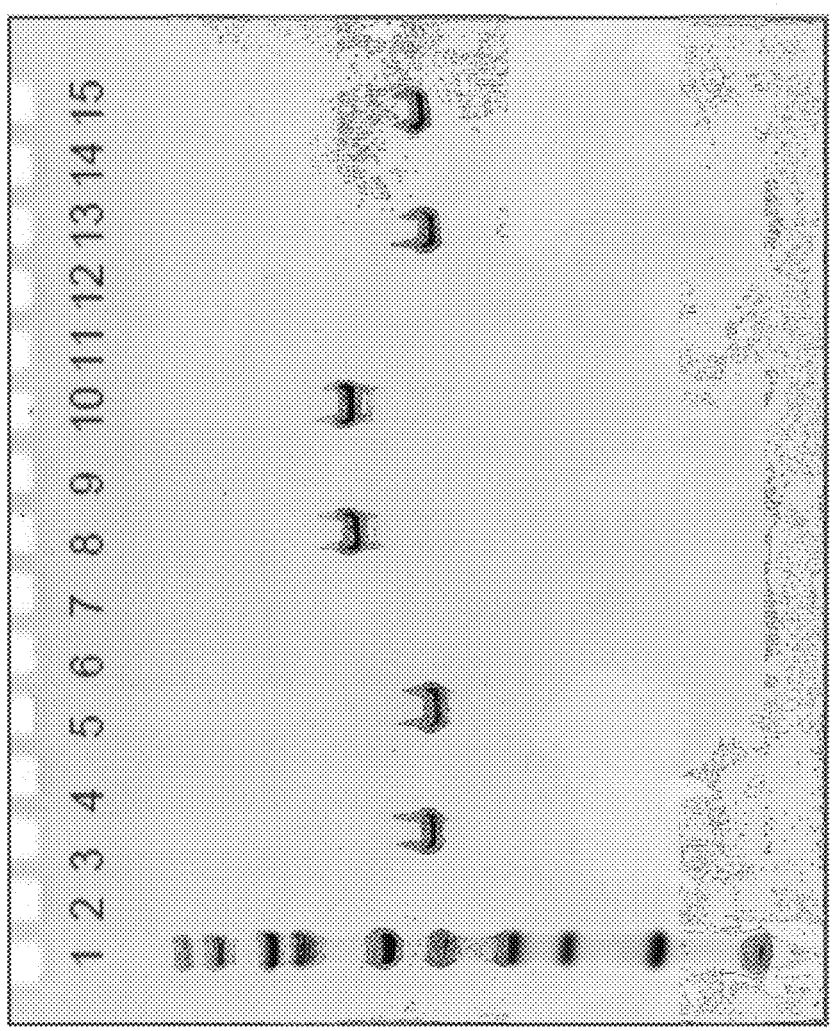
FIG. 7: shows the results of the following experiment: Proteins and ADJU-PHOS® that were incubated at RT for 30 min while mixing gently. After incubation, the samples were centrifuged for 3 min. and subsequently analyzed by SDS-Page Lane 1) pageRuler Prestained Protein Ladder; 2) iMAT-Cul o3 Supernatant; 3) iMAT-Cul o3 Pellet in Urea 4) iMAT-Cul o3 Supernatant; 5) iMAT-Cul o3 Pellet in Urea; 6) Empty; 7) iMAT-Cul o2 Supernatant 8) iMAT-Cul o2 Pellet in Urea 9) iMAT-Cul o2 Supernatant 10) iMAT-Cul o2 Pellet in Urea; 11) Empty; 12) iMAT-Cul o4 Supernatant; 13) iMAT-Cul o4 Pellet in Urea 14) iMAT-Cul o4 Supernatant; 15) iMAT-Cul o4 Pellet in Urea; (2, 3, 7, 8, 12, 13 w/o freeze thaw); (4, 5, 9, 10, 14, 15 after two times freeze thaw process).
Figure 8:
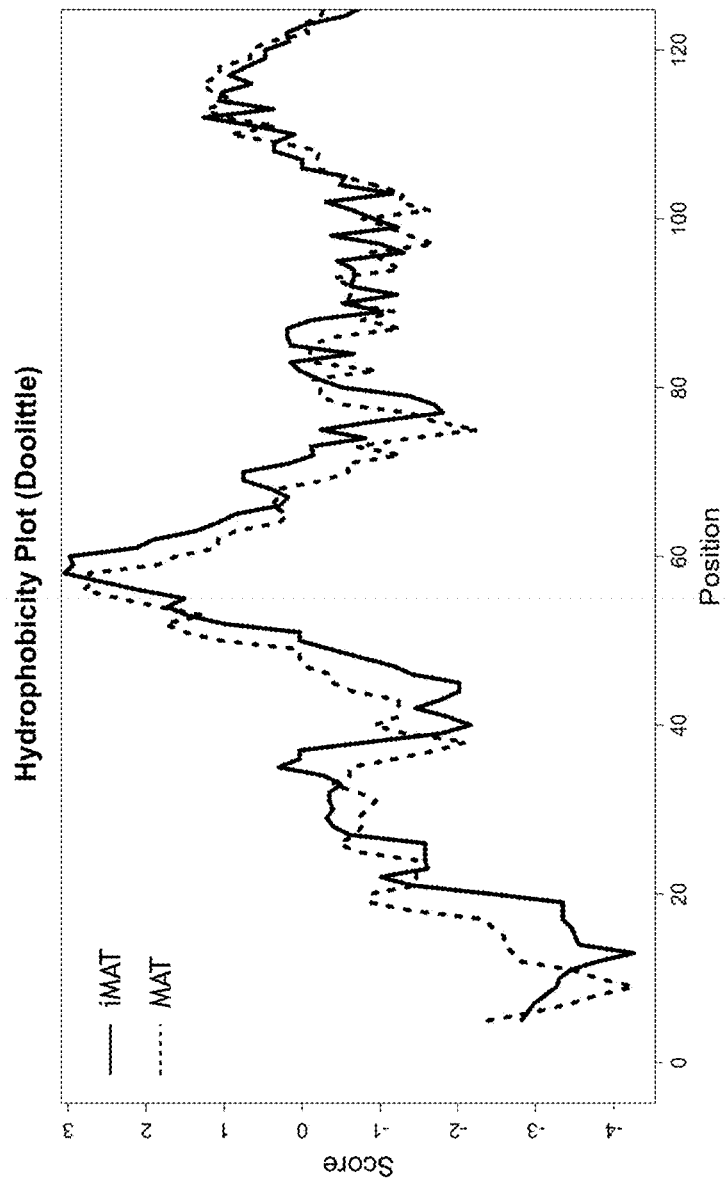
FIG. 8: shows the Kyte-Doolittle hydrophobicity plot of MAT molecules versus iMAT molecules in the generic part of the respective fusion proteins [i.e. without the respective antigen module(s)]. The hydrophobicity index is shown on the Y-axis versus the amino acid position on the X-axis. Positive numbers in the index indicate hydrophobicity. The shift of the graph of the iMAT molecule at the beginning of the hydrophobicity plot as compared to the MAT molecule is due to the additional N-terminal presence of a His-tag and one methionine residue in the iMAT molecule as well as the absence of any spacer module(s).

However, the iMAT molecule does not show such gel shifting and exhibits a peak in RP-HPLC chromatogram in the native (oxidized) form of the protein. Furthermore, the Kyte-Doolittle plots of MAT and iMAT molecules are nearly identical at the N-terminus covering the sequence of His-tag, TAT and targeting domain (FIG. 8). Consequently, a person skilled in the art would not be motivated to construct a MAT molecule according to the prior art with cysteine residues substituted with other amino acid residues in order to overcome the disadvantages of the prior art.

iMAT molecules can be constructed by the "bioinformatical engineering" procedures according to Example 5 below and produced by recombinant expression technology in *E. coli*. As an example three iMAT molecules, as shown in FIG. 7 are stable in buffer (20 mM citrate, 1 M arginine, pH 6.0) after freezing and thawing twice and could be adsorbed to ADJU-PHOS® (Brenntag, Denmark) as adjuvant, so that the iMAT molecules can be used as a vaccine. The proteins are desorbed from ADJU-PHOS® without degradation in the same buffer system (FIG. 7).

Example 5—"Bioinformatical Engineering" of iMAT Molecules: Selection of Proteins for the Antigen Module and Optimization of the Full iMAT Molecule In order to, for example, treat dogs and/or cats with allergic disorders using the iMAT technology effectively, it is further advisable:
a) to select a protein as allergen module in iMAT molecules that is an allergen and thus has a high potential to cause hypersensitivity in affected subjects and thus can also be the target for tolerance induction, and
b) to construct an iMAT molecule with said allergens that is thermodynamically stable and can be produced efficiently by protein engineering and can additionally be analyzed with standard methods to ensure sufficient enough quality (i.e. identity, purity and potency).

In order to fulfil these requirements a bioinformatics approach is chosen for the selection of the allergen to be included into the iMAT molecules according to the invention. The objective of the selection is (i) to choose one or more allergens to be expected to be of relevance in a given allergic disorder, i.e. that the majority of individuals suffering from allergic disorder are sensitized to the respective allergen, and (ii) to choose the allergen with the highest probability of comprising linear epitopes of allergen characteristics, i.e. comprising high numbers of short peptide sequences (7 to 13 amino acid residues) homologue to those in published allergens.

To select appropriate antigens for pharmaceutical preparations, a homology comparison based on local sequence alignments to known allergens is chosen. Often epitope detection for antibody recognition (mostly conformational epitopes) is achieved by functional analysis (e.g. peptide microarrays) or for T-cells epitopes (linear epitopes) by calculation of peptide binding probabilities to MHC molecules. The therapeutic principle of the iMAT technology inter alia is based on endocytosis and degradation by acid-dependent proteases in endosomes followed by MHC Class II binding and antigen presentation.

Thus a different—non experimental but bioinformatics—approach for allergen selection is chosen that is based on local homology searches of peptides derived from given proteins to known allergenic proteins, most of which are known to raise allergies in humans. Amino acid sequences of proteins suspected to have allergenic properties are exported from publicly available databases (e.g. UNIPROT) and redundancies are determined by analysis of sequences homologies within the exported dataset. Highly homologue sequence counterparts are eliminated and the resulting remainder of sequences served as the canonical sequence database of probable valid antigens for subsequent analyses. To determine proteins with putative high allergenic potential, proteins are in silico cleaved into peptides with lengths of 6 to 15 amino acids with a one amino acid shifting. Next, local-pairwise alignments of e.g. *dermatophagoides* proteins and the corresponding peptides to the canonical sequence database are performed. Following this, a scaling of obtained alignment hits is conducted by setting the self-alignment score of a given protein to one and alignment hits of the corresponding peptides accordingly. Thereafter the number of alignment hits exceeding a given threshold are counted for each peptide and compared by local-pairwise alignment to a randomly generated database of protein sequences with no known allergenic properties, and subsequently scaled and counted. The resulting "non allergic protein" counts are subtracted from those of the allergen results and cumulative hit scores for each protein based on the number of hits for all corresponding peptides are calculated. Proteins with highest counts are selected as iMAT antigen module candidates.

Each of the selected allergens are integrated into separate iMAT molecules as the antigen module and subsequently the full iMAT molecule is optimized for thermodynamic stability by iterative modeling of three-dimensional protein structures and calculation of changes of free energies after substitution of single amino acids. Physicochemical properties and stability is influenced by substituting different amino acid residue(s) within the primary amino acid sequence.

The results of the herein described analyses (antigen search and modeling) are transformed into an iMAT amino acid sequence suitable for pharmacological production and application.

In a specific example, this bioinformatics engineering approach identifies Zen 1 and Der f 15 to be of relevance in the allergic disorder atopic dermatitis elicited by proteins derived from the mite species *dermatophagoides farinae*. Furthermore, the bioinformatics analysis reveals stable iMAT molecules with cysteines substituted by other amino acid residues. Examples of such stable iMAT molecules are SEQ ID NO: 39 (Dog Zen1) and SEQ ID NO: 57 (Dog Der f 15).

Example 6—Construction of Mosaic-Like iMAT Molecules According to the Invention

It is expected that iMAT molecules according to the invention is further improved if components of more than one allergen are included into the antigen module. For this purpose, it is possible to apply the basic principle of the above described bioinformatics selection approach (Example 5) in a different way. Instead of selecting complete allergens based on the hit count of allergen peptides found in the allergen data base, only the most abundant peptides of several of such allergens are used to engineer an iMAT antigen module. Thus, such an iMAT molecule consists of an antigen module of peptides that stem from several allergens. This allows broadening of the spectrum of a single iMAT molecule with respect to its targeted allergic profile and is thus beneficial for pharmacological drug development.

In order to find short peptide sequences that qualify for such mosaic-like iMAT molecule proteins from e.g. *dermatophagoides* are analyzed by homology comparison as described above. Briefly in silico cleaved proteins with peptide lengths of 6-15 amino acid residues are locally aligned to a canonical sequence database of allergen-related proteins and a random database of non-allergy-related proteins. The number of differences of significant homologies for each peptide found within the canonical database is determined. Subsequently, each peptide is locally aligned to a random database triple the size of the canonical database to reduce false positive hits. The top (e.g. tenth percentile) of remaining homologies for each peptide length is especially suitable to serve as a base for construction of a mosaic-like or hybrid allergen carrying iMAT molecule. To construct a mosaic-like iMAT molecule a protein precursor is chosen (for example from the list of precursor proteins corresponding to top ranking peptides) as a scaffold protein for embedding top ranking peptides. The signal peptide sequence is removed from the scaffold protein and top ranking peptides, optionally with additional adjacent N- or C-terminal amino acids, can be inserted within the original sequence of the scaffold protein or can replace parts of the original sequence of the scaffold protein. The position for insertion or replacement is determined using similarity alignments or the reference position of the peptide in the corresponding precursor protein. As a next step, His-Tag, the TAT and targeting domain are added. Finally, cysteine residues are replaced by most stabilizing residues as described above.

In a specific example (hybrid 1), this bioinformatics engineering approach identifies a combination of SEQ ID NO: 84 (A1KXC1_DERFA DFP1 OS=*Dermatophagoides farina*), SEQ ID NO: 10 (Q86R84_DERFA 60 kDa allergen Der f 18p OS=*Dermatophagoides farinae* GN=Der f 18 PE=2 SV=1), SEQ ID NO: 85 (A0A088SAS1_DERFA Der f 28 allergen OS=*Dermatophagoides farinae* PE=2 SV=1), SEQ ID NO: 88: (A7XXV2_DERFA Der f 2 allergen OS=*Dermatophagoides farinae* PE=4 SV=1), SEQ ID NO: 86 (B7U5T1_DERFA Der f 6 allergen OS=*Dermatophagoides farinae* PE=2 SV=1), SEQ ID NO: 87 (T2B4F3_DERPT LytFM OS=*Dermatophagoides pteronyssinus* GN=lytFM PE=4 SV=1), SEQ ID NO: 11 (Q9U6R7_DERFA 98 kDa HDM allergen OS=*Dermatophagoides farinae* PE=2 SV=1)

to be of relevance in the allergic disorder atopic dermatitis elicited by proteins derived from the mite species *dermatophagoides farinae*. Furthermore, the bioinformatics analysis reveals stable iMAT molecules with cysteines substituted by other amino acid residues. Examples of such stable mosaic-like iMAT molecules are SEQ ID NOS: 75 (Dog Hybrid 1) and SEQ ID NO: 66 (Cat Hybrid 1).

Example 7—Therapeutic Vaccine/Prophylaxis of Allergic Asthma in Cats

A single iMAT molecule or a combination of iMAT molecules containing different antigen modules according to the present invention can be employed for treating prophylactically or therapeutically a cat suffering from or being at risk of allergic asthma. In cats iMAT molecules according to the present invention are administered as described in Example 3.

Adult cats with a known history of allergic asthma will be included in the study, i.e. cats reported to exhibit clinical signs as spastic coughing episodes, wheezing and expiratory dyspnea.

Bronchoalveolar lavage fluids (BALF) are collected prior to treatment start and e.g. 2, 3, and 6 months during/after treatment. BALF is used for cytologic examination and nucleated cell counts.

Cats are sedated with e.g. Ketamine HCl intravenously. Bronchoalveolar lavage fluid is collected by gently inserting e.g. a 7 Fr polypropylene catheter through the endotracheal tube. When resistance is felt, an up to 20 ml aliquot of warmed sterile saline is lavaged through the catheter and retrieved by manual suction. After centrifugation and resuspension, a smear cytology of the collected BALF cells is prepared, the presence of significant numbers of eosinophils support a diagnosis of feline asthma. Differential cell counts can quantitatively evaluate the ratio (%) of eosinophils in BAL fluids.

Alternatively or in addition, employing certain recombinant allergens an intradermal provocation test, skin prick test or also allergen specific IgE and/or IgG determination in BAL fluid or serum can be monitored in said cats (Norris et al., Vet Immunol Immunopathol. 2003, 96(3-4): 119-127). A reduced response (immediate and/or late phase reactivity) and/or changes of the antibody titers indicate a therapy and/or prevention effects of the iMAT molecule treatment.

Clinical signs as the respiratory rate and scores to account for respiratory effort/difficulty are employed. Said "respiratory scoring system" can be employed also e.g. in response to an aerosol challenge. Briefly, awake, spontaneously breathing cats in a sealed chamber are exposed for different time length and/or different concentrations of aerosolized recombinant allergens. Alternatively, quantitative measures of the airway hyper-responsiveness can be performed in anesthetized cats. Pneumotachograph measurements can be done baseline and in a broncho-provocation protocol e.g. a dose response of the pulmonary resistance to methacholine and/or selected recombinant allergens.

Thus, throughout the treatment period and/or thereafter the efficacy of a therapy or the prevention of allergic asthma is investigated clinically by quantitative, semi-quantitative or qualitative assessments.

The parameters can be compared in the individual cat to the severity prior to the start of a therapeutic intervention. Alternatively, a comparison to cats with allergic asthma that are not treated or treated with placebo demonstrates the efficacy of the iMAT molecule-mediated treatment and/or prevention of clinical signs of feline allergic asthma.

Example 8—Therapeutic Vaccine/Prophylaxis of Flea Allergy in Cats and/or Dogs

A single iMAT molecule or a combination of iMAT molecules containing different antigen modules according to the present invention can be employed for treating prophylactically or therapeutically a cat and/or a dog suffering from or being at risk of flea atopic dermatitis.

In a first example the iMAT molecule according to SEQ ID NO: 42 (Cat Cte f 1) is administered into the popliteal lymph node of cats suffering from or being at risk of flea atopic dermatitis.

In a second example the iMAT molecule according to SEQ ID NO: 63 (Dog Cte f 1) is administered into the popliteal lymph node of dogs suffering from or being at risk of flea atopic dermatitis.

The further treatment details are as described in Example 3 above.

The efficacy of said iMAT treatment is evaluated by an intradermal test (IDT), T-cell analyses and measurement of flea allergen specific IgE and IgG (Gerber, J. D. Vaccine 1990-12-8(6):536-542) in treated cats and/or dogs before and after iMAT treatment as described by Jin (Jin J et al., Vaccine 28 (2010) 1997-2004). Intradermal tests (IDTs) are done following the protocol from Hillier and DeBoer, (DeBoer, D. J., Hillier, A. Veterinary Immunology and Immunopathology 2001, 81 (3-4), 271-276). 4 weeks after the last immunization, the cats and/or dogs are injected with 100 μl PBS containing 100 μg of flea extract on the lateral thorax skin of the cats and/or dogs intradermally; histamine is used as positive control, BSA used as an irrelevant stimulator, and saline used as the negative control. The size of reactive bleb on the skin is marked with a marker pen and measured perpendicularly and horizontally within 20 min after the challenge by a micrometer. The results are calculated as an average of the three measurements. A reduced response (immediate and/or late phase reactivity) and/or changes of the antibody titers or Th1 or Treg skewed T-cell responses indicate a therapy and/or prevention effects of the iMAT molecule treatment.

REFERENCES (1) 3$^{rd}$ Havemeyer workshop, Hólar, Iceland, June 2007, Veterinary Immunology and Immunotherapy 2008, 126: 351-361
(2) Allergome (www.allergome.org)
(3) Crameri R. et al., Allergy 2007, 62: 197-206
(4) DeBoer, D. J., Hillier, A. Veterinary Immunology and Immunopathology 2001, 81(3-4): 271-276
(5) Gadermaier G et al., Molecular Immunology 2010, 47: 1292-1298
(6) Gerber J. D. Vaccine 1990-12-8(6):536-542
(7) Griffin C E. Diagnosis of canine atopic dermatitis in Veterinary Allergy DOI: 10.1002/9781118738818.ch10
(8) Guaguere E et al. EJCAP, 2009, 19 (3), 234-241
(9) Hill et al. Vet Immunol Immunopathol, 2001; 81(3-4): 169-186
(10) Hobi S, Mueller R S; Tierarztliche Praxis. Ausgabe K, Kleintiere/Heimtiere 2014, 42(3):167-173
(11) Jackson H A, EJCAP, 2009, 19 (3), 230-233
(12) Jin J. et al. Vaccine 2010, 28: 1997-2004
(13) Klein J S et al., Protein Eng Des Sel 2014, 27(10): 325-330
(14) Kyte J, Doolittle R F, Journal of Molecular Biology 1982, 157(1): 105-132
(15) Martínez-Gómez J M et al., Allergy 2009, 64(1): 172-178
(16) McCall C et al., Vet Immunol Immunopath 2001; 78:231-247
(17) McDermott M J et al. Molecular Immunology 2000, 37: 361-375

(18) Norris et al., Vet Immunol Immunopathol. 2003, 96(3-4): 119-127
(19) Nuttall T. J. et al., Veterinary immunology and Immunopathology 2002; 84: 143-150
(20) Pires D E et al. Bioinformatics 2014, 30(3): 335-342
(21) Prost C, Rev Fr Allergol Immunol Clin, 2008, 48(5), 409-413
(22) Rath A et al., PNAS 2009, 106(6): 1760-1765
(23) Rose H, Arb Paul Ehrlich Inst Bundesinstitut Impfstoffe Biomed Arzneim Langen Hess 2009, 96: 319-327
(24) Senna G et al., Curr Opin Allergy Clin Immunol. 2011, 11(4): 375-380
(25) Senti G et al., J Allergy Clin Immunol. 2012, 129(5): 1290-1296
(26) SIAF Annual Report 2010
(27) SIAF Annual Report 2011
(28) Thomas W R et al., Chang Gung Med J 2004; 27: 563-569
(29) Thompson J et al., J Biol Chem 2002, 277: 34310-34331
(30) US 2005/0281816
(31) U.S. Pat. No. 7,629,446
(32) U.S. Pat. No. 7,653,866
(33) WHO PD-VAC 2014—Status of Vaccine Research and Development of Vaccines for Leishmaniasis
(34) WO 2004/035793
(35) Zhao et al. Int J Clin Exp Med 2015; 8(4):6436-6443

The invention claimed is:

1. A method of prophylactically and/or therapeutically treating one or more allergic diseases in a dog or a cat, comprising administering an effective amount of an improved modular antigen transportation (iMAT) molecule, wherein said iMAT molecule comprises:
   (i) at least one first module, wherein said at least one first module comprises an amino acid sequence allowing the translocation of the iMAT molecule from the extracellular space into the interior of cells, wherein said at least one first module is selected from the group consisting of:
      (a) the amino acid sequence of HIV-tat, VP22, Antennapedia, or a partial sequence thereof;
   (ii) at least one second module, wherein said at least one second module comprises an amino acid sequence allowing species-specific intracellular targeting of the iMAT molecule to the cell organelles which are involved in the processing of antigens and/or the loading of major histocompatibility complex (MHC) molecules with antigens, preferably processed antigens, wherein said at least one second module is selected from the group consisting of:
      (a) the invariant chain selected from the canine and/or feline species' or a partial sequence thereof; and
   (iii) at least one third module, wherein said at least one third module is an antigen module having an amino acid sequence of at least one epitope of at least one allergen eliciting an immune response in dogs and/or cats in response to allergens derived from fleas and/or mites, wherein the antigen module determines the specificity of an immune response modulated by such iMAT molecule, characterized in that in the entire iMAT molecule all cysteine residues are substituted with a different amino acid residue.

2. A method of prophylactically and/or therapeutically treating one or more allergic diseases in a cat or a dog comprising administering an effective amount of an improved MAT (iMAT) molecule, wherein said iMAT molecule comprises:
   (i) at least one first module, wherein said at least one first module comprises an amino acid sequence allowing the translocation of the iMAT molecule from the extracellular space into the interior of cells, wherein said at least one first module is selected from the group consisting of:
      (a) the amino acid sequence of HIV-tat, VP22, Antennapedia, or a partial sequence thereof,
   (ii) at least one second module, wherein said at least one second module comprises an amino acid sequence allowing species-specific intracellular targeting of the iMAT molecule to the cell organelles which are involved in the processing of antigens and/or the loading of major histocompatibility complex (MHC) molecules with antigens, wherein said at least one second module is selected from the group consisting of:
the invariant chain selected from the canine and/or feline species' or a partial sequence thereof; and
(iii) at least one third module, wherein said at least one third module is an antigen module having an amino acid sequence of at least one epitope of at least one allergen eliciting an allergic disease in cats or dogs, wherein the allergic disease is selected from the group consisting of: allergies to flea bites, allergies to mite derived allergens, food allergies, atopic dermatitis, atopic dermatitis caused by flea bites, allergic asthma, allergic airway inflammation and/or obstruction; characterized in that in the entire iMAT molecule all cysteine residues are substituted with a different amino acid residue.

3. The method of claim 1 or claim 2, wherein the modules of the iMAT molecule are covalently linked to each other, and wherein no additional spacer module(s) between two or more adjacent modules of said first, second and/or third modules are present at all.

4. The method of claim 1 or claim 2, wherein said at least one antigen module comprises Der f 15 allergen according to SEQ ID NO: 11, 18, and/or Cte f1 allergen according to SEQ ID NO: 13 and/or 20.

5. The method of claim 1 or claim 2, wherein said iMAT molecule further comprises at least one His-tag module, wherein the at least one His-tag module is present N-terminally and/or C-terminally.

6. The method of claim 1 or claim 2, wherein said at least one first module consists of SEQ ID NO: 1.

7. The method of claim 1 or claim 2, wherein said at least one third module consists of an amino acid sequence selected from the group consisting of SEQ ID NOs: 7 to 23.

8. The method of claim 1 or claim 2, wherein said iMAT molecule consists of an amino acid sequence selected from the group consisting of SEQ ID NOS: 24 to 83.

9. The method of claim 1 or claim 2, wherein said iMAT molecule, comprises:
(i) said at least one first module, wherein said at least one module consists of SEQ ID NO: 1;
(ii) said at least one second module, wherein said second module is selected from a group consisting of SEQ ID NOs: 4 or 5; and
(iii) said at least one third module, wherein said at least one third module is selected from a group consisting of SEQ ID NOs: 14 to 23.

10. The method of claim 1 or claim 2, wherein said iMAT molecule, comprises:
(i) said at least one first module, wherein said at least one module consists of SEQ ID NO: 1;
(ii) said at least one second module, wherein said second module is selected from a group consisting of SEQ ID NOs: 4 or 5; and
(iii) said at least one third module, wherein said at least one third module is an antigen module having an amino acid sequence of at least one epitope, selected from the group consisting of: SEQ ID NO: 7, 8, 9, 10, 11, 12, 13, 84, 85, 86, 87, and 88.

11. The method of claim 1 or claim 2, wherein said iMAT molecule, comprises:
(i) said at least one first module, wherein said at least one module consists of SEQ ID NO: 1;
(ii) said at least one second module, wherein said second module is selected from a group consisting of SEQ ID NOs: 4 or 5; and
(iii) said at least one third module, wherein said at least one third module is an antigen module having an amino acid sequence of at least one epitope, selected from the group consisting of two or more antigens selected from the group consisting of: SEQ ID NO: 10, 11, 84, 85, 86, 87, and 88, or any combination of two or more antigens selected from the group consisting of: SEQ ID NO: 7, 8, 9, 10, 11, and 12, or any combination of two or more antigens selected from the group consisting of: SEQ ID NO: 7, 8, 10, and 11.

12. The method of claim 1 or claim 2, wherein said iMAT molecule further comprises at least one His-tag module, wherein the at least one His-tag module is present N-terminally after one methionine residue.

13. The method of claim 1 or claim 2, wherein said amino acid sequence of said at least one first module is selected from the group consisting of the amino acid sequence of HIV-tat or a partial sequence thereof.

14. The method of claim 1 or 2, wherein said amino acid sequence of said at least one first module is selected from the group consisting of the amino acid sequence having at least 95% sequence identity with the amino acid sequence set forth in SEQ ID NO: 1.

15. The method of claim 1 or claim 2, wherein said amino acid sequence of said at least one second module is selected from the group consisting of the sequence according to SEQ ID NO: 2, SEQ ID NO: 3, SEQ ID NO: 4, SEQ ID NO: 5, and fragments thereof.

16. The method of claim 1 or claim 2, wherein said amino acid sequence of at least one allergen of said at least one third module is selected from the group consisting of the amino acid sequence for Der f 1, Der f 2, Der f 23, Der f 18/Der f 18p, Der f 15, Zen 1, Cte f1, and fragments thereof.

17. The method of claim 1 or claim 2, wherein said amino acid sequence of at least one allergen of said at least one third module is selected from the group consisting of the amino acid sequence having at least 95% sequence identity with the amino acid sequence set forth in SEQ ID NOs: 7-23.

18. The method of claim 1 or claim 2, wherein said iMAT molecule consists of an amino acid sequence having at least 95% sequence identity with an amino acid sequence selected from the group consisting of SEQ ID NOS: 24 to 83.

19. The method of claim 1 or claim 2, wherein the dog or the cat is suffering from or being at risk of said one or more allergic diseases.

* * * * *

SEQUENCE LISTING

<160> NUMBER OF SEQ ID NOS: 102

<210> SEQ ID NO 1
<211> LENGTH: 11
<212> TYPE: PRT
<213> ORGANISM: Artificial Sequence
<220> FEATURE:
<223> OTHER INFORMATION: TAT sequence

<400> SEQUENCE: 1

Tyr Gly Arg Lys Lys Arg Arg Gln Arg Arg Arg
1               5                   10

<210> SEQ ID NO 2
<211> LENGTH: 272
<212> TYPE: PRT
<213> ORGANISM: Canis lupus familiaris

<400> SEQUENCE: 2

Met Glu Asp Gln Arg Asp Leu Ile Ser Asn His Glu Gln Leu Pro Ile
1               5                   10                  15

Leu Gly Gln Arg Pro Gly Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Ser Leu Arg Met Lys
65                  70                  75                  80

Leu Pro Lys Pro Pro Lys Pro Leu Ser Lys Met Arg Val Ala Thr Pro
                85                  90                  95

Met Met Met Gln Ala Leu Pro Ile Gln Ser Leu Pro Gln Gly Pro Thr
            100                 105                 110

Gln Asn Ala Thr Glu Tyr Gly Asn Met Thr Gln Asp His Val Met His
        115                 120                 125

Leu Leu Leu Glu Ala Asp Pro Leu Lys Val Tyr Pro Lys Leu Lys Gly
    130                 135                 140

Ser Phe Pro Glu Asn Leu Lys His Leu Lys Asn Thr Met Glu Thr Leu
145                 150                 155                 160

Asp Trp Lys Val Phe Glu Asn Trp Met Tyr Gln Trp Leu Leu Phe Glu
                165                 170                 175

Met Ser Lys Asn Ser Leu Glu Lys Lys Ser Thr Glu Val Pro Leu Lys
            180                 185                 190

Ala Leu Thr Lys Cys Gln Glu Glu Val Ser Arg Ile Pro Asp Val His
        195                 200                 205

Pro Gly Met Phe Arg Pro Gln Cys Asp Glu Asn Gly Asn Tyr Lys Pro
    210                 215                 220

Leu Gln Cys Tyr Gly Ser Thr Gly Tyr Cys Trp Cys Val Phe Pro Asn
225                 230                 235                 240

Gly Thr Glu Val Pro His Thr Arg Ser His Gly His His Asn Cys Ser
                245                 250                 255

Glu Pro Leu Asp Met Glu Asp Leu Ser Ser Gly Leu Gly Met Ala Lys
            260                 265                 270

<210> SEQ ID NO 3
<211> LENGTH: 280
<212> TYPE: PRT
<213> ORGANISM: Felis catus

<400> SEQUENCE: 3

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
50                  55                  60

Leu Thr Val Thr Ala Gln Asn Leu Gln Leu Glu Asn Leu Arg Met Lys
65                  70                  75                  80

Leu Pro Lys Pro Ala Lys Pro Leu Asn Lys Leu Arg Val Ala Thr Pro
            85                  90                  95

Met Leu Met Gln Thr Met Pro Val Arg Gly Leu Leu Gln Ala Pro Met
            100                 105                 110

Gln Asn Ala Thr Lys Tyr Gly Asn Met Thr Gln Asp His Val Met His
        115                 120                 125

Met Leu Leu Glu Gly Asp Pro Leu Lys Val Tyr Pro Gln Leu Lys Gly
    130                 135                 140

Asn Phe Pro Glu Asn Leu Lys His Leu Lys Asn Thr Met Gly Thr Leu
145                 150                 155                 160

Asp Trp Lys Val Phe Glu Asn Trp Met Tyr Gln Trp Leu Leu Phe Glu
                165                 170                 175

Met Ser Lys Asn Ser Leu Glu Lys His Pro Ala Asp Ile Pro Leu Lys
            180                 185                 190

Val Leu Thr Lys Cys Gln Glu Glu Val Ser Arg Ile Pro Ala Val His
        195                 200                 205

Pro Gly Thr Phe Arg Pro Gln Cys Asp Glu Asn Gly Asn Tyr Lys Pro
    210                 215                 220

Leu Gln Cys Tyr Gly Ser Thr Gly Tyr Cys Trp Cys Val Phe Pro Asn
225                 230                 235                 240

Gly Thr Glu Val Pro His Ser Arg Ser His Gly His Arg Asn Cys Ser
                245                 250                 255

Glu Ser Val Asp Val Glu Asp Leu Ser Ser Gly Leu Gly Met Thr Lys
            260                 265                 270

Pro Asp Leu Gly Gln Val Val Met
    275                 280

<210> SEQ ID NO 4
<211> LENGTH: 110
<212> TYPE: PRT

```
<213> ORGANISM: Artificial sequence
<220> FEATURE:
<223> OTHER INFORMATION: Invariant Chain Dog [110 AA]

<400> SEQUENCE: 4

Met Glu Asp Gln Arg Asp Leu Ile Ser Asn His Glu Gln Leu Pro Ile
1               5                   10                  15

Leu Gly Gln Arg Pro Gly Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Ser Leu Arg Met Lys
65                  70                  75                  80

Leu Pro Lys Pro Pro Lys Pro Leu Ser Lys Met Arg Val Ala Thr Pro
                85                  90                  95

Met Met Met Gln Ala Leu Pro Ile Gln Ser Leu Pro Gln Gly
            100                 105                 110

<210> SEQ ID NO 5
<211> LENGTH: 110
<212> TYPE: PRT
<213> ORGANISM: Artificial Sequence
<220> FEATURE:
<223> OTHER INFORMATION: Invariant Chain Cat [110 AA]

<400> SEQUENCE: 5

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ala Gln Asn Leu Gln Leu Glu Asn Leu Arg Met Lys
65                  70                  75                  80

Leu Pro Lys Pro Ala Lys Pro Leu Asn Lys Leu Arg Val Ala Thr Pro
                85                  90                  95

Met Leu Met Gln Thr Met Pro Val Arg Gly Leu Leu Gln Ala
            100                 105                 110

<210> SEQ ID NO 6
<211> LENGTH: 22
<212> TYPE: PRT
<213> ORGANISM: Artificial sequence
<220> FEATURE:
<223> OTHER INFORMATION: N-Term Marker [22 AA]

<400> SEQUENCE: 6

Met His His His His His His Tyr Gly Arg Lys Lys Arg Arg Gln Arg
1               5                   10                  15

Arg Arg Met Glu Asp Gln
            20

<210> SEQ ID NO 7
<211> LENGTH: 321
<212> TYPE: PRT
<213> ORGANISM: Dermatophagoides farinae
```

<400> SEQUENCE: 7

```
Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
            35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
            115                 120                 125

Gly Cys Gly Ser Cys Trp Ala Phe Ser Gly Val Ala Ala Thr Glu Ser
130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
            195                 200                 205

His Tyr Gly Ile Ser Asn Tyr Cys Gln Ile Tyr Pro Pro Asp Val Lys
210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Tyr Trp Ile Val Arg
            275                 280                 285

Asn Ser Trp Asp Thr Thr Trp Gly Asp Ser Gly Tyr Gly Tyr Phe Gln
            290                 295                 300

Ala Gly Asn Asn Leu Met Met Ile Glu Gln Tyr Pro Tyr Val Val Ile
305                 310                 315                 320

Met
```

<210> SEQ ID NO 8
<211> LENGTH: 146
<212> TYPE: PRT
<213> ORGANISM: Dermatophagoides farinae

<400> SEQUENCE: 8

```
Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30
```

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
 50                  55                  60

Lys Thr Ala Lys Ile Glu Ile Lys Ala Ser Leu Asp Gly Leu Glu Ile
 65                  70                  75                  80

Asp Val Pro Gly Ile Asp Thr Asn Ala Cys His Phe Met Lys Cys Pro
                 85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Leu Ile
        115                 120                 125

Gly Asp Asn Gly Val Leu Ala Cys Ala Ile Ala Thr His Gly Lys Ile
130                 135                 140

Arg Asp
145

<210> SEQ ID NO 9
<211> LENGTH: 91
<212> TYPE: PRT
<213> ORGANISM: Dermatophagoides farinae

<400> SEQUENCE: 9

Met Lys Phe Asn Ile Thr Ile Ala Phe Val Ser Leu Ala Ile Leu Ile
 1               5                  10                  15

His Ser Ser Tyr Ala Asp Ile Asp His Asp Asp Pro Thr Thr Met
            20                  25                  30

Ile Asp Val Gln Thr Thr Thr Val Gln Pro Ser Asp Glu Phe Glu Cys
        35                  40                  45

Pro Thr Arg Phe Gly Tyr Phe Ala Asp Pro Lys Asp Pro Cys Lys Phe
 50                  55                  60

Tyr Ile Cys Ser Asn Trp Glu Ala Ile His Lys Ser Cys Pro Gly Asn
 65                  70                  75                  80

Thr Arg Trp Asn Glu Lys Glu Leu Thr Cys Thr
            85                  90

<210> SEQ ID NO 10
<211> LENGTH: 462
<212> TYPE: PRT
<213> ORGANISM: Dermatophagoides farinae

<400> SEQUENCE: 10

Met Thr Arg Phe Ser Leu Thr Val Leu Ala Val Leu Ala Ala Cys Phe
 1               5                  10                  15

Gly Ser Asn Ile Arg Pro Asn Val Ala Thr Leu Glu Pro Lys Thr Val
            20                  25                  30

Cys Tyr Tyr Glu Ser Trp Val His Trp Arg Gln Gly Glu Gly Lys Met
        35                  40                  45

Asp Pro Glu Asp Ile Asp Thr Ser Leu Cys Thr His Ile Val Tyr Ser
 50                  55                  60

Tyr Phe Gly Ile Asp Ala Ala Thr His Glu Ile Lys Leu Leu Asp Glu
 65                  70                  75                  80

Tyr Leu Met Lys Asp Leu His Asp Met Glu His Phe Thr Gln His Lys
            85                  90                  95

Gly Asn Ala Lys Ala Met Ile Ala Val Gly Gly Ser Thr Met Ser Asp
            100                 105                 110

```
Gln Phe Ser Lys Thr Ala Ala Val Glu His Tyr Arg Glu Thr Phe Val
            115                 120                 125

Val Ser Thr Val Asp Leu Met Thr Arg Tyr Gly Phe Asp Gly Val Met
        130                 135                 140

Ile Asp Trp Ser Gly Met Gln Ala Lys Asp Ser Asp Asn Phe Ile Lys
145                 150                 155                 160

Leu Leu Asp Lys Phe Asp Glu Lys Phe Ala His Thr Ser Phe Val Met
                165                 170                 175

Gly Val Thr Leu Pro Ala Thr Ile Ala Ser Tyr Asp Asn Tyr Asn Ile
                180                 185                 190

Pro Ala Ile Ser Asn Tyr Val Asp Phe Met Asn Val Leu Ser Leu Asp
                195                 200                 205

Tyr Thr Gly Ser Trp Ala His Thr Val Gly His Ala Ser Pro Phe Pro
    210                 215                 220

Glu Gln Leu Lys Thr Leu Glu Ala Tyr His Lys Arg Gly Ala Pro Arg
225                 230                 235                 240

His Lys Met Val Met Ala Val Pro Phe Tyr Ala Arg Thr Trp Ile Leu
                245                 250                 255

Glu Lys Met Asn Lys Gln Asp Ile Gly Asp Lys Ala Ser Gly Pro Gly
                260                 265                 270

Pro Arg Gly Gln Phe Thr Gln Thr Asp Gly Phe Leu Ser Tyr Asn Glu
    275                 280                 285

Leu Cys Val Gln Ile Gln Ala Glu Thr Asn Ala Phe Thr Ile Thr Arg
    290                 295                 300

Asp His Asp Asn Thr Ala Ile Tyr Ala Val Tyr Val His Ser Asn His
305                 310                 315                 320

Ala Glu Trp Ile Ser Phe Glu Asp Arg His Thr Leu Gly Glu Lys Ala
                325                 330                 335

Lys Asn Ile Thr Gln Gln Gly Tyr Ala Gly Met Ser Val Tyr Thr Leu
                340                 345                 350

Ser Asn Glu Asp Val His Gly Val Cys Gly Asp Lys Asn Pro Leu Leu
    355                 360                 365

His Ala Ile Gln Ser Asn Tyr Tyr His Gly Val Val Thr Glu Pro Thr
370                 375                 380

Val Val Thr Leu Pro Pro Val Thr His Thr Glu His Val Thr Asp
385                 390                 395                 400

Ile Pro Gly Val Phe His Cys His Glu Glu Gly Phe Phe Arg Asp Lys
                405                 410                 415

Thr Tyr Cys Ala Thr Tyr Tyr Glu Cys Lys Lys Gly Asp Phe Gly Leu
                420                 425                 430

Glu Lys Thr Val His His Cys Ala Asn His Leu Gln Ala Phe Asp Glu
                435                 440                 445

Val Ser Arg Thr Cys Ile Asp His Thr Lys Ile Pro Gly Cys
    450                 455                 460

<210> SEQ ID NO 11
<211> LENGTH: 555
<212> TYPE: PRT
<213> ORGANISM: Dermatophagoides farinae

<400> SEQUENCE: 11

Met Lys Thr Ile Tyr Ala Ile Leu Ser Ile Met Ala Cys Ile Gly Leu
1               5                   10                  15

Met Asn Ala Ser Ile Lys Arg Asp His Asn Asp Tyr Ser Lys Asn Pro
                20                  25                  30
```

Met Arg Ile Val Cys Tyr Val Gly Thr Trp Ser Val Tyr His Lys Val
            35                  40                  45

Asp Pro Tyr Thr Ile Glu Ile Asp Pro Phe Lys Cys Thr His Leu
 50                  55                  60

Met Tyr Gly Phe Ala Lys Ile Asp Glu Tyr Lys Tyr Thr Ile Gln Val
 65                  70                  75                  80

Phe Asp Pro Tyr Gln Asp Asp Asn His Asn Ser Trp Glu Lys Arg Gly
                     85                  90                  95

Tyr Glu Arg Phe Asn Asn Leu Arg Leu Lys Asn Pro Glu Leu Thr Thr
                100                 105                 110

Met Ile Ser Leu Gly Gly Trp Tyr Glu Gly Ser Glu Lys Tyr Ser Asp
            115                 120                 125

Met Ala Ala Asn Pro Thr Tyr Arg Gln Gln Phe Ile Gln Ser Val Leu
            130                 135                 140

Asp Phe Leu Gln Glu Tyr Lys Phe Asp Gly Leu Asp Leu Asp Trp Glu
145                 150                 155                 160

Tyr Pro Gly Ser Arg Leu Gly Asn Pro Lys Ile Asp Lys Gln Asn Tyr
                165                 170                 175

Leu Ala Leu Val Arg Glu Leu Lys Asp Ala Phe Glu Pro His Gly Tyr
            180                 185                 190

Leu Leu Thr Ala Ala Val Ser Pro Gly Lys Asp Lys Ile Asp Arg Ala
            195                 200                 205

Tyr Asp Ile Lys Glu Leu Asn Lys Leu Phe Asp Trp Met Asn Val Met
210                 215                 220

Thr Tyr Asp Tyr His Gly Gly Trp Glu Asn Phe Tyr Gly His Asn Ala
225                 230                 235                 240

Pro Leu Tyr Lys Arg Pro Asp Glu Thr Asp Glu Leu His Thr Tyr Phe
                245                 250                 255

Asn Val Asn Tyr Thr Met His Tyr Tyr Leu Asn Asn Gly Ala Thr Arg
                260                 265                 270

Asp Lys Leu Val Met Gly Val Pro Phe Tyr Gly Arg Ala Trp Ser Ile
            275                 280                 285

Glu Asp Arg Ser Lys Leu Lys Leu Gly Asp Pro Ala Lys Gly Met Ser
            290                 295                 300

Pro Pro Gly Phe Ile Ser Gly Glu Glu Gly Val Leu Ser Tyr Ile Glu
305                 310                 315                 320

Leu Cys Gln Leu Phe Gln Lys Glu Glu Trp His Ile Gln Tyr Asp Glu
                325                 330                 335

Tyr Tyr Asn Ala Pro Tyr Gly Tyr Asn Asp Lys Ile Trp Val Gly Tyr
                340                 345                 350

Asp Asp Leu Ala Ser Ile Ser Cys Lys Leu Ala Phe Leu Lys Glu Leu
            355                 360                 365

Gly Val Ser Gly Val Met Val Trp Ser Leu Glu Asn Asp Asp Phe Lys
            370                 375                 380

Gly His Cys Gly Pro Lys Asn Pro Leu Leu Asn Lys Val His Asn Met
385                 390                 395                 400

Ile Asn Gly Asp Glu Lys Asn Ser Phe Glu Cys Ile Leu Gly Pro Ser
                405                 410                 415

Thr Thr Thr Pro Thr Pro Thr Thr Pro Thr Thr Pro Thr Thr
            420                 425                 430

Pro Thr Thr Pro Ser Pro Thr Thr Pro Thr Thr Pro Ser Pro Thr
            435                 440                 445

```
Thr Pro Thr Thr Thr Pro Ser Pro Thr Thr Pro Thr Thr Pro Ser
    450                 455                 460

Pro Thr Thr Pro Thr Pro Thr Thr Pro Thr Pro Ala Pro Thr Thr Ser
465                 470                 475                 480

Thr Pro Ser Pro Thr Thr Thr Glu His Thr Ser Glu Thr Pro Lys Tyr
                485                 490                 495

Thr Thr Tyr Val Asp Gly His Leu Ile Lys Cys Tyr Lys Glu Gly Asp
            500                 505                 510

Ile Pro His Pro Thr Asn Ile His Lys Tyr Leu Val Cys Glu Phe Val
        515                 520                 525

Asn Gly Gly Trp Trp Val His Ile Met Pro Cys Pro Pro Gly Thr Ile
530                 535                 540

Trp Cys Gln Glu Lys Leu Thr Cys Ile Gly Glu
545                 550                 555

<210> SEQ ID NO 12
<211> LENGTH: 500
<212> TYPE: PRT
<213> ORGANISM: Dermatophagoides farinae

<400> SEQUENCE: 12

Met Lys Leu Thr Ala Thr Leu Leu Ile Leu Thr Leu Ser Trp Ala
1               5                   10                  15

Gly Ile Phe Val Asp Ala Asn Pro Arg Phe Lys Arg Asp Asn Arg Asp
            20                  25                  30

Asp Val Leu Lys Gln Thr Glu Glu Leu Ile Lys Ser Ala Gln Asp Val
            35                  40                  45

Leu Glu Lys Leu Pro Asp Ser Asp Leu Lys Asp Glu Ile Ala Glu Lys
50                  55                  60

Leu Ala Thr Met Lys His Tyr Lys His Glu Leu Glu Asn Ala Lys Asn
65                  70                  75                  80

Pro Ile Lys Ile Ala His Phe Glu Leu Glu Leu Leu Thr Met Phe Lys
            85                  90                  95

Lys Phe Gln Ser Leu Leu Asn Glu Ala Asn Glu Ile Ile Lys Ser Leu
            100                 105                 110

Thr Thr Thr Thr Thr Glu Pro Thr Thr Pro Thr Pro Glu Pro Thr Thr
            115                 120                 125

Thr Thr Pro Glu Pro Thr Thr Lys Thr Pro Glu Pro Thr Thr Lys Thr
            130                 135                 140

Pro Glu Pro Thr Thr Pro Thr Pro Glu Pro Thr Thr Lys Thr Pro Glu
145                 150                 155                 160

Pro Thr Thr Lys Thr Pro Glu Pro Thr Thr Pro Thr Pro Glu Pro Thr
                165                 170                 175

Thr Lys Thr Pro Glu Pro Thr Thr Thr Pro Glu Pro Thr Thr Thr Lys
            180                 185                 190

Thr Pro Glu Pro Thr Thr Lys Thr Pro Glu Pro Ser Thr Pro Thr Pro
            195                 200                 205

Glu Pro Thr Thr Lys Thr Pro Glu Pro Thr Thr Lys Thr Pro Glu Pro
            210                 215                 220

Ser Thr Pro Thr Pro Glu Pro Thr Thr Lys Thr Pro Glu Pro Ser Thr
225                 230                 235                 240

Pro Thr Pro Glu Pro Thr Thr Lys Thr Pro Glu Pro Thr Thr Lys Thr
                245                 250                 255

Pro Glu Pro Ser Thr Pro Thr Pro Glu Pro Thr Thr Lys Thr Pro Glu
            260                 265                 270
```

```
Pro Ser Thr Pro Thr Pro Glu Pro Thr Thr Lys Thr Pro Glu Pro Ser
        275                 280                 285

Thr Thr Lys Lys Pro Asn Arg Asp Asp Val Leu Lys Gln Ala Glu Glu
290                 295                 300

Leu Ile Lys Arg Ala Glu Asp Val Phe Glu Lys Leu Pro Asp Ser Asp
305                 310                 315                 320

Leu Lys Asn Glu Ile Ala Glu Lys Leu Ala Thr Met Lys Asn Tyr Lys
                325                 330                 335

His Glu Leu Glu Asn Ala Lys Asn Pro Ile Lys Ile Ala His Leu Glu
            340                 345                 350

Ser Glu Leu Leu Thr Met Phe Lys Met Phe Gln Ser Leu Leu Asn Glu
        355                 360                 365

Ala Asp Glu Ile Ile Arg Ser Leu Thr Thr Thr Thr Glu Pro Thr Thr
    370                 375                 380

Leu Asn Ser Thr Thr Pro Glu Pro Thr Thr Leu Asn Ser Thr Thr Pro
385                 390                 395                 400

Glu Pro Thr Thr Leu Asn Ser Thr Thr Pro Glu Pro Thr Thr Leu Asn
                405                 410                 415

Ser Thr Thr Pro Glu Pro Thr Thr Leu Asn Ser Thr Thr Pro Glu Pro
            420                 425                 430

Thr Thr Leu Asn Ser Thr Thr Pro Glu Pro Thr Thr Leu Asn Ser Thr
        435                 440                 445

Thr Pro Glu Pro Thr Thr Leu Asn Ser Thr Thr Pro Glu Pro Thr Thr
    450                 455                 460

Ser Asn Ser Thr Thr Ser Glu Pro Thr Asn Ser Ile Asn Arg Lys Thr
465                 470                 475                 480

Ser Glu Ile Ser Phe Leu Ser Asp Trp Phe His Lys Ile Arg Thr Arg
                485                 490                 495

Phe Asn Ile Phe
            500

<210> SEQ ID NO 13
<211> LENGTH: 176
<212> TYPE: PRT
<213> ORGANISM: Ctenocephalides felis

<400> SEQUENCE: 13

Met Asn Tyr Cys Phe Leu Val Phe Leu Val Tyr Leu Val Phe Ala Val
1               5                   10                  15

Asn Gly Glu Asp Ile Trp Lys Val Asn Lys Lys Cys Thr Ser Gly Gly
            20                  25                  30

Lys Asn Gln Asp Arg Lys Leu Asp Gln Ile Ile Gln Lys Gly Gln Gln
        35                  40                  45

Val Lys Ile Gln Asn Ile Cys Lys Leu Ile Arg Asp Lys Pro His Thr
    50                  55                  60

Asn Gln Glu Lys Glu Lys Cys Met Lys Phe Cys Lys Lys Val Cys Lys
65                  70                  75                  80

Gly Tyr Arg Gly Ala Cys Asp Gly Asn Ile Cys Tyr Cys Ser Arg Pro
                85                  90                  95

Ser Asn Leu Gly Pro Asp Trp Lys Val Ser Lys Glu Cys Lys Asp Pro
            100                 105                 110

Asn Asn Lys Asp Ser Arg Pro Thr Glu Ile Val Pro Tyr Arg Gln Gln
        115                 120                 125

Leu Ala Ile Pro Asn Ile Cys Lys Leu Lys Asn Ser Glu Thr Asn Glu
```

```
                130               135                140
Asp Ser Lys Cys Lys His Cys Lys Glu Lys Cys Arg Gly Gly Asn
145                 150                 155                 160

Asp Ala Gly Cys Asp Gly Asn Phe Cys Tyr Cys Arg Pro Lys Asn Lys
                165                 170                 175
```

<210> SEQ ID NO 14
<211> LENGTH: 223
<212> TYPE: PRT
<213> ORGANISM: Artificial sequence
<220> FEATURE:
<223> OTHER INFORMATION: IMAT_Allergen from Q58A71 Der f 1 allergen
      preproenzyme Dermatophagoides farinae (American house dust mite)

<400> SEQUENCE: 14

```
Thr Ser Ala Ile Arg Ile Asn Ser Val Asn Val Pro Ser Glu Leu Asp
1               5                   10                  15

Leu Arg Ser Leu Arg Thr Val Thr Pro Ile Arg Met Gln Gly Gly Ile
                20                  25                  30

Gly Ser Leu Trp Ala Phe Ser Gly Val Ala Ala Thr Glu Ser Ala Tyr
            35                  40                  45

Leu Ala Tyr Arg Asn Thr Ser Leu Asp Leu Ser Glu Gln Glu Leu Val
50                  55                  60

Asp Arg Ala Ser Gln His Gly Arg His Gly Asp Thr Ile Pro Arg Gly
65                  70                  75                  80

Ile Glu Tyr Ile Gln Gln Asn Gly Val Val Glu Glu Arg Ser Tyr Pro
                85                  90                  95

Tyr Val Ala Arg Glu Gln Gln Ser Arg Arg Pro Asn Ser Gln His Tyr
                100                 105                 110

Gly Ile Ser Asn Tyr Ile Gln Ile Tyr Pro Pro Asp Val Lys Gln Ile
            115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
                180                 185                 190

Trp Asp Thr Thr Trp Gly Asp Ser Gly Tyr Gly Tyr Phe Gln Ala Gly
            195                 200                 205

Asn Asn Leu Met Met Ile Glu Gln Tyr Pro Tyr Val Val Ile Met
    210                 215                 220
```

<210> SEQ ID NO 15
<211> LENGTH: 129
<212> TYPE: PRT
<213> ORGANISM: Artificial sequence
<220> FEATURE:
<223> OTHER INFORMATION: IMAT_Allergen from Q00855 Mite group 2
      allergen Der f 2 (Allergen Der f II) (allergen Der f 2)
      Dermatophagoides farinae (American house dust mite)

<400> SEQUENCE: 15

```
Asp Gln Val Asp Val Lys Asp Ser Ala Asn Asn Glu Ile Lys Lys Val
1               5                   10                  15

Met Val Asp Gly Ile His Gly Ser Asp Pro Leu Ile Ile His Arg Gly
                20                  25                  30
```

```
Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
 50                  55                  60

Val Pro Gly Ile Asp Thr Asn Ala Ile His Phe Met Lys Leu Pro Leu
 65                  70                  75                  80

Val Lys Gly Gln Gln Tyr Asp Ile Lys Tyr Thr Trp Asn Val Pro Lys
                 85                  90                  95

Ile Ala Pro Lys Ser Glu Asn Val Val Thr Val Lys Leu Ile Gly
             100                 105                 110

Asp Asn Gly Val Leu Ala Leu Ala Ile Ala Thr His Gly Lys Ile Arg
         115                 120                 125

Asp

<210> SEQ ID NO 16
<211> LENGTH: 70
<212> TYPE: PRT
<213> ORGANISM: Artificial sequence
<220> FEATURE:
<223> OTHER INFORMATION: IMAT_Allergen from A0A088SAW7 Der f 23
      allergen Dermatophagoides farinae (American house dust mite)

<400> SEQUENCE: 16

Asp Ile Asp His Asp Asp Pro Thr Thr Met Ile Asp Val Gln Thr
 1               5                  10                  15

Thr Thr Val Gln Pro Ser Asp Glu Phe Glu Leu Pro Thr Arg Phe Gly
                 20                  25                  30

Tyr Phe Ala Asp Pro Lys Asp Pro Leu Lys Phe Tyr Ile Ile Ser Asn
             35                  40                  45

Trp Glu Ala Ile His Lys Ser Leu Pro Gly Asn Thr Arg Trp Asn Glu
 50                  55                  60

Lys Glu Leu Thr Ile Thr
 65                  70

<210> SEQ ID NO 17
<211> LENGTH: 445
<212> TYPE: PRT
<213> ORGANISM: Artificial sequence
<220> FEATURE:
<223> OTHER INFORMATION: IMAT_Allergen from Q86R84 60 kDa allergen Der
      f 18p Dermatophagoides farinae (American house dust mite)

<400> SEQUENCE: 17

Ser Asn Ile Arg Pro Asn Val Ala Thr Leu Glu Pro Lys Thr Val Leu
 1               5                  10                  15

Tyr Tyr Glu Ser Trp Val His Trp Arg Gln Gly Glu Gly Lys Met Asp
                 20                  25                  30

Pro Glu Asp Ile Asp Thr Ser Leu Met Thr His Ile Val Tyr Ser Tyr
             35                  40                  45

Phe Gly Ile Asp Ala Ala Thr His Glu Ile Lys Leu Leu Asp Glu Tyr
 50                  55                  60

Leu Met Lys Asp Leu His Asp Met Glu His Phe Thr Gln His Lys Gly
 65                  70                  75                  80

Asn Ala Lys Ala Met Ile Ala Val Gly Gly Ser Thr Met Ser Asp Gln
                 85                  90                  95

Phe Ser Lys Thr Ala Ala Val Glu His Tyr Arg Glu Thr Phe Val Val
             100                 105                 110

Ser Thr Val Asp Leu Met Thr Arg Tyr Gly Phe Asp Gly Val Met Ile
```

```
            115                 120                 125
Asp Trp Ser Gly Met Gln Ala Lys Asp Ser Asp Asn Phe Ile Lys Leu
        130                 135                 140

Leu Asp Lys Phe Asp Glu Lys Phe Ala His Thr Ser Phe Val Met Gly
145                 150                 155                 160

Val Thr Leu Pro Ala Thr Ile Ala Ser Tyr Asp Asn Tyr Asn Ile Pro
                165                 170                 175

Ala Ile Ser Asn Tyr Val Asp Phe Met Asn Val Leu Ser Leu Asp Tyr
            180                 185                 190

Thr Gly Ser Trp Ala His Thr Val Gly His Ala Ser Pro Phe Pro Glu
        195                 200                 205

Gln Leu Lys Thr Leu Glu Ala Tyr His Lys Arg Gly Ala Pro Arg His
    210                 215                 220

Lys Met Val Met Ala Val Pro Phe Tyr Ala Arg Thr Trp Ile Leu Glu
225                 230                 235                 240

Lys Met Asn Lys Gln Asp Ile Gly Asp Lys Ala Ser Gly Pro Gly Pro
                245                 250                 255

Arg Gly Gln Phe Thr Gln Thr Asp Gly Phe Leu Ser Tyr Asn Glu Leu
            260                 265                 270

Ser Val Gln Ile Gln Ala Glu Thr Asn Ala Phe Thr Ile Thr Arg Asp
        275                 280                 285

His Asp Asn Thr Ala Ile Tyr Ala Val Tyr Val His Ser Asn His Ala
    290                 295                 300

Glu Trp Ile Ser Phe Glu Asp Arg His Thr Leu Gly Glu Lys Ala Lys
305                 310                 315                 320

Asn Ile Thr Gln Gln Gly Tyr Ala Gly Met Ser Val Tyr Thr Leu Ser
                325                 330                 335

Asn Glu Asp Val His Gly Val Arg Gly Asp Lys Asn Pro Leu Leu His
            340                 345                 350

Ala Ile Gln Ser Asn Tyr Tyr His Gly Val Val Thr Glu Pro Thr Val
        355                 360                 365

Val Thr Leu Pro Pro Val Thr His Thr Thr Glu His Val Thr Asp Ile
    370                 375                 380

Pro Gly Val Phe His Leu His Glu Glu Gly Phe Phe Arg Asp Lys Thr
385                 390                 395                 400

Tyr Ser Ala Thr Tyr Tyr Glu Ile Lys Lys Gly Asp Phe Gly Leu Glu
                405                 410                 415

Lys Thr Val His His Leu Ala Asn His Leu Gln Ala Phe Asp Glu Val
            420                 425                 430

Ser Arg Thr Arg Ile Asp His Thr Lys Ile Pro Gly Ser
        435                 440                 445

<210> SEQ ID NO 18
<211> LENGTH: 536
<212> TYPE: PRT
<213> ORGANISM: Artificial sequence
<220> FEATURE:
<223> OTHER INFORMATION: IMAT_Allergen from Q9U6R7 98kDa HDM allergen
      (Der f 15 allergen) (Group 15 allergen Der f 15) Dermatophagoides
      farinae (American house dust mite)

<400> SEQUENCE: 18

Ser Ile Lys Arg Asp His Asn Asp Tyr Ser Lys Asn Pro Met Arg Ile
1               5                   10                  15

Val Leu Tyr Val Gly Thr Trp Ser Val Tyr His Lys Val Asp Pro Tyr
            20                  25                  30
```

-continued

```
Thr Ile Glu Asp Ile Asp Pro Phe Lys Ser Thr His Leu Met Tyr Gly
            35                  40                  45

Phe Ala Lys Ile Asp Glu Tyr Lys Tyr Thr Ile Gln Val Phe Asp Pro
 50                  55                  60

Tyr Gln Asp Asp Asn His Asn Ser Trp Glu Lys Arg Gly Tyr Glu Arg
 65                  70                  75                  80

Phe Asn Asn Leu Arg Leu Lys Asn Pro Glu Leu Thr Thr Met Ile Ser
                 85                  90                  95

Leu Gly Gly Trp Tyr Glu Gly Ser Glu Lys Tyr Ser Asp Met Ala Ala
                100                 105                 110

Asn Pro Thr Tyr Arg Gln Phe Ile Gln Ser Val Leu Asp Phe Leu
                115                 120                 125

Gln Glu Tyr Lys Phe Asp Gly Leu Asp Leu Asp Trp Glu Tyr Pro Gly
130                 135                 140

Ser Arg Leu Gly Asn Pro Lys Ile Asp Lys Gln Asn Tyr Leu Ala Leu
145                 150                 155                 160

Val Arg Glu Leu Lys Asp Ala Phe Glu Pro His Gly Tyr Leu Leu Thr
                165                 170                 175

Ala Ala Val Ser Pro Gly Lys Asp Lys Ile Asp Arg Ala Tyr Asp Ile
                180                 185                 190

Lys Glu Leu Asn Lys Leu Phe Asp Trp Met Asn Val Met Thr Tyr Asp
                195                 200                 205

Tyr His Gly Gly Trp Glu Asn Phe Tyr Gly His Asn Ala Pro Leu Tyr
                210                 215                 220

Lys Arg Pro Asp Glu Thr Asp Glu Leu His Thr Tyr Phe Asn Val Asn
225                 230                 235                 240

Tyr Thr Met His Tyr Tyr Leu Asn Asn Gly Ala Thr Arg Asp Lys Leu
                245                 250                 255

Val Met Gly Val Pro Phe Tyr Gly Arg Ala Trp Ser Ile Glu Asp Arg
                260                 265                 270

Ser Lys Leu Lys Leu Gly Asp Pro Ala Lys Gly Met Ser Pro Pro Gly
                275                 280                 285

Phe Ile Ser Gly Glu Glu Gly Val Leu Ser Tyr Ile Glu Leu Ser Gln
                290                 295                 300

Leu Phe Gln Lys Glu Glu Trp His Ile Gln Tyr Asp Glu Tyr Tyr Asn
305                 310                 315                 320

Ala Pro Tyr Gly Tyr Asn Asp Lys Ile Trp Val Gly Tyr Asp Asp Leu
                325                 330                 335

Ala Ser Ile Ser Ser Lys Leu Ala Phe Leu Lys Glu Leu Gly Val Ser
                340                 345                 350

Gly Val Met Val Trp Ser Leu Glu Asn Asp Asp Phe Lys Gly His Leu
                355                 360                 365

Gly Pro Lys Asn Pro Leu Leu Asn Lys Val His Asn Met Ile Asn Gly
                370                 375                 380

Asp Glu Lys Asn Ser Phe Glu Ile Ile Leu Gly Pro Ser Thr Thr Thr
385                 390                 395                 400

Pro Thr Pro Thr Thr Thr Pro Thr Thr Pro Thr Thr Thr Pro Thr Thr
                405                 410                 415

Pro Ser Pro Thr Thr Pro Thr Thr Thr Pro Ser Pro Thr Thr Pro Thr
                420                 425                 430

Thr Thr Pro Ser Pro Thr Thr Pro Thr Thr Thr Pro Ser Pro Thr Thr
                435                 440                 445
```

```
Pro Thr Pro Thr Thr Pro Thr Pro Ala Pro Thr Thr Ser Thr Pro Ser
    450                 455                 460

Pro Thr Thr Thr Glu His Thr Ser Glu Thr Pro Lys Tyr Thr Thr Tyr
465                 470                 475                 480

Val Asp Gly His Leu Ile Lys Ser Tyr Lys Glu Gly Asp Ile Pro His
                485                 490                 495

Pro Thr Asn Ile His Lys Tyr Leu Val Ile Glu Phe Val Asn Gly Gly
            500                 505                 510

Trp Trp Val His Ile Met Pro Ser Pro Gly Thr Ile Trp Ser Gln
        515                 520                 525

Glu Lys Leu Thr Ser Ile Gly Glu
530                 535

<210> SEQ ID NO 19
<211> LENGTH: 478
<212> TYPE: PRT
<213> ORGANISM: Artificial sequence
<220> FEATURE:
<223> OTHER INFORMATION: IMAT_Allergen from I7HDR2 Zen 1 protein
      Dermatophagoides farinae (American house dust mite)

<400> SEQUENCE: 19

Asn Pro Arg Phe Lys Arg Asp Asn Arg Asp Val Leu Lys Gln Thr
1               5                   10                  15

Glu Glu Leu Ile Lys Ser Ala Gln Asp Val Leu Glu Lys Leu Pro Asp
                20                  25                  30

Ser Asp Leu Lys Asp Glu Ile Ala Glu Lys Leu Ala Thr Met Lys His
            35                  40                  45

Tyr Lys His Glu Leu Glu Asn Ala Lys Asn Pro Ile Lys Ile Ala His
    50                  55                  60

Phe Glu Leu Glu Leu Leu Thr Met Phe Lys Lys Phe Gln Ser Leu Leu
65                  70                  75                  80

Asn Glu Ala Asn Glu Ile Ile Lys Ser Leu Thr Thr Thr Thr Thr Glu
                85                  90                  95

Pro Thr Thr Pro Thr Pro Glu Pro Thr Thr Thr Thr Pro Glu Pro Thr
            100                 105                 110

Thr Lys Thr Pro Glu Pro Thr Thr Lys Thr Pro Glu Pro Thr Thr Pro
        115                 120                 125

Thr Pro Glu Pro Thr Thr Lys Thr Pro Glu Pro Thr Thr Lys Thr Pro
    130                 135                 140

Glu Pro Thr Thr Pro Thr Pro Glu Pro Thr Thr Lys Thr Pro Glu Pro
145                 150                 155                 160

Thr Thr Pro Thr Pro Glu Pro Thr Thr Lys Thr Pro Glu Pro Thr Thr
                165                 170                 175

Lys Thr Pro Glu Pro Ser Thr Pro Thr Pro Glu Pro Thr Thr Lys Thr
            180                 185                 190

Pro Glu Pro Thr Thr Lys Thr Pro Glu Pro Ser Thr Pro Thr Pro Glu
        195                 200                 205

Pro Thr Thr Lys Thr Pro Glu Pro Ser Thr Thr Pro Glu Pro Thr
    210                 215                 220

Thr Lys Thr Pro Glu Pro Thr Thr Lys Thr Pro Glu Pro Ser Thr Pro
225                 230                 235                 240

Thr Pro Glu Pro Thr Thr Lys Thr Pro Glu Pro Ser Thr Thr Pro
                245                 250                 255

Glu Pro Thr Thr Lys Thr Pro Glu Pro Ser Thr Thr Lys Lys Pro Asn
            260                 265                 270
```

```
Arg Asp Asp Val Leu Lys Gln Ala Glu Glu Leu Ile Lys Arg Ala Glu
            275                 280                 285

Asp Val Phe Glu Lys Leu Pro Asp Ser Asp Leu Lys Asn Glu Ile Ala
290                 295                 300

Glu Lys Leu Ala Thr Met Lys Asn Tyr Lys His Glu Leu Glu Asn Ala
305                 310                 315                 320

Lys Asn Pro Ile Lys Ile Ala His Leu Glu Ser Glu Leu Leu Thr Met
                325                 330                 335

Phe Lys Met Phe Gln Ser Leu Leu Asn Glu Ala Asp Glu Ile Ile Arg
            340                 345                 350

Ser Leu Thr Thr Thr Thr Glu Pro Thr Thr Leu Asn Ser Thr Thr Pro
            355                 360                 365

Glu Pro Thr Thr Leu Asn Ser Thr Thr Pro Glu Pro Thr Thr Leu Asn
        370                 375                 380

Ser Thr Thr Pro Glu Pro Thr Thr Leu Asn Ser Thr Thr Pro Glu Pro
385                 390                 395                 400

Thr Thr Leu Asn Ser Thr Thr Pro Glu Pro Thr Thr Leu Asn Ser Thr
                405                 410                 415

Thr Pro Glu Pro Thr Thr Leu Asn Ser Thr Thr Pro Glu Pro Thr Thr
            420                 425                 430

Leu Asn Ser Thr Thr Pro Glu Pro Thr Thr Ser Asn Ser Thr Thr Ser
            435                 440                 445

Glu Pro Thr Asn Ser Ile Asn Arg Lys Thr Ser Glu Ile Ser Phe Leu
        450                 455                 460

Ser Asp Trp Phe His Lys Ile Arg Thr Arg Phe Asn Ile Phe
465                 470                 475

<210> SEQ ID NO 20
<211> LENGTH: 158
<212> TYPE: PRT
<213> ORGANISM: Artificial sequence
<220> FEATURE:
<223> OTHER INFORMATION: IMAT_Allergen  from Q94424 Salivary antigen 1
      (FS-I) (allergen Cte f 1) Ctenocephalides felis (Cat flea)

<400> SEQUENCE: 20

Glu Asp Ile Trp Lys Val Asn Lys Lys Arg Thr Ser Gly Gly Lys Asn
1               5                   10                  15

Gln Asp Arg Lys Leu Asp Gln Ile Ile Gln Lys Gly Gln Gln Val Lys
            20                  25                  30

Ile Gln Asn Ile Leu Lys Leu Ile Arg Asp Lys Pro His Thr Asn Gln
        35                  40                  45

Glu Lys Glu Lys Leu Met Lys Phe Leu Lys Lys Val Leu Lys Gly Tyr
    50                  55                  60

Arg Gly Ala Arg Asp Gly Asn Ile Leu Tyr Leu Ser Arg Pro Ser Asn
65                  70                  75                  80

Leu Gly Pro Asp Trp Lys Val Ser Lys Glu Arg Lys Asp Pro Asn Asn
                85                  90                  95

Lys Asp Ser Arg Pro Thr Glu Ile Val Pro Tyr Arg Gln Gln Leu Ala
            100                 105                 110

Ile Pro Asn Ile Leu Lys Leu Lys Asn Ser Glu Thr Asn Glu Asp Ser
        115                 120                 125

Lys Leu Lys Lys His Met Lys Glu Lys Ser Arg Gly Gly Asn Asp Ala
    130                 135                 140

Gly Ile Asp Gly Asn Phe Leu Tyr Leu Arg Pro Lys Asn Lys
```

145          150          155

<210> SEQ ID NO 21
<211> LENGTH: 383
<212> TYPE: PRT
<213> ORGANISM: Artificial sequence
<220> FEATURE:
<223> OTHER INFORMATION: IMAT_Allergen from Hybrid1

<400> SEQUENCE: 21

Gln Ser His Gln Tyr Tyr His Thr Ser Gly Leu Arg Asn Leu Gly Gly
1               5                   10                  15

Ser Tyr Tyr Arg Ser Gly Asn Ala Lys Ala Met Ile Ala Val Gly Gly
            20                  25                  30

Ser Thr Met Ile Val Asp Gly Asp Lys Val Thr Ile Tyr Gly Trp Gly
        35                  40                  45

Ser Gly Leu Gly Tyr Gly Leu Gly Tyr Gly Leu Gly Tyr Gly Gln Ala
    50                  55                  60

Val Ala Leu Ala Pro Ala Gln Ala Val Gly Tyr Val Ala Ala Ala Pro
65                  70                  75                  80

Ala Val Ala Val Gln Ala Pro Ala Val Ser Tyr Ala Ala Ala Ala Pro
                85                  90                  95

Ala Val Gln Thr Val Ala Val Gln Ala Pro Ala Val Ser Tyr Ala Ala
            100                 105                 110

Ala Pro Ala Val Ala Val Gln Ala His Thr Ala Gln Val Ser Gly Pro
        115                 120                 125

Ile His Ala Ala Ile Glu Ser Arg Arg Thr Val Glu Val Ile Asp Gly
    130                 135                 140

Pro Ser Thr Gly Asp Ala Pro Val Ala Ser Thr Val Ile Gly Pro
145                 150                 155                 160

Asn Val Gln Pro Ile Asn Leu Glu Phe Gln Thr Gln Ala Ser Pro Leu
                165                 170                 175

Ala Ala Thr Gln Asn His Val Pro Thr Thr Pro Thr Thr Pro Thr Pro
            180                 185                 190

Ala Pro Thr Thr Ser Thr Pro Asp Leu Leu Arg Gln Asp Ile Val Lys
        195                 200                 205

Pro Val Val Gln Asp Val His Glu Phe Leu Val Tyr Ile His Ile Ala
    210                 215                 220

Asn Asn Glu Ile Lys Lys Val Gln Glu Ser Val His Gln Ile Leu Pro
225                 230                 235                 240

Arg Gly Gln Met Met Lys Ile Tyr Gln Gln Gln Gln Gln His His
                245                 250                 255

Pro Gln Arg Glu Glu Asn Ile Trp Ser Asp His Ile Ala Asn Val Ala
            260                 265                 270

Gln Ala Ala Pro Ala Ile Ser Ala Val Arg Val Ala Ala Ala Pro Ala
        275                 280                 285

Val Ala Tyr Ala Ala Pro Ala Val Ser Thr Val Ser Ala Ala Pro Ala
    290                 295                 300

Ala Ile Gly Val Ile Gly Val Gln Pro Val Ala Gly Tyr Ile Gly Tyr
305                 310                 315                 320

Gly Ala Gly Tyr Gly Thr Gly Tyr Gly Thr Gly Tyr Gly Val Ala Lys
                325                 330                 335

Tyr Gly Thr Gly Tyr Gly Leu Thr Ser Gly Leu Ile Gly Gly Ser
            340                 345                 350

Tyr Gly Ser Ser Tyr Ser Val Gln Pro Ala Ser Tyr Gly Thr Gly Tyr 355                 360                 365
Gly Tyr Thr Thr Tyr Ser Ser Asp Ala Tyr Pro Ile Arg Lys Lys
    370                 375                 380

<210> SEQ ID NO 22
<211> LENGTH: 517
<212> TYPE: PRT
<213> ORGANISM: Artificial sequence
<220> FEATURE:
<223> OTHER INFORMATION: IMAT_Allergen from Hybrid2

<400> SEQUENCE: 22

Thr Ser Ala Ser Arg Ile Asn Ser Val Asn Val Pro Ser Glu Leu Asp
1               5                   10                  15

Leu Arg Ser Leu Arg Thr Val Thr Pro Ile Arg Met Gln Gly Gly Ser
            20                  25                  30

Gly Ser Ser Trp Ala Phe Ser Gly Val Ala Ala Thr Glu Ser Ala Tyr
        35                  40                  45

Leu Ala Tyr Arg Asn Thr Ser Leu Asp Leu Ser Glu Gln Glu Leu Val
    50                  55                  60

Asp Ser Ala Ser Gln His Gly Ser His Gly Asp Thr Ile Pro Arg Gly
65                  70                  75                  80

Ile Glu Tyr Ile Gln Gln Asn Gly Val Val Glu Arg Ser Tyr Pro
                85                  90                  95

Tyr Val Ala Arg Glu Gln Gln Ser Arg Arg Pro Asn Ser Gln His Tyr
            100                 105                 110

Gly Ile Ser Asn Tyr Ser Gln Ile Tyr Pro Pro Asp Val Lys Gln Ile
        115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
            180                 185                 190

Trp Asp Thr Thr Trp Gly Asp Ser Gly Tyr Gly Tyr Phe Gln Ala Gly
        195                 200                 205

Asn Asn Leu Met Met Ile Glu Gln Tyr Pro Tyr Val Val Ile Met Phe
    210                 215                 220

Thr Gln Thr Asp Gly Phe Leu Ser Tyr Asn Glu Leu Ser Val Gln Ile
225                 230                 235                 240

Gln Ala Glu Thr Asn Ala Phe Thr Ile Thr Arg Glu Pro Thr Thr Pro
                245                 250                 255

Thr Pro Glu Pro Thr Thr Lys Thr Pro Glu Pro Thr Thr Lys Thr Pro
            260                 265                 270

Glu Pro Ser Thr Pro Thr Pro Glu Pro Thr Thr Lys Thr Pro Glu Pro
        275                 280                 285

Thr Thr Lys Asp Ile Asp His Asp Asp Pro Thr Thr Met Ile Asp
    290                 295                 300

Val Gln Thr Thr Val Gln Pro Ser Asp Phe Glu Ser Pro Thr
305                 310                 315                 320

Arg Phe Gly Tyr Phe Ala Asp Pro Lys Asp Pro Ile Lys Phe Tyr Ile
                325                 330                 335

Ser Ser Asn Trp Glu Ala Ile His Lys Ser Ser Pro Gly Asn Thr Arg

```
                340             345             350
Trp Asn Glu Lys Glu Leu Thr Ser Thr Ser Pro Thr Thr Pro Thr Thr
            355                 360                 365

Thr Pro Ser Pro Thr Thr Pro Thr Thr Thr Pro Ser Pro Thr Thr Pro
        370                 375                 380

Thr Thr Thr Pro Asp Gln Val Asp Val Lys Asp Leu Ala Asn Asn Glu
385                 390                 395                 400

Ile Lys Lys Val Met Val Asp Gly Ile His Gly Ser Asp Pro Ser Ile
            405                 410                 415

Ile His Arg Gly Lys Pro Phe Thr Leu Glu Ala Leu Phe Asp Ala Asn
            420                 425                 430

Gln Asn Thr Lys Thr Ala Lys Ile Glu Ile Lys Ala Ser Leu Asp Gly
            435                 440                 445

Leu Glu Ile Asp Val Pro Gly Ile Asp Thr Asn Ala Leu His Phe Met
        450                 455                 460

Lys Ile Pro Leu Val Lys Gly Gln Gln Tyr Asp Ile Lys Tyr Thr Trp
465                 470                 475                 480

Asn Val Pro Lys Ile Ala Pro Lys Ser Glu Asn Val Val Thr Val
            485                 490                 495

Lys Leu Ile Gly Asp Asn Gly Val Leu Ala Ser Ala Ile Ala Thr His
            500                 505                 510

Gly Lys Ile Arg Asp
        515
```

<210> SEQ ID NO 23
<211> LENGTH: 407
<212> TYPE: PRT
<213> ORGANISM: Artificial sequence
<220> FEATURE:
<223> OTHER INFORMATION: IMAT_Allergen from Hybrid3

<400> SEQUENCE: 23

```
Thr Ser Ala Ser Arg Ile Asn Ser Val Asn Val Pro Ser Glu Leu Asp
1               5                   10                  15

Leu Arg Ser Leu Arg Thr Val Thr Pro Ile Arg Met Gln Gly Gly Ser
            20                  25                  30

Gly Ser Leu Trp Ala Phe Ser Gly Val Ala Ala Thr Glu Ser Ala Tyr
        35                  40                  45

Leu Ala Tyr Arg Asn Thr Ser Leu Asp Leu Ser Glu Gln Glu Leu Val
    50                  55                  60

Asp Ile Ala Ser Gln His Gly Leu His Gly Asp Thr Ile Pro Arg Gly
65                  70                  75                  80

Ile Glu Tyr Ile Gln Gln Asn Gly Val Val Glu Glu Arg Ser Tyr Pro
                85                  90                  95

Tyr Val Ala Arg Glu Gln Gln Ser Arg Arg Pro Asn Ser Gln His Tyr
            100                 105                 110

Gly Ile Ser Asn Tyr Leu Gln Ile Tyr Pro Pro Asp Val Lys Gln Ile
        115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
```

```
                180                 185                 190
Trp Asp Thr Thr Trp Gly Asp Ser Gly Tyr Gly Tyr Phe Gln Ala Gly
            195                 200                 205

Asn Asn Leu Met Met Ile Glu Gln Tyr Pro Tyr Val Val Ile Met Phe
        210                 215                 220

Thr Gln Thr Asp Gly Phe Leu Ser Tyr Asn Glu Leu Ser Val Gln Ile
225                 230                 235                 240

Gln Ala Glu Thr Asn Ala Phe Thr Ile Thr Arg Ser Pro Thr Thr Pro
                245                 250                 255

Thr Thr Thr Pro Ser Pro Thr Thr Pro Thr Thr Thr Pro Ser Pro Thr
            260                 265                 270

Thr Pro Thr Thr Thr Pro Asp Gln Val Asp Val Lys Asp Ser Ala Asn
        275                 280                 285

Asn Glu Ile Lys Lys Val Met Val Asp Gly Ile His Gly Ser Asp Pro
290                 295                 300

Ser Ile Ile His Arg Gly Lys Pro Phe Thr Leu Glu Ala Leu Phe Asp
305                 310                 315                 320

Ala Asn Gln Asn Thr Lys Thr Ala Lys Ile Glu Ile Lys Ala Ser Leu
                325                 330                 335

Asp Gly Leu Glu Ile Asp Val Pro Gly Ile Asp Thr Asn Ala Ser His
            340                 345                 350

Phe Met Lys Ser Pro Leu Val Lys Gly Gln Gln Tyr Asp Ile Lys Tyr
        355                 360                 365

Thr Trp Asn Val Pro Lys Ile Ala Pro Lys Ser Glu Asn Val Val Val
    370                 375                 380

Thr Val Lys Leu Ile Gly Asp Asn Gly Val Leu Ala Ser Ala Ile Ala
385                 390                 395                 400

Thr His Gly Lys Ile Arg Asp
                405

<210> SEQ ID NO 24
<211> LENGTH: 351
<212> TYPE: PRT
<213> ORGANISM: Artificial sequence
<220> FEATURE:
<223> OTHER INFORMATION: IMAT_NTERM Cat from Q58A71 Der f 1 allergen
      preproenzyme Dermatophagoides farinae (American house dust mite)

<400> SEQUENCE: 24

Met His His His His His Tyr Gly Arg Lys Lys Arg Gln Arg
1               5                   10                  15

Arg Arg Met Glu Asp Gln Arg Asp Leu Ile Ser Asn His Glu Gln Leu
                20                  25                  30

Pro Ile Leu Gly Gln Arg Pro Ala Ala Pro Glu Ser Lys Ser Ser Arg
            35                  40                  45

Gly Ala Leu Tyr Thr Gly Phe Ser Val Leu Val Ala Leu Leu Leu Ala
        50                  55                  60

Gly Gln Ala Thr Thr Ala Tyr Phe Leu Tyr Gln Gln Gly Arg Leu
65                  70                  75                  80

Asp Lys Leu Thr Val Thr Ala Gln Asn Leu Gln Leu Glu Asn Leu Arg
                85                  90                  95

Met Lys Leu Pro Lys Pro Ala Lys Pro Leu Asn Lys Leu Arg Val Ala
            100                 105                 110

Thr Pro Met Leu Met Gln Thr Met Pro Val Arg Gly Leu Leu Gln Ala
        115                 120                 125
```

-continued

```
        Thr Ser Ala Ile Arg Ile Asn Ser Val Asn Val Pro Ser Glu Leu Asp
            130                 135                 140

Leu Arg Ser Leu Arg Thr Val Thr Pro Ile Arg Met Gln Gly Gly Ile
        145                 150                 155                 160

Gly Ser Leu Trp Ala Phe Ser Gly Val Ala Ala Thr Glu Ser Ala Tyr
                        165                 170                 175

Leu Ala Tyr Arg Asn Thr Ser Leu Asp Leu Ser Glu Gln Glu Leu Val
                    180                 185                 190

Asp Arg Ala Ser Gln His Gly Arg His Gly Asp Thr Ile Pro Arg Gly
                195                 200                 205

Ile Glu Tyr Ile Gln Gln Asn Gly Val Val Glu Arg Ser Tyr Pro
            210                 215                 220

Tyr Val Ala Arg Glu Gln Gln Ser Arg Arg Pro Asn Ser Gln His Tyr
        225                 230                 235                 240

Gly Ile Ser Asn Tyr Ile Gln Ile Tyr Pro Pro Asp Val Lys Gln Ile
                        245                 250                 255

Arg Glu Ala Leu Thr Gln Thr His Thr Ala Ile Ala Val Ile Ile Gly
                    260                 265                 270

Ile Lys Asp Leu Arg Ala Phe Gln His Tyr Asp Gly Arg Thr Ile Ile
            275                 280                 285

Gln His Asp Asn Gly Tyr Gln Pro Asn Tyr His Ala Val Asn Ile Val
            290                 295                 300

Gly Tyr Gly Ser Thr Gln Gly Val Asp Tyr Trp Ile Val Arg Asn Ser
        305                 310                 315                 320

Trp Asp Thr Thr Trp Gly Asp Ser Gly Tyr Gly Tyr Phe Gln Ala Gly
                        325                 330                 335

Asn Asn Leu Met Met Ile Glu Gln Tyr Pro Tyr Val Val Ile Met
                    340                 345                 350

<210> SEQ ID NO 25
<211> LENGTH: 351
<212> TYPE: PRT
<213> ORGANISM: Artificial sequence
<220> FEATURE:
<223> OTHER INFORMATION: IMAT_CTERM Cat from Q58A71 Der f 1 allergen
      preproenzyme Dermatophagoides farinae (American house dust mite)

<400> SEQUENCE: 25

Met Tyr Gly Arg Lys Lys Arg Gln Arg Arg Met Glu Asp Gln
        1               5                   10                  15

Arg Asp Leu Ile Ser Asn His Glu Gln Leu Pro Ile Leu Gly Gln Arg
                    20                  25                  30

Pro Ala Ala Pro Glu Ser Lys Ser Ser Arg Gly Ala Leu Tyr Thr Gly
                35                  40                  45

Phe Ser Val Leu Val Ala Leu Leu Ala Gly Gln Ala Thr Thr Ala
        50                  55                  60

Tyr Phe Leu Tyr Gln Gln Gln Gly Arg Leu Asp Lys Leu Thr Val Thr
        65                  70                  75                  80

Ala Gln Asn Leu Gln Leu Glu Asn Leu Arg Met Lys Leu Pro Lys Pro
                        85                  90                  95

Ala Lys Pro Leu Asn Lys Leu Arg Val Ala Thr Pro Met Leu Met Gln
                    100                 105                 110

Thr Met Pro Val Arg Gly Leu Leu Gln Ala Thr Ser Ala Ile Arg Ile
                115                 120                 125

Asn Ser Val Asn Val Pro Ser Glu Leu Asp Leu Arg Ser Leu Arg Thr
            130                 135                 140
```

```
Val Thr Pro Ile Arg Met Gln Gly Gly Ile Gly Ser Leu Trp Ala Phe
145                 150                 155                 160

Ser Gly Val Ala Ala Thr Glu Ser Ala Tyr Leu Ala Tyr Arg Asn Thr
                165                 170                 175

Ser Leu Asp Leu Ser Glu Gln Glu Leu Val Asp Arg Ala Ser Gln His
            180                 185                 190

Gly Arg His Gly Asp Thr Ile Pro Arg Gly Ile Glu Tyr Ile Gln Gln
        195                 200                 205

Asn Gly Val Val Glu Glu Arg Ser Tyr Pro Tyr Val Ala Arg Glu Gln
210                 215                 220

Gln Ser Arg Arg Pro Asn Ser Gln His Tyr Gly Ile Ser Asn Tyr Ile
225                 230                 235                 240

Gln Ile Tyr Pro Pro Asp Val Lys Gln Ile Arg Glu Ala Leu Thr Gln
                245                 250                 255

Thr His Thr Ala Ile Ala Val Ile Ile Gly Ile Lys Asp Leu Arg Ala
            260                 265                 270

Phe Gln His Tyr Asp Gly Arg Thr Ile Ile Gln His Asp Asn Gly Tyr
        275                 280                 285

Gln Pro Asn Tyr His Ala Val Asn Ile Val Gly Tyr Gly Ser Thr Gln
290                 295                 300

Gly Val Asp Tyr Trp Ile Val Arg Asn Ser Trp Asp Thr Thr Trp Gly
305                 310                 315                 320

Asp Ser Gly Tyr Gly Tyr Phe Gln Ala Gly Asn Asn Leu Met Met Ile
                325                 330                 335

Glu Gln Tyr Pro Tyr Val Val Ile Met His His His His His His
            340                 345                 350

<210> SEQ ID NO 26
<211> LENGTH: 344
<212> TYPE: PRT
<213> ORGANISM: Artificial sequence
<220> FEATURE:
<223> OTHER INFORMATION: IMAT_PURE Cat from Q58A71 Der f 1 allergen
      preproenzyme Dermatophagoides farinae (American house dust mite)

<400> SEQUENCE: 26

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Ala Ala Pro Glu Ser Lys Ser Ser Arg Gly Ala Leu Tyr Thr Gly Phe
            35                  40                  45

Ser Val Leu Val Ala Leu Leu Leu Ala Gly Gln Ala Thr Thr Ala Tyr
        50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
                100                 105                 110

Met Pro Val Arg Gly Leu Leu Gln Ala Thr Ser Ala Ile Arg Ile Asn
            115                 120                 125

Ser Val Asn Val Pro Ser Glu Leu Asp Leu Arg Ser Leu Arg Thr Val
        130                 135                 140

Thr Pro Ile Arg Met Gln Gly Gly Ile Gly Ser Leu Trp Ala Phe Ser
```

```
            145                 150                 155                 160
Gly Val Ala Ala Thr Glu Ser Ala Tyr Leu Ala Tyr Arg Asn Thr Ser
                165                 170                 175

Leu Asp Leu Ser Glu Gln Glu Leu Val Asp Arg Ala Ser Gln His Gly
                180                 185                 190

Arg His Gly Asp Thr Ile Pro Arg Gly Ile Glu Tyr Ile Gln Gln Asn
                195                 200                 205

Gly Val Val Glu Glu Arg Ser Tyr Pro Tyr Val Ala Arg Glu Gln Gln
    210                 215                 220

Ser Arg Arg Pro Asn Ser Gln His Tyr Gly Ile Ser Asn Tyr Ile Gln
225                 230                 235                 240

Ile Tyr Pro Pro Asp Val Lys Gln Ile Arg Glu Ala Leu Thr Gln Thr
                245                 250                 255

His Thr Ala Ile Ala Val Ile Ile Gly Ile Lys Asp Leu Arg Ala Phe
                260                 265                 270

Gln His Tyr Asp Gly Arg Thr Ile Ile Gln His Asp Asn Gly Tyr Gln
                275                 280                 285

Pro Asn Tyr His Ala Val Asn Ile Val Gly Tyr Gly Ser Thr Gln Gly
                290                 295                 300

Val Asp Tyr Trp Ile Val Arg Asn Ser Trp Asp Thr Thr Trp Gly Asp
305                 310                 315                 320

Ser Gly Tyr Gly Tyr Phe Gln Ala Gly Asn Asn Leu Met Met Ile Glu
                325                 330                 335

Gln Tyr Pro Tyr Val Val Ile Met
                340

<210> SEQ ID NO 27
<211> LENGTH: 257
<212> TYPE: PRT
<213> ORGANISM: Artificial sequence
<220> FEATURE:
<223> OTHER INFORMATION: IMAT_NTERM Cat from Q00855 Mite group 2
      allergen Der f 2 (Allergen Der f II) (allergen Der f 2)
      Dermatophagoides farinae (American house dust mite)

<400> SEQUENCE: 27

Met His His His His His Tyr Gly Arg Lys Lys Arg Gln Arg
1               5                   10                  15

Arg Arg Met Glu Asp Gln Arg Asp Leu Ile Ser Asn His Glu Gln Leu
                20                  25                  30

Pro Ile Leu Gly Gln Arg Pro Ala Ala Pro Glu Ser Lys Ser Ser Arg
                35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gly Arg Leu
65                  70                  75                  80

Asp Lys Leu Thr Val Thr Ala Gln Asn Leu Gln Leu Glu Asn Leu Arg
                85                  90                  95

Met Lys Leu Pro Lys Pro Ala Lys Pro Leu Asn Lys Leu Arg Val Ala
                100                 105                 110

Thr Pro Met Leu Met Gln Thr Met Pro Val Arg Gly Leu Leu Gln Ala
                115                 120                 125

Asp Gln Val Asp Val Lys Asp Ser Ala Asn Asn Glu Ile Lys Lys Val
    130                 135                 140

Met Val Asp Gly Ile His Gly Ser Asp Pro Leu Ile Ile His Arg Gly
145                 150                 155                 160
```

Lys Pro Phe Thr Leu Glu Ala Leu Phe Asp Ala Asn Gln Asn Thr Lys
            165                 170                 175

Thr Ala Lys Ile Glu Ile Lys Ala Ser Leu Asp Gly Leu Glu Ile Asp
        180                 185                 190

Val Pro Gly Ile Asp Thr Asn Ala Ile His Phe Met Lys Leu Pro Leu
        195                 200                 205

Val Lys Gly Gln Gln Tyr Asp Ile Lys Tyr Thr Trp Asn Val Pro Lys
    210                 215                 220

Ile Ala Pro Lys Ser Glu Asn Val Val Thr Val Lys Leu Ile Gly
225                 230                 235                 240

Asp Asn Gly Val Leu Ala Leu Ala Ile Ala Thr His Gly Lys Ile Arg
                245                 250                 255

Asp

<210> SEQ ID NO 28
<211> LENGTH: 257
<212> TYPE: PRT
<213> ORGANISM: Artificial sequence
<220> FEATURE:
<223> OTHER INFORMATION: IMAT_CTERM Cat from Q00855 Mite group 2
      allergen Der f 2 (Allergen Der f II) (allergen Der f 2)
      Dermatophagoides farinae (American house dust mite)

<400> SEQUENCE: 28

Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Ala Ala Pro Glu Ser Lys Ser Ser Arg Gly Ala Leu Tyr Thr Gly
        35                  40                  45

Phe Ser Val Leu Val Ala Leu Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Asp Gln Val Asp Val Lys
        115                 120                 125

Asp Ser Ala Asn Asn Glu Ile Lys Lys Val Met Val Asp Gly Ile His
    130                 135                 140

Gly Ser Asp Pro Leu Ile Ile His Arg Gly Lys Pro Phe Thr Leu Glu
145                 150                 155                 160

Ala Leu Phe Asp Ala Asn Gln Asn Thr Lys Thr Ala Lys Ile Glu Ile
                165                 170                 175

Lys Ala Ser Leu Asp Gly Leu Glu Ile Asp Val Pro Gly Ile Asp Thr
            180                 185                 190

Asn Ala Ile His Phe Met Lys Leu Pro Leu Val Lys Gly Gln Gln Tyr
        195                 200                 205

Asp Ile Lys Tyr Thr Trp Asn Val Pro Lys Ile Ala Pro Lys Ser Glu
    210                 215                 220

Asn Val Val Thr Val Lys Leu Ile Gly Asp Asn Gly Val Leu Ala
225                 230                 235                 240

Leu Ala Ile Ala Thr His Gly Lys Ile Arg Asp His His His His His

<210> SEQ ID NO 29
<211> LENGTH: 250
<212> TYPE: PRT
<213> ORGANISM: Artificial sequence
<220> FEATURE:
<223> OTHER INFORMATION: IMAT_PURE Cat from Q00855 Mite group 2 allergen
      Der f 2 (Allergen Der f II) (allergen Der f 2) Dermatophagoides
      farinae (American house dust mite)

<400> SEQUENCE: 29

```
Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Ala Ala Pro Glu Ser Lys Ser Ser Arg Gly Ala Leu Tyr Thr Gly Phe
            35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
            100                 105                 110

Met Pro Val Arg Gly Leu Leu Gln Ala Asp Gln Val Asp Val Lys Asp
        115                 120                 125

Ser Ala Asn Asn Glu Ile Lys Lys Val Met Val Asp Gly Ile His Gly
    130                 135                 140

Ser Asp Pro Leu Ile Ile His Arg Gly Lys Pro Phe Thr Leu Glu Ala
145                 150                 155                 160

Leu Phe Asp Ala Asn Gln Asn Thr Lys Thr Ala Lys Ile Glu Ile Lys
                165                 170                 175

Ala Ser Leu Asp Gly Leu Glu Ile Asp Val Pro Gly Ile Asp Thr Asn
            180                 185                 190

Ala Ile His Phe Met Lys Leu Pro Leu Val Lys Gly Gln Gln Tyr Asp
        195                 200                 205

Ile Lys Tyr Thr Trp Asn Val Pro Lys Ile Ala Pro Lys Ser Glu Asn
    210                 215                 220

Val Val Val Thr Val Lys Leu Ile Gly Asp Asn Gly Val Leu Ala Leu
225                 230                 235                 240

Ala Ile Ala Thr His Gly Lys Ile Arg Asp
                245                 250
```

<210> SEQ ID NO 30
<211> LENGTH: 198
<212> TYPE: PRT
<213> ORGANISM: Artificial sequence
<220> FEATURE:
<223> OTHER INFORMATION: IMAT_NTERM Cat from A0A088SAW7 Der f 23
      allergen Dermatophagoides farinae (American house dust mite)

<400> SEQUENCE: 30

```
Met His His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
```

```
                    20                  25                  30
Pro Ile Leu Gly Gln Arg Pro Ala Ala Pro Glu Ser Lys Glu Ser Arg
                35                  40                  45

Gly Ala Leu Tyr Thr Gly Phe Ser Val Leu Val Ala Leu Leu Leu Ala
            50                  55                  60

Gly Gln Ala Thr Thr Ala Tyr Phe Leu Tyr Gln Gln Gly Arg Leu
65                  70                  75                  80

Asp Lys Leu Thr Val Thr Ala Gln Asn Leu Gln Leu Glu Asn Leu Arg
                85                  90                  95

Met Lys Leu Pro Lys Pro Ala Lys Pro Leu Asn Lys Leu Arg Val Ala
                100                 105                 110

Thr Pro Met Leu Met Gln Thr Met Pro Val Arg Gly Leu Leu Gln Ala
            115                 120                 125

Asp Ile Asp His Asp Asp Pro Thr Thr Met Ile Asp Val Gln Thr
130                 135                 140

Thr Thr Val Gln Pro Ser Asp Glu Phe Glu Leu Pro Thr Arg Phe Gly
145                 150                 155                 160

Tyr Phe Ala Asp Pro Lys Asp Pro Leu Lys Phe Tyr Ile Ile Ser Asn
                165                 170                 175

Trp Glu Ala Ile His Lys Ser Leu Pro Gly Asn Thr Arg Trp Asn Glu
                180                 185                 190

Lys Glu Leu Thr Ile Thr
            195

<210> SEQ ID NO 31
<211> LENGTH: 198
<212> TYPE: PRT
<213> ORGANISM: Artificial sequence
<220> FEATURE:
<223> OTHER INFORMATION: IMAT_CTERM Cat from A0A088SAW7 Der f 23
      allergen Dermatophagoides farinae (American house dust mite)

<400> SEQUENCE: 31

Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
                20                  25                  30

Pro Ala Ala Pro Glu Ser Lys Glu Ser Arg Gly Ala Leu Tyr Thr Gly
            35                  40                  45

Phe Ser Val Leu Val Ala Leu Leu Leu Ala Gly Gln Ala Thr Thr Ala
        50                  55                  60

Tyr Phe Leu Tyr Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
                100                 105                 110

Thr Met Pro Val Arg Gly Leu Leu Gln Ala Asp Ile Asp His Asp Asp
            115                 120                 125

Asp Pro Thr Thr Met Ile Asp Val Gln Thr Thr Thr Val Gln Pro Ser
130                 135                 140

Asp Glu Phe Glu Leu Pro Thr Arg Phe Gly Tyr Phe Ala Asp Pro Lys
145                 150                 155                 160

Asp Pro Leu Lys Phe Tyr Ile Ile Ser Asn Trp Glu Ala Ile His Lys
                165                 170                 175
```

Ser Leu Pro Gly Asn Thr Arg Trp Asn Glu Lys Glu Leu Thr Ile Thr
            180                 185                 190

His His His His His His
        195

<210> SEQ ID NO 32
<211> LENGTH: 191
<212> TYPE: PRT
<213> ORGANISM: Artificial sequence
<220> FEATURE:
<223> OTHER INFORMATION: IMAT_PURE Cat from A0A088SAW7 Der f 23 allergen
      Dermatophagoides farinae (American house dust mite)

<400> SEQUENCE: 32

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Ala Ala Pro Glu Ser Lys Glu Ser Arg Gly Ala Leu Tyr Thr Gly Phe
        35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
            100                 105                 110

Met Pro Val Arg Gly Leu Leu Gln Ala Asp Ile Asp His Asp Asp Asp
        115                 120                 125

Pro Thr Thr Met Ile Asp Val Gln Thr Thr Val Gln Pro Ser Asp
    130                 135                 140

Glu Phe Glu Leu Pro Thr Arg Phe Gly Tyr Phe Ala Asp Pro Lys Asp
145                 150                 155                 160

Pro Leu Lys Phe Tyr Ile Ile Ser Asn Trp Glu Ala Ile His Lys Ser
                165                 170                 175

Leu Pro Gly Asn Thr Arg Trp Asn Glu Lys Glu Leu Thr Ile Thr
            180                 185                 190

<210> SEQ ID NO 33
<211> LENGTH: 573
<212> TYPE: PRT
<213> ORGANISM: Artificial sequence
<220> FEATURE:
<223> OTHER INFORMATION: IMAT_NTERM Cat from Q86R84 60 kDa allergen Der
      f 18p Dermatophagoides farinae (American house dust mite)

<400> SEQUENCE: 33

Met His His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Ala Ala Pro Glu Ser Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gln Gly Arg Leu
65                  70                  75                  80

```
Asp Lys Leu Thr Val Thr Ala Gln Asn Leu Gln Leu Glu Asn Leu Arg
            85                  90                  95
Met Lys Leu Pro Lys Pro Ala Lys Pro Leu Asn Lys Leu Arg Val Ala
        100                 105                 110
Thr Pro Met Leu Met Gln Thr Met Pro Val Arg Gly Leu Leu Gln Ala
            115                 120                 125
Ser Asn Ile Arg Pro Asn Val Ala Thr Leu Glu Pro Lys Thr Val Leu
    130                 135                 140
Tyr Tyr Glu Ser Trp Val His Trp Arg Gln Gly Glu Gly Lys Met Asp
145                 150                 155                 160
Pro Glu Asp Ile Asp Thr Ser Leu Met Thr His Ile Val Tyr Ser Tyr
                165                 170                 175
Phe Gly Ile Asp Ala Ala Thr His Glu Ile Lys Leu Leu Asp Glu Tyr
            180                 185                 190
Leu Met Lys Asp Leu His Asp Met Glu His Phe Thr Gln His Lys Gly
        195                 200                 205
Asn Ala Lys Ala Met Ile Ala Val Gly Gly Ser Thr Met Ser Asp Gln
    210                 215                 220
Phe Ser Lys Thr Ala Ala Val Glu His Tyr Arg Glu Thr Phe Val Val
225                 230                 235                 240
Ser Thr Val Asp Leu Met Thr Arg Tyr Gly Phe Asp Gly Val Met Ile
                245                 250                 255
Asp Trp Ser Gly Met Gln Ala Lys Ser Asp Asn Phe Ile Lys Leu
            260                 265                 270
Leu Asp Lys Phe Asp Glu Lys Phe Ala His Thr Ser Phe Val Met Gly
        275                 280                 285
Val Thr Leu Pro Ala Thr Ile Ala Ser Tyr Asp Asn Tyr Asn Ile Pro
    290                 295                 300
Ala Ile Ser Asn Tyr Val Asp Phe Met Asn Val Leu Ser Leu Asp Tyr
305                 310                 315                 320
Thr Gly Ser Trp Ala His Thr Val Gly His Ala Ser Pro Phe Pro Glu
                325                 330                 335
Gln Leu Lys Thr Leu Glu Ala Tyr His Lys Arg Gly Ala Pro Arg His
            340                 345                 350
Lys Met Val Met Ala Val Pro Phe Tyr Ala Arg Thr Trp Ile Leu Glu
        355                 360                 365
Lys Met Asn Lys Gln Asp Ile Gly Asp Lys Ala Ser Gly Pro Gly Pro
    370                 375                 380
Arg Gly Gln Phe Thr Gln Thr Asp Gly Phe Leu Ser Tyr Asn Glu Leu
385                 390                 395                 400
Ser Val Gln Ile Gln Ala Glu Thr Asn Ala Phe Thr Ile Thr Arg Asp
                405                 410                 415
His Asp Asn Thr Ala Ile Tyr Ala Val Tyr Val His Ser Asn His Ala
            420                 425                 430
Glu Trp Ile Ser Phe Glu Asp Arg His Thr Leu Gly Glu Lys Ala Lys
        435                 440                 445
Asn Ile Thr Gln Gln Gly Tyr Ala Gly Met Ser Val Tyr Thr Leu Ser
    450                 455                 460
Asn Glu Asp Val His Gly Val Arg Gly Asp Lys Asn Pro Leu Leu His
465                 470                 475                 480
Ala Ile Gln Ser Asn Tyr Tyr His Gly Val Val Thr Glu Pro Thr Val
                485                 490                 495
Val Thr Leu Pro Pro Val Thr His Thr Thr Glu His Val Thr Asp Ile
```

```
                500                 505                 510
Pro Gly Val Phe His Leu His Glu Glu Gly Phe Phe Arg Asp Lys Thr
            515                 520                 525

Tyr Ser Ala Thr Tyr Tyr Glu Ile Lys Lys Gly Asp Phe Gly Leu Glu
            530                 535                 540

Lys Thr Val His His Leu Ala Asn His Leu Gln Ala Phe Asp Glu Val
545                 550                 555                 560

Ser Arg Thr Arg Ile Asp His Thr Lys Ile Pro Gly Ser
            565                 570

<210> SEQ ID NO 34
<211> LENGTH: 573
<212> TYPE: PRT
<213> ORGANISM: Artificial sequence
<220> FEATURE:
<223> OTHER INFORMATION: IMAT_CTERM Cat from Q86R84 60 kDa allergen Der
      f 18p Dermatophagoides farinae (American house dust mite)

<400> SEQUENCE: 34

Met Tyr Gly Arg Lys Arg Gln Arg Arg Met Glu Asp Gln
1               5                   10              15

Arg Asp Leu Ile Ser Asn His Glu Gln Leu Pro Ile Leu Gly Gln Arg
            20                  25                  30

Pro Ala Ala Pro Glu Ser Lys Ser Arg Gly Ala Leu Tyr Thr Gly
            35                  40                  45

Phe Ser Val Leu Val Ala Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Ser Asn Ile Arg Pro Asn
            115                 120                 125

Val Ala Thr Leu Glu Pro Lys Thr Val Leu Tyr Tyr Glu Ser Trp Val
        130                 135                 140

His Trp Arg Gln Gly Glu Gly Lys Met Asp Pro Glu Asp Ile Asp Thr
145                 150                 155                 160

Ser Leu Met Thr His Ile Val Tyr Ser Tyr Phe Gly Ile Asp Ala Ala
                165                 170                 175

Thr His Glu Ile Lys Leu Leu Asp Glu Tyr Leu Met Lys Asp Leu His
            180                 185                 190

Asp Met Glu His Phe Thr Gln His Lys Gly Asn Ala Lys Ala Met Ile
            195                 200                 205

Ala Val Gly Gly Ser Thr Met Ser Asp Gln Phe Ser Lys Thr Ala Ala
        210                 215                 220

Val Glu His Tyr Arg Glu Thr Phe Val Val Ser Thr Val Asp Leu Met
225                 230                 235                 240

Thr Arg Tyr Gly Phe Asp Gly Val Met Ile Asp Trp Ser Gly Met Gln
                245                 250                 255

Ala Lys Asp Ser Asp Asn Phe Ile Lys Leu Leu Asp Lys Phe Asp Glu
            260                 265                 270

Lys Phe Ala His Thr Ser Phe Val Met Gly Val Thr Leu Pro Ala Thr
            275                 280                 285
```

-continued

```
Ile Ala Ser Tyr Asp Asn Tyr Asn Ile Pro Ala Ile Ser Asn Tyr Val
    290                 295                 300

Asp Phe Met Asn Val Leu Ser Leu Asp Tyr Thr Gly Ser Trp Ala His
305                 310                 315                 320

Thr Val Gly His Ala Ser Pro Phe Pro Glu Gln Leu Lys Thr Leu Glu
                325                 330                 335

Ala Tyr His Lys Arg Gly Ala Pro Arg His Lys Met Val Met Ala Val
            340                 345                 350

Pro Phe Tyr Ala Arg Thr Trp Ile Leu Glu Lys Met Asn Lys Gln Asp
        355                 360                 365

Ile Gly Asp Lys Ala Ser Gly Pro Gly Pro Arg Gly Gln Phe Thr Gln
    370                 375                 380

Thr Asp Gly Phe Leu Ser Tyr Asn Glu Leu Ser Val Gln Ile Gln Ala
385                 390                 395                 400

Glu Thr Asn Ala Phe Thr Ile Thr Arg Asp His Asp Asn Thr Ala Ile
                405                 410                 415

Tyr Ala Val Tyr Val His Ser Asn His Ala Glu Trp Ile Ser Phe Glu
            420                 425                 430

Asp Arg His Thr Leu Gly Glu Lys Ala Lys Asn Ile Thr Gln Gln Gly
        435                 440                 445

Tyr Ala Gly Met Ser Val Tyr Thr Leu Ser Asn Glu Asp Val His Gly
    450                 455                 460

Val Arg Gly Asp Lys Asn Pro Leu Leu His Ala Ile Gln Ser Asn Tyr
465                 470                 475                 480

Tyr His Gly Val Val Thr Glu Pro Thr Val Val Thr Leu Pro Pro Val
                485                 490                 495

Thr His Thr Thr Glu His Val Thr Asp Ile Pro Gly Val Phe His Leu
            500                 505                 510

His Glu Glu Gly Phe Phe Arg Asp Lys Thr Tyr Ser Ala Thr Tyr Tyr
        515                 520                 525

Glu Ile Lys Lys Gly Asp Phe Gly Leu Glu Lys Thr Val His His Leu
    530                 535                 540

Ala Asn His Leu Gln Ala Phe Asp Glu Val Ser Arg Thr Arg Ile Asp
545                 550                 555                 560

His Thr Lys Ile Pro Gly Ser His His His His His
                565                 570
```

<210> SEQ ID NO 35
<211> LENGTH: 566
<212> TYPE: PRT
<213> ORGANISM: Artificial sequence
<220> FEATURE:
<223> OTHER INFORMATION: IMAT_PURE Cat from Q86R84 60 kDa allergen Der f
      18p Dermatophagoides farinae (American house dust mite)

<400> SEQUENCE: 35

```
Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Ala Ala Pro Glu Ser Lys Ser Ser Arg Gly Ala Leu Tyr Thr Gly Phe
            35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ala
65                  70                  75                  80
```

```
Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
            100                 105                 110

Met Pro Val Arg Gly Leu Leu Gln Ala Ser Asn Ile Arg Pro Asn Val
        115                 120                 125

Ala Thr Leu Glu Pro Lys Thr Val Leu Tyr Tyr Glu Ser Trp Val His
    130                 135                 140

Trp Arg Gln Gly Glu Gly Lys Met Asp Pro Glu Asp Ile Asp Thr Ser
145                 150                 155                 160

Leu Met Thr His Ile Val Tyr Ser Tyr Phe Gly Ile Asp Ala Ala Thr
                165                 170                 175

His Glu Ile Lys Leu Leu Asp Glu Tyr Leu Met Lys Asp Leu His Asp
            180                 185                 190

Met Glu His Phe Thr Gln His Lys Gly Asn Ala Lys Ala Met Ile Ala
        195                 200                 205

Val Gly Gly Ser Thr Met Ser Asp Gln Phe Ser Lys Thr Ala Ala Val
    210                 215                 220

Glu His Tyr Arg Glu Thr Phe Val Val Ser Thr Val Asp Leu Met Thr
225                 230                 235                 240

Arg Tyr Gly Phe Asp Gly Val Met Ile Asp Trp Ser Gly Met Gln Ala
                245                 250                 255

Lys Asp Ser Asp Asn Phe Ile Lys Leu Leu Asp Lys Phe Asp Glu Lys
            260                 265                 270

Phe Ala His Thr Ser Phe Val Met Gly Val Thr Leu Pro Ala Thr Ile
        275                 280                 285

Ala Ser Tyr Asp Asn Tyr Asn Ile Pro Ala Ile Ser Asn Tyr Val Asp
    290                 295                 300

Phe Met Asn Val Leu Ser Leu Asp Tyr Thr Gly Ser Trp Ala His Thr
305                 310                 315                 320

Val Gly His Ala Ser Pro Phe Pro Glu Gln Leu Lys Thr Leu Glu Ala
                325                 330                 335

Tyr His Lys Arg Gly Ala Pro Arg His Lys Met Val Met Ala Val Pro
            340                 345                 350

Phe Tyr Ala Arg Thr Trp Ile Leu Glu Lys Met Asn Lys Gln Asp Ile
        355                 360                 365

Gly Asp Lys Ala Ser Gly Pro Gly Pro Arg Gly Gln Phe Thr Gln Thr
    370                 375                 380

Asp Gly Phe Leu Ser Tyr Asn Glu Leu Ser Val Gln Ile Gln Ala Glu
385                 390                 395                 400

Thr Asn Ala Phe Thr Ile Thr Arg Asp His Asp Asn Thr Ala Ile Tyr
                405                 410                 415

Ala Val Tyr Val His Ser Asn His Ala Glu Trp Ile Ser Phe Glu Asp
            420                 425                 430

Arg His Thr Leu Gly Glu Lys Ala Lys Asn Ile Thr Gln Gln Gly Tyr
        435                 440                 445

Ala Gly Met Ser Val Tyr Thr Leu Ser Asn Glu Asp Val His Gly Val
    450                 455                 460

Arg Gly Asp Lys Asn Pro Leu Leu His Ala Ile Gln Ser Asn Tyr Tyr
465                 470                 475                 480

His Gly Val Val Thr Glu Pro Thr Val Val Thr Leu Pro Pro Val Thr
                485                 490                 495
```

-continued

```
His Thr Thr Glu His Val Thr Asp Ile Pro Gly Val Phe His Leu His
                500                 505                 510

Glu Glu Gly Phe Phe Arg Asp Lys Thr Tyr Ser Ala Thr Tyr Tyr Glu
            515                 520                 525

Ile Lys Lys Gly Asp Phe Gly Leu Glu Lys Thr Val His His Leu Ala
        530                 535                 540

Asn His Leu Gln Ala Phe Asp Glu Val Ser Arg Thr Arg Ile Asp His
545                 550                 555                 560

Thr Lys Ile Pro Gly Ser
                565

<210> SEQ ID NO 36
<211> LENGTH: 664
<212> TYPE: PRT
<213> ORGANISM: Artificial sequence
<220> FEATURE:
<223> OTHER INFORMATION: IMAT_NTERM Cat from Q9U6R7 98kDa HDM allergen
      (Der f 15 allergen) (Group 15 allergen Der f 15) Dermatophagoides
      farinae (American house dust mite)

<400> SEQUENCE: 36

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Ala Pro Glu Ser Lys Ser Ser Arg
        35                  40                  45

Gly Ala Leu Tyr Thr Gly Phe Ser Val Leu Val Ala Leu Leu Leu Ala
50                  55                  60

Gly Gln Ala Thr Thr Ala Tyr Phe Leu Tyr Gln Gln Gln Gly Arg Leu
65                  70                  75                  80

Asp Lys Leu Thr Val Thr Ala Gln Asn Leu Gln Leu Glu Asn Leu Arg
                85                  90                  95

Met Lys Leu Pro Lys Pro Ala Lys Pro Leu Asn Lys Leu Arg Val Ala
            100                 105                 110

Thr Pro Met Leu Met Gln Thr Met Pro Val Arg Gly Leu Leu Gln Ala
        115                 120                 125

Ser Ile Lys Arg Asp His Asn Asp Tyr Ser Lys Asn Pro Met Arg Ile
130                 135                 140

Val Leu Tyr Val Gly Thr Trp Ser Val Tyr His Lys Val Asp Pro Tyr
145                 150                 155                 160

Thr Ile Glu Asp Ile Asp Pro Phe Lys Ser Thr His Leu Met Tyr Gly
                165                 170                 175

Phe Ala Lys Ile Asp Glu Tyr Lys Tyr Thr Ile Gln Val Phe Asp Pro
            180                 185                 190

Tyr Gln Asp Asp Asn His Asn Ser Trp Glu Lys Arg Gly Tyr Glu Arg
        195                 200                 205

Phe Asn Asn Leu Arg Leu Lys Asn Pro Glu Leu Thr Thr Met Ile Ser
210                 215                 220

Leu Gly Gly Trp Tyr Glu Gly Ser Glu Lys Tyr Ser Asp Met Ala Ala
225                 230                 235                 240

Asn Pro Thr Tyr Arg Gln Phe Ile Gln Ser Val Leu Asp Phe Leu
                245                 250                 255

Gln Glu Tyr Lys Phe Asp Gly Leu Asp Leu Asp Trp Glu Tyr Pro Gly
            260                 265                 270

Ser Arg Leu Gly Asn Pro Lys Ile Asp Lys Gln Asn Tyr Leu Ala Leu
```

```
            275                 280                 285
Val Arg Glu Leu Lys Asp Ala Phe Glu Pro His Gly Tyr Leu Leu Thr
290                 295                 300

Ala Ala Val Ser Pro Gly Lys Asp Lys Ile Asp Arg Ala Tyr Asp Ile
305                 310                 315                 320

Lys Glu Leu Asn Lys Leu Phe Asp Trp Met Asn Val Met Thr Tyr Asp
                325                 330                 335

Tyr His Gly Gly Trp Glu Asn Phe Tyr Gly His Asn Ala Pro Leu Tyr
            340                 345                 350

Lys Arg Pro Asp Glu Thr Asp Glu Leu His Thr Tyr Phe Asn Val Asn
        355                 360                 365

Tyr Thr Met His Tyr Tyr Leu Asn Asn Gly Ala Thr Arg Asp Lys Leu
370                 375                 380

Val Met Gly Val Pro Phe Tyr Gly Arg Ala Trp Ser Ile Glu Asp Arg
385                 390                 395                 400

Ser Lys Leu Lys Leu Gly Asp Pro Ala Lys Gly Met Ser Pro Pro Gly
                405                 410                 415

Phe Ile Ser Gly Glu Glu Gly Val Leu Ser Tyr Ile Glu Leu Ser Gln
            420                 425                 430

Leu Phe Gln Lys Glu Trp His Ile Gln Tyr Asp Glu Tyr Tyr Asn
        435                 440                 445

Ala Pro Tyr Gly Tyr Asn Asp Lys Ile Trp Val Gly Tyr Asp Asp Leu
450                 455                 460

Ala Ser Ile Ser Ser Lys Leu Ala Phe Leu Lys Glu Leu Gly Val Ser
465                 470                 475                 480

Gly Val Met Val Trp Ser Leu Glu Asn Asp Asp Phe Lys Gly His Leu
                485                 490                 495

Gly Pro Lys Asn Pro Leu Leu Asn Lys Val His Asn Met Ile Asn Gly
            500                 505                 510

Asp Glu Lys Asn Ser Phe Glu Ile Ile Leu Gly Pro Ser Thr Thr Thr
        515                 520                 525

Pro Thr Pro Thr Thr Thr Pro Thr Thr Pro Thr Thr Thr Pro Thr Thr
530                 535                 540

Pro Ser Pro Thr Thr Pro Thr Thr Pro Ser Pro Thr Thr Pro Thr
545                 550                 555                 560

Thr Thr Pro Ser Pro Thr Thr Pro Thr Thr Pro Ser Pro Thr Thr
                565                 570                 575

Pro Thr Pro Thr Thr Pro Thr Pro Ala Pro Thr Thr Ser Thr Pro Ser
            580                 585                 590

Pro Thr Thr Thr Glu His Thr Ser Glu Thr Pro Lys Tyr Thr Thr Tyr
        595                 600                 605

Val Asp Gly His Leu Ile Lys Ser Tyr Lys Glu Gly Asp Ile Pro His
610                 615                 620

Pro Thr Asn Ile His Lys Tyr Leu Val Ile Glu Phe Val Asn Gly Gly
625                 630                 635                 640

Trp Trp Val His Ile Met Pro Ser Pro Pro Gly Thr Ile Trp Ser Gln
                645                 650                 655

Glu Lys Leu Thr Ser Ile Gly Glu
            660

<210> SEQ ID NO 37
<211> LENGTH: 664
<212> TYPE: PRT
<213> ORGANISM: Artificial sequence
```

<220> FEATURE:
<223> OTHER INFORMATION: IMAT_CTERM Cat from Q9U6R7 98kDa HDM allergen
     (Der f 15 allergen) (Group 15 allergen Der f 15) Dermatophagoides
     farinae (American house dust mite)

<400> SEQUENCE: 37

```
Met Tyr Gly Arg Lys Lys Arg Arg Gln Arg Arg Met Glu Asp Gln
 1               5                  10                  15

Arg Asp Leu Ile Ser Asn His Glu Gln Leu Pro Ile Leu Gly Gln Arg
             20                  25                  30

Pro Ala Ala Pro Glu Ser Lys Ser Ser Arg Gly Ala Leu Tyr Thr Gly
         35                  40                  45

Phe Ser Val Leu Val Ala Leu Leu Leu Ala Gly Gln Ala Thr Thr Ala
     50                  55                  60

Tyr Phe Leu Tyr Gln Gln Gln Gly Arg Leu Asp Lys Leu Thr Val Thr
 65                  70                  75                  80

Ala Gln Asn Leu Gln Leu Glu Asn Leu Arg Met Lys Leu Pro Lys Pro
                 85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Ser Ile Lys Arg Asp His
        115                 120                 125

Asn Asp Tyr Ser Lys Asn Pro Met Arg Ile Val Leu Tyr Val Gly Thr
130                 135                 140

Trp Ser Val Tyr His Lys Val Asp Pro Tyr Thr Ile Glu Asp Ile Asp
145                 150                 155                 160

Pro Phe Lys Ser Thr His Leu Met Tyr Gly Phe Ala Lys Ile Asp Glu
                165                 170                 175

Tyr Lys Tyr Thr Ile Gln Val Phe Asp Pro Tyr Gln Asp Asp Asn His
            180                 185                 190

Asn Ser Trp Glu Lys Arg Gly Tyr Glu Arg Phe Asn Asn Leu Arg Leu
        195                 200                 205

Lys Asn Pro Glu Leu Thr Thr Met Ile Ser Leu Gly Gly Trp Tyr Glu
210                 215                 220

Gly Ser Glu Lys Tyr Ser Asp Met Ala Ala Asn Pro Thr Tyr Arg Gln
225                 230                 235                 240

Gln Phe Ile Gln Ser Val Leu Asp Phe Leu Gln Glu Tyr Lys Phe Asp
                245                 250                 255

Gly Leu Asp Leu Asp Trp Glu Tyr Pro Gly Ser Arg Leu Gly Asn Pro
            260                 265                 270

Lys Ile Asp Lys Gln Asn Tyr Leu Ala Leu Val Arg Glu Leu Lys Asp
        275                 280                 285

Ala Phe Glu Pro His Gly Tyr Leu Leu Thr Ala Ala Val Ser Pro Gly
290                 295                 300

Lys Asp Lys Ile Asp Arg Ala Tyr Asp Ile Lys Glu Leu Asn Lys Leu
305                 310                 315                 320

Phe Asp Trp Met Asn Val Met Thr Tyr Asp Tyr His Gly Gly Trp Glu
                325                 330                 335

Asn Phe Tyr Gly His Asn Ala Pro Leu Tyr Lys Arg Pro Asp Glu Thr
            340                 345                 350

Asp Glu Leu His Thr Tyr Phe Asn Val Asn Tyr Thr Met His Tyr Tyr
        355                 360                 365

Leu Asn Asn Gly Ala Thr Arg Asp Lys Leu Val Met Gly Val Pro Phe
370                 375                 380
```

-continued

```
Tyr Gly Arg Ala Trp Ser Ile Glu Asp Arg Ser Lys Leu Lys Leu Gly
385                 390                 395                 400

Asp Pro Ala Lys Gly Met Ser Pro Gly Phe Ile Ser Gly Glu Glu
            405                 410                 415

Gly Val Leu Ser Tyr Ile Glu Leu Ser Gln Leu Phe Gln Lys Glu Glu
            420                 425                 430

Trp His Ile Gln Tyr Asp Glu Tyr Asn Ala Pro Tyr Gly Tyr Asn
            435                 440                 445

Asp Lys Ile Trp Val Gly Tyr Asp Asp Leu Ala Ser Ile Ser Ser Lys
    450                 455                 460

Leu Ala Phe Leu Lys Glu Leu Gly Val Ser Gly Val Met Val Trp Ser
465                 470                 475                 480

Leu Glu Asn Asp Asp Phe Lys Gly His Leu Gly Pro Lys Asn Pro Leu
                485                 490                 495

Leu Asn Lys Val His Asn Met Ile Asn Gly Asp Glu Lys Asn Ser Phe
            500                 505                 510

Glu Ile Ile Leu Gly Pro Ser Thr Thr Pro Thr Pro Thr Thr Thr
            515                 520                 525

Pro Thr Thr Pro Thr Thr Thr Pro Thr Thr Pro Ser Pro Thr Thr Pro
530                 535                 540

Thr Thr Thr Pro Ser Pro Thr Thr Pro Thr Thr Thr Pro Ser Pro Thr
545                 550                 555                 560

Thr Pro Thr Thr Thr Pro Ser Pro Thr Thr Pro Thr Thr Thr Pro
                565                 570                 575

Thr Pro Ala Pro Thr Thr Ser Thr Pro Ser Pro Thr Thr Thr Glu His
            580                 585                 590

Thr Ser Glu Thr Pro Lys Tyr Thr Thr Tyr Val Asp Gly His Leu Ile
            595                 600                 605

Lys Ser Tyr Lys Glu Gly Asp Ile Pro His Pro Thr Asn Ile His Lys
    610                 615                 620

Tyr Leu Val Ile Glu Phe Val Asn Gly Gly Trp Trp Val His Ile Met
625                 630                 635                 640

Pro Ser Pro Pro Gly Thr Ile Trp Ser Gln Glu Lys Leu Thr Ser Ile
                645                 650                 655

Gly Glu His His His His His His
            660

<210> SEQ ID NO 38
<211> LENGTH: 657
<212> TYPE: PRT
<213> ORGANISM: Artificial sequence
<220> FEATURE:
<223> OTHER INFORMATION: IMAT_PURE Cat from Q9U6R7 98kDa HDM allergen
      (Der f 15 allergen) (Group 15 allergen Der f 15) Dermatophagoides
      farinae (American house dust mite)

<400> SEQUENCE: 38

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Ala Ala Pro Glu Ser Lys Ser Ser Arg Gly Ala Leu Tyr Thr Gly Phe
            35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ala
```

-continued

```
                65                  70                  75                  80
        Gln Asn Leu Gln Leu Glu Asn Leu Arg Met Lys Leu Pro Lys Pro Ala
                        85                  90                  95
        Lys Pro Leu Asn Lys Leu Arg Val Ala Thr Pro Met Leu Met Gln Thr
                        100                 105                 110
        Met Pro Val Arg Gly Leu Leu Gln Ala Ser Ile Lys Arg Asp His Asn
                        115                 120                 125
        Asp Tyr Ser Lys Asn Pro Met Arg Ile Val Leu Tyr Val Gly Thr Trp
                130                 135                 140
        Ser Val Tyr His Lys Val Asp Pro Tyr Thr Ile Glu Asp Ile Asp Pro
        145                 150                 155                 160
        Phe Lys Ser Thr His Leu Met Tyr Gly Phe Ala Lys Ile Asp Glu Tyr
                        165                 170                 175
        Lys Tyr Thr Ile Gln Val Phe Asp Pro Tyr Gln Asp Asp Asn His Asn
                        180                 185                 190
        Ser Trp Glu Lys Arg Gly Tyr Glu Arg Phe Asn Asn Leu Arg Leu Lys
                        195                 200                 205
        Asn Pro Glu Leu Thr Thr Met Ile Ser Leu Gly Gly Trp Tyr Glu Gly
                210                 215                 220
        Ser Glu Lys Tyr Ser Asp Met Ala Ala Asn Pro Thr Tyr Arg Gln Gln
        225                 230                 235                 240
        Phe Ile Gln Ser Val Leu Asp Phe Leu Gln Glu Tyr Lys Phe Asp Gly
                        245                 250                 255
        Leu Asp Leu Asp Trp Glu Tyr Pro Gly Ser Arg Leu Gly Asn Pro Lys
                        260                 265                 270
        Ile Asp Lys Gln Asn Tyr Leu Ala Leu Val Arg Glu Leu Lys Asp Ala
                        275                 280                 285
        Phe Glu Pro His Gly Tyr Leu Leu Thr Ala Ala Val Ser Pro Gly Lys
                290                 295                 300
        Asp Lys Ile Asp Arg Ala Tyr Asp Ile Lys Glu Leu Asn Lys Leu Phe
        305                 310                 315                 320
        Asp Trp Met Asn Val Met Thr Tyr Asp Tyr His Gly Gly Trp Glu Asn
                        325                 330                 335
        Phe Tyr Gly His Asn Ala Pro Leu Tyr Lys Arg Pro Asp Glu Thr Asp
                        340                 345                 350
        Glu Leu His Thr Tyr Phe Asn Val Asn Tyr Thr Met His Tyr Tyr Leu
                        355                 360                 365
        Asn Asn Gly Ala Thr Arg Asp Lys Leu Val Met Gly Val Pro Phe Tyr
                370                 375                 380
        Gly Arg Ala Trp Ser Ile Glu Asp Arg Ser Lys Leu Lys Leu Gly Asp
        385                 390                 395                 400
        Pro Ala Lys Gly Met Ser Pro Gly Phe Ile Ser Gly Glu Glu Gly
                        405                 410                 415
        Val Leu Ser Tyr Ile Glu Leu Ser Gln Leu Phe Gln Lys Glu Glu Trp
                        420                 425                 430
        His Ile Gln Tyr Asp Glu Tyr Tyr Asn Ala Pro Tyr Gly Tyr Asn Asp
                        435                 440                 445
        Lys Ile Trp Val Gly Tyr Asp Asp Leu Ala Ser Ile Ser Ser Lys Leu
                450                 455                 460
        Ala Phe Leu Lys Glu Leu Gly Val Ser Gly Val Met Val Trp Ser Leu
        465                 470                 475                 480
        Glu Asn Asp Asp Phe Lys Gly His Leu Gly Pro Lys Asn Pro Leu Leu
                        485                 490                 495
```

```
Asn Lys Val His Asn Met Ile Asn Gly Asp Glu Lys Asn Ser Phe Glu
            500                 505                 510

Ile Ile Leu Gly Pro Ser Thr Thr Pro Thr Pro Thr Thr Thr Pro
            515                 520                 525

Thr Thr Pro Thr Thr Thr Pro Thr Thr Pro Ser Pro Thr Thr Pro Thr
530                 535                 540

Thr Thr Pro Ser Pro Thr Thr Pro Thr Thr Pro Ser Pro Thr Thr
545                 550                 555                 560

Pro Thr Thr Thr Pro Ser Pro Thr Thr Pro Thr Pro Thr Thr Pro Thr
            565                 570                 575

Pro Ala Pro Thr Thr Ser Thr Pro Ser Pro Thr Thr Thr Glu His Thr
            580                 585                 590

Ser Glu Thr Pro Lys Tyr Thr Thr Tyr Val Asp Gly His Leu Ile Lys
            595                 600                 605

Ser Tyr Lys Glu Gly Asp Ile Pro His Pro Thr Asn Ile His Lys Tyr
            610                 615                 620

Leu Val Ile Glu Phe Val Asn Gly Gly Trp Trp Val His Ile Met Pro
625                 630                 635                 640

Ser Pro Pro Gly Thr Ile Trp Ser Gln Glu Lys Leu Thr Ser Ile Gly
            645                 650                 655

Glu

<210> SEQ ID NO 39
<211> LENGTH: 606
<212> TYPE: PRT
<213> ORGANISM: Artificial sequence
<220> FEATURE:
<223> OTHER INFORMATION: IMAT_NTERM Cat from I7HDR2 Zen 1 protein
      Dermatophagoides farinae (American house dust mite)

<400> SEQUENCE: 39

Met His His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Ala Ala Pro Glu Ser Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gln Gly Arg Leu
65                  70                  75                  80

Asp Lys Leu Thr Val Thr Ala Gln Asn Leu Gln Leu Glu Asn Leu Arg
                85                  90                  95

Met Lys Leu Pro Lys Pro Ala Lys Pro Leu Asn Lys Leu Arg Val Ala
            100                 105                 110

Thr Pro Met Leu Met Gln Thr Met Pro Val Arg Gly Leu Leu Gln Ala
            115                 120                 125

Asn Pro Arg Phe Lys Arg Asp Asn Arg Asp Asp Val Leu Lys Gln Thr
        130                 135                 140

Glu Glu Leu Ile Lys Ser Ala Gln Asp Val Leu Glu Lys Leu Pro Asp
145                 150                 155                 160

Ser Asp Leu Lys Asp Glu Ile Ala Glu Lys Leu Ala Thr Met Lys His
                165                 170                 175

Tyr Lys His Glu Leu Glu Asn Ala Lys Asn Pro Ile Lys Ile Ala His
            180                 185                 190
```

-continued

```
Phe Glu Leu Glu Leu Leu Thr Met Phe Lys Lys Phe Gln Ser Leu Leu
            195                 200                 205

Asn Glu Ala Asn Glu Ile Ile Lys Ser Leu Thr Thr Thr Thr Thr Glu
210                 215                 220

Pro Thr Pro Thr Pro Glu Pro Thr Thr Thr Pro Glu Pro Thr
225                 230                 235                 240

Thr Lys Thr Pro Glu Pro Thr Thr Lys Thr Pro Glu Pro Thr Thr Pro
                245                 250                 255

Thr Pro Glu Pro Thr Thr Lys Thr Pro Glu Pro Thr Thr Lys Thr Pro
                260                 265                 270

Glu Pro Thr Thr Pro Thr Pro Glu Pro Thr Thr Lys Thr Pro Glu Pro
                275                 280                 285

Thr Thr Pro Thr Pro Glu Pro Thr Thr Lys Thr Pro Glu Pro Thr Thr
                290                 295                 300

Lys Thr Pro Glu Pro Ser Thr Pro Thr Pro Glu Pro Thr Thr Lys Thr
305                 310                 315                 320

Pro Glu Pro Thr Thr Lys Thr Pro Glu Pro Ser Thr Pro Thr Pro Glu
                325                 330                 335

Pro Thr Thr Lys Thr Pro Glu Pro Ser Thr Pro Thr Pro Glu Pro Thr
                340                 345                 350

Thr Lys Thr Pro Glu Pro Thr Thr Lys Thr Pro Glu Pro Ser Thr Pro
                355                 360                 365

Thr Pro Glu Pro Thr Thr Lys Thr Pro Glu Pro Ser Thr Pro Thr Pro
                370                 375                 380

Glu Pro Thr Thr Lys Thr Pro Glu Pro Ser Thr Pro Thr Lys Lys Pro Asn
385                 390                 395                 400

Arg Asp Asp Val Leu Lys Gln Ala Glu Glu Leu Ile Lys Arg Ala Glu
                405                 410                 415

Asp Val Phe Glu Lys Leu Pro Asp Ser Asp Leu Lys Asn Glu Ile Ala
                420                 425                 430

Glu Lys Leu Ala Thr Met Lys Asn Tyr Lys His Glu Leu Glu Asn Ala
                435                 440                 445

Lys Asn Pro Ile Lys Ile Ala His Leu Glu Ser Glu Leu Leu Thr Met
450                 455                 460

Phe Lys Met Phe Gln Ser Leu Leu Asn Glu Ala Asp Glu Ile Ile Arg
465                 470                 475                 480

Ser Leu Thr Thr Thr Thr Glu Pro Thr Thr Leu Asn Ser Thr Thr Pro
                485                 490                 495

Glu Pro Thr Thr Leu Asn Ser Thr Thr Pro Glu Pro Thr Thr Leu Asn
                500                 505                 510

Ser Thr Thr Pro Glu Pro Thr Thr Leu Asn Ser Thr Thr Pro Glu Pro
                515                 520                 525

Thr Thr Leu Asn Ser Thr Thr Pro Glu Pro Thr Thr Leu Asn Ser Thr
                530                 535                 540

Thr Pro Glu Pro Thr Thr Leu Asn Ser Thr Thr Pro Glu Pro Thr Thr
545                 550                 555                 560

Leu Asn Ser Thr Thr Pro Glu Pro Thr Thr Ser Asn Ser Thr Thr Ser
                565                 570                 575

Glu Pro Thr Asn Ser Ile Asn Arg Lys Thr Ser Glu Ile Ser Phe Leu
                580                 585                 590

Ser Asp Trp Phe His Lys Ile Arg Thr Arg Phe Asn Ile Phe
                595                 600                 605
```

<210> SEQ ID NO 40
<211> LENGTH: 606
<212> TYPE: PRT
<213> ORGANISM: Artificial sequence
<220> FEATURE:
<223> OTHER INFORMATION: IMAT_CTERM Cat from I7HDR2 Zen 1 protein
Dermatophagoides farinae (American house dust mite)

<400> SEQUENCE: 40

```
Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Ala Ala Pro Glu Ser Lys Ser Ser Arg Gly Ala Leu Tyr Thr Gly
        35                  40                  45

Phe Ser Val Leu Val Ala Leu Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Asn Pro Arg Phe Lys Arg
        115                 120                 125

Asp Asn Arg Asp Asp Val Leu Lys Gln Thr Glu Glu Leu Ile Lys Ser
130                 135                 140

Ala Gln Asp Val Leu Glu Lys Leu Pro Asp Ser Asp Leu Lys Asp Glu
145                 150                 155                 160

Ile Ala Glu Lys Leu Ala Thr Met Lys His Tyr Lys His Glu Leu Glu
                165                 170                 175

Asn Ala Lys Asn Pro Ile Lys Ile Ala His Phe Glu Leu Glu Leu Leu
            180                 185                 190

Thr Met Phe Lys Lys Phe Gln Ser Leu Leu Asn Glu Ala Asn Glu Ile
        195                 200                 205

Ile Lys Ser Leu Thr Thr Thr Thr Glu Pro Thr Thr Pro Thr Pro
210                 215                 220

Glu Pro Thr Thr Thr Thr Pro Glu Pro Thr Thr Lys Thr Pro Glu Pro
225                 230                 235                 240

Thr Thr Lys Thr Pro Glu Pro Thr Thr Pro Thr Pro Glu Pro Thr Thr
                245                 250                 255

Lys Thr Pro Glu Pro Thr Thr Lys Thr Pro Glu Pro Thr Thr Pro Thr
            260                 265                 270

Pro Glu Pro Thr Thr Lys Thr Pro Glu Pro Thr Thr Pro Thr Pro Glu
        275                 280                 285

Pro Thr Thr Lys Thr Pro Glu Pro Thr Thr Lys Thr Pro Glu Pro Ser
290                 295                 300

Thr Pro Thr Pro Glu Pro Thr Thr Lys Thr Pro Glu Pro Thr Thr Lys
305                 310                 315                 320

Thr Pro Glu Pro Ser Thr Pro Thr Pro Glu Pro Thr Thr Lys Thr Pro
                325                 330                 335

Glu Pro Ser Thr Pro Thr Pro Glu Pro Thr Thr Lys Thr Pro Glu Pro
            340                 345                 350

Thr Thr Lys Thr Pro Glu Pro Ser Thr Pro Thr Pro Glu Pro Thr Thr
        355                 360                 365
```

Lys Thr Pro Glu Pro Ser Thr Pro Thr Pro Glu Pro Thr Thr Lys Thr
370                 375                 380

Pro Glu Pro Ser Thr Thr Lys Lys Pro Asn Arg Asp Asp Val Leu Lys
385                 390                 395                 400

Gln Ala Glu Glu Leu Ile Lys Arg Ala Glu Asp Val Phe Glu Lys Leu
            405                 410                 415

Pro Asp Ser Asp Leu Lys Asn Glu Ile Ala Glu Lys Leu Ala Thr Met
            420                 425                 430

Lys Asn Tyr Lys His Glu Leu Glu Asn Ala Lys Asn Pro Ile Lys Ile
        435                 440                 445

Ala His Leu Glu Ser Glu Leu Leu Thr Met Phe Lys Met Phe Gln Ser
    450                 455                 460

Leu Leu Asn Glu Ala Asp Glu Ile Ile Arg Ser Leu Thr Thr Thr Thr
465                 470                 475                 480

Glu Pro Thr Thr Leu Asn Ser Thr Thr Pro Glu Pro Thr Thr Leu Asn
            485                 490                 495

Ser Thr Thr Pro Glu Pro Thr Thr Leu Asn Ser Thr Thr Pro Glu Pro
            500                 505                 510

Thr Thr Leu Asn Ser Thr Thr Pro Glu Pro Thr Thr Leu Asn Ser Thr
        515                 520                 525

Thr Pro Glu Pro Thr Thr Leu Asn Ser Thr Thr Pro Glu Pro Thr Thr
    530                 535                 540

Leu Asn Ser Thr Thr Pro Glu Pro Thr Thr Leu Asn Ser Thr Thr Pro
545                 550                 555                 560

Glu Pro Thr Thr Ser Asn Ser Thr Thr Ser Glu Pro Thr Asn Ser Ile
            565                 570                 575

Asn Arg Lys Thr Ser Glu Ile Ser Phe Leu Ser Asp Trp Phe His Lys
        580                 585                 590

Ile Arg Thr Arg Phe Asn Ile Phe His His His His His
        595                 600                 605

<210> SEQ ID NO 41
<211> LENGTH: 599
<212> TYPE: PRT
<213> ORGANISM: Artificial sequence
<220> FEATURE:
<223> OTHER INFORMATION: IMAT_PURE Cat from I7HDR2 Zen 1 protein
      Dermatophagoides farinae (American house dust mite)

<400> SEQUENCE: 41

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Ala Ala Pro Glu Ser Lys Ser Ser Arg Gly Ala Leu Tyr Thr Gly Phe
        35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
            85                  90                  95

Lys Pro Leu Asn Lys Leu Arg Val Ala Thr Pro Met Leu Met Gln Thr
            100                 105                 110

Met Pro Val Arg Gly Leu Leu Gln Ala Asn Pro Arg Phe Lys Arg Asp

```
            115                 120                 125
Asn Arg Asp Asp Val Leu Lys Gln Thr Glu Leu Ile Lys Ser Ala
    130                 135                 140
Gln Asp Val Leu Glu Lys Leu Pro Asp Ser Asp Leu Lys Asp Glu Ile
145                 150                 155                 160
Ala Glu Lys Leu Ala Thr Met Lys His Tyr Lys His Glu Leu Glu Asn
                165                 170                 175
Ala Lys Asn Pro Ile Lys Ile Ala His Phe Glu Leu Glu Leu Leu Thr
            180                 185                 190
Met Phe Lys Lys Phe Gln Ser Leu Leu Asn Glu Ala Asn Glu Ile Ile
            195                 200                 205
Lys Ser Leu Thr Thr Thr Thr Thr Glu Pro Thr Thr Pro Thr Pro Glu
210                 215                 220
Pro Thr Thr Thr Thr Pro Glu Pro Thr Thr Lys Thr Pro Glu Pro Thr
225                 230                 235                 240
Thr Lys Thr Pro Glu Pro Thr Thr Pro Thr Pro Glu Pro Thr Thr Lys
                245                 250                 255
Thr Pro Glu Pro Thr Thr Lys Thr Pro Glu Pro Thr Thr Pro Thr Pro
                260                 265                 270
Glu Pro Thr Thr Lys Thr Pro Glu Pro Thr Thr Pro Thr Pro Glu Pro
            275                 280                 285
Thr Thr Lys Thr Pro Glu Pro Thr Thr Lys Thr Pro Glu Pro Ser Thr
            290                 295                 300
Pro Thr Pro Glu Pro Thr Thr Lys Thr Pro Glu Pro Thr Thr Lys Thr
305                 310                 315                 320
Pro Glu Pro Ser Thr Pro Thr Pro Glu Pro Thr Thr Lys Thr Pro Glu
                325                 330                 335
Pro Ser Thr Pro Thr Pro Glu Pro Thr Thr Lys Thr Pro Glu Pro Thr
                340                 345                 350
Thr Lys Thr Pro Glu Pro Ser Thr Pro Thr Pro Glu Pro Thr Thr Lys
            355                 360                 365
Thr Pro Glu Pro Ser Thr Pro Thr Pro Glu Pro Thr Thr Lys Thr Pro
            370                 375                 380
Glu Pro Ser Thr Thr Lys Lys Pro Asn Arg Asp Asp Val Leu Lys Gln
385                 390                 395                 400
Ala Glu Glu Leu Ile Lys Arg Ala Glu Asp Val Phe Glu Lys Leu Pro
                405                 410                 415
Asp Ser Asp Leu Lys Asn Glu Ile Ala Glu Lys Leu Ala Thr Met Lys
            420                 425                 430
Asn Tyr Lys His Glu Leu Glu Asn Ala Lys Asn Pro Ile Lys Ile Ala
            435                 440                 445
His Leu Glu Ser Glu Leu Leu Thr Met Phe Lys Met Phe Gln Ser Leu
            450                 455                 460
Leu Asn Glu Ala Asp Glu Ile Ile Arg Ser Leu Thr Thr Thr Thr Glu
465                 470                 475                 480
Pro Thr Thr Leu Asn Ser Thr Thr Pro Glu Pro Thr Thr Leu Asn Ser
                485                 490                 495
Thr Thr Pro Glu Pro Thr Thr Leu Asn Ser Thr Thr Pro Glu Pro Thr
                500                 505                 510
Thr Leu Asn Ser Thr Thr Pro Glu Pro Thr Thr Leu Asn Ser Thr Thr
            515                 520                 525
Pro Glu Pro Thr Thr Leu Asn Ser Thr Thr Pro Glu Pro Thr Thr Leu
            530                 535                 540
```

```
Asn Ser Thr Thr Pro Glu Pro Thr Thr Leu Asn Ser Thr Thr Pro Glu
545                 550                 555                 560

Pro Thr Thr Ser Asn Ser Thr Ser Glu Pro Thr Asn Ser Ile Asn
            565                 570                 575

Arg Lys Thr Ser Glu Ile Ser Phe Leu Ser Asp Trp Phe His Lys Ile
        580                 585                 590

Arg Thr Arg Phe Asn Ile Phe
        595
```

<210> SEQ ID NO 42
<211> LENGTH: 286
<212> TYPE: PRT
<213> ORGANISM: Artificial sequence
<220> FEATURE:
<223> OTHER INFORMATION: IMAT_NTERM Cat from Q94424 Salivary antigen 1
      (FS-I) (allergen Cte f 1) Ctenocephalides felis (Cat flea)

<400> SEQUENCE: 42

```
Met His His His His His Tyr Gly Arg Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Ala Pro Glu Ser Lys Arg Ser Arg
        35                  40                  45

Gly Ala Leu Tyr Thr Gly Phe Ser Val Leu Val Ala Leu Leu Leu Ala
50                  55                  60

Gly Gln Ala Thr Thr Ala Tyr Phe Leu Tyr Gln Gln Gln Gly Arg Leu
65                  70                  75                  80

Asp Lys Leu Thr Val Thr Ala Gln Asn Leu Gln Leu Glu Asn Leu Arg
                85                  90                  95

Met Lys Leu Pro Lys Pro Ala Lys Pro Leu Asn Lys Leu Arg Val Ala
            100                 105                 110

Thr Pro Met Leu Met Gln Thr Met Pro Val Arg Gly Leu Leu Gln Ala
        115                 120                 125

Glu Asp Ile Trp Lys Val Asn Lys Lys Arg Thr Ser Gly Gly Lys Asn
130                 135                 140

Gln Asp Arg Lys Leu Asp Gln Ile Ile Gln Lys Gly Gln Val Lys
145                 150                 155                 160

Ile Gln Asn Ile Leu Lys Leu Ile Arg Asp Lys Pro His Thr Asn Gln
                165                 170                 175

Glu Lys Glu Lys Leu Met Lys Phe Leu Lys Val Leu Lys Gly Tyr
            180                 185                 190

Arg Gly Ala Arg Asp Gly Asn Ile Leu Tyr Leu Ser Arg Pro Ser Asn
        195                 200                 205

Leu Gly Pro Asp Trp Lys Val Ser Lys Glu Arg Lys Asp Pro Asn Asn
210                 215                 220

Lys Asp Ser Arg Pro Thr Glu Ile Val Pro Tyr Arg Gln Gln Leu Ala
225                 230                 235                 240

Ile Pro Asn Ile Leu Lys Leu Lys Asn Ser Glu Thr Asn Glu Asp Ser
                245                 250                 255

Lys Leu Lys Lys His Met Lys Glu Lys Ser Arg Gly Gly Asn Asp Ala
            260                 265                 270

Gly Ile Asp Gly Asn Phe Leu Tyr Leu Arg Pro Lys Asn Lys
        275                 280                 285
```

-continued

```
<210> SEQ ID NO 43
<211> LENGTH: 286
<212> TYPE: PRT
<213> ORGANISM: Artificial sequence
<220> FEATURE:
<223> OTHER INFORMATION: IMAT_CTERM Cat from Q94424 Salivary antigen 1
      (FS-I) (allergen Cte f 1) Ctenocephalides felis (Cat flea)

<400> SEQUENCE: 43

Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Ala Ala Pro Glu Ser Lys Arg Ser Arg Gly Ala Leu Tyr Thr Gly
        35                  40                  45

Phe Ser Val Leu Val Ala Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Glu Asp Ile Trp Lys Val
        115                 120                 125

Asn Lys Lys Arg Thr Ser Gly Gly Lys Asn Gln Asp Arg Lys Leu Asp
130                 135                 140

Gln Ile Ile Gln Lys Gly Gln Gln Val Lys Ile Gln Asn Ile Leu Lys
145                 150                 155                 160

Leu Ile Arg Asp Lys Pro His Thr Asn Gln Glu Lys Glu Lys Leu Met
                165                 170                 175

Lys Phe Leu Lys Lys Val Leu Lys Gly Tyr Arg Gly Ala Arg Asp Gly
            180                 185                 190

Asn Ile Leu Tyr Leu Ser Arg Pro Ser Asn Leu Gly Pro Asp Trp Lys
        195                 200                 205

Val Ser Lys Glu Arg Lys Asp Pro Asn Lys Asp Ser Arg Pro Thr
    210                 215                 220

Glu Ile Val Pro Tyr Arg Gln Gln Leu Ala Ile Pro Asn Ile Leu Lys
225                 230                 235                 240

Leu Lys Asn Ser Glu Thr Asn Glu Asp Ser Lys Leu Lys Lys His Met
                245                 250                 255

Lys Glu Lys Ser Arg Gly Gly Asn Asp Ala Gly Ile Asp Gly Asn Phe
            260                 265                 270

Leu Tyr Leu Arg Pro Lys Asn Lys His His His His His
        275                 280                 285

<210> SEQ ID NO 44
<211> LENGTH: 279
<212> TYPE: PRT
<213> ORGANISM: Artificial sequence
<220> FEATURE:
<223> OTHER INFORMATION: IMAT_PURE Cat from Q94424 Salivary antigen 1
      (FS-I) (allergen Cte f 1) Ctenocephalides felis (Cat flea)

<400> SEQUENCE: 44

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
```

```
                     20                  25                  30

Ala Ala Pro Glu Ser Lys Arg Ser Arg Gly Ala Leu Tyr Thr Gly Phe
            35                  40                  45

Ser Val Leu Val Ala Leu Leu Leu Ala Gly Gln Ala Thr Thr Ala Tyr
        50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
            100                 105                 110

Met Pro Val Arg Gly Leu Leu Gln Ala Glu Asp Ile Trp Lys Val Asn
        115                 120                 125

Lys Lys Arg Thr Ser Gly Gly Lys Asn Gln Asp Arg Lys Leu Asp Gln
    130                 135                 140

Ile Ile Gln Lys Gly Gln Gln Val Lys Ile Gln Asn Ile Leu Lys Leu
145                 150                 155                 160

Ile Arg Asp Lys Pro His Thr Asn Gln Glu Lys Glu Lys Leu Met Lys
                165                 170                 175

Phe Leu Lys Lys Val Leu Lys Gly Tyr Arg Gly Ala Arg Asp Gly Asn
            180                 185                 190

Ile Leu Tyr Leu Ser Arg Pro Ser Asn Leu Gly Pro Asp Trp Lys Val
        195                 200                 205

Ser Lys Glu Arg Lys Asp Pro Asn Asn Lys Asp Ser Arg Pro Thr Glu
    210                 215                 220

Ile Val Pro Tyr Arg Gln Gln Leu Ala Ile Pro Asn Ile Leu Lys Leu
225                 230                 235                 240

Lys Asn Ser Glu Thr Asn Glu Asp Ser Lys Leu Lys Lys His Met Lys
                245                 250                 255

Glu Lys Ser Arg Gly Gly Asn Asp Ala Gly Ile Asp Gly Asn Phe Leu
            260                 265                 270

Tyr Leu Arg Pro Lys Asn Lys
        275

<210> SEQ ID NO 45
<211> LENGTH: 351
<212> TYPE: PRT
<213> ORGANISM: Artificial sequence
<220> FEATURE:
<223> OTHER INFORMATION: IMAT_NTERM Dog from Q58A71 Der f 1 allergen
      preproenzyme Dermatophagoides farinae (American house dust mite)

<400> SEQUENCE: 45

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gln Gly Arg Leu
65                  70                  75                  80

Asp Lys Leu Thr Val Thr Ser Gln Asn Leu Gln Leu Glu Ser Leu Arg
                85                  90                  95
```

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
            115                 120                 125

Thr Ser Ala Ile Arg Ile Asn Ser Val Asn Val Pro Ser Glu Leu Asp
        130                 135                 140

Leu Arg Ser Leu Arg Thr Val Thr Pro Ile Arg Met Gln Gly Gly Ile
145                 150                 155                 160

Gly Ser Leu Trp Ala Phe Ser Gly Val Ala Ala Thr Glu Ser Ala Tyr
                165                 170                 175

Leu Ala Tyr Arg Asn Thr Ser Leu Asp Leu Ser Glu Gln Glu Leu Val
            180                 185                 190

Asp Arg Ala Ser Gln His Gly Arg His Gly Asp Thr Ile Pro Arg Gly
        195                 200                 205

Ile Glu Tyr Ile Gln Gln Asn Gly Val Val Glu Glu Arg Ser Tyr Pro
    210                 215                 220

Tyr Val Ala Arg Glu Gln Gln Ser Arg Arg Pro Asn Ser Gln His Tyr
225                 230                 235                 240

Gly Ile Ser Asn Tyr Ile Gln Ile Tyr Pro Pro Asp Val Lys Gln Ile
                245                 250                 255

Arg Glu Ala Leu Thr Gln Thr His Thr Ala Ile Ala Val Ile Ile Gly
            260                 265                 270

Ile Lys Asp Leu Arg Ala Phe Gln His Tyr Asp Gly Arg Thr Ile Ile
        275                 280                 285

Gln His Asp Asn Gly Tyr Gln Pro Asn Tyr His Ala Val Asn Ile Val
    290                 295                 300

Gly Tyr Gly Ser Thr Gln Gly Val Asp Tyr Trp Ile Val Arg Asn Ser
305                 310                 315                 320

Trp Asp Thr Thr Trp Gly Asp Ser Gly Tyr Gly Tyr Phe Gln Ala Gly
                325                 330                 335

Asn Asn Leu Met Met Ile Glu Gln Tyr Pro Tyr Val Val Ile Met
            340                 345                 350

<210> SEQ ID NO 46
<211> LENGTH: 351
<212> TYPE: PRT
<213> ORGANISM: Artificial sequence
<220> FEATURE:
<223> OTHER INFORMATION: IMAT_CTERM Dog from Q58A71 Der f 1 allergen
      preproenzyme Dermatophagoides farinae (American house dust mite)

<400> SEQUENCE: 46

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Ser Arg Gly Ala Leu Tyr Thr Gly
        35                  40                  45

Phe Ser Val Leu Val Ala Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
            100                 105                 110

```
Ala Leu Pro Ile Gln Ser Leu Pro Gln Gly Thr Ser Ala Ile Arg Ile
            115                 120                 125

Asn Ser Val Asn Val Pro Ser Glu Leu Asp Leu Arg Ser Leu Arg Thr
        130                 135                 140

Val Thr Pro Ile Arg Met Gln Gly Gly Ile Gly Ser Leu Trp Ala Phe
145                 150                 155                 160

Ser Gly Val Ala Ala Thr Glu Ser Ala Tyr Leu Ala Tyr Arg Asn Thr
                165                 170                 175

Ser Leu Asp Leu Ser Glu Gln Glu Leu Val Asp Arg Ala Ser Gln His
            180                 185                 190

Gly Arg His Gly Asp Thr Ile Pro Arg Gly Ile Glu Tyr Ile Gln Gln
        195                 200                 205

Asn Gly Val Val Glu Glu Arg Ser Tyr Pro Tyr Val Ala Arg Glu Gln
    210                 215                 220

Gln Ser Arg Arg Pro Asn Ser Gln His Tyr Gly Ile Ser Asn Tyr Ile
225                 230                 235                 240

Gln Ile Tyr Pro Pro Asp Val Lys Gln Ile Arg Glu Ala Leu Thr Gln
                245                 250                 255

Thr His Thr Ala Ile Ala Val Ile Ile Gly Ile Lys Asp Leu Arg Ala
            260                 265                 270

Phe Gln His Tyr Asp Gly Arg Thr Ile Ile Gln His Asp Asn Gly Tyr
        275                 280                 285

Gln Pro Asn Tyr His Ala Val Asn Ile Val Gly Tyr Gly Ser Thr Gln
    290                 295                 300

Gly Val Asp Tyr Trp Ile Val Arg Asn Ser Trp Asp Thr Thr Trp Gly
305                 310                 315                 320

Asp Ser Gly Tyr Gly Tyr Phe Gln Ala Gly Asn Asn Leu Met Met Ile
                325                 330                 335

Glu Gln Tyr Pro Tyr Val Val Ile Met His His His His His His
            340                 345                 350

<210> SEQ ID NO 47
<211> LENGTH: 344
<212> TYPE: PRT
<213> ORGANISM: Artificial sequence
<220> FEATURE:
<223> OTHER INFORMATION: IMAT_PURE Dog from Q58A71 Der f 1 allergen
      preproenzyme Dermatophagoides farinae (American house dust mite)

<400> SEQUENCE: 47

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Gly Ala Pro Glu Ser Lys Ser Ser Arg Gly Ala Leu Tyr Thr Gly Phe
        35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ser
65                  70                  75                  80

Gln Asn Leu Gln Leu Glu Ser Leu Arg Met Lys Leu Pro Lys Pro Pro
                85                  90                  95

Lys Pro Leu Ser Lys Met Arg Val Ala Thr Pro Met Met Met Gln Ala
            100                 105                 110

Leu Pro Ile Gln Ser Leu Pro Gln Gly Thr Ser Ala Ile Arg Ile Asn
```

```
            115                 120                 125
Ser Val Asn Val Pro Ser Glu Leu Asp Leu Arg Ser Leu Arg Thr Val
        130                 135                 140

Thr Pro Ile Arg Met Gln Gly Gly Ile Gly Ser Leu Trp Ala Phe Ser
145                 150                 155                 160

Gly Val Ala Ala Thr Glu Ser Ala Tyr Leu Ala Tyr Arg Asn Thr Ser
                165                 170                 175

Leu Asp Leu Ser Glu Gln Glu Leu Val Asp Arg Ala Ser Gln His Gly
            180                 185                 190

Arg His Gly Asp Thr Ile Pro Arg Gly Ile Glu Tyr Ile Gln Gln Asn
        195                 200                 205

Gly Val Val Glu Glu Arg Ser Tyr Pro Tyr Val Ala Arg Glu Gln Gln
    210                 215                 220

Ser Arg Arg Pro Asn Ser Gln His Tyr Gly Ile Ser Asn Tyr Ile Gln
225                 230                 235                 240

Ile Tyr Pro Pro Asp Val Lys Gln Ile Arg Glu Ala Leu Thr Gln Thr
                245                 250                 255

His Thr Ala Ile Ala Val Ile Ile Gly Ile Lys Asp Leu Arg Ala Phe
            260                 265                 270

Gln His Tyr Asp Gly Arg Thr Ile Ile Gln His Asp Asn Gly Tyr Gln
        275                 280                 285

Pro Asn Tyr His Ala Val Asn Ile Val Gly Tyr Gly Ser Thr Gln Gly
    290                 295                 300

Val Asp Tyr Trp Ile Val Arg Asn Ser Trp Asp Thr Thr Trp Gly Asp
305                 310                 315                 320

Ser Gly Tyr Gly Tyr Phe Gln Ala Gly Asn Asn Leu Met Met Ile Glu
                325                 330                 335

Gln Tyr Pro Tyr Val Val Ile Met
            340

<210> SEQ ID NO 48
<211> LENGTH: 257
<212> TYPE: PRT
<213> ORGANISM: Artificial sequence
<220> FEATURE:
<223> OTHER INFORMATION: IMAT_NTERM Dog from Q00855 Mite group 2
      allergen Der f 2 (Allergen Der f II) (allergen Der f 2)
      Dermatophagoides farinae (American house dust mite)

<400> SEQUENCE: 48

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
        115                 120                 125
```

```
Asp Gln Val Asp Val Lys Asp Ser Ala Asn Asn Glu Ile Lys Lys Val
        130                 135                 140

Met Val Asp Gly Ile His Gly Ser Asp Pro Leu Ile Ile His Arg Gly
145                 150                 155                 160

Lys Pro Phe Thr Leu Glu Ala Leu Phe Asp Ala Asn Gln Asn Thr Lys
                165                 170                 175

Thr Ala Lys Ile Glu Ile Lys Ala Ser Leu Asp Gly Leu Glu Ile Asp
            180                 185                 190

Val Pro Gly Ile Asp Thr Asn Ala Ile His Phe Met Lys Leu Pro Leu
        195                 200                 205

Val Lys Gly Gln Gln Tyr Asp Ile Lys Tyr Thr Trp Asn Val Pro Lys
    210                 215                 220

Ile Ala Pro Lys Ser Glu Asn Val Val Thr Val Lys Leu Ile Gly
225                 230                 235                 240

Asp Asn Gly Val Leu Ala Leu Ala Ile Ala Thr His Gly Lys Ile Arg
                245                 250                 255

Asp

<210> SEQ ID NO 49
<211> LENGTH: 257
<212> TYPE: PRT
<213> ORGANISM: Artificial sequence
<220> FEATURE:
<223> OTHER INFORMATION: IMAT_CTERM Dog from Q00855 Mite group 2
      allergen Der f 2 (Allergen Der f II) (allergen Der f 2)
      Dermatophagoides farinae (American house dust mite)

<400> SEQUENCE: 49

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Ser Arg Gly Ala Leu Tyr Thr Gly
        35                  40                  45

Phe Ser Val Leu Val Ala Leu Leu Ala Gly Gln Ala Thr Thr Ala
50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
            100                 105                 110

Ala Leu Pro Ile Gln Ser Leu Pro Gln Gly Asp Gln Val Asp Val Lys
        115                 120                 125

Asp Ser Ala Asn Asn Glu Ile Lys Lys Val Met Val Asp Gly Ile His
    130                 135                 140

Gly Ser Asp Pro Leu Ile Ile His Arg Gly Lys Pro Phe Thr Leu Glu
145                 150                 155                 160

Ala Leu Phe Asp Ala Asn Gln Asn Thr Lys Thr Ala Lys Ile Glu Ile
                165                 170                 175

Lys Ala Ser Leu Asp Gly Leu Glu Ile Asp Val Pro Gly Ile Asp Thr
            180                 185                 190

Asn Ala Ile His Phe Met Lys Leu Pro Leu Val Lys Gly Gln Gln Tyr
        195                 200                 205

Asp Ile Lys Tyr Thr Trp Asn Val Pro Lys Ile Ala Pro Lys Ser Glu
```

Asn Val Val Thr Val Lys Leu Ile Gly Asp Asn Gly Val Leu Ala
225                 230                 235                 240

Leu Ala Ile Ala Thr His Gly Lys Ile Arg Asp His His His His
                245                 250                 255

His

<210> SEQ ID NO 50
<211> LENGTH: 250
<212> TYPE: PRT
<213> ORGANISM: Artificial sequence
<220> FEATURE:
<223> OTHER INFORMATION: IMAT_PURE Dog from Q00855 Mite group 2 allergen
      Der f 2 (Allergen Der f II) (allergen Der f 2) Dermatophagoides
      farinae (American house dust mite)

<400> SEQUENCE: 50

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Gly Ala Pro Glu Ser Lys Ser Ser Arg Gly Ala Leu Tyr Thr Gly Phe
            35                  40                  45

Ser Val Leu Val Ala Leu Leu Leu Ala Gly Gln Ala Thr Thr Ala Tyr
50                  55                  60

Phe Leu Tyr Gln Gln Gln Gly Arg Leu Asp Lys Leu Thr Val Thr Ser
65                  70                  75                  80

Gln Asn Leu Gln Leu Glu Ser Leu Arg Met Lys Leu Pro Lys Pro Pro
                85                  90                  95

Lys Pro Leu Ser Lys Met Arg Val Ala Thr Pro Met Met Met Gln Ala
            100                 105                 110

Leu Pro Ile Gln Ser Leu Pro Gln Gly Asp Gln Val Asp Val Lys Asp
        115                 120                 125

Ser Ala Asn Asn Glu Ile Lys Lys Val Met Val Asp Gly Ile His Gly
130                 135                 140

Ser Asp Pro Leu Ile Ile His Arg Gly Lys Pro Phe Thr Leu Glu Ala
145                 150                 155                 160

Leu Phe Asp Ala Asn Gln Asn Thr Lys Thr Ala Lys Ile Glu Ile Lys
                165                 170                 175

Ala Ser Leu Asp Gly Leu Glu Ile Asp Val Pro Gly Ile Asp Thr Asn
            180                 185                 190

Ala Ile His Phe Met Lys Leu Pro Leu Val Lys Gly Gln Gln Tyr Asp
        195                 200                 205

Ile Lys Tyr Thr Trp Asn Val Pro Lys Ile Ala Pro Lys Ser Glu Asn
    210                 215                 220

Val Val Thr Val Lys Leu Ile Gly Asp Asn Gly Val Leu Ala Leu
225                 230                 235                 240

Ala Ile Ala Thr His Gly Lys Ile Arg Asp
                245                 250

<210> SEQ ID NO 51
<211> LENGTH: 198
<212> TYPE: PRT
<213> ORGANISM: Artificial sequence
<220> FEATURE:
<223> OTHER INFORMATION: IMAT_NTERM Dog from A0A088SAW7 Der f 23
      allergen Dermatophagoides farinae (American house dust mite)

-continued

```
<400> SEQUENCE: 51

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Glu Ser Arg
        35                  40                  45

Gly Ala Leu Tyr Thr Gly Phe Ser Val Leu Val Ala Leu Leu Leu Ala
50                  55                  60

Gly Gln Ala Thr Thr Ala Tyr Phe Leu Tyr Gln Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
        115                 120                 125

Asp Ile Asp His Asp Asp Asp Pro Thr Thr Met Ile Asp Val Gln Thr
130                 135                 140

Thr Thr Val Gln Pro Ser Asp Glu Phe Glu Leu Pro Thr Arg Phe Gly
145                 150                 155                 160

Tyr Phe Ala Asp Pro Lys Asp Pro Leu Lys Phe Tyr Ile Ile Ser Asn
                165                 170                 175

Trp Glu Ala Ile His Lys Ser Leu Pro Gly Asn Thr Arg Trp Asn Glu
            180                 185                 190

Lys Glu Leu Thr Ile Thr
        195

<210> SEQ ID NO 52
<211> LENGTH: 198
<212> TYPE: PRT
<213> ORGANISM: Artificial sequence
<220> FEATURE:
<223> OTHER INFORMATION: IMAT_CTERM Dog from A0A088SAW7 Der f 23
      allergen Dermatophagoides farinae (American house dust mite)

<400> SEQUENCE: 52

Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Glu Ser Arg Gly Ala Leu Tyr Thr Gly
        35                  40                  45

Phe Ser Val Leu Val Ala Leu Leu Leu Ala Gly Gln Ala Thr Thr Ala
50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
            100                 105                 110

Ala Leu Pro Ile Gln Ser Leu Pro Gln Gly Asp Ile Asp His Asp Asp
        115                 120                 125

Asp Pro Thr Thr Met Ile Asp Val Gln Thr Thr Thr Val Gln Pro Ser
130                 135                 140
```

Asp Glu Phe Glu Leu Pro Thr Arg Phe Gly Tyr Phe Ala Asp Pro Lys
145                 150                 155                 160

Asp Pro Leu Lys Phe Tyr Ile Ile Ser Asn Trp Glu Ala Ile His Lys
                165                 170                 175

Ser Leu Pro Gly Asn Thr Arg Trp Asn Glu Lys Glu Leu Thr Ile Thr
            180                 185                 190

His His His His His His
        195

<210> SEQ ID NO 53
<211> LENGTH: 191
<212> TYPE: PRT
<213> ORGANISM: Artificial sequence
<220> FEATURE:
<223> OTHER INFORMATION: IMAT_PURE Dog from A0A088SAW7 Der f 23 allergen
      Dermatophagoides farinae (American house dust mite)

<400> SEQUENCE: 53

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Gly Ala Pro Glu Ser Lys Glu Ser Arg Gly Ala Leu Tyr Thr Gly Phe
        35                  40                  45

Ser Val Leu Val Ala Leu Leu Ala Gly Gln Ala Thr Thr Ala Tyr
    50                  55                  60

Phe Leu Tyr Gln Gln Gln Gly Arg Leu Asp Lys Leu Thr Val Thr Ser
65                  70                  75                  80

Gln Asn Leu Gln Leu Glu Ser Leu Arg Met Lys Leu Pro Lys Pro Pro
                85                  90                  95

Lys Pro Leu Ser Lys Met Arg Val Ala Thr Pro Met Met Met Gln Ala
            100                 105                 110

Leu Pro Ile Gln Ser Leu Pro Gln Gly Asp Ile Asp His Asp Asp Asp
        115                 120                 125

Pro Thr Thr Met Ile Asp Val Gln Thr Thr Thr Val Gln Pro Ser Asp
130                 135                 140

Glu Phe Glu Leu Pro Thr Arg Phe Gly Tyr Phe Ala Asp Pro Lys Asp
145                 150                 155                 160

Pro Leu Lys Phe Tyr Ile Ile Ser Asn Trp Glu Ala Ile His Lys Ser
                165                 170                 175

Leu Pro Gly Asn Thr Arg Trp Asn Glu Lys Glu Leu Thr Ile Thr
            180                 185                 190

<210> SEQ ID NO 54
<211> LENGTH: 573
<212> TYPE: PRT
<213> ORGANISM: Artificial sequence
<220> FEATURE:
<223> OTHER INFORMATION: IMAT_NTERM Dog from Q86R84 60 kDa allergen Der
      f 18p Dermatophagoides farinae (American house dust mite)

<400> SEQUENCE: 54

Met His His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
        35                  40                  45

```
Gly Ala Leu Tyr Thr Gly Phe Ser Val Leu Val Ala Leu Leu Ala
 50                  55                  60

Gly Gln Ala Thr Thr Ala Tyr Phe Leu Tyr Gln Gln Gly Arg Leu
 65                  70                  75                  80

Asp Lys Leu Thr Val Thr Ser Gln Asn Leu Gln Leu Glu Ser Leu Arg
                 85                  90                  95

Met Lys Leu Pro Lys Pro Pro Lys Pro Leu Ser Lys Met Arg Val Ala
                100                 105                 110

Thr Pro Met Met Met Gln Ala Leu Pro Ile Gln Ser Leu Pro Gln Gly
            115                 120                 125

Ser Asn Ile Arg Pro Asn Val Ala Thr Leu Glu Pro Lys Thr Val Leu
130                 135                 140

Tyr Tyr Glu Ser Trp Val His Trp Arg Gln Gly Glu Gly Lys Met Asp
145                 150                 155                 160

Pro Glu Asp Ile Asp Thr Ser Leu Met Thr His Ile Val Tyr Ser Tyr
                165                 170                 175

Phe Gly Ile Asp Ala Ala Thr His Glu Ile Lys Leu Leu Asp Glu Tyr
                180                 185                 190

Leu Met Lys Asp Leu His Asp Met Glu His Phe Thr Gln His Lys Gly
                195                 200                 205

Asn Ala Lys Ala Met Ile Ala Val Gly Gly Ser Thr Met Ser Asp Gln
210                 215                 220

Phe Ser Lys Thr Ala Ala Val Glu His Tyr Arg Glu Thr Phe Val Val
225                 230                 235                 240

Ser Thr Val Asp Leu Met Thr Arg Tyr Gly Phe Asp Gly Val Met Ile
                245                 250                 255

Asp Trp Ser Gly Met Gln Ala Lys Asp Ser Asp Asn Phe Ile Lys Leu
                260                 265                 270

Leu Asp Lys Phe Asp Glu Lys Phe Ala His Thr Ser Phe Val Met Gly
                275                 280                 285

Val Thr Leu Pro Ala Thr Ile Ala Ser Tyr Asp Asn Tyr Asn Ile Pro
290                 295                 300

Ala Ile Ser Asn Tyr Val Asp Phe Met Asn Val Leu Ser Leu Asp Tyr
305                 310                 315                 320

Thr Gly Ser Trp Ala His Thr Val Gly His Ala Ser Pro Phe Pro Glu
                325                 330                 335

Gln Leu Lys Thr Leu Glu Ala Tyr His Lys Arg Gly Ala Pro Arg His
                340                 345                 350

Lys Met Val Met Ala Val Pro Phe Tyr Ala Arg Thr Trp Ile Leu Glu
                355                 360                 365

Lys Met Asn Lys Gln Asp Ile Gly Asp Lys Ala Ser Gly Pro Gly Pro
370                 375                 380

Arg Gly Gln Phe Thr Gln Thr Asp Gly Phe Leu Ser Tyr Asn Glu Leu
385                 390                 395                 400

Ser Val Gln Ile Gln Ala Glu Thr Asn Ala Phe Thr Ile Thr Arg Asp
                405                 410                 415

His Asp Asn Thr Ala Ile Tyr Ala Val Tyr Val His Ser Asn His Ala
                420                 425                 430

Glu Trp Ile Ser Phe Glu Asp Arg His Thr Leu Gly Glu Lys Ala Lys
                435                 440                 445

Asn Ile Thr Gln Gln Gly Tyr Ala Gly Met Ser Val Tyr Thr Leu Ser
450                 455                 460

Asn Glu Asp Val His Gly Val Arg Gly Asp Lys Asn Pro Leu Leu His
```

-continued

```
            465                 470                 475                 480
        Ala Ile Gln Ser Asn Tyr Tyr His Gly Val Val Thr Glu Pro Thr Val
                        485                 490                 495

Val Thr Leu Pro Pro Val Thr His Thr Glu His Val Thr Asp Ile
                        500                 505                 510

Pro Gly Val Phe His Leu His Glu Glu Gly Phe Phe Arg Asp Lys Thr
                        515                 520                 525

Tyr Ser Ala Thr Tyr Tyr Glu Ile Lys Lys Gly Asp Phe Gly Leu Glu
                        530                 535                 540

Lys Thr Val His His Leu Ala Asn His Leu Gln Ala Phe Asp Glu Val
        545                 550                 555                 560

Ser Arg Thr Arg Ile Asp His Thr Lys Ile Pro Gly Ser
                        565                 570

<210> SEQ ID NO 55
<211> LENGTH: 573
<212> TYPE: PRT
<213> ORGANISM: Artificial sequence
<220> FEATURE:
<223> OTHER INFORMATION: IMAT_CTERM Dog from Q86R84 60 kDa allergen Der
      f 18p Dermatophagoides farinae (American house dust mite)

<400> SEQUENCE: 55

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
                20                  25                  30

Pro Gly Ala Pro Glu Ser Lys Ser Arg Gly Ala Leu Tyr Thr Gly
            35                  40                  45

Phe Ser Val Leu Val Ala Leu Leu Ala Gly Gln Ala Thr Thr Ala
50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
            100                 105                 110

Ala Leu Pro Ile Gln Ser Leu Pro Gln Gly Ser Asn Ile Arg Pro Asn
        115                 120                 125

Val Ala Thr Leu Glu Pro Lys Thr Val Leu Tyr Tyr Glu Ser Trp Val
    130                 135                 140

His Trp Arg Gln Gly Glu Gly Lys Met Asp Pro Glu Asp Ile Asp Thr
145                 150                 155                 160

Ser Leu Met Thr His Ile Val Tyr Ser Tyr Phe Gly Ile Asp Ala Ala
                165                 170                 175

Thr His Glu Ile Lys Leu Leu Asp Glu Tyr Leu Met Lys Asp Leu His
            180                 185                 190

Asp Met Glu His Phe Thr Gln His Lys Gly Asn Ala Lys Ala Met Ile
        195                 200                 205

Ala Val Gly Gly Ser Thr Met Ser Asp Gln Phe Ser Lys Thr Ala Ala
    210                 215                 220

Val Glu His Tyr Arg Glu Thr Phe Val Val Ser Thr Val Asp Leu Met
225                 230                 235                 240

Thr Arg Tyr Gly Phe Asp Gly Val Met Ile Asp Trp Ser Gly Met Gln
                245                 250                 255
```

Ala Lys Asp Ser Asp Asn Phe Ile Lys Leu Leu Asp Lys Phe Asp Glu
            260                 265                 270

Lys Phe Ala His Thr Ser Phe Val Met Gly Val Thr Leu Pro Ala Thr
        275                 280                 285

Ile Ala Ser Tyr Asp Asn Tyr Asn Ile Pro Ala Ile Ser Asn Tyr Val
    290                 295                 300

Asp Phe Met Asn Val Leu Ser Leu Asp Tyr Thr Gly Ser Trp Ala His
305                 310                 315                 320

Thr Val Gly His Ala Ser Pro Phe Pro Glu Gln Leu Lys Thr Leu Glu
                325                 330                 335

Ala Tyr His Lys Arg Gly Ala Pro Arg His Lys Met Val Met Ala Val
            340                 345                 350

Pro Phe Tyr Ala Arg Thr Trp Ile Leu Glu Lys Met Asn Lys Gln Asp
        355                 360                 365

Ile Gly Asp Lys Ala Ser Gly Pro Gly Pro Arg Gly Gln Phe Thr Gln
    370                 375                 380

Thr Asp Gly Phe Leu Ser Tyr Asn Glu Leu Ser Val Gln Ile Gln Ala
385                 390                 395                 400

Glu Thr Asn Ala Phe Thr Ile Thr Arg Asp His Asp Asn Thr Ala Ile
                405                 410                 415

Tyr Ala Val Tyr Val His Ser Asn His Ala Glu Trp Ile Ser Phe Glu
            420                 425                 430

Asp Arg His Thr Leu Gly Glu Lys Ala Lys Asn Ile Thr Gln Gln Gly
        435                 440                 445

Tyr Ala Gly Met Ser Val Tyr Thr Leu Ser Asn Glu Asp Val His Gly
    450                 455                 460

Val Arg Gly Asp Lys Asn Pro Leu Leu His Ala Ile Gln Ser Asn Tyr
465                 470                 475                 480

Tyr His Gly Val Val Thr Glu Pro Thr Val Val Thr Leu Pro Pro Val
                485                 490                 495

Thr His Thr Thr Glu His Val Thr Asp Ile Pro Gly Val Phe His Leu
            500                 505                 510

His Glu Glu Gly Phe Phe Arg Asp Lys Thr Tyr Ser Ala Thr Tyr Tyr
        515                 520                 525

Glu Ile Lys Lys Gly Asp Phe Gly Leu Glu Lys Thr Val His His Leu
    530                 535                 540

Ala Asn His Leu Gln Ala Phe Asp Glu Val Ser Arg Thr Arg Ile Asp
545                 550                 555                 560

His Thr Lys Ile Pro Gly Ser His His His His His
                565                 570

<210> SEQ ID NO 56
<211> LENGTH: 566
<212> TYPE: PRT
<213> ORGANISM: Artificial sequence
<220> FEATURE:
<223> OTHER INFORMATION: IMAT_PURE Dog from Q86R84 60 kDa allergen Der f
    18p Dermatophagoides farinae (American house dust mite)

<400> SEQUENCE: 56

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Gly Ala Pro Glu Ser Lys Ser Ser Arg Gly Ala Leu Tyr Thr Gly Phe
            35                  40                  45

-continued

Ser Val Leu Val Ala Leu Leu Ala Gly Gln Ala Thr Thr Ala Tyr
 50                 55                  60

Phe Leu Tyr Gln Gln Gln Gly Arg Leu Asp Lys Leu Thr Val Thr Ser
 65                 70                  75                  80

Gln Asn Leu Gln Leu Glu Ser Leu Arg Met Lys Leu Pro Lys Pro Pro
                 85                  90                  95

Lys Pro Leu Ser Lys Met Arg Val Ala Thr Pro Met Met Met Gln Ala
                100                 105                 110

Leu Pro Ile Gln Ser Leu Pro Gln Gly Ser Asn Ile Arg Pro Asn Val
            115                 120                 125

Ala Thr Leu Glu Pro Lys Thr Val Leu Tyr Tyr Glu Ser Trp Val His
            130                 135                 140

Trp Arg Gln Gly Glu Gly Lys Met Asp Pro Glu Asp Ile Asp Thr Ser
145                 150                 155                 160

Leu Met Thr His Ile Val Tyr Ser Tyr Phe Gly Ile Asp Ala Ala Thr
                165                 170                 175

His Glu Ile Lys Leu Leu Asp Glu Tyr Leu Met Lys Asp Leu His Asp
                180                 185                 190

Met Glu His Phe Thr Gln His Lys Gly Asn Ala Lys Ala Met Ile Ala
            195                 200                 205

Val Gly Gly Ser Thr Met Ser Asp Gln Phe Ser Lys Thr Ala Ala Val
            210                 215                 220

Glu His Tyr Arg Glu Thr Phe Val Val Ser Thr Val Asp Leu Met Thr
225                 230                 235                 240

Arg Tyr Gly Phe Asp Gly Val Met Ile Asp Trp Ser Gly Met Gln Ala
                245                 250                 255

Lys Asp Ser Asp Asn Phe Ile Lys Leu Leu Asp Lys Phe Asp Glu Lys
                260                 265                 270

Phe Ala His Thr Ser Phe Val Met Gly Val Thr Leu Pro Ala Thr Ile
            275                 280                 285

Ala Ser Tyr Asp Asn Tyr Asn Ile Pro Ala Ile Ser Asn Tyr Val Asp
            290                 295                 300

Phe Met Asn Val Leu Ser Leu Asp Tyr Thr Gly Ser Trp Ala His Thr
305                 310                 315                 320

Val Gly His Ala Ser Pro Phe Pro Glu Gln Leu Lys Thr Leu Glu Ala
                325                 330                 335

Tyr His Lys Arg Gly Ala Pro Arg His Lys Met Val Met Ala Val Pro
                340                 345                 350

Phe Tyr Ala Arg Thr Trp Ile Leu Glu Lys Met Asn Lys Gln Asp Ile
            355                 360                 365

Gly Asp Lys Ala Ser Gly Pro Gly Pro Arg Gly Gln Phe Thr Gln Thr
            370                 375                 380

Asp Gly Phe Leu Ser Tyr Asn Glu Leu Ser Val Gln Ile Gln Ala Glu
385                 390                 395                 400

Thr Asn Ala Phe Thr Ile Thr Arg Asp His Asp Asn Thr Ala Ile Tyr
                405                 410                 415

Ala Val Tyr Val His Ser Asn His Ala Glu Trp Ile Ser Phe Glu Asp
                420                 425                 430

Arg His Thr Leu Gly Glu Lys Ala Lys Asn Ile Thr Gln Gln Gly Tyr
            435                 440                 445

Ala Gly Met Ser Val Tyr Thr Leu Ser Asn Glu Asp Val His Gly Val
            450                 455                 460

-continued

Arg Gly Asp Lys Asn Pro Leu Leu His Ala Ile Gln Ser Asn Tyr Tyr
465                 470                 475                 480

His Gly Val Val Thr Glu Pro Thr Val Val Thr Leu Pro Pro Val Thr
            485                 490                 495

His Thr Thr Glu His Val Thr Asp Ile Pro Gly Val Phe His Leu His
            500                 505                 510

Glu Glu Gly Phe Phe Arg Asp Lys Thr Tyr Ser Ala Thr Tyr Tyr Glu
            515                 520                 525

Ile Lys Lys Gly Asp Phe Gly Leu Glu Lys Thr Val His His Leu Ala
        530                 535                 540

Asn His Leu Gln Ala Phe Asp Glu Val Ser Arg Thr Arg Ile Asp His
545                 550                 555                 560

Thr Lys Ile Pro Gly Ser
            565

<210> SEQ ID NO 57
<211> LENGTH: 664
<212> TYPE: PRT
<213> ORGANISM: Artificial sequence
<220> FEATURE:
<223> OTHER INFORMATION: IMAT_NTERM Dog from Q9U6R7 98kDa HDM allergen
      (Der f 15 allergen) (Group 15 allergen Der f 15) Dermatophagoides
      farinae (American house dust mite)

<400> SEQUENCE: 57

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
            115                 120                 125

Ser Ile Lys Arg Asp His Asn Asp Tyr Ser Lys Asn Pro Met Arg Ile
    130                 135                 140

Val Leu Tyr Val Gly Thr Trp Ser Val Tyr His Lys Val Asp Pro Tyr
145                 150                 155                 160

Thr Ile Glu Asp Ile Asp Pro Phe Lys Ser Thr His Leu Met Tyr Gly
                165                 170                 175

Phe Ala Lys Ile Asp Glu Tyr Lys Tyr Thr Ile Gln Val Phe Asp Pro
            180                 185                 190

Tyr Gln Asp Asp Asn His Asn Ser Trp Glu Lys Arg Gly Tyr Glu Arg
        195                 200                 205

Phe Asn Asn Leu Arg Leu Lys Asn Pro Glu Leu Thr Thr Met Ile Ser
    210                 215                 220

Leu Gly Gly Trp Tyr Glu Gly Ser Glu Lys Tyr Ser Asp Met Ala Ala
225                 230                 235                 240

Asn Pro Thr Tyr Arg Gln Gln Phe Ile Gln Ser Val Leu Asp Phe Leu

```
                    245                 250                 255
Gln Glu Tyr Lys Phe Asp Gly Leu Asp Leu Asp Trp Glu Tyr Pro Gly
                260                 265                 270

Ser Arg Leu Gly Asn Pro Lys Ile Asp Lys Gln Asn Tyr Leu Ala Leu
            275                 280                 285

Val Arg Glu Leu Lys Asp Ala Phe Glu Pro His Gly Tyr Leu Leu Thr
        290                 295                 300

Ala Ala Val Ser Pro Gly Lys Asp Lys Ile Asp Arg Ala Tyr Asp Ile
305                 310                 315                 320

Lys Glu Leu Asn Lys Leu Phe Asp Trp Met Asn Val Met Thr Tyr Asp
                325                 330                 335

Tyr His Gly Gly Trp Glu Asn Phe Tyr Gly His Asn Ala Pro Leu Tyr
            340                 345                 350

Lys Arg Pro Asp Glu Thr Asp Glu Leu His Thr Tyr Phe Asn Val Asn
        355                 360                 365

Tyr Thr Met His Tyr Tyr Leu Asn Asn Gly Ala Thr Arg Asp Lys Leu
    370                 375                 380

Val Met Gly Val Pro Phe Tyr Gly Arg Ala Trp Ser Ile Glu Asp Arg
385                 390                 395                 400

Ser Lys Leu Lys Leu Gly Asp Pro Ala Lys Gly Met Ser Pro Pro Gly
                405                 410                 415

Phe Ile Ser Gly Glu Glu Gly Val Leu Ser Tyr Ile Glu Leu Ser Gln
            420                 425                 430

Leu Phe Gln Lys Glu Glu Trp His Ile Gln Tyr Asp Glu Tyr Tyr Asn
        435                 440                 445

Ala Pro Tyr Gly Tyr Asn Asp Lys Ile Trp Val Gly Tyr Asp Asp Leu
    450                 455                 460

Ala Ser Ile Ser Ser Lys Leu Ala Phe Leu Lys Glu Leu Gly Val Ser
465                 470                 475                 480

Gly Val Met Val Trp Ser Leu Glu Asn Asp Asp Phe Lys Gly His Leu
                485                 490                 495

Gly Pro Lys Asn Pro Leu Leu Asn Lys Val His Asn Met Ile Asn Gly
            500                 505                 510

Asp Glu Lys Asn Ser Phe Glu Ile Ile Leu Gly Pro Ser Thr Thr Thr
        515                 520                 525

Pro Thr Pro Thr Thr Thr Pro Thr Thr Pro Thr Thr Thr Pro Thr Thr
    530                 535                 540

Pro Ser Pro Thr Thr Pro Thr Thr Thr Pro Ser Pro Thr Thr Pro Thr
545                 550                 555                 560

Thr Thr Pro Ser Pro Thr Thr Pro Thr Thr Thr Pro Ser Pro Thr Thr
                565                 570                 575

Pro Thr Pro Thr Thr Pro Thr Pro Ala Pro Thr Thr Ser Thr Pro Ser
            580                 585                 590

Pro Thr Thr Thr Glu His Thr Ser Glu Thr Pro Lys Tyr Thr Thr Tyr
        595                 600                 605

Val Asp Gly His Leu Ile Lys Ser Tyr Lys Glu Gly Asp Ile Pro His
    610                 615                 620

Pro Thr Asn Ile His Lys Tyr Leu Val Ile Glu Phe Val Asn Gly Gly
625                 630                 635                 640

Trp Trp Val His Ile Met Pro Ser Pro Pro Gly Thr Ile Trp Ser Gln
                645                 650                 655

Glu Lys Leu Thr Ser Ile Gly Glu
            660
```

<210> SEQ ID NO 58
<211> LENGTH: 664
<212> TYPE: PRT
<213> ORGANISM: Artificial sequence
<220> FEATURE:
<223> OTHER INFORMATION: IMAT_CTERM Dog from Q9U6R7 98kDa HDM allergen
(Der f 15 allergen) (Group 15 allergen Der f 15) Dermatophagoides
farinae (American house dust mite)

<400> SEQUENCE: 58

```
Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Ser Arg Gly Ala Leu Tyr Thr Gly
        35                  40                  45

Phe Ser Val Leu Val Ala Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
            100                 105                 110

Ala Leu Pro Ile Gln Ser Leu Pro Gln Gly Ser Ile Lys Arg Asp His
        115                 120                 125

Asn Asp Tyr Ser Lys Asn Pro Met Arg Ile Val Leu Tyr Val Gly Thr
130                 135                 140

Trp Ser Val Tyr His Lys Val Asp Pro Tyr Thr Ile Glu Asp Ile Asp
145                 150                 155                 160

Pro Phe Lys Ser Thr His Leu Met Tyr Gly Phe Ala Lys Ile Asp Glu
                165                 170                 175

Tyr Lys Tyr Thr Ile Gln Val Phe Asp Pro Tyr Gln Asp Asp Asn His
            180                 185                 190

Asn Ser Trp Glu Lys Arg Gly Tyr Glu Arg Phe Asn Asn Leu Arg Leu
        195                 200                 205

Lys Asn Pro Glu Leu Thr Thr Met Ile Ser Leu Gly Gly Trp Tyr Glu
    210                 215                 220

Gly Ser Glu Lys Tyr Ser Asp Met Ala Ala Asn Pro Thr Tyr Arg Gln
225                 230                 235                 240

Gln Phe Ile Gln Ser Val Leu Asp Phe Leu Gln Glu Tyr Lys Phe Asp
                245                 250                 255

Gly Leu Asp Leu Asp Trp Glu Tyr Pro Gly Ser Arg Leu Gly Asn Pro
            260                 265                 270

Lys Ile Asp Lys Gln Asn Tyr Leu Ala Leu Val Arg Glu Leu Lys Asp
        275                 280                 285

Ala Phe Glu Pro His Gly Tyr Leu Leu Thr Ala Ala Val Ser Pro Gly
    290                 295                 300

Lys Asp Lys Ile Asp Arg Ala Tyr Asp Ile Lys Glu Leu Asn Lys Leu
305                 310                 315                 320

Phe Asp Trp Met Asn Val Met Thr Tyr Asp Tyr His Gly Gly Trp Glu
                325                 330                 335

Asn Phe Tyr Gly His Asn Ala Pro Leu Tyr Lys Arg Pro Asp Glu Thr
            340                 345                 350
```

```
Asp Glu Leu His Thr Tyr Phe Asn Val Asn Tyr Thr Met His Tyr Tyr
            355                 360                 365

Leu Asn Asn Gly Ala Thr Arg Asp Lys Leu Val Met Gly Val Pro Phe
    370                 375                 380

Tyr Gly Arg Ala Trp Ser Ile Glu Asp Arg Ser Lys Leu Lys Leu Gly
385                 390                 395                 400

Asp Pro Ala Lys Gly Met Ser Pro Gly Phe Ile Ser Gly Glu Glu
                405                 410                 415

Gly Val Leu Ser Tyr Ile Glu Leu Ser Gln Leu Phe Gln Lys Glu Glu
                420                 425                 430

Trp His Ile Gln Tyr Asp Glu Tyr Asn Ala Pro Tyr Gly Tyr Asn
            435                 440                 445

Asp Lys Ile Trp Val Gly Tyr Asp Asp Leu Ala Ser Ile Ser Ser Lys
    450                 455                 460

Leu Ala Phe Leu Lys Glu Leu Gly Val Ser Gly Val Met Val Trp Ser
465                 470                 475                 480

Leu Glu Asn Asp Asp Phe Lys Gly His Leu Gly Pro Lys Asn Pro Leu
                485                 490                 495

Leu Asn Lys Val His Asn Met Ile Asn Gly Asp Glu Lys Asn Ser Phe
            500                 505                 510

Glu Ile Ile Leu Gly Pro Ser Thr Thr Thr Pro Thr Pro Thr Thr Thr
            515                 520                 525

Pro Thr Thr Pro Thr Thr Thr Pro Thr Thr Pro Ser Pro Thr Thr Pro
    530                 535                 540

Thr Thr Thr Pro Ser Pro Thr Thr Pro Thr Thr Thr Pro Ser Pro Thr
545                 550                 555                 560

Thr Pro Thr Thr Thr Pro Ser Pro Thr Thr Pro Thr Pro Thr Thr Pro
                565                 570                 575

Thr Pro Ala Pro Thr Thr Ser Thr Pro Ser Pro Thr Thr Thr Glu His
            580                 585                 590

Thr Ser Glu Thr Pro Lys Tyr Thr Thr Tyr Val Asp Gly His Leu Ile
    595                 600                 605

Lys Ser Tyr Lys Glu Gly Asp Ile Pro His Pro Thr Asn Ile His Lys
610                 615                 620

Tyr Leu Val Ile Glu Phe Val Asn Gly Gly Trp Trp Val His Ile Met
625                 630                 635                 640

Pro Ser Pro Pro Gly Thr Ile Trp Ser Gln Glu Lys Leu Thr Ser Ile
                645                 650                 655

Gly Glu His His His His His His
            660

<210> SEQ ID NO 59
<211> LENGTH: 657
<212> TYPE: PRT
<213> ORGANISM: Artificial sequence
<220> FEATURE:
<223> OTHER INFORMATION: IMAT_PURE Dog from Q9U6R7 98kDa HDM allergen
      (Der f 15 allergen) (Group 15 allergen Der f 15) Dermatophagoides
      farinae (American house dust mite)

<400> SEQUENCE: 59

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Gly Ala Pro Glu Ser Lys Ser Ser Arg Gly Ala Leu Tyr Thr Gly Phe
```

```
              35                  40                  45
Ser Val Leu Val Ala Leu Leu Ala Gly Gln Ala Thr Thr Ala Tyr
 50                  55                  60

Phe Leu Tyr Gln Gln Gln Gly Arg Leu Asp Lys Leu Thr Val Thr Ser
 65                  70                  75                  80

Gln Asn Leu Gln Leu Glu Ser Leu Arg Met Lys Leu Pro Lys Pro Pro
                     85                  90                  95

Lys Pro Leu Ser Lys Met Arg Val Ala Thr Pro Met Met Met Gln Ala
                    100                 105                 110

Leu Pro Ile Gln Ser Leu Pro Gln Gly Ser Ile Lys Arg Asp His Asn
                    115                 120                 125

Asp Tyr Ser Lys Asn Pro Met Arg Ile Val Leu Tyr Val Gly Thr Trp
                    130                 135                 140

Ser Val Tyr His Lys Val Asp Pro Tyr Thr Ile Glu Asp Ile Asp Pro
145                 150                 155                 160

Phe Lys Ser Thr His Leu Met Tyr Gly Phe Ala Lys Ile Asp Glu Tyr
                    165                 170                 175

Lys Tyr Thr Ile Gln Val Phe Asp Pro Tyr Gln Asp Asp Asn His Asn
                    180                 185                 190

Ser Trp Glu Lys Arg Gly Tyr Glu Arg Phe Asn Asn Leu Arg Leu Lys
                    195                 200                 205

Asn Pro Glu Leu Thr Thr Met Ile Ser Leu Gly Gly Trp Tyr Glu Gly
210                 215                 220

Ser Glu Lys Tyr Ser Asp Met Ala Ala Asn Pro Thr Tyr Arg Gln Gln
225                 230                 235                 240

Phe Ile Gln Ser Val Leu Asp Phe Leu Gln Glu Tyr Lys Phe Asp Gly
                    245                 250                 255

Leu Asp Leu Asp Trp Glu Tyr Pro Gly Ser Arg Leu Gly Asn Pro Lys
                    260                 265                 270

Ile Asp Lys Gln Asn Tyr Leu Ala Leu Val Arg Glu Leu Lys Asp Ala
                    275                 280                 285

Phe Glu Pro His Gly Tyr Leu Leu Thr Ala Ala Val Ser Pro Gly Lys
                    290                 295                 300

Asp Lys Ile Asp Arg Ala Tyr Asp Ile Lys Glu Leu Asn Lys Leu Phe
305                 310                 315                 320

Asp Trp Met Asn Val Met Thr Tyr Asp Tyr His Gly Gly Trp Glu Asn
                    325                 330                 335

Phe Tyr Gly His Asn Ala Pro Leu Tyr Lys Arg Pro Asp Glu Thr Asp
                    340                 345                 350

Glu Leu His Thr Tyr Phe Asn Val Asn Tyr Thr Met His Tyr Tyr Leu
                    355                 360                 365

Asn Asn Gly Ala Thr Arg Asp Lys Leu Val Met Gly Val Pro Phe Tyr
                    370                 375                 380

Gly Arg Ala Trp Ser Ile Glu Asp Arg Ser Lys Leu Lys Leu Gly Asp
385                 390                 395                 400

Pro Ala Lys Gly Met Ser Pro Gly Phe Ile Ser Gly Glu Glu Gly
                    405                 410                 415

Val Leu Ser Tyr Ile Glu Leu Ser Gln Leu Phe Gln Lys Glu Glu Trp
                    420                 425                 430

His Ile Gln Tyr Asp Glu Tyr Tyr Asn Ala Pro Tyr Gly Tyr Asn Asp
                    435                 440                 445

Lys Ile Trp Val Gly Tyr Asp Asp Leu Ala Ser Ile Ser Ser Lys Leu
                    450                 455                 460
```

```
Ala Phe Leu Lys Glu Leu Gly Val Ser Gly Val Met Val Trp Ser Leu
465                 470                 475                 480

Glu Asn Asp Asp Phe Lys Gly His Leu Gly Pro Lys Asn Pro Leu Leu
            485                 490                 495

Asn Lys Val His Asn Met Ile Asn Gly Asp Glu Lys Asn Ser Phe Glu
            500                 505                 510

Ile Ile Leu Gly Pro Ser Thr Thr Thr Pro Thr Pro Thr Thr Thr Pro
            515                 520                 525

Thr Thr Pro Thr Thr Thr Pro Thr Thr Pro Ser Pro Thr Thr Pro Thr
            530                 535                 540

Thr Thr Pro Ser Pro Thr Thr Pro Thr Thr Pro Ser Pro Thr Thr
545                 550                 555                 560

Pro Thr Thr Thr Pro Ser Pro Thr Thr Pro Thr Pro Thr Thr Pro Thr
                565                 570                 575

Pro Ala Pro Thr Thr Ser Thr Pro Ser Pro Thr Thr Thr Glu His Thr
            580                 585                 590

Ser Glu Thr Pro Lys Tyr Thr Thr Tyr Val Asp Gly His Leu Ile Lys
            595                 600                 605

Ser Tyr Lys Glu Gly Asp Ile Pro His Pro Thr Asn Ile His Lys Tyr
            610                 615                 620

Leu Val Ile Glu Phe Val Asn Gly Gly Trp Trp Val His Ile Met Pro
625                 630                 635                 640

Ser Pro Pro Gly Thr Ile Trp Ser Gln Glu Lys Leu Thr Ser Ile Gly
                645                 650                 655

Glu

<210> SEQ ID NO 60
<211> LENGTH: 606
<212> TYPE: PRT
<213> ORGANISM: Artificial sequence
<220> FEATURE:
<223> OTHER INFORMATION: IMAT_NTERM Dog from I7HDR2 Zen 1 protein
      Dermatophagoides farinae (American house dust mite)

<400> SEQUENCE: 60

Met His His His His His Tyr Gly Arg Lys Lys Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
            35                  40                  45

Gly Ala Leu Tyr Thr Gly Phe Ser Val Leu Val Ala Leu Leu Leu Ala
        50                  55                  60

Gly Gln Ala Thr Thr Ala Tyr Phe Leu Tyr Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
            115                 120                 125

Asn Pro Arg Phe Lys Arg Asp Asn Arg Asp Asp Val Leu Lys Gln Thr
        130                 135                 140

Glu Glu Leu Ile Lys Ser Ala Gln Asp Val Leu Glu Lys Leu Pro Asp
145                 150                 155                 160
```

-continued

```
Ser Asp Leu Lys Asp Glu Ile Ala Glu Lys Leu Ala Thr Met Lys His
            165                 170                 175

Tyr Lys His Glu Leu Glu Asn Ala Lys Asn Pro Ile Lys Ile Ala His
            180                 185                 190

Phe Glu Leu Glu Leu Leu Thr Met Phe Lys Lys Phe Gln Ser Leu Leu
            195                 200                 205

Asn Glu Ala Asn Glu Ile Ile Lys Ser Leu Thr Thr Thr Thr Thr Glu
            210                 215                 220

Pro Thr Thr Pro Thr Pro Glu Pro Thr Thr Thr Thr Pro Glu Pro Thr
225                 230                 235                 240

Thr Lys Thr Pro Glu Pro Thr Thr Lys Thr Pro Glu Pro Thr Thr Pro
            245                 250                 255

Thr Pro Glu Pro Thr Thr Lys Thr Pro Glu Pro Thr Thr Lys Thr Pro
            260                 265                 270

Glu Pro Thr Thr Pro Thr Pro Glu Pro Thr Thr Lys Thr Pro Glu Pro
            275                 280                 285

Thr Thr Pro Thr Pro Glu Pro Thr Thr Lys Thr Pro Glu Pro Thr Thr
            290                 295                 300

Lys Thr Pro Glu Pro Ser Thr Pro Thr Pro Glu Pro Thr Thr Lys Thr
305                 310                 315                 320

Pro Glu Pro Thr Thr Lys Thr Pro Glu Pro Ser Thr Pro Thr Pro Glu
            325                 330                 335

Pro Thr Thr Lys Thr Pro Glu Pro Ser Thr Pro Thr Pro Glu Pro Thr
            340                 345                 350

Thr Lys Thr Pro Glu Pro Thr Thr Lys Thr Pro Glu Pro Ser Thr Pro
            355                 360                 365

Thr Pro Glu Pro Thr Thr Lys Thr Pro Glu Pro Ser Thr Pro Thr Pro
            370                 375                 380

Glu Pro Thr Thr Lys Thr Pro Glu Pro Ser Thr Lys Lys Pro Asn
385                 390                 395                 400

Arg Asp Asp Val Leu Lys Gln Ala Glu Glu Leu Ile Lys Arg Ala Glu
            405                 410                 415

Asp Val Phe Glu Lys Leu Pro Asp Ser Asp Leu Lys Asn Glu Ile Ala
            420                 425                 430

Glu Lys Leu Ala Thr Met Lys Asn Tyr Lys His Glu Leu Glu Asn Ala
            435                 440                 445

Lys Asn Pro Ile Lys Ile Ala His Leu Glu Ser Glu Leu Leu Thr Met
450                 455                 460

Phe Lys Met Phe Gln Ser Leu Leu Asn Glu Ala Asp Glu Ile Ile Arg
465                 470                 475                 480

Ser Leu Thr Thr Thr Thr Glu Pro Thr Thr Leu Asn Ser Thr Thr Pro
            485                 490                 495

Glu Pro Thr Thr Leu Asn Ser Thr Thr Pro Glu Pro Thr Thr Leu Asn
            500                 505                 510

Ser Thr Thr Pro Glu Pro Thr Thr Leu Asn Ser Thr Thr Pro Glu Pro
            515                 520                 525

Thr Thr Leu Asn Ser Thr Thr Pro Glu Pro Thr Thr Leu Asn Ser Thr
            530                 535                 540

Thr Pro Glu Pro Thr Thr Leu Asn Ser Thr Thr Pro Glu Pro Thr Thr
545                 550                 555                 560

Leu Asn Ser Thr Thr Pro Glu Pro Thr Thr Ser Asn Ser Thr Thr Ser
            565                 570                 575
```

```
Glu Pro Thr Asn Ser Ile Asn Arg Lys Thr Ser Glu Ile Ser Phe Leu
                580                 585                 590

Ser Asp Trp Phe His Lys Ile Arg Thr Arg Phe Asn Ile Phe
            595                 600                 605

<210> SEQ ID NO 61
<211> LENGTH: 606
<212> TYPE: PRT
<213> ORGANISM: Artificial sequence
<220> FEATURE:
<223> OTHER INFORMATION: IMAT_CTERM Dog from I7HDR2 Zen 1 protein
      Dermatophagoides farinae (American house dust mite)

<400> SEQUENCE: 61

Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Ser Arg Gly Ala Leu Tyr Thr Gly
                35                  40                  45

Phe Ser Val Leu Val Ala Leu Leu Ala Gly Gln Ala Thr Thr Ala
        50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
                100                 105                 110

Ala Leu Pro Ile Gln Ser Leu Pro Gln Gly Asn Pro Arg Phe Lys Arg
                115                 120                 125

Asp Asn Arg Asp Asp Val Leu Lys Gln Thr Glu Glu Leu Ile Lys Ser
                130                 135                 140

Ala Gln Asp Val Leu Glu Lys Leu Pro Asp Ser Asp Leu Lys Asp Glu
145                 150                 155                 160

Ile Ala Glu Lys Leu Ala Thr Met Lys His Tyr Lys His Glu Leu Glu
                165                 170                 175

Asn Ala Lys Asn Pro Ile Lys Ile Ala His Phe Glu Leu Glu Leu Leu
                180                 185                 190

Thr Met Phe Lys Lys Phe Gln Ser Leu Leu Asn Glu Ala Asn Glu Ile
                195                 200                 205

Ile Lys Ser Leu Thr Thr Thr Thr Thr Glu Pro Thr Thr Pro Thr Pro
210                 215                 220

Glu Pro Thr Thr Thr Thr Pro Glu Pro Thr Thr Lys Thr Pro Glu Pro
225                 230                 235                 240

Thr Thr Lys Thr Pro Glu Pro Thr Thr Pro Thr Pro Glu Pro Thr Thr
                245                 250                 255

Lys Thr Pro Glu Pro Thr Thr Lys Thr Pro Glu Pro Thr Thr Pro Thr
                260                 265                 270

Pro Glu Pro Thr Thr Lys Thr Pro Glu Pro Thr Thr Pro Thr Pro Glu
                275                 280                 285

Pro Thr Thr Lys Thr Pro Glu Pro Thr Thr Lys Thr Pro Glu Pro Ser
                290                 295                 300

Thr Pro Thr Pro Glu Pro Thr Thr Lys Thr Pro Glu Pro Thr Thr Lys
305                 310                 315                 320

Thr Pro Glu Pro Ser Thr Pro Thr Pro Glu Pro Thr Thr Lys Thr Pro
                325                 330                 335
```

-continued

```
Glu Pro Ser Thr Pro Thr Pro Glu Pro Thr Thr Lys Thr Pro Glu Pro
                340                 345                 350
Thr Thr Lys Thr Pro Glu Pro Ser Thr Pro Thr Pro Glu Pro Thr Thr
            355                 360                 365
Lys Thr Pro Glu Pro Ser Thr Pro Thr Pro Glu Pro Thr Thr Lys Thr
        370                 375                 380
Pro Glu Pro Ser Thr Thr Lys Lys Pro Asn Arg Asp Val Leu Lys
385                 390                 395                 400
Gln Ala Glu Glu Leu Ile Lys Arg Ala Glu Asp Val Phe Glu Lys Leu
                405                 410                 415
Pro Asp Ser Asp Leu Lys Asn Glu Ile Ala Glu Lys Leu Ala Thr Met
            420                 425                 430
Lys Asn Tyr Lys His Glu Leu Glu Asn Ala Lys Asn Pro Ile Lys Ile
        435                 440                 445
Ala His Leu Glu Ser Glu Leu Leu Thr Met Phe Lys Met Phe Gln Ser
    450                 455                 460
Leu Leu Asn Glu Ala Asp Glu Ile Ile Arg Ser Leu Thr Thr Thr Thr
465                 470                 475                 480
Glu Pro Thr Thr Leu Asn Ser Thr Thr Pro Glu Pro Thr Thr Leu Asn
                485                 490                 495
Ser Thr Thr Pro Glu Pro Thr Thr Leu Asn Ser Thr Thr Pro Glu Pro
            500                 505                 510
Thr Thr Leu Asn Ser Thr Thr Pro Glu Pro Thr Thr Leu Asn Ser Thr
        515                 520                 525
Thr Pro Glu Pro Thr Thr Leu Asn Ser Thr Thr Pro Glu Pro Thr Thr
    530                 535                 540
Leu Asn Ser Thr Thr Pro Glu Pro Thr Thr Leu Asn Ser Thr Thr Pro
545                 550                 555                 560
Glu Pro Thr Thr Ser Asn Ser Thr Thr Ser Glu Pro Thr Asn Ser Ile
                565                 570                 575
Asn Arg Lys Thr Ser Glu Ile Ser Phe Leu Ser Asp Trp Phe His Lys
            580                 585                 590
Ile Arg Thr Arg Phe Asn Ile Phe His His His His His
        595                 600                 605
```

<210> SEQ ID NO 62
<211> LENGTH: 599
<212> TYPE: PRT
<213> ORGANISM: Artificial sequence
<220> FEATURE:
<223> OTHER INFORMATION: IMAT_PURE Dog from I7HDR2 Zen 1 protein
      Dermatophagoides farinae (American house dust mite)

<400> SEQUENCE: 62

```
Tyr Gly Arg Lys Lys Arg Arg Gln Arg Arg Met Glu Asp Gln Arg
1               5                   10                  15
Asp Leu Ile Ser Asn His Glu Gln Leu Pro Ile Leu Gly Gln Arg Pro
                20                  25                  30
Gly Ala Pro Glu Ser Lys Ser Ser Arg Gly Ala Leu Tyr Thr Gly Phe
            35                  40                  45
Ser Val Leu Val Ala Leu Leu Ala Gly Gln Ala Thr Thr Ala Tyr
        50                  55                  60
Phe Leu Tyr Gln Gln Gln Gly Arg Leu Asp Lys Leu Thr Val Thr Ser
65                  70                  75                  80
Gln Asn Leu Gln Leu Glu Ser Leu Arg Met Lys Leu Pro Lys Pro Pro
```

-continued

```
                85                  90                  95
Lys Pro Leu Ser Lys Met Arg Val Ala Thr Pro Met Met Gln Ala
            100                 105                 110
Leu Pro Ile Gln Ser Leu Pro Gln Gly Asn Pro Arg Phe Lys Arg Asp
            115                 120                 125
Asn Arg Asp Asp Val Leu Lys Gln Thr Glu Glu Leu Ile Lys Ser Ala
130                 135                 140
Gln Asp Val Leu Glu Lys Leu Pro Asp Ser Asp Leu Lys Asp Glu Ile
145                 150                 155                 160
Ala Glu Lys Leu Ala Thr Met Lys His Tyr Lys His Glu Leu Glu Asn
                165                 170                 175
Ala Lys Asn Pro Ile Lys Ile Ala His Phe Glu Leu Glu Leu Leu Thr
                180                 185                 190
Met Phe Lys Lys Phe Gln Ser Leu Leu Asn Glu Ala Asn Glu Ile Ile
                195                 200                 205
Lys Ser Leu Thr Thr Thr Thr Thr Glu Pro Thr Thr Pro Thr Pro Glu
            210                 215                 220
Pro Thr Thr Thr Thr Pro Glu Pro Thr Thr Lys Thr Pro Glu Pro Thr
225                 230                 235                 240
Thr Lys Thr Pro Glu Pro Thr Thr Pro Thr Pro Glu Pro Thr Thr Lys
                245                 250                 255
Thr Pro Glu Pro Thr Thr Lys Thr Pro Glu Pro Thr Thr Pro Thr Pro
            260                 265                 270
Glu Pro Thr Thr Lys Thr Pro Glu Pro Thr Thr Pro Thr Pro Glu Pro
            275                 280                 285
Thr Thr Lys Thr Pro Glu Pro Thr Thr Lys Thr Pro Glu Pro Ser Thr
            290                 295                 300
Pro Thr Pro Glu Pro Thr Thr Lys Thr Pro Glu Pro Thr Thr Lys Thr
305                 310                 315                 320
Pro Glu Pro Ser Thr Pro Thr Pro Glu Pro Thr Thr Lys Thr Pro Glu
                325                 330                 335
Pro Ser Thr Pro Thr Pro Glu Pro Thr Thr Lys Thr Pro Glu Pro Thr
            340                 345                 350
Thr Lys Thr Pro Glu Pro Ser Thr Pro Thr Pro Glu Pro Thr Thr Lys
            355                 360                 365
Thr Pro Glu Pro Ser Thr Pro Glu Pro Thr Thr Lys Thr Pro
            370                 375                 380
Glu Pro Ser Thr Thr Lys Lys Pro Asn Arg Asp Asp Val Leu Lys Gln
385                 390                 395                 400
Ala Glu Glu Leu Ile Lys Arg Ala Glu Asp Val Phe Glu Lys Leu Pro
                405                 410                 415
Asp Ser Asp Leu Lys Asn Glu Ile Ala Glu Lys Leu Ala Thr Met Lys
            420                 425                 430
Asn Tyr Lys His Glu Leu Glu Asn Ala Lys Asn Pro Ile Lys Ile Ala
            435                 440                 445
His Leu Glu Ser Glu Leu Leu Thr Met Phe Lys Met Phe Gln Ser Leu
    450                 455                 460
Leu Asn Glu Ala Asp Glu Ile Ile Arg Ser Leu Thr Thr Thr Thr Glu
465                 470                 475                 480
Pro Thr Thr Leu Asn Ser Thr Thr Pro Glu Pro Thr Thr Leu Asn Ser
            485                 490                 495
Thr Thr Pro Glu Pro Thr Thr Leu Asn Ser Thr Thr Pro Glu Pro Thr
            500                 505                 510
```

```
Thr Leu Asn Ser Thr Thr Pro Glu Pro Thr Thr Leu Asn Ser Thr Thr
        515                 520                 525

Pro Glu Pro Thr Thr Leu Asn Ser Thr Thr Pro Glu Pro Thr Thr Leu
    530                 535                 540

Asn Ser Thr Thr Pro Glu Pro Thr Thr Leu Asn Ser Thr Thr Pro Glu
545                 550                 555                 560

Pro Thr Thr Ser Asn Ser Thr Thr Ser Glu Pro Thr Asn Ser Ile Asn
                565                 570                 575

Arg Lys Thr Ser Glu Ile Ser Phe Leu Ser Asp Trp Phe His Lys Ile
                580                 585                 590

Arg Thr Arg Phe Asn Ile Phe
        595

<210> SEQ ID NO 63
<211> LENGTH: 286
<212> TYPE: PRT
<213> ORGANISM: Artificial sequence
<220> FEATURE:
<223> OTHER INFORMATION: IMAT_NTERM Dog from Q94424 Salivary antigen 1
      (FS-I) (allergen Cte f 1) Ctenocephalides felis (Cat flea)

<400> SEQUENCE: 63

Met His His His His His His Tyr Gly Arg Lys Lys Arg Gln Arg
1               5                   10                  15

Arg Arg Met Glu Asp Gln Arg Asp Leu Ile Ser Asn His Glu Gln Leu
                20                  25                  30

Pro Ile Leu Gly Gln Arg Pro Gly Ala Pro Glu Ser Lys Arg Ser Arg
            35                  40                  45

Gly Ala Leu Tyr Thr Gly Phe Ser Val Leu Val Ala Leu Leu Leu Ala
        50                  55                  60

Gly Gln Ala Thr Thr Ala Tyr Phe Leu Tyr Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
                100                 105                 110

Thr Pro Met Met Met Gln Ala Leu Pro Ile Gln Ser Leu Pro Gln Gly
            115                 120                 125

Glu Asp Ile Trp Lys Val Asn Lys Lys Arg Thr Ser Gly Gly Lys Asn
    130                 135                 140

Gln Asp Arg Lys Leu Asp Gln Ile Ile Gln Lys Gly Gln Gln Val Lys
145                 150                 155                 160

Ile Gln Asn Ile Leu Lys Leu Ile Arg Asp Lys Pro His Thr Asn Gln
                165                 170                 175

Glu Lys Glu Lys Leu Met Lys Phe Leu Lys Lys Val Leu Lys Gly Tyr
            180                 185                 190

Arg Gly Ala Arg Asp Gly Asn Ile Leu Tyr Leu Ser Arg Pro Ser Asn
        195                 200                 205

Leu Gly Pro Asp Trp Lys Val Ser Lys Glu Arg Lys Asp Pro Asn Asn
    210                 215                 220

Lys Asp Ser Arg Pro Thr Glu Ile Val Pro Tyr Arg Gln Gln Leu Ala
225                 230                 235                 240

Ile Pro Asn Ile Leu Lys Leu Lys Asn Ser Glu Thr Asn Glu Asp Ser
                245                 250                 255

Lys Leu Lys Lys His Met Lys Glu Lys Ser Arg Gly Gly Asn Asp Ala
```

```
                260                 265                 270
Gly Ile Asp Gly Asn Phe Leu Tyr Leu Arg Pro Lys Asn Lys
            275                 280                 285

<210> SEQ ID NO 64
<211> LENGTH: 286
<212> TYPE: PRT
<213> ORGANISM: Artificial sequence
<220> FEATURE:
<223> OTHER INFORMATION: IMAT_CTERM Dog from Q94424 Salivary antigen 1
      (FS-I) (allergen Cte f 1) Ctenocephalides felis (Cat flea)

<400> SEQUENCE: 64

Met Tyr Gly Arg Lys Lys Arg Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Arg Ser Arg Gly Ala Leu Tyr Thr Gly
        35                  40                  45

Phe Ser Val Leu Val Ala Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
                85                  90                  95

Pro Lys Pro Leu Ser Lys Met Arg Val Ala Thr Pro Met Met Met Gln
            100                 105                 110

Ala Leu Pro Ile Gln Ser Leu Pro Gln Gly Glu Asp Ile Trp Lys Val
        115                 120                 125

Asn Lys Lys Arg Thr Ser Gly Gly Lys Asn Gln Asp Arg Lys Leu Asp
130                 135                 140

Gln Ile Ile Gln Lys Gly Gln Gln Val Lys Ile Gln Asn Ile Leu Lys
145                 150                 155                 160

Leu Ile Arg Asp Lys Pro His Thr Asn Gln Glu Lys Glu Lys Leu Met
                165                 170                 175

Lys Phe Leu Lys Lys Val Leu Lys Gly Tyr Arg Gly Ala Arg Asp Gly
            180                 185                 190

Asn Ile Leu Tyr Leu Ser Arg Pro Ser Asn Leu Gly Pro Asp Trp Lys
        195                 200                 205

Val Ser Lys Glu Arg Lys Asp Pro Asn Asn Lys Asp Ser Arg Pro Thr
210                 215                 220

Glu Ile Val Pro Tyr Arg Gln Gln Leu Ala Ile Pro Asn Ile Leu Lys
225                 230                 235                 240

Leu Lys Asn Ser Glu Thr Asn Glu Asp Ser Lys Leu Lys Lys His Met
                245                 250                 255

Lys Glu Lys Ser Arg Gly Gly Asn Asp Ala Gly Ile Asp Gly Asn Phe
            260                 265                 270

Leu Tyr Leu Arg Pro Lys Asn Lys His His His His His His
        275                 280                 285

<210> SEQ ID NO 65
<211> LENGTH: 279
<212> TYPE: PRT
<213> ORGANISM: Artificial sequence
<220> FEATURE:
<223> OTHER INFORMATION: IMAT_PURE Dog from Q94424 Salivary antigen 1
      (FS-I) (allergen Cte f 1) Ctenocephalides felis (Cat flea)
```

<400> SEQUENCE: 65

```
Tyr Gly Arg Lys Lys Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Gly Ala Pro Glu Ser Lys Arg Ser Arg Gly Ala Leu Tyr Thr Gly Phe
            35                  40                  45

Ser Val Leu Val Ala Leu Leu Leu Ala Gly Gln Ala Thr Thr Ala Tyr
        50                  55                  60

Phe Leu Tyr Gln Gln Gln Gly Arg Leu Asp Lys Leu Thr Val Thr Ser
65                  70                  75                  80

Gln Asn Leu Gln Leu Glu Ser Leu Arg Met Lys Leu Pro Lys Pro Pro
                85                  90                  95

Lys Pro Leu Ser Lys Met Arg Val Ala Thr Pro Met Met Met Gln Ala
            100                 105                 110

Leu Pro Ile Gln Ser Leu Pro Gln Gly Glu Asp Ile Trp Lys Val Asn
        115                 120                 125

Lys Lys Arg Thr Ser Gly Gly Lys Asn Gln Asp Arg Lys Leu Asp Gln
    130                 135                 140

Ile Ile Gln Lys Gly Gln Gln Val Lys Ile Gln Asn Ile Leu Lys Leu
145                 150                 155                 160

Ile Arg Asp Lys Pro His Thr Asn Gln Glu Lys Glu Lys Leu Met Lys
                165                 170                 175

Phe Leu Lys Lys Val Leu Lys Gly Tyr Arg Gly Ala Arg Asp Gly Asn
            180                 185                 190

Ile Leu Tyr Leu Ser Arg Pro Ser Asn Leu Gly Pro Asp Trp Lys Val
        195                 200                 205

Ser Lys Glu Arg Lys Asp Pro Asn Asn Lys Asp Ser Arg Pro Thr Glu
    210                 215                 220

Ile Val Pro Tyr Arg Gln Gln Leu Ala Ile Pro Asn Ile Leu Lys Leu
225                 230                 235                 240

Lys Asn Ser Glu Thr Asn Glu Asp Ser Lys Leu Lys Lys His Met Lys
                245                 250                 255

Glu Lys Ser Arg Gly Gly Asn Asp Ala Gly Ile Asp Gly Asn Phe Leu
            260                 265                 270

Tyr Leu Arg Pro Lys Asn Lys
        275
```

<210> SEQ ID NO 66
<211> LENGTH: 511
<212> TYPE: PRT
<213> ORGANISM: Artificial sequence
<220> FEATURE:
<223> OTHER INFORMATION: IMAT_NTERM Cat Hybrid1

<400> SEQUENCE: 66

```
Met His His His His His Tyr Gly Arg Lys Lys Arg Gln Arg
1               5                   10                  15

Arg Arg Met Glu Asp Gln Arg Asp Leu Ile Ser Asn His Glu Gln Leu
                20                  25                  30

Pro Ile Leu Gly Gln Arg Pro Ala Ala Pro Glu Ser Lys Ser Ser Arg
            35                  40                  45

Gly Ala Leu Tyr Thr Gly Phe Ser Val Leu Val Ala Leu Leu Leu Ala
        50                  55                  60

Gly Gln Ala Thr Thr Ala Tyr Phe Leu Tyr Gln Gln Gln Gly Arg Leu
```

```
            65                  70                  75                  80
Asp Lys Leu Thr Val Thr Ala Gln Asn Leu Gln Leu Glu Asn Leu Arg
                    85                  90                  95

Met Lys Leu Pro Lys Pro Ala Lys Pro Leu Asn Lys Leu Arg Val Ala
                100                 105                 110

Thr Pro Met Leu Met Gln Thr Met Pro Val Arg Gly Leu Leu Gln Ala
                115                 120                 125

Gln Ser His Gln Tyr Tyr His Thr Ser Gly Leu Arg Asn Leu Gly Gly
            130                 135                 140

Ser Tyr Tyr Arg Ser Gly Asn Ala Lys Ala Met Ile Ala Val Gly Gly
145                 150                 155                 160

Ser Thr Met Ile Val Asp Gly Asp Lys Val Thr Ile Tyr Gly Trp Gly
                165                 170                 175

Ser Gly Leu Gly Tyr Gly Leu Gly Tyr Gly Leu Gly Tyr Gly Gln Ala
            180                 185                 190

Val Ala Leu Ala Pro Ala Gln Ala Val Gly Tyr Val Ala Ala Ala Pro
            195                 200                 205

Ala Val Ala Val Gln Ala Pro Ala Val Ser Tyr Ala Ala Ala Ala Pro
210                 215                 220

Ala Val Gln Thr Val Ala Val Gln Ala Pro Ala Val Ser Tyr Ala Ala
225                 230                 235                 240

Ala Pro Ala Val Ala Val Gln Ala His Thr Ala Gln Val Ser Gly Pro
                245                 250                 255

Ile His Ala Ala Ile Glu Ser Arg Arg Thr Val Glu Val Ile Asp Gly
            260                 265                 270

Pro Ser Thr Gly Asp Ala Pro Val Ala Ser Thr Val Ile Gly Pro
            275                 280                 285

Asn Val Gln Pro Ile Asn Leu Glu Phe Gln Thr Gln Ala Ser Pro Leu
            290                 295                 300

Ala Ala Thr Gln Asn His Val Pro Thr Thr Pro Thr Thr Pro Thr Pro
305                 310                 315                 320

Ala Pro Thr Thr Ser Thr Pro Asp Leu Leu Arg Gln Asp Ile Val Lys
                325                 330                 335

Pro Val Val Gln Asp Val His Glu Phe Leu Val Tyr Ile His Ile Ala
                340                 345                 350

Asn Asn Glu Ile Lys Lys Val Gln Glu Ser Val His Gln Ile Leu Pro
            355                 360                 365

Arg Gly Gln Met Met Lys Ile Tyr Gln Gln Gln Gln Gln His His
            370                 375                 380

Pro Gln Arg Glu Glu Asn Ile Trp Ser Asp His Ile Ala Asn Val Ala
385                 390                 395                 400

Gln Ala Ala Pro Ala Ile Ser Ala Val Arg Val Ala Ala Pro Ala
                405                 410                 415

Val Ala Tyr Ala Ala Pro Ala Val Ser Thr Val Ser Ala Ala Pro Ala
                420                 425                 430

Ala Ile Gly Val Ile Gly Val Gln Pro Val Ala Gly Tyr Ile Gly Tyr
            435                 440                 445

Gly Ala Gly Tyr Gly Thr Gly Tyr Gly Thr Gly Tyr Gly Val Ala Lys
            450                 455                 460

Tyr Gly Thr Gly Tyr Gly Leu Thr Ser Gly Leu Ile Gly Gly Ser
465                 470                 475                 480

Tyr Gly Ser Ser Tyr Ser Val Gln Pro Ala Ser Tyr Gly Thr Gly Tyr
                485                 490                 495
```

```
Gly Tyr Thr Thr Tyr Ser Ser Asp Ala Tyr Pro Ile Arg Lys Lys
            500                 505                 510
```

<210> SEQ ID NO 67
<211> LENGTH: 511
<212> TYPE: PRT
<213> ORGANISM: Artificial sequence
<220> FEATURE:
<223> OTHER INFORMATION: IMAT_CTERM Cat Hybrid1

<400> SEQUENCE: 67

```
Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
                20                  25                  30

Pro Ala Ala Pro Glu Ser Lys Ser Ser Arg Gly Ala Leu Tyr Thr Gly
            35                  40                  45

Phe Ser Val Leu Val Ala Leu Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Gln Ser His Gln Tyr Tyr
        115                 120                 125

His Thr Ser Gly Leu Arg Asn Leu Gly Gly Ser Tyr Tyr Arg Ser Gly
    130                 135                 140

Asn Ala Lys Ala Met Ile Ala Val Gly Gly Ser Thr Met Ile Val Asp
145                 150                 155                 160

Gly Asp Lys Val Thr Ile Tyr Gly Trp Gly Ser Gly Leu Gly Tyr Gly
                165                 170                 175

Leu Gly Tyr Gly Leu Gly Tyr Gly Gln Ala Val Ala Leu Ala Pro Ala
            180                 185                 190

Gln Ala Val Gly Tyr Val Ala Ala Pro Ala Val Ala Val Gln Ala
        195                 200                 205

Pro Ala Val Ser Tyr Ala Ala Ala Pro Ala Val Gln Thr Val Ala
    210                 215                 220

Val Gln Ala Pro Ala Val Ser Tyr Ala Ala Pro Ala Val Ala Val
225                 230                 235                 240

Gln Ala His Thr Ala Gln Val Ser Gly Pro Ile His Ala Ala Ile Glu
                245                 250                 255

Ser Arg Arg Thr Val Glu Val Ile Asp Gly Pro Ser Thr Gly Asp Ala
            260                 265                 270

Pro Val Ala Ser Thr Val Ile Gly Pro Asn Val Gln Pro Ile Asn
        275                 280                 285

Leu Glu Phe Gln Thr Gln Ala Ser Pro Leu Ala Ala Thr Gln Asn His
    290                 295                 300

Val Pro Thr Thr Pro Thr Thr Pro Thr Pro Ala Pro Thr Thr Ser Thr
305                 310                 315                 320

Pro Asp Leu Leu Arg Gln Asp Ile Val Lys Pro Val Val Gln Asp Val
                325                 330                 335

His Glu Phe Leu Val Tyr Ile His Ile Ala Asn Asn Glu Ile Lys Lys
            340                 345                 350
```

-continued

```
Val Gln Glu Ser Val His Gln Ile Leu Pro Arg Gly Gln Met Met Lys
            355                 360                 365

Ile Tyr Gln Gln Gln Gln Gln His His Pro Gln Arg Glu Glu Asn
        370                 375                 380

Ile Trp Ser Asp His Ile Ala Asn Val Ala Gln Ala Ala Pro Ala Ile
385                 390                 395                 400

Ser Ala Val Arg Val Ala Ala Pro Ala Val Ala Tyr Ala Ala Pro
                405                 410                 415

Ala Val Ser Thr Val Ser Ala Ala Pro Ala Ala Ile Gly Val Ile Gly
            420                 425                 430

Val Gln Pro Val Ala Gly Tyr Ile Gly Tyr Gly Ala Gly Tyr Gly Thr
            435                 440                 445

Gly Tyr Gly Thr Gly Tyr Gly Val Ala Lys Tyr Gly Thr Gly Tyr Gly
        450                 455                 460

Leu Thr Ser Gly Leu Ile Gly Gly Ser Tyr Gly Ser Ser Tyr Ser
465                 470                 475                 480

Val Gln Pro Ala Ser Tyr Gly Thr Gly Tyr Gly Tyr Thr Thr Tyr Ser
                485                 490                 495

Ser Asp Ala Tyr Pro Ile Arg Lys Lys His His His His His His
            500                 505                 510

<210> SEQ ID NO 68
<211> LENGTH: 504
<212> TYPE: PRT
<213> ORGANISM: Artificial sequence
<220> FEATURE:
<223> OTHER INFORMATION: Hybrid 1 iMAT molecule (cat) without tag

<400> SEQUENCE: 68

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Ala Ala Pro Glu Ser Lys Cys Ser Arg Gly Ala Leu Tyr Thr Gly Phe
            35                  40                  45

Ser Val Leu Val Ala Leu Leu Leu Ala Gly Gln Ala Thr Thr Ala Tyr
        50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
            100                 105                 110

Met Pro Val Arg Gly Leu Leu Gln Ala Gln Ser His Gln Tyr Tyr His
        115                 120                 125

Thr Ser Gly Leu Arg Asn Leu Gly Gly Ser Tyr Tyr Arg Ser Gly Asn
130                 135                 140

Ala Lys Ala Met Ile Ala Val Gly Gly Ser Thr Met Ile Val Asp Gly
145                 150                 155                 160

Asp Lys Val Thr Ile Tyr Gly Trp Gly Ser Gly Leu Tyr Gly Leu
                165                 170                 175

Gly Tyr Gly Leu Gly Tyr Gly Gln Ala Val Ala Leu Ala Pro Ala Gln
            180                 185                 190

Ala Val Gly Tyr Val Ala Ala Pro Ala Val Ala Val Gln Ala Pro
        195                 200                 205
```

```
Ala Val Ser Tyr Ala Ala Ala Pro Ala Val Gln Thr Val Ala Val
        210                 215                 220

Gln Ala Pro Ala Val Ser Tyr Ala Ala Pro Ala Val Ala Val Gln
225                 230                 235                 240

Ala His Thr Ala Gln Val Ser Gly Pro Ile His Ala Ala Ile Glu Ser
                245                 250                 255

Arg Arg Thr Val Glu Val Ile Asp Gly Pro Ser Thr Gly Asp Ala Pro
                260                 265                 270

Val Ala Ser Thr Val Val Ile Gly Pro Asn Val Gln Pro Ile Asn Leu
                275                 280                 285

Glu Phe Gln Thr Gln Ala Ser Pro Leu Ala Ala Thr Gln Asn His Val
                290                 295                 300

Pro Thr Thr Pro Thr Thr Pro Thr Pro Ala Pro Thr Thr Ser Thr Pro
305                 310                 315                 320

Asp Leu Leu Arg Gln Asp Ile Val Lys Pro Val Val Gln Asp Val His
                325                 330                 335

Glu Phe Leu Val Tyr Ile His Ile Ala Asn Asn Glu Ile Lys Lys Val
                340                 345                 350

Gln Glu Ser Val His Gln Ile Leu Pro Arg Gly Gln Met Met Lys Ile
                355                 360                 365

Tyr Gln Gln Gln Gln Gln His His Pro Gln Arg Glu Glu Asn Ile
                370                 375                 380

Trp Ser Asp His Ile Ala Asn Val Ala Gln Ala Ala Pro Ala Ile Ser
385                 390                 395                 400

Ala Val Arg Val Ala Ala Ala Pro Ala Val Ala Tyr Ala Ala Pro Ala
                405                 410                 415

Val Ser Thr Val Ser Ala Ala Pro Ala Ala Ile Gly Val Ile Gly Val
                420                 425                 430

Gln Pro Val Ala Gly Tyr Ile Gly Tyr Gly Ala Gly Tyr Gly Thr Gly
                435                 440                 445

Tyr Gly Thr Gly Tyr Gly Val Ala Lys Tyr Gly Thr Gly Tyr Gly Leu
                450                 455                 460

Thr Ser Gly Leu Ile Gly Gly Gly Ser Tyr Gly Ser Ser Tyr Ser Val
465                 470                 475                 480

Gln Pro Ala Ser Tyr Gly Thr Gly Tyr Gly Tyr Thr Thr Tyr Ser Ser
                485                 490                 495

Asp Ala Tyr Pro Ile Arg Lys Lys
                500

<210> SEQ ID NO 69
<211> LENGTH: 645
<212> TYPE: PRT
<213> ORGANISM: Artificial sequence
<220> FEATURE:
<223> OTHER INFORMATION: IMAT_NTERM Cat Hybrid2

<400> SEQUENCE: 69

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
                20                  25                  30

Pro Ile Leu Gly Gln Arg Pro Ala Ala Pro Glu Ser Lys Ser Ser Arg
            35                  40                  45

Gly Ala Leu Tyr Thr Gly Phe Ser Val Leu Val Ala Leu Leu Leu Ala
        50                  55                  60
```

```
Gly Gln Ala Thr Thr Ala Tyr Phe Leu Tyr Gln Gln Gly Arg Leu
 65                  70                  75                  80

Asp Lys Leu Thr Val Thr Ala Gln Asn Leu Gln Leu Glu Asn Leu Arg
             85                  90                  95

Met Lys Leu Pro Lys Pro Ala Lys Pro Leu Asn Lys Leu Arg Val Ala
            100                 105                 110

Thr Pro Met Leu Met Gln Thr Met Pro Val Arg Gly Leu Leu Gln Ala
            115                 120                 125

Thr Ser Ala Ser Arg Ile Asn Ser Val Asn Val Pro Ser Glu Leu Asp
            130                 135                 140

Leu Arg Ser Leu Arg Thr Val Thr Pro Ile Arg Met Gln Gly Gly Ser
145                 150                 155                 160

Gly Ser Ser Trp Ala Phe Ser Gly Val Ala Ala Thr Glu Ser Ala Tyr
                165                 170                 175

Leu Ala Tyr Arg Asn Thr Ser Leu Asp Leu Ser Glu Gln Glu Leu Val
                180                 185                 190

Asp Ser Ala Ser Gln His Gly Ser His Gly Asp Thr Ile Pro Arg Gly
            195                 200                 205

Ile Glu Tyr Ile Gln Gln Asn Gly Val Val Glu Arg Ser Tyr Pro
210                 215                 220

Tyr Val Ala Arg Glu Gln Gln Ser Arg Arg Pro Asn Ser Gln His Tyr
225                 230                 235                 240

Gly Ile Ser Asn Tyr Ser Gln Ile Tyr Pro Pro Asp Val Lys Gln Ile
                245                 250                 255

Arg Glu Ala Leu Thr Gln Thr His Thr Ala Ile Ala Val Ile Ile Gly
            260                 265                 270

Ile Lys Asp Leu Arg Ala Phe Gln His Tyr Asp Gly Arg Thr Ile Ile
            275                 280                 285

Gln His Asp Asn Gly Tyr Gln Pro Asn Tyr His Ala Val Asn Ile Val
            290                 295                 300

Gly Tyr Gly Ser Thr Gln Gly Val Asp Tyr Trp Ile Val Arg Asn Ser
305                 310                 315                 320

Trp Asp Thr Thr Trp Gly Asp Ser Gly Tyr Gly Tyr Phe Gln Ala Gly
                325                 330                 335

Asn Asn Leu Met Met Ile Glu Gln Tyr Pro Tyr Val Val Ile Met Phe
            340                 345                 350

Thr Gln Thr Asp Gly Phe Leu Ser Tyr Asn Glu Leu Ser Val Gln Ile
            355                 360                 365

Gln Ala Glu Thr Asn Ala Phe Thr Ile Thr Arg Glu Pro Thr Thr Pro
            370                 375                 380

Thr Pro Glu Pro Thr Thr Lys Thr Pro Glu Pro Thr Thr Lys Thr Pro
385                 390                 395                 400

Glu Pro Ser Thr Pro Thr Pro Glu Pro Thr Thr Lys Thr Pro Glu Pro
                405                 410                 415

Thr Thr Lys Asp Ile Asp His Asp Asp Pro Thr Thr Met Ile Asp
            420                 425                 430

Val Gln Thr Thr Thr Val Gln Pro Ser Asp Glu Phe Glu Ser Pro Thr
            435                 440                 445

Arg Phe Gly Tyr Phe Ala Asp Pro Lys Asp Pro Ile Lys Phe Tyr Ile
            450                 455                 460

Ser Ser Asn Trp Glu Ala Ile His Lys Ser Ser Pro Gly Asn Thr Arg
465                 470                 475                 480
```

```
Trp Asn Glu Lys Glu Leu Thr Ser Thr Ser Pro Thr Thr Pro Thr Thr
                485                 490                 495

Thr Pro Ser Pro Thr Thr Pro Thr Thr Thr Pro Ser Pro Thr Thr Pro
            500                 505                 510

Thr Thr Thr Pro Asp Gln Val Asp Val Lys Asp Leu Ala Asn Asn Glu
            515                 520                 525

Ile Lys Lys Val Met Val Asp Gly Ile His Gly Ser Asp Pro Ser Ile
    530                 535                 540

Ile His Arg Gly Lys Pro Phe Thr Leu Glu Ala Leu Phe Asp Ala Asn
545                 550                 555                 560

Gln Asn Thr Lys Thr Ala Lys Ile Glu Ile Lys Ala Ser Leu Asp Gly
                565                 570                 575

Leu Glu Ile Asp Val Pro Gly Ile Asp Thr Asn Ala Leu His Phe Met
            580                 585                 590

Lys Ile Pro Leu Val Lys Gly Gln Gln Tyr Asp Ile Lys Tyr Thr Trp
            595                 600                 605

Asn Val Pro Lys Ile Ala Pro Lys Ser Glu Asn Val Val Thr Val
    610                 615                 620

Lys Leu Ile Gly Asp Asn Gly Val Leu Ala Ser Ala Ile Ala Thr His
625                 630                 635                 640

Gly Lys Ile Arg Asp
            645

<210> SEQ ID NO 70
<211> LENGTH: 645
<212> TYPE: PRT
<213> ORGANISM: Artificial sequence
<220> FEATURE:
<223> OTHER INFORMATION: IMAT_CTERM Cat Hybrid2

<400> SEQUENCE: 70

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Ala Ala Pro Glu Ser Lys Ser Arg Gly Ala Leu Tyr Thr Gly
            35                  40                  45

Phe Ser Val Leu Val Ala Leu Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ala Gln Asn Leu Gln Leu Glu Asn Leu Arg Met Lys Leu Pro Lys Pro
                85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Thr Ser Ala Ser Arg Ile
            115                 120                 125

Asn Ser Val Asn Val Pro Ser Glu Leu Asp Leu Arg Ser Leu Arg Thr
    130                 135                 140

Val Thr Pro Ile Arg Met Gln Gly Gly Ser Gly Ser Ser Trp Ala Phe
145                 150                 155                 160

Ser Gly Val Ala Ala Thr Glu Ser Ala Tyr Leu Ala Tyr Arg Asn Thr
            165                 170                 175

Ser Leu Asp Leu Ser Glu Gln Glu Leu Val Asp Ser Ala Ser Gln His
            180                 185                 190
```

```
Gly Ser His Gly Asp Thr Ile Pro Arg Gly Ile Glu Tyr Ile Gln Gln
            195                 200                 205
Asn Gly Val Val Glu Glu Arg Ser Tyr Pro Tyr Val Ala Arg Glu Gln
210                 215                 220
Gln Ser Arg Arg Pro Asn Ser Gln His Tyr Gly Ile Ser Asn Tyr Ser
225                 230                 235                 240
Gln Ile Tyr Pro Pro Asp Val Lys Gln Ile Arg Glu Ala Leu Thr Gln
                245                 250                 255
Thr His Thr Ala Ile Ala Val Ile Ile Gly Ile Lys Asp Leu Arg Ala
            260                 265                 270
Phe Gln His Tyr Asp Gly Arg Thr Ile Ile Gln His Asp Asn Gly Tyr
        275                 280                 285
Gln Pro Asn Tyr His Ala Val Asn Ile Val Gly Tyr Gly Ser Thr Gln
    290                 295                 300
Gly Val Asp Tyr Trp Ile Val Arg Asn Ser Trp Asp Thr Thr Trp Gly
305                 310                 315                 320
Asp Ser Gly Tyr Gly Tyr Phe Gln Ala Gly Asn Asn Leu Met Met Ile
                325                 330                 335
Glu Gln Tyr Pro Tyr Val Val Ile Met Phe Thr Gln Thr Asp Gly Phe
            340                 345                 350
Leu Ser Tyr Asn Glu Leu Ser Val Gln Ile Gln Ala Glu Thr Asn Ala
        355                 360                 365
Phe Thr Ile Thr Arg Glu Pro Thr Thr Pro Thr Pro Glu Pro Thr Thr
    370                 375                 380
Lys Thr Pro Glu Pro Thr Thr Lys Thr Pro Glu Pro Ser Thr Pro Thr
385                 390                 395                 400
Pro Glu Pro Thr Thr Lys Thr Pro Glu Pro Thr Thr Lys Asp Ile Asp
                405                 410                 415
His Asp Asp Asp Pro Thr Thr Met Ile Asp Val Gln Thr Thr Thr Val
            420                 425                 430
Gln Pro Ser Asp Glu Phe Glu Ser Pro Thr Arg Phe Gly Tyr Phe Ala
        435                 440                 445
Asp Pro Lys Asp Pro Ile Lys Phe Tyr Ile Ser Ser Asn Trp Glu Ala
    450                 455                 460
Ile His Lys Ser Ser Pro Gly Asn Thr Arg Trp Asn Glu Lys Glu Leu
465                 470                 475                 480
Thr Ser Thr Ser Pro Thr Thr Pro Thr Thr Pro Ser Pro Thr Thr
                485                 490                 495
Pro Thr Thr Thr Pro Ser Pro Thr Thr Pro Thr Thr Thr Pro Asp Gln
            500                 505                 510
Val Asp Val Lys Asp Leu Ala Asn Asn Glu Ile Lys Lys Val Met Val
        515                 520                 525
Asp Gly Ile His Gly Ser Asp Pro Ser Ile Ile His Arg Gly Lys Pro
    530                 535                 540
Phe Thr Leu Glu Ala Leu Phe Asp Ala Asn Gln Asn Thr Lys Thr Ala
545                 550                 555                 560
Lys Ile Glu Ile Lys Ala Ser Leu Asp Gly Leu Glu Ile Asp Val Pro
                565                 570                 575
Gly Ile Asp Thr Asn Ala Leu His Phe Met Lys Ile Pro Leu Val Lys
            580                 585                 590
Gly Gln Gln Tyr Asp Ile Lys Tyr Thr Trp Asn Val Pro Lys Ile Ala
        595                 600                 605
Pro Lys Ser Glu Asn Val Val Val Thr Val Lys Leu Ile Gly Asp Asn
```

```
            610                 615                 620
Gly Val Leu Ala Ser Ala Ile Ala Thr His Gly Lys Ile Arg Asp His
625                 630                 635                 640

His His His His His
                645

<210> SEQ ID NO 71
<211> LENGTH: 638
<212> TYPE: PRT
<213> ORGANISM: Artificial sequence
<220> FEATURE:
<223> OTHER INFORMATION: Hybrid 2 iMAT molecule (cat) without tag

<400> SEQUENCE: 71

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
                20                  25                  30

Ala Ala Pro Glu Ser Lys Cys Ser Arg Gly Ala Leu Tyr Thr Gly Phe
            35                  40                  45

Ser Val Leu Val Ala Leu Leu Leu Ala Gly Gln Ala Thr Thr Ala Tyr
50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
                85                  90                  95

Lys Pro Leu Asn Lys Leu Arg Val Ala Thr Pro Met Leu Met Gln Thr
            100                 105                 110

Met Pro Val Arg Gly Leu Leu Gln Ala Thr Ser Ala Ser Arg Ile Asn
        115                 120                 125

Ser Val Asn Val Pro Ser Glu Leu Asp Leu Arg Ser Leu Arg Thr Val
    130                 135                 140

Thr Pro Ile Arg Met Gln Gly Gly Ser Gly Ser Ser Trp Ala Phe Ser
145                 150                 155                 160

Gly Val Ala Ala Thr Glu Ser Ala Tyr Leu Ala Tyr Arg Asn Thr Ser
                165                 170                 175

Leu Asp Leu Ser Glu Gln Glu Leu Val Asp Ser Ala Ser Gln His Gly
            180                 185                 190

Ser His Gly Asp Thr Ile Pro Arg Gly Ile Glu Tyr Ile Gln Gln Asn
        195                 200                 205

Gly Val Val Glu Glu Arg Ser Tyr Pro Tyr Val Ala Arg Glu Gln Gln
    210                 215                 220

Ser Arg Arg Pro Asn Ser Gln His Tyr Gly Ile Ser Asn Tyr Ser Gln
225                 230                 235                 240

Ile Tyr Pro Pro Asp Val Lys Gln Ile Arg Glu Ala Leu Thr Gln Thr
                245                 250                 255

His Thr Ala Ile Ala Val Ile Ile Gly Ile Lys Asp Leu Arg Ala Phe
            260                 265                 270

Gln His Tyr Asp Gly Arg Thr Ile Ile Gln His Asp Asn Gly Tyr Gln
        275                 280                 285

Pro Asn Tyr His Ala Val Asn Ile Val Gly Tyr Gly Ser Thr Gln Gly
    290                 295                 300

Val Asp Tyr Trp Ile Val Arg Asn Ser Trp Asp Thr Thr Trp Gly Asp
305                 310                 315                 320

Ser Gly Tyr Gly Tyr Phe Gln Ala Gly Asn Asn Leu Met Met Ile Glu
```

```
                    325                 330                 335
Gln Tyr Pro Tyr Val Ile Met Phe Thr Gln Thr Asp Gly Phe Leu
                340                 345                 350

Ser Tyr Asn Glu Leu Ser Val Gln Ile Gln Ala Glu Thr Asn Ala Phe
            355                 360                 365

Thr Ile Thr Arg Glu Pro Thr Thr Pro Thr Glu Pro Thr Thr Lys
        370                 375                 380

Thr Pro Glu Pro Thr Thr Lys Thr Pro Glu Pro Ser Thr Pro Thr Pro
385                 390                 395                 400

Glu Pro Thr Thr Lys Thr Pro Glu Pro Thr Thr Lys Asp Ile Asp His
                405                 410                 415

Asp Asp Asp Pro Thr Thr Met Ile Asp Val Gln Thr Thr Val Gln
            420                 425                 430

Pro Ser Asp Glu Phe Glu Ser Pro Thr Arg Phe Gly Tyr Phe Ala Asp
                435                 440                 445

Pro Lys Asp Pro Ile Lys Phe Tyr Ile Ser Ser Asn Trp Glu Ala Ile
            450                 455                 460

His Lys Ser Ser Pro Gly Asn Thr Arg Trp Asn Glu Lys Glu Leu Thr
465                 470                 475                 480

Ser Thr Ser Pro Thr Thr Pro Thr Thr Thr Pro Ser Pro Thr Thr Pro
                485                 490                 495

Thr Thr Thr Pro Ser Pro Thr Thr Pro Thr Thr Thr Pro Asp Gln Val
            500                 505                 510

Asp Val Lys Asp Leu Ala Asn Asn Glu Ile Lys Lys Val Met Val Asp
                515                 520                 525

Gly Ile His Gly Ser Asp Pro Ser Ile Ile His Arg Gly Lys Pro Phe
            530                 535                 540

Thr Leu Glu Ala Leu Phe Asp Ala Asn Gln Asn Thr Lys Thr Ala Lys
545                 550                 555                 560

Ile Glu Ile Lys Ala Ser Leu Asp Gly Leu Glu Ile Asp Val Pro Gly
                565                 570                 575

Ile Asp Thr Asn Ala Leu His Phe Met Lys Ile Pro Leu Val Lys Gly
            580                 585                 590

Gln Gln Tyr Asp Ile Lys Tyr Thr Trp Asn Val Pro Lys Ile Ala Pro
                595                 600                 605

Lys Ser Glu Asn Val Val Val Thr Val Lys Leu Ile Gly Asp Asn Gly
            610                 615                 620

Val Leu Ala Ser Ala Ile Ala Thr His Gly Lys Ile Arg Asp
625                 630                 635

<210> SEQ ID NO 72
<211> LENGTH: 535
<212> TYPE: PRT
<213> ORGANISM: Artificial sequence
<220> FEATURE:
<223> OTHER INFORMATION: IMAT_NTERM Cat Hybrid3

<400> SEQUENCE: 72

Met His His His His His Tyr Gly Arg Lys Lys Arg Arg Gln Arg
1               5                   10                  15

Arg Arg Met Glu Asp Gln Arg Asp Leu Ile Ser Asn His Glu Gln Leu
                20                  25                  30

Pro Ile Leu Gly Gln Arg Pro Ala Ala Pro Glu Ser Lys Ser Ser Arg
            35                  40                  45

Gly Ala Leu Tyr Thr Gly Phe Ser Val Leu Val Ala Leu Leu Leu Ala
```

-continued

```
            50                  55                  60
Gly Gln Ala Thr Thr Ala Tyr Phe Leu Tyr Gln Gln Gly Arg Leu
 65                  70                  75                  80

Asp Lys Leu Thr Val Thr Ala Gln Asn Leu Gln Leu Glu Asn Leu Arg
                 85                  90                  95

Met Lys Leu Pro Lys Pro Ala Lys Pro Leu Asn Lys Leu Arg Val Ala
                100                 105                 110

Thr Pro Met Leu Met Gln Thr Met Pro Val Arg Gly Leu Leu Gln Ala
                115                 120                 125

Thr Ser Ala Ser Arg Ile Asn Ser Val Asn Val Pro Ser Glu Leu Asp
            130                 135                 140

Leu Arg Ser Leu Arg Thr Val Thr Pro Ile Arg Met Gln Gly Gly Ser
145                 150                 155                 160

Gly Ser Leu Trp Ala Phe Ser Gly Val Ala Ala Thr Glu Ser Ala Tyr
                165                 170                 175

Leu Ala Tyr Arg Asn Thr Ser Leu Asp Leu Ser Glu Gln Glu Leu Val
                180                 185                 190

Asp Ile Ala Ser Gln His Gly Leu His Gly Asp Thr Ile Pro Arg Gly
                195                 200                 205

Ile Glu Tyr Ile Gln Gln Asn Gly Val Val Glu Arg Ser Tyr Pro
            210                 215                 220

Tyr Val Ala Arg Glu Gln Gln Ser Arg Arg Pro Asn Ser Gln His Tyr
225                 230                 235                 240

Gly Ile Ser Asn Tyr Leu Gln Ile Tyr Pro Pro Asp Val Lys Gln Ile
                245                 250                 255

Arg Glu Ala Leu Thr Gln Thr His Thr Ala Ile Ala Val Ile Ile Gly
                260                 265                 270

Ile Lys Asp Leu Arg Ala Phe Gln His Tyr Asp Gly Arg Thr Ile Ile
                275                 280                 285

Gln His Asp Asn Gly Tyr Gln Pro Asn Tyr His Ala Val Asn Ile Val
                290                 295                 300

Gly Tyr Gly Ser Thr Gln Gly Val Asp Tyr Trp Ile Val Arg Asn Ser
305                 310                 315                 320

Trp Asp Thr Thr Trp Gly Asp Ser Gly Tyr Gly Tyr Phe Gln Ala Gly
                325                 330                 335

Asn Asn Leu Met Met Ile Glu Gln Tyr Pro Tyr Val Val Ile Met Phe
                340                 345                 350

Thr Gln Thr Asp Gly Phe Leu Ser Tyr Asn Glu Leu Ser Val Gln Ile
                355                 360                 365

Gln Ala Glu Thr Asn Ala Phe Thr Ile Thr Arg Ser Pro Thr Thr Pro
                370                 375                 380

Thr Thr Thr Pro Ser Pro Thr Thr Pro Thr Thr Pro Ser Pro Thr
385                 390                 395                 400

Thr Pro Thr Thr Thr Pro Asp Gln Val Asp Val Lys Asp Ser Ala Asn
                405                 410                 415

Asn Glu Ile Lys Lys Val Met Val Asp Gly Ile His Gly Ser Asp Pro
                420                 425                 430

Ser Ile Ile His Arg Gly Lys Pro Phe Thr Leu Glu Ala Leu Phe Asp
                435                 440                 445

Ala Asn Gln Asn Thr Lys Thr Ala Lys Ile Glu Ile Lys Ala Ser Leu
                450                 455                 460

Asp Gly Leu Glu Ile Asp Val Pro Gly Ile Asp Thr Asn Ala Ser His
465                 470                 475                 480
```

```
Phe Met Lys Ser Pro Leu Val Lys Gly Gln Gln Tyr Asp Ile Lys Tyr
            485                 490                 495

Thr Trp Asn Val Pro Lys Ile Ala Pro Lys Ser Glu Asn Val Val Val
            500                 505                 510

Thr Val Lys Leu Ile Gly Asp Asn Gly Val Leu Ala Ser Ala Ile Ala
            515                 520                 525

Thr His Gly Lys Ile Arg Asp
            530                 535

<210> SEQ ID NO 73
<211> LENGTH: 535
<212> TYPE: PRT
<213> ORGANISM: Artificial sequence
<220> FEATURE:
<223> OTHER INFORMATION: IMAT_CTERM Cat Hybrid3

<400> SEQUENCE: 73

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Ala Ala Pro Glu Ser Lys Ser Ser Arg Gly Ala Leu Tyr Thr Gly
            35                  40                  45

Phe Ser Val Leu Val Ala Leu Leu Leu Gly Gln Ala Thr Thr Ala
        50                  55                  60

Tyr Phe Leu Tyr Gln Gln Gln Gly Arg Leu Asp Lys Leu Thr Val Thr
65              70                  75                  80

Ala Gln Asn Leu Gln Leu Glu Asn Leu Arg Met Lys Leu Pro Lys Pro
            85                  90                  95

Ala Lys Pro Leu Asn Lys Leu Arg Val Ala Thr Pro Met Leu Met Gln
            100                 105                 110

Thr Met Pro Val Arg Gly Leu Leu Gln Ala Thr Ser Ala Ser Arg Ile
            115                 120                 125

Asn Ser Val Asn Val Pro Ser Glu Leu Asp Leu Arg Ser Leu Arg Thr
            130                 135                 140

Val Thr Pro Ile Arg Met Gln Gly Gly Ser Gly Ser Leu Trp Ala Phe
145                 150                 155                 160

Ser Gly Val Ala Ala Thr Glu Ser Ala Tyr Leu Ala Tyr Arg Asn Thr
            165                 170                 175

Ser Leu Asp Leu Ser Glu Gln Glu Leu Val Asp Ile Ala Ser Gln His
            180                 185                 190

Gly Leu His Gly Asp Thr Ile Pro Arg Gly Ile Glu Tyr Ile Gln Gln
            195                 200                 205

Asn Gly Val Val Glu Glu Arg Ser Tyr Pro Tyr Val Ala Arg Glu Gln
            210                 215                 220

Gln Ser Arg Arg Pro Asn Ser Gln His Tyr Gly Ile Ser Asn Tyr Leu
225                 230                 235                 240

Gln Ile Tyr Pro Pro Asp Val Lys Gln Ile Arg Glu Ala Leu Thr Gln
            245                 250                 255

Thr His Thr Ala Ile Ala Val Ile Ile Gly Ile Lys Asp Leu Arg Ala
            260                 265                 270

Phe Gln His Tyr Asp Gly Arg Thr Ile Ile Gln His Asp Asn Gly Tyr
            275                 280                 285

Gln Pro Asn Tyr His Ala Val Asn Ile Val Gly Tyr Gly Ser Thr Gln
            290                 295                 300
```

```
Gly Val Asp Tyr Trp Ile Val Arg Asn Ser Trp Asp Thr Thr Trp Gly
305                 310                 315                 320

Asp Ser Gly Tyr Gly Tyr Phe Gln Ala Gly Asn Asn Leu Met Met Ile
            325                 330                 335

Glu Gln Tyr Pro Tyr Val Val Ile Met Phe Thr Gln Thr Asp Gly Phe
            340                 345                 350

Leu Ser Tyr Asn Glu Leu Ser Val Gln Ile Gln Ala Glu Thr Asn Ala
            355                 360                 365

Phe Thr Ile Thr Arg Ser Pro Thr Pro Thr Thr Pro Ser Pro
370                 375                 380

Thr Thr Pro Thr Thr Pro Ser Pro Thr Thr Pro Thr Thr Pro
385                 390                 395                 400

Asp Gln Val Asp Val Lys Asp Ser Ala Asn Asn Glu Ile Lys Lys Val
            405                 410                 415

Met Val Asp Gly Ile His Gly Ser Asp Pro Ser Ile Ile His Arg Gly
            420                 425                 430

Lys Pro Phe Thr Leu Glu Ala Leu Phe Asp Ala Asn Gln Asn Thr Lys
            435                 440                 445

Thr Ala Lys Ile Glu Ile Lys Ala Ser Leu Asp Gly Leu Glu Ile Asp
            450                 455                 460

Val Pro Gly Ile Asp Thr Asn Ala Ser His Phe Met Lys Ser Pro Leu
465                 470                 475                 480

Val Lys Gly Gln Gln Tyr Asp Ile Lys Tyr Thr Trp Asn Val Pro Lys
            485                 490                 495

Ile Ala Pro Lys Ser Glu Asn Val Val Val Thr Val Lys Leu Ile Gly
            500                 505                 510

Asp Asn Gly Val Leu Ala Ser Ala Ile Ala Thr His Gly Lys Ile Arg
            515                 520                 525

Asp His His His His His
            530                 535

<210> SEQ ID NO 74
<211> LENGTH: 528
<212> TYPE: PRT
<213> ORGANISM: Artificial sequence
<220> FEATURE:
<223> OTHER INFORMATION: Hybrid 3 iMAT molecule (cat) without tag

<400> SEQUENCE: 74

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Ala Ala Pro Glu Ser Lys Cys Ser Arg Gly Ala Leu Tyr Thr Gly Phe
            35                  40                  45

Ser Val Leu Val Ala Leu Leu Ala Gly Gln Ala Thr Thr Ala Tyr
            50                  55                  60

Phe Leu Tyr Gln Gln Gln Gly Arg Leu Asp Lys Leu Thr Val Thr Ala
65                  70                  75                  80

Gln Asn Leu Gln Leu Glu Asn Leu Arg Met Lys Leu Pro Lys Pro Ala
            85                  90                  95

Lys Pro Leu Asn Lys Leu Arg Val Ala Thr Pro Met Leu Met Gln Thr
            100                 105                 110

Met Pro Val Arg Gly Leu Leu Gln Ala Thr Ser Ala Ser Arg Ile Asn
            115                 120                 125
```

Ser Val Asn Val Pro Ser Glu Leu Asp Leu Arg Ser Leu Arg Thr Val
130                 135                 140

Thr Pro Ile Arg Met Gln Gly Gly Ser Gly Ser Leu Trp Ala Phe Ser
145                 150                 155                 160

Gly Val Ala Ala Thr Glu Ser Ala Tyr Leu Ala Tyr Arg Asn Thr Ser
                165                 170                 175

Leu Asp Leu Ser Glu Gln Glu Leu Val Asp Ile Ala Ser Gln His Gly
                180                 185                 190

Leu His Gly Asp Thr Ile Pro Arg Gly Ile Glu Tyr Ile Gln Gln Asn
            195                 200                 205

Gly Val Val Glu Glu Arg Ser Tyr Pro Tyr Val Ala Arg Glu Gln Gln
210                 215                 220

Ser Arg Arg Pro Asn Ser Gln His Tyr Gly Ile Ser Asn Tyr Leu Gln
225                 230                 235                 240

Ile Tyr Pro Pro Asp Val Lys Gln Ile Arg Glu Ala Leu Thr Gln Thr
                245                 250                 255

His Thr Ala Ile Ala Val Ile Ile Gly Ile Lys Asp Leu Arg Ala Phe
            260                 265                 270

Gln His Tyr Asp Gly Arg Thr Ile Ile Gln His Asp Asn Gly Tyr Gln
            275                 280                 285

Pro Asn Tyr His Ala Val Asn Ile Val Gly Tyr Gly Ser Thr Gln Gly
290                 295                 300

Val Asp Tyr Trp Ile Val Arg Asn Ser Trp Asp Thr Thr Trp Gly Asp
305                 310                 315                 320

Ser Gly Tyr Gly Tyr Phe Gln Ala Gly Asn Asn Leu Met Met Ile Glu
                325                 330                 335

Gln Tyr Pro Tyr Val Val Ile Met Phe Thr Gln Thr Asp Gly Phe Leu
            340                 345                 350

Ser Tyr Asn Glu Leu Ser Val Gln Ile Gln Ala Glu Thr Asn Ala Phe
            355                 360                 365

Thr Ile Thr Arg Ser Pro Thr Thr Pro Thr Thr Thr Pro Ser Pro Thr
370                 375                 380

Thr Pro Thr Thr Pro Ser Pro Thr Thr Pro Thr Thr Thr Pro Asp
385                 390                 395                 400

Gln Val Asp Val Lys Asp Ser Ala Asn Asn Glu Ile Lys Lys Val Met
                405                 410                 415

Val Asp Gly Ile His Gly Ser Asp Pro Ser Ile Ile His Arg Gly Lys
            420                 425                 430

Pro Phe Thr Leu Glu Ala Leu Phe Asp Ala Asn Gln Asn Thr Lys Thr
            435                 440                 445

Ala Lys Ile Glu Ile Lys Ala Ser Leu Asp Gly Leu Glu Ile Asp Val
450                 455                 460

Pro Gly Ile Asp Thr Asn Ala Ser His Phe Met Lys Ser Pro Leu Val
465                 470                 475                 480

Lys Gly Gln Gln Tyr Asp Ile Lys Tyr Thr Trp Asn Val Pro Lys Ile
                485                 490                 495

Ala Pro Lys Ser Glu Asn Val Val Thr Val Lys Leu Ile Gly Asp
            500                 505                 510

Asn Gly Val Leu Ala Ser Ala Ile Ala Thr His Gly Lys Ile Arg Asp
            515                 520                 525

<210> SEQ ID NO 75
<211> LENGTH: 511

```
<212> TYPE: PRT
<213> ORGANISM: Artificial sequence
<220> FEATURE:
<223> OTHER INFORMATION: IMAT_NTERM Dog Hybrid1

<400> SEQUENCE: 75
```

| | | | | | | | | | | | | | | |
|---|---|---|---|---|---|---|---|---|---|---|---|---|---|---|
| Met | His | His | His | His | His | Tyr | Gly | Arg | Lys | Lys | Arg | Arg | Gln | Arg |
| 1 | | | | 5 | | | | | 10 | | | | | 15 |
| Arg | Arg | Met | Glu | Asp | Gln | Arg | Asp | Leu | Ile | Ser | Asn | His | Glu | Gln | Leu |
| | | | 20 | | | | | 25 | | | | | 30 | | |
| Pro | Ile | Leu | Gly | Gln | Arg | Pro | Gly | Ala | Pro | Glu | Ser | Lys | Ser | Ser | Arg |
| | | | 35 | | | | | 40 | | | | | 45 | | |
| Gly | Ala | Leu | Tyr | Thr | Gly | Phe | Ser | Val | Leu | Val | Ala | Leu | Leu | Leu | Ala |
| | 50 | | | | | 55 | | | | | 60 | | | | |
| Gly | Gln | Ala | Thr | Thr | Ala | Tyr | Phe | Leu | Tyr | Gln | Gln | Gln | Gly | Arg | Leu |
| 65 | | | | | 70 | | | | | 75 | | | | | 80 |
| Asp | Lys | Leu | Thr | Val | Thr | Ser | Gln | Asn | Leu | Gln | Leu | Glu | Ser | Leu | Arg |
| | | | | 85 | | | | | 90 | | | | | 95 | |
| Met | Lys | Leu | Pro | Lys | Pro | Pro | Lys | Pro | Leu | Ser | Lys | Met | Arg | Val | Ala |
| | | | | 100 | | | | | 105 | | | | | 110 | |
| Thr | Pro | Met | Met | Met | Gln | Ala | Leu | Pro | Ile | Gln | Ser | Leu | Pro | Gln | Gly |
| | | | 115 | | | | | 120 | | | | | 125 | | |
| Gln | Ser | His | Gln | Tyr | Tyr | His | Thr | Ser | Gly | Leu | Arg | Asn | Leu | Gly | Gly |
| | 130 | | | | | 135 | | | | | 140 | | | | |
| Ser | Tyr | Tyr | Arg | Ser | Gly | Asn | Ala | Lys | Ala | Met | Ile | Ala | Val | Gly | Gly |
| 145 | | | | | 150 | | | | | 155 | | | | | 160 |
| Ser | Thr | Met | Ile | Val | Asp | Gly | Asp | Lys | Val | Thr | Ile | Tyr | Gly | Trp | Gly |
| | | | | 165 | | | | | 170 | | | | | 175 | |
| Ser | Gly | Leu | Gly | Tyr | Gly | Leu | Gly | Tyr | Gly | Leu | Gly | Tyr | Gly | Gln | Ala |
| | | | 180 | | | | | 185 | | | | | 190 | | |
| Val | Ala | Leu | Ala | Pro | Ala | Gln | Ala | Val | Gly | Tyr | Val | Ala | Ala | Pro |
| | 195 | | | | | 200 | | | | | 205 | | | | |
| Ala | Val | Ala | Val | Gln | Ala | Pro | Ala | Val | Ser | Tyr | Ala | Ala | Ala | Pro |
| 210 | | | | | 215 | | | | | 220 | | | | | |
| Ala | Val | Gln | Thr | Val | Ala | Val | Gln | Ala | Pro | Ala | Val | Ser | Tyr | Ala | Ala |
| 225 | | | | | 230 | | | | | 235 | | | | | 240 |
| Ala | Pro | Ala | Val | Ala | Val | Gln | Ala | His | Thr | Ala | Gln | Val | Ser | Gly | Pro |
| | | | | 245 | | | | | 250 | | | | | 255 | |
| Ile | His | Ala | Ala | Ile | Glu | Ser | Arg | Arg | Thr | Val | Glu | Val | Ile | Asp | Gly |
| | | | 260 | | | | | 265 | | | | | 270 | | |
| Pro | Ser | Thr | Gly | Asp | Ala | Pro | Val | Ala | Ser | Thr | Val | Val | Ile | Gly | Pro |
| | | 275 | | | | | 280 | | | | | 285 | | | |
| Asn | Val | Gln | Pro | Ile | Asn | Leu | Glu | Phe | Gln | Thr | Gln | Ala | Ser | Pro | Leu |
| | 290 | | | | | 295 | | | | | 300 | | | | |
| Ala | Ala | Thr | Gln | Asn | His | Val | Pro | Thr | Thr | Pro | Thr | Thr | Pro | Thr | Pro |
| 305 | | | | | 310 | | | | | 315 | | | | | 320 |
| Ala | Pro | Thr | Thr | Ser | Thr | Pro | Asp | Leu | Leu | Arg | Gln | Asp | Ile | Val | Lys |
| | | | | 325 | | | | | 330 | | | | | 335 | |
| Pro | Val | Val | Gln | Asp | Val | His | Glu | Phe | Leu | Val | Tyr | Ile | His | Ile | Ala |
| | | | 340 | | | | | 345 | | | | | 350 | | |
| Asn | Asn | Glu | Ile | Lys | Lys | Val | Gln | Glu | Ser | Val | His | Gln | Ile | Leu | Pro |
| | | 355 | | | | | 360 | | | | | 365 | | | |
| Arg | Gly | Gln | Met | Met | Lys | Ile | Tyr | Gln | Gln | Gln | Gln | Gln | His | His |
| | 370 | | | | | 375 | | | | | 380 | | | | |

```
Pro Gln Arg Glu Glu Asn Ile Trp Ser Asp His Ile Ala Asn Val Ala
385                 390                 395                 400

Gln Ala Ala Pro Ala Ile Ser Ala Val Arg Val Ala Ala Ala Pro Ala
            405                 410                 415

Val Ala Tyr Ala Ala Pro Ala Val Ser Thr Val Ser Ala Ala Pro Ala
            420                 425                 430

Ala Ile Gly Val Ile Gly Val Gln Pro Val Ala Gly Tyr Ile Gly Tyr
        435                 440                 445

Gly Ala Gly Tyr Gly Thr Gly Tyr Gly Thr Gly Tyr Gly Val Ala Lys
        450                 455                 460

Tyr Gly Thr Gly Tyr Gly Leu Thr Ser Gly Leu Ile Gly Gly Gly Ser
465                 470                 475                 480

Tyr Gly Ser Ser Tyr Ser Val Gln Pro Ala Ser Tyr Gly Thr Gly Tyr
            485                 490                 495

Gly Tyr Thr Thr Tyr Ser Ser Asp Ala Tyr Pro Ile Arg Lys Lys
            500                 505                 510

<210> SEQ ID NO 76
<211> LENGTH: 511
<212> TYPE: PRT
<213> ORGANISM: Artificial sequence
<220> FEATURE:
<223> OTHER INFORMATION: IMAT_CTERM Dog Hybrid1

<400> SEQUENCE: 76

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Ser Arg Gly Ala Leu Tyr Thr Gly
        35                  40                  45

Phe Ser Val Leu Val Ala Leu Leu Leu Ala Gly Gln Ala Thr Thr Ala
    50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
            85                  90                  95

Pro Lys Pro Leu Ser Lys Met Arg Val Ala Thr Pro Met Met Met Gln
        100                 105                 110

Ala Leu Pro Ile Gln Ser Leu Pro Gln Gly Gln Ser His Gln Tyr Tyr
    115                 120                 125

His Thr Ser Gly Leu Arg Asn Leu Gly Gly Ser Tyr Tyr Arg Ser Gly
130                 135                 140

Asn Ala Lys Ala Met Ile Ala Val Gly Gly Ser Thr Met Ile Val Asp
145                 150                 155                 160

Gly Asp Lys Val Thr Ile Tyr Gly Trp Gly Ser Gly Leu Gly Tyr Gly
                165                 170                 175

Leu Gly Tyr Gly Leu Gly Tyr Gly Gln Ala Val Ala Leu Ala Pro Ala
            180                 185                 190

Gln Ala Val Gly Tyr Val Ala Ala Pro Ala Val Ala Val Gln Ala
        195                 200                 205

Pro Ala Val Ser Tyr Ala Ala Ala Pro Ala Val Gln Thr Val Ala
    210                 215                 220

Val Gln Ala Pro Ala Val Ser Tyr Ala Ala Ala Pro Ala Val Ala Val
225                 230                 235                 240
```

```
Gln Ala His Thr Ala Gln Val Ser Gly Pro Ile His Ala Ala Ile Glu
            245                 250                 255

Ser Arg Arg Thr Val Glu Val Ile Asp Gly Pro Ser Thr Gly Asp Ala
        260                 265                 270

Pro Val Ala Ser Thr Val Val Ile Gly Pro Asn Val Gln Pro Ile Asn
    275                 280                 285

Leu Glu Phe Gln Thr Gln Ala Ser Pro Leu Ala Ala Thr Gln Asn His
290                 295                 300

Val Pro Thr Thr Pro Thr Pro Thr Pro Ala Pro Thr Thr Ser Thr
305                 310                 315                 320

Pro Asp Leu Leu Arg Gln Asp Ile Val Lys Pro Val Val Gln Asp Val
                325                 330                 335

His Glu Phe Leu Val Tyr Ile His Ile Ala Asn Asn Glu Ile Lys Lys
            340                 345                 350

Val Gln Glu Ser Val His Gln Ile Leu Pro Arg Gly Gln Met Met Lys
        355                 360                 365

Ile Tyr Gln Gln Gln Gln Gln His His Pro Gln Arg Glu Glu Asn
    370                 375                 380

Ile Trp Ser Asp His Ile Ala Asn Val Ala Gln Ala Ala Pro Ala Ile
385                 390                 395                 400

Ser Ala Val Arg Val Ala Ala Pro Ala Val Ala Tyr Ala Ala Pro
                405                 410                 415

Ala Val Ser Thr Val Ser Ala Ala Pro Ala Ala Ile Gly Val Ile Gly
            420                 425                 430

Val Gln Pro Val Ala Gly Tyr Ile Gly Tyr Gly Ala Tyr Gly Thr
        435                 440                 445

Gly Tyr Gly Thr Gly Tyr Gly Val Ala Lys Tyr Gly Thr Gly Tyr Gly
450                 455                 460

Leu Thr Ser Gly Leu Ile Gly Gly Ser Tyr Gly Ser Ser Tyr Ser
465                 470                 475                 480

Val Gln Pro Ala Ser Tyr Gly Thr Gly Tyr Gly Tyr Thr Thr Tyr Ser
                485                 490                 495

Ser Asp Ala Tyr Pro Ile Arg Lys Lys His His His His His
            500                 505                 510

<210> SEQ ID NO 77
<211> LENGTH: 504
<212> TYPE: PRT
<213> ORGANISM: Artificial sequence
<220> FEATURE:
<223> OTHER INFORMATION: Hybrid 1 iMAT molecule (dog) without tag

<400> SEQUENCE: 77

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Gly Ala Pro Glu Ser Lys Cys Ser Arg Gly Ala Leu Tyr Thr Gly Phe
        35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ser
65                  70                  75                  80

Gln Asn Leu Gln Leu Glu Ser Leu Arg Met Lys Leu Pro Lys Pro Pro
                85                  90                  95
```

```
Lys Pro Leu Ser Lys Met Arg Val Ala Thr Pro Met Met Gln Ala
            100                 105                 110
Leu Pro Ile Gln Ser Leu Pro Gln Gly Gln Ser His Gln Tyr Tyr His
            115                 120                 125
Thr Ser Gly Leu Arg Asn Leu Gly Gly Ser Tyr Tyr Arg Ser Gly Asn
        130                 135                 140
Ala Lys Ala Met Ile Ala Val Gly Gly Ser Thr Met Ile Val Asp Gly
145                 150                 155                 160
Asp Lys Val Thr Ile Tyr Gly Trp Gly Ser Gly Leu Gly Tyr Gly Leu
                165                 170                 175
Gly Tyr Gly Leu Gly Tyr Gly Gln Ala Val Ala Leu Ala Pro Ala Gln
            180                 185                 190
Ala Val Gly Tyr Val Ala Ala Pro Ala Val Ala Val Gln Ala Pro
            195                 200                 205
Ala Val Ser Tyr Ala Ala Ala Pro Ala Val Gln Thr Val Ala Val
        210                 215                 220
Gln Ala Pro Ala Val Ser Tyr Ala Ala Ala Pro Ala Val Ala Val Gln
225                 230                 235                 240
Ala His Thr Ala Gln Val Ser Gly Pro Ile His Ala Ala Ile Glu Ser
                245                 250                 255
Arg Arg Thr Val Glu Val Ile Asp Gly Pro Ser Thr Gly Asp Ala Pro
            260                 265                 270
Val Ala Ser Thr Val Val Ile Gly Pro Asn Val Gln Pro Ile Asn Leu
        275                 280                 285
Glu Phe Gln Thr Gln Ala Ser Pro Leu Ala Ala Thr Gln Asn His Val
290                 295                 300
Pro Thr Thr Pro Thr Thr Pro Thr Pro Ala Pro Thr Thr Ser Thr Pro
305                 310                 315                 320
Asp Leu Leu Arg Gln Asp Ile Val Lys Pro Val Val Gln Asp Val His
                325                 330                 335
Glu Phe Leu Val Tyr Ile His Ile Ala Asn Asn Glu Ile Lys Lys Val
            340                 345                 350
Gln Glu Ser Val His Gln Ile Leu Pro Arg Gly Gln Met Met Lys Ile
        355                 360                 365
Tyr Gln Gln Gln Gln Gln His His Pro Gln Arg Glu Glu Asn Ile
370                 375                 380
Trp Ser Asp His Ile Ala Asn Val Ala Gln Ala Ala Pro Ala Ile Ser
385                 390                 395                 400
Ala Val Arg Val Ala Ala Pro Ala Val Ala Tyr Ala Ala Pro Ala
                405                 410                 415
Val Ser Thr Val Ser Ala Ala Pro Ala Ala Ile Gly Val Ile Gly Val
            420                 425                 430
Gln Pro Val Ala Gly Tyr Ile Gly Tyr Gly Ala Gly Tyr Gly Thr Gly
        435                 440                 445
Tyr Gly Thr Gly Tyr Gly Val Ala Lys Tyr Gly Thr Gly Tyr Gly Leu
450                 455                 460
Thr Ser Gly Leu Ile Gly Gly Ser Tyr Gly Ser Ser Tyr Ser Val
465                 470                 475                 480
Gln Pro Ala Ser Tyr Gly Thr Gly Tyr Gly Tyr Thr Thr Tyr Ser Ser
                485                 490                 495
Asp Ala Tyr Pro Ile Arg Lys Lys
                500
```

```
<210> SEQ ID NO 78
<211> LENGTH: 645
<212> TYPE: PRT
<213> ORGANISM: Artificial sequence
<220> FEATURE:
<223> OTHER INFORMATION: IMAT_NTERM Dog Hybrid2

<400> SEQUENCE: 78

Met His His His His His Tyr Gly Arg Lys Lys Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
        35                  40                  45

Gly Ala Leu Tyr Thr Gly Phe Ser Val Leu Val Ala Leu Leu Leu Ala
50                  55                  60

Gly Gln Ala Thr Thr Ala Tyr Phe Leu Tyr Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
        115                 120                 125

Thr Ser Ala Ser Arg Ile Asn Ser Val Asn Val Pro Ser Glu Leu Asp
130                 135                 140

Leu Arg Ser Leu Arg Thr Val Thr Pro Ile Arg Met Gln Gly Gly Ser
145                 150                 155                 160

Gly Ser Ser Trp Ala Phe Ser Gly Val Ala Ala Thr Glu Ser Ala Tyr
                165                 170                 175

Leu Ala Tyr Arg Asn Thr Ser Leu Asp Leu Ser Glu Gln Glu Leu Val
            180                 185                 190

Asp Ser Ala Ser Gln His Gly Ser His Gly Asp Thr Ile Pro Arg Gly
        195                 200                 205

Ile Glu Tyr Ile Gln Gln Asn Gly Val Val Glu Glu Arg Ser Tyr Pro
210                 215                 220

Tyr Val Ala Arg Glu Gln Gln Ser Arg Arg Pro Asn Ser Gln His Tyr
225                 230                 235                 240

Gly Ile Ser Asn Tyr Ser Gln Ile Tyr Pro Pro Asp Val Lys Gln Ile
                245                 250                 255

Arg Glu Ala Leu Thr Gln Thr His Thr Ala Ile Ala Val Ile Ile Gly
            260                 265                 270

Ile Lys Asp Leu Arg Ala Phe Gln His Tyr Asp Gly Arg Thr Ile Ile
        275                 280                 285

Gln His Asp Asn Gly Tyr Gln Pro Asn Tyr His Ala Val Asn Ile Val
290                 295                 300

Gly Tyr Gly Ser Thr Gln Gly Val Asp Tyr Trp Ile Val Arg Asn Ser
305                 310                 315                 320

Trp Asp Thr Thr Trp Gly Asp Ser Gly Tyr Gly Tyr Phe Gln Ala Gly
                325                 330                 335

Asn Asn Leu Met Met Ile Glu Gln Tyr Pro Tyr Val Val Ile Met Phe
            340                 345                 350

Thr Gln Thr Asp Gly Phe Leu Ser Tyr Asn Glu Leu Ser Val Gln Ile
        355                 360                 365

Gln Ala Glu Thr Asn Ala Phe Thr Ile Thr Arg Glu Pro Thr Thr Pro
```

```
            370                 375                 380
Thr Pro Glu Pro Thr Thr Lys Thr Pro Glu Pro Thr Thr Lys Thr Pro
385                 390                 395                 400

Glu Pro Ser Thr Pro Thr Pro Glu Pro Thr Thr Lys Thr Pro Glu Pro
                    405                 410                 415

Thr Thr Lys Asp Ile Asp His Asp Asp Pro Thr Thr Met Ile Asp
            420                 425                 430

Val Gln Thr Thr Thr Val Gln Pro Ser Asp Glu Phe Glu Ser Pro Thr
                435                 440                 445

Arg Phe Gly Tyr Phe Ala Asp Pro Lys Asp Pro Ile Lys Phe Tyr Ile
            450                 455                 460

Ser Ser Asn Trp Glu Ala Ile His Lys Ser Ser Pro Gly Asn Thr Arg
465                 470                 475                 480

Trp Asn Glu Lys Glu Leu Thr Ser Thr Ser Pro Thr Thr Pro Thr Thr
                485                 490                 495

Thr Pro Ser Pro Thr Thr Pro Thr Thr Thr Pro Ser Pro Thr Thr Pro
                500                 505                 510

Thr Thr Thr Pro Asp Gln Val Asp Val Lys Asp Leu Ala Asn Asn Glu
                515                 520                 525

Ile Lys Lys Val Met Val Asp Gly Ile His Gly Ser Asp Pro Ser Ile
            530                 535                 540

Ile His Arg Gly Lys Pro Phe Thr Leu Glu Ala Leu Phe Asp Ala Asn
545                 550                 555                 560

Gln Asn Thr Lys Thr Ala Lys Ile Glu Ile Lys Ala Ser Leu Asp Gly
                565                 570                 575

Leu Glu Ile Asp Val Pro Gly Ile Asp Thr Asn Ala Leu His Phe Met
                580                 585                 590

Lys Ile Pro Leu Val Lys Gly Gln Gln Tyr Asp Ile Lys Tyr Thr Trp
            595                 600                 605

Asn Val Pro Lys Ile Ala Pro Lys Ser Glu Asn Val Val Thr Val
            610                 615                 620

Lys Leu Ile Gly Asp Asn Gly Val Leu Ala Ser Ala Ile Ala Thr His
625                 630                 635                 640

Gly Lys Ile Arg Asp
                645

<210> SEQ ID NO 79
<211> LENGTH: 645
<212> TYPE: PRT
<213> ORGANISM: Artificial sequence
<220> FEATURE:
<223> OTHER INFORMATION: IMAT_CTERM Dog Hybrid2

<400> SEQUENCE: 79

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Ser Arg Gly Ala Leu Tyr Thr Gly
            35                  40                  45

Phe Ser Val Leu Val Ala Leu Leu Ala Gly Gln Ala Thr Thr Ala
            50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
```

```
                85                  90                  95
Pro Lys Pro Leu Ser Lys Met Arg Val Ala Thr Pro Met Met Met Gln
            100                 105                 110
Ala Leu Pro Ile Gln Ser Leu Pro Gln Gly Thr Ser Ala Ser Arg Ile
            115                 120                 125
Asn Ser Val Asn Val Pro Ser Glu Leu Asp Leu Arg Ser Leu Arg Thr
130                 135                 140
Val Thr Pro Ile Arg Met Gln Gly Gly Ser Gly Ser Ser Trp Ala Phe
145                 150                 155                 160
Ser Gly Val Ala Ala Thr Glu Ser Ala Tyr Leu Ala Tyr Arg Asn Thr
                165                 170                 175
Ser Leu Asp Leu Ser Glu Gln Glu Leu Val Asp Ser Ala Ser Gln His
            180                 185                 190
Gly Ser His Gly Asp Thr Ile Pro Arg Gly Ile Glu Tyr Ile Gln Gln
            195                 200                 205
Asn Gly Val Val Glu Glu Arg Ser Tyr Pro Tyr Val Ala Arg Glu Gln
            210                 215                 220
Gln Ser Arg Arg Pro Asn Ser Gln His Tyr Gly Ile Ser Asn Tyr Ser
225                 230                 235                 240
Gln Ile Tyr Pro Pro Asp Val Lys Gln Ile Arg Glu Ala Leu Thr Gln
                245                 250                 255
Thr His Thr Ala Ile Ala Val Ile Ile Gly Ile Lys Asp Leu Arg Ala
            260                 265                 270
Phe Gln His Tyr Asp Gly Arg Thr Ile Ile Gln His Asp Asn Gly Tyr
            275                 280                 285
Gln Pro Asn Tyr His Ala Val Asn Ile Val Gly Tyr Gly Ser Thr Gln
            290                 295                 300
Gly Val Asp Tyr Trp Ile Val Arg Asn Ser Trp Asp Thr Thr Trp Gly
305                 310                 315                 320
Asp Ser Gly Tyr Gly Tyr Phe Gln Ala Gly Asn Asn Leu Met Met Ile
                325                 330                 335
Glu Gln Tyr Pro Tyr Val Val Ile Met Phe Thr Gln Thr Asp Gly Phe
            340                 345                 350
Leu Ser Tyr Asn Glu Leu Ser Val Gln Ile Gln Ala Glu Thr Asn Ala
            355                 360                 365
Phe Thr Ile Thr Arg Glu Pro Thr Thr Pro Thr Pro Glu Pro Thr Thr
            370                 375                 380
Lys Thr Pro Glu Pro Thr Thr Lys Thr Pro Glu Pro Ser Thr Pro Thr
385                 390                 395                 400
Pro Glu Pro Thr Thr Lys Thr Pro Glu Pro Thr Thr Lys Asp Ile Asp
                405                 410                 415
His Asp Asp Pro Thr Thr Met Ile Asp Val Gln Thr Thr Thr Val
            420                 425                 430
Gln Pro Ser Asp Glu Phe Glu Ser Pro Thr Arg Phe Gly Tyr Phe Ala
            435                 440                 445
Asp Pro Lys Asp Pro Ile Lys Phe Tyr Ile Ser Ser Asn Trp Glu Ala
            450                 455                 460
Ile His Lys Ser Ser Pro Gly Asn Thr Arg Trp Asn Glu Lys Glu Leu
465                 470                 475                 480
Thr Ser Thr Ser Pro Thr Thr Pro Thr Thr Pro Ser Pro Thr Thr
                485                 490                 495
Pro Thr Thr Thr Pro Ser Pro Thr Thr Pro Thr Thr Thr Pro Asp Gln
            500                 505                 510
```

```
Val Asp Val Lys Asp Leu Ala Asn Asn Glu Ile Lys Lys Val Met Val
            515                 520                 525

Asp Gly Ile His Gly Ser Asp Pro Ser Ile Ile His Arg Gly Lys Pro
        530                 535                 540

Phe Thr Leu Glu Ala Leu Phe Asp Ala Asn Gln Asn Thr Lys Thr Ala
545                 550                 555                 560

Lys Ile Glu Ile Lys Ala Ser Leu Asp Gly Leu Glu Ile Asp Val Pro
                565                 570                 575

Gly Ile Asp Thr Asn Ala Leu His Phe Met Lys Ile Pro Leu Val Lys
            580                 585                 590

Gly Gln Gln Tyr Asp Ile Lys Tyr Thr Trp Asn Val Pro Lys Ile Ala
        595                 600                 605

Pro Lys Ser Glu Asn Val Val Val Thr Val Lys Leu Ile Gly Asp Asn
    610                 615                 620

Gly Val Leu Ala Ser Ala Ile Ala Thr His Gly Lys Ile Arg Asp His
625                 630                 635                 640

His His His His His
            645

<210> SEQ ID NO 80
<211> LENGTH: 638
<212> TYPE: PRT
<213> ORGANISM: Artificial sequence
<220> FEATURE:
<223> OTHER INFORMATION: Hybrid 2 iMAT molecule (dog) without tag

<400> SEQUENCE: 80

Tyr Gly Arg Lys Lys Arg Arg Gln Arg Arg Met Glu Asp Gln Arg
1               5                   10                  15

Asp Leu Ile Ser Asn His Glu Gln Leu Pro Ile Leu Gly Gln Arg Pro
            20                  25                  30

Gly Ala Pro Glu Ser Lys Cys Ser Arg Gly Ala Leu Tyr Thr Gly Phe
        35                  40                  45

Ser Val Leu Val Ala Leu Leu Leu Ala Gly Gln Ala Thr Thr Ala Tyr
    50                  55                  60

Phe Leu Tyr Gln Gln Gln Gly Arg Leu Asp Lys Leu Thr Val Thr Ser
65                  70                  75                  80

Gln Asn Leu Gln Leu Glu Ser Leu Arg Met Lys Leu Pro Lys Pro Pro
            85                  90                  95

Lys Pro Leu Ser Lys Met Arg Val Ala Thr Pro Met Met Met Gln Ala
        100                 105                 110

Leu Pro Ile Gln Ser Leu Pro Gln Gly Thr Ser Ala Ser Arg Ile Asn
    115                 120                 125

Ser Val Asn Val Pro Ser Glu Leu Asp Leu Arg Ser Leu Arg Thr Val
    130                 135                 140

Thr Pro Ile Arg Met Gln Gly Ser Gly Ser Ser Trp Ala Phe Ser
145                 150                 155                 160

Gly Val Ala Ala Thr Glu Ser Ala Tyr Leu Ala Tyr Arg Asn Thr Ser
            165                 170                 175

Leu Asp Leu Ser Glu Gln Glu Leu Val Asp Ser Ala Ser Gln His Gly
        180                 185                 190

Ser His Gly Asp Thr Ile Pro Arg Gly Ile Glu Tyr Ile Gln Gln Asn
    195                 200                 205

Gly Val Val Glu Glu Arg Ser Tyr Pro Tyr Val Ala Arg Glu Gln Gln
    210                 215                 220
```

```
Ser Arg Arg Pro Asn Ser Gln His Tyr Gly Ile Ser Asn Tyr Ser Gln
225                 230                 235                 240

Ile Tyr Pro Pro Asp Val Lys Gln Ile Arg Glu Ala Leu Thr Gln Thr
            245                 250                 255

His Thr Ala Ile Ala Val Ile Ile Gly Ile Lys Asp Leu Arg Ala Phe
        260                 265                 270

Gln His Tyr Asp Gly Arg Thr Ile Ile Gln His Asp Asn Gly Tyr Gln
    275                 280                 285

Pro Asn Tyr His Ala Val Asn Ile Val Gly Tyr Gly Ser Thr Gln Gly
290                 295                 300

Val Asp Tyr Trp Ile Val Arg Asn Ser Trp Asp Thr Thr Trp Gly Asp
305                 310                 315                 320

Ser Gly Tyr Gly Tyr Phe Gln Ala Gly Asn Asn Leu Met Met Ile Glu
            325                 330                 335

Gln Tyr Pro Tyr Val Val Ile Met Phe Thr Gln Thr Asp Gly Phe Leu
            340                 345                 350

Ser Tyr Asn Glu Leu Ser Val Gln Ile Gln Ala Glu Thr Asn Ala Phe
        355                 360                 365

Thr Ile Thr Arg Glu Pro Thr Thr Pro Thr Pro Glu Pro Thr Thr Lys
370                 375                 380

Thr Pro Glu Pro Thr Thr Lys Thr Pro Glu Pro Ser Thr Pro Thr Pro
385                 390                 395                 400

Glu Pro Thr Thr Lys Thr Pro Glu Pro Thr Thr Lys Asp Ile Asp His
            405                 410                 415

Asp Asp Asp Pro Thr Thr Met Ile Asp Val Gln Thr Thr Thr Val Gln
            420                 425                 430

Pro Ser Asp Glu Phe Glu Ser Pro Thr Arg Phe Gly Tyr Phe Ala Asp
        435                 440                 445

Pro Lys Asp Pro Ile Lys Phe Tyr Ile Ser Ser Asn Trp Glu Ala Ile
450                 455                 460

His Lys Ser Ser Pro Gly Asn Thr Arg Trp Asn Glu Lys Glu Leu Thr
465                 470                 475                 480

Ser Thr Ser Pro Thr Thr Pro Thr Thr Pro Ser Pro Thr Thr Pro
            485                 490                 495

Thr Thr Thr Pro Ser Pro Thr Thr Pro Thr Thr Thr Pro Asp Gln Val
            500                 505                 510

Asp Val Lys Asp Leu Ala Asn Asn Glu Ile Lys Lys Val Met Val Asp
        515                 520                 525

Gly Ile His Gly Ser Asp Pro Ser Ile Ile His Arg Gly Lys Pro Phe
530                 535                 540

Thr Leu Glu Ala Leu Phe Asp Ala Asn Gln Asn Thr Lys Thr Ala Lys
545                 550                 555                 560

Ile Glu Ile Lys Ala Ser Leu Asp Gly Leu Glu Ile Asp Val Pro Gly
            565                 570                 575

Ile Asp Thr Asn Ala Leu His Phe Met Lys Ile Pro Leu Val Lys Gly
            580                 585                 590

Gln Gln Tyr Asp Ile Lys Tyr Thr Trp Asn Val Pro Lys Ile Ala Pro
        595                 600                 605

Lys Ser Glu Asn Val Val Thr Val Lys Leu Ile Gly Asp Asn Gly
610                 615                 620

Val Leu Ala Ser Ala Ile Ala Thr His Gly Lys Ile Arg Asp
625                 630                 635
```

```
<210> SEQ ID NO 81
<211> LENGTH: 535
<212> TYPE: PRT
<213> ORGANISM: Artificial sequence
<220> FEATURE:
<223> OTHER INFORMATION: IMAT_NTERM Dog Hybrid3

<400> SEQUENCE: 81

Met His His His His His Tyr Gly Arg Lys Lys Arg Gln Arg
1               5                   10                  15

Arg Arg Met Glu Asp Gln Arg Asp Leu Ile Ser Asn His Glu Gln Leu
            20                  25                  30

Pro Ile Leu Gly Gln Arg Pro Gly Ala Pro Glu Ser Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Tyr Gln Gln Gln Gly Arg Leu
65                  70                  75                  80

Asp Lys Leu Thr Val Thr Ser Gln Asn Leu Gln Leu Glu Ser Leu Arg
                85                  90                  95

Met Lys Leu Pro Lys Pro Pro Lys Pro Leu Ser Lys Met Arg Val Ala
            100                 105                 110

Thr Pro Met Met Met Gln Ala Leu Pro Ile Gln Ser Leu Pro Gln Gly
        115                 120                 125

Thr Ser Ala Ser Arg Ile Asn Ser Val Asn Val Pro Ser Glu Leu Asp
    130                 135                 140

Leu Arg Ser Leu Arg Thr Val Thr Pro Ile Arg Met Gln Gly Gly Ser
145                 150                 155                 160

Gly Ser Leu Trp Ala Phe Ser Gly Val Ala Ala Thr Glu Ser Ala Tyr
                165                 170                 175

Leu Ala Tyr Arg Asn Thr Ser Leu Asp Leu Ser Glu Gln Glu Leu Val
            180                 185                 190

Asp Ile Ala Ser Gln His Gly Leu His Gly Asp Thr Ile Pro Arg Gly
        195                 200                 205

Ile Glu Tyr Ile Gln Gln Asn Gly Val Val Glu Glu Arg Ser Tyr Pro
    210                 215                 220

Tyr Val Ala Arg Glu Gln Gln Ser Arg Arg Pro Asn Ser Gln His Tyr
225                 230                 235                 240

Gly Ile Ser Asn Tyr Leu Gln Ile Tyr Pro Pro Asp Val Lys Gln Ile
                245                 250                 255

Arg Glu Ala Leu Thr Gln Thr His Thr Ala Ile Ala Val Ile Ile Gly
            260                 265                 270

Ile Lys Asp Leu Arg Ala Phe Gln His Tyr Asp Gly Arg Thr Ile Ile
        275                 280                 285

Gln His Asp Asn Gly Tyr Gln Pro Asn Tyr His Ala Val Asn Ile Val
    290                 295                 300

Gly Tyr Gly Ser Thr Gln Gly Val Asp Tyr Trp Ile Val Arg Asn Ser
305                 310                 315                 320

Trp Asp Thr Thr Trp Gly Asp Ser Gly Tyr Gly Tyr Phe Gln Ala Gly
                325                 330                 335

Asn Asn Leu Met Met Ile Glu Gln Tyr Pro Tyr Val Val Ile Met Phe
            340                 345                 350

Thr Gln Thr Asp Gly Phe Leu Ser Tyr Asn Glu Leu Ser Val Gln Ile
        355                 360                 365
```

Gln Ala Glu Thr Asn Ala Phe Thr Ile Thr Arg Ser Pro Thr Thr Pro
370                 375                 380

Thr Thr Thr Pro Ser Pro Thr Thr Pro Thr Thr Thr Pro Ser Pro Thr
385                 390                 395                 400

Thr Pro Thr Thr Thr Pro Asp Gln Val Asp Val Lys Asp Ser Ala Asn
            405                 410                 415

Asn Glu Ile Lys Lys Val Met Val Asp Gly Ile His Gly Ser Asp Pro
            420                 425                 430

Ser Ile Ile His Arg Gly Lys Pro Phe Thr Leu Glu Ala Leu Phe Asp
            435                 440                 445

Ala Asn Gln Asn Thr Lys Thr Ala Lys Ile Glu Ile Lys Ala Ser Leu
450                 455                 460

Asp Gly Leu Glu Ile Asp Val Pro Gly Ile Asp Thr Asn Ala Ser His
465                 470                 475                 480

Phe Met Lys Ser Pro Leu Val Lys Gly Gln Gln Tyr Asp Ile Lys Tyr
            485                 490                 495

Thr Trp Asn Val Pro Lys Ile Ala Pro Lys Ser Glu Asn Val Val Val
            500                 505                 510

Thr Val Lys Leu Ile Gly Asp Asn Gly Val Leu Ala Ser Ala Ile Ala
            515                 520                 525

Thr His Gly Lys Ile Arg Asp
530                 535

<210> SEQ ID NO 82
<211> LENGTH: 535
<212> TYPE: PRT
<213> ORGANISM: Artificial sequence
<220> FEATURE:
<223> OTHER INFORMATION: IMAT_CTERM Dog Hybrid3

<400> SEQUENCE: 82

Met Tyr Gly Arg Lys Lys Arg Gln Arg Arg Met Glu Asp Gln
1               5                   10                  15

Arg Asp Leu Ile Ser Asn His Glu Gln Leu Pro Ile Leu Gly Gln Arg
            20                  25                  30

Pro Gly Ala Pro Glu Ser Lys Ser Arg Gly Ala Leu Tyr Thr Gly
        35                  40                  45

Phe Ser Val Leu Val Ala Leu Leu Leu Ala Gly Gln Ala Thr Thr Ala
50                  55                  60

Tyr Phe Leu Tyr Gln Gln Gln Gly Arg Leu Asp Lys Leu Thr Val Thr
65                  70                  75                  80

Ser Gln Asn Leu Gln Leu Glu Ser Leu Arg Met Lys Leu Pro Lys Pro
            85                  90                  95

Pro Lys Pro Leu Ser Lys Met Arg Val Ala Thr Pro Met Met Met Gln
        100                 105                 110

Ala Leu Pro Ile Gln Ser Leu Pro Gln Gly Thr Ser Ala Ser Arg Ile
        115                 120                 125

Asn Ser Val Asn Val Pro Ser Glu Leu Asp Leu Arg Ser Leu Arg Thr
130                 135                 140

Val Thr Pro Ile Arg Met Gln Gly Gly Ser Gly Ser Leu Trp Ala Phe
145                 150                 155                 160

Ser Gly Val Ala Ala Thr Glu Ser Ala Tyr Leu Ala Tyr Arg Asn Thr
            165                 170                 175

Ser Leu Asp Leu Ser Glu Gln Glu Leu Val Asp Ile Ala Ser Gln His
            180                 185                 190

```
Gly Leu His Gly Asp Thr Ile Pro Arg Gly Ile Glu Tyr Ile Gln Gln
            195                 200                 205

Asn Gly Val Val Glu Glu Arg Ser Tyr Pro Tyr Val Ala Arg Glu Gln
        210                 215                 220

Gln Ser Arg Arg Pro Asn Ser Gln His Tyr Gly Ile Ser Asn Tyr Leu
225                 230                 235                 240

Gln Ile Tyr Pro Pro Asp Val Lys Gln Ile Arg Glu Ala Leu Thr Gln
            245                 250                 255

Thr His Thr Ala Ile Ala Val Ile Ile Gly Ile Lys Asp Leu Arg Ala
        260                 265                 270

Phe Gln His Tyr Asp Gly Arg Thr Ile Ile Gln His Asp Asn Gly Tyr
            275                 280                 285

Gln Pro Asn Tyr His Ala Val Asn Ile Val Gly Tyr Gly Ser Thr Gln
        290                 295                 300

Gly Val Asp Tyr Trp Ile Val Arg Asn Ser Trp Asp Thr Thr Trp Gly
305                 310                 315                 320

Asp Ser Gly Tyr Gly Tyr Phe Gln Ala Gly Asn Asn Leu Met Met Ile
            325                 330                 335

Glu Gln Tyr Pro Tyr Val Val Ile Met Phe Thr Gln Thr Asp Gly Phe
        340                 345                 350

Leu Ser Tyr Asn Glu Leu Ser Val Gln Ile Gln Ala Glu Thr Asn Ala
            355                 360                 365

Phe Thr Ile Thr Arg Ser Pro Thr Thr Pro Thr Thr Pro Ser Pro
            370                 375                 380

Thr Thr Pro Thr Thr Thr Pro Ser Pro Thr Thr Pro Thr Thr Thr Pro
385                 390                 395                 400

Asp Gln Val Asp Val Lys Asp Ser Ala Asn Asn Glu Ile Lys Lys Val
            405                 410                 415

Met Val Asp Gly Ile His Gly Ser Asp Pro Ser Ile Ile His Arg Gly
        420                 425                 430

Lys Pro Phe Thr Leu Glu Ala Leu Phe Asp Ala Asn Gln Asn Thr Lys
            435                 440                 445

Thr Ala Lys Ile Glu Ile Lys Ala Ser Leu Asp Gly Leu Glu Ile Asp
450                 455                 460

Val Pro Gly Ile Asp Thr Asn Ala Ser His Phe Met Lys Ser Pro Leu
465                 470                 475                 480

Val Lys Gly Gln Gln Tyr Asp Ile Lys Tyr Thr Trp Asn Val Pro Lys
            485                 490                 495

Ile Ala Pro Lys Ser Glu Asn Val Val Val Thr Val Lys Leu Ile Gly
        500                 505                 510

Asp Asn Gly Val Leu Ala Ser Ala Ile Ala Thr His Gly Lys Ile Arg
            515                 520                 525

Asp His His His His His His
530                 535

<210> SEQ ID NO 83
<211> LENGTH: 528
<212> TYPE: PRT
<213> ORGANISM: Artificial sequence
<220> FEATURE:
<223> OTHER INFORMATION: Hybrid 3 iMAT molecule (dog) without tag

<400> SEQUENCE: 83

Tyr Gly Arg Lys Lys Arg Arg Gln Arg Arg Met Glu Asp Gln Arg
1               5                   10                  15
```

-continued

```
Asp Leu Ile Ser Asn His Glu Gln Leu Pro Ile Leu Gly Gln Arg Pro
             20                  25                  30

Gly Ala Pro Glu Ser Lys Cys Ser Arg Gly Ala Leu Tyr Thr Gly Phe
         35                  40                  45

Ser Val Leu Val Ala Leu Leu Leu Ala Gly Gln Ala Thr Thr Ala Tyr
     50                  55                  60

Phe Leu Tyr Gln Gln Gln Gly Arg Leu Asp Lys Leu Thr Val Thr Ser
 65                  70                  75                  80

Gln Asn Leu Gln Leu Glu Ser Leu Arg Met Lys Leu Pro Lys Pro Pro
                 85                  90                  95

Lys Pro Leu Ser Lys Met Arg Val Ala Thr Pro Met Met Met Gln Ala
            100                 105                 110

Leu Pro Ile Gln Ser Leu Pro Gln Gly Thr Ser Ala Ser Arg Ile Asn
        115                 120                 125

Ser Val Asn Val Pro Ser Glu Leu Asp Leu Arg Ser Leu Arg Thr Val
    130                 135                 140

Thr Pro Ile Arg Met Gln Gly Gly Ser Gly Ser Leu Trp Ala Phe Ser
145                 150                 155                 160

Gly Val Ala Ala Thr Glu Ser Ala Tyr Leu Ala Tyr Arg Asn Thr Ser
                165                 170                 175

Leu Asp Leu Ser Glu Gln Glu Leu Val Asp Ile Ala Ser Gln His Gly
            180                 185                 190

Leu His Gly Asp Thr Ile Pro Arg Gly Ile Glu Tyr Ile Gln Gln Asn
        195                 200                 205

Gly Val Val Glu Glu Arg Ser Tyr Pro Tyr Val Ala Arg Glu Gln Gln
    210                 215                 220

Ser Arg Arg Pro Asn Ser Gln His Tyr Gly Ile Ser Asn Tyr Leu Gln
225                 230                 235                 240

Ile Tyr Pro Pro Asp Val Lys Gln Ile Arg Glu Ala Leu Thr Gln Thr
                245                 250                 255

His Thr Ala Ile Ala Val Ile Ile Gly Ile Lys Asp Leu Arg Ala Phe
            260                 265                 270

Gln His Tyr Asp Gly Arg Thr Ile Ile Gln His Asp Asn Gly Tyr Gln
        275                 280                 285

Pro Asn Tyr His Ala Val Asn Ile Val Gly Tyr Gly Ser Thr Gln Gly
    290                 295                 300

Val Asp Tyr Trp Ile Val Arg Asn Ser Trp Asp Thr Thr Trp Gly Asp
305                 310                 315                 320

Ser Gly Tyr Gly Tyr Phe Gln Ala Gly Asn Asn Leu Met Met Ile Glu
                325                 330                 335

Gln Tyr Pro Tyr Val Val Ile Met Phe Thr Gln Thr Asp Gly Phe Leu
            340                 345                 350

Ser Tyr Asn Glu Leu Ser Val Gln Ile Gln Ala Glu Thr Asn Ala Phe
        355                 360                 365

Thr Ile Thr Arg Ser Pro Thr Thr Pro Thr Thr Thr Pro Ser Pro Thr
    370                 375                 380

Thr Pro Thr Thr Thr Pro Ser Pro Thr Thr Pro Thr Thr Thr Pro Asp
385                 390                 395                 400

Gln Val Asp Val Lys Asp Ser Ala Asn Asn Glu Ile Lys Lys Val Met
                405                 410                 415

Val Asp Gly Ile His Gly Ser Asp Pro Ser Ile Ile His Arg Gly Lys
            420                 425                 430

Pro Phe Thr Leu Glu Ala Leu Phe Asp Ala Asn Gln Asn Thr Lys Thr
```

```
            435                 440                 445
Ala Lys Ile Glu Ile Lys Ala Ser Leu Asp Gly Leu Glu Ile Asp Val
    450                 455                 460

Pro Gly Ile Asp Thr Asn Ala Ser His Phe Met Lys Ser Pro Leu Val
465                 470                 475                 480

Lys Gly Gln Gln Tyr Asp Ile Lys Tyr Thr Trp Asn Val Pro Lys Ile
                    485                 490                 495

Ala Pro Lys Ser Glu Asn Val Val Val Thr Val Lys Leu Ile Gly Asp
                500                 505                 510

Asn Gly Val Leu Ala Ser Ala Ile Ala Thr His Gly Lys Ile Arg Asp
            515                 520                 525

<210> SEQ ID NO 84
<211> LENGTH: 400
<212> TYPE: PRT
<213> ORGANISM: Artificial sequence
<220> FEATURE:
<223> OTHER INFORMATION: tr_KXC1_KXC1_DERFA DFP1 OS=Dermatophagoides
      farinae GN=DFP1 PE=2 SV=1

<400> SEQUENCE: 84

Met Lys Phe Ala Leu Phe Val Val Ala Ser Leu Ile Ala Thr Val Tyr
1               5                   10                  15

Gly Gln Ser His Gln Tyr Tyr His Thr Ser Gly Leu Arg Asn Leu Gly
            20                  25                  30

Gly Ser Tyr Tyr Arg Ser Ala Gly Ile Ser Gly Val Ala Gly Leu Gly
        35                  40                  45

Gly Leu Ala Tyr Gly Thr Gly Leu Gly Tyr Gly Thr Arg Tyr Gly Tyr
    50                  55                  60

Gly Ser Gly Leu Gly Tyr Gly Leu Gly Tyr Gly Leu Gly Tyr Gly Gln
65                  70                  75                  80

Ala Val Ala Leu Ala Pro Ala Gln Ala Val Gly Tyr Val Ala Ala Ala
                85                  90                  95

Pro Ala Val Ala Val Gln Ala Pro Ala Val Ser Tyr Ala Ala Ala Ala
            100                 105                 110

Pro Ala Val Gln Thr Val Ala Val Gln Ala Pro Ala Val Ser Tyr Ala
        115                 120                 125

Ala Ala Pro Ala Val Ala Val Gln Ala His Thr Ala Gln Val Ser Gly
    130                 135                 140

Pro Ile His Ala Ala Ile Glu Ser Arg Arg Thr Val Glu Val Ile Asp
145                 150                 155                 160

Gly Pro Ser Thr Gly Asp Ala Pro Val Ala Ser Thr Val Val Ile Gly
                165                 170                 175

Pro Asn Val Gln Pro Ile Asn Leu Glu Phe Gln Thr Gln Ala Ser Pro
            180                 185                 190

Leu Ala Ala Thr Gln Asn His Val Pro Thr Ala Pro Ala Glu Pro Gln
        195                 200                 205

Gln Ser Ser Tyr Glu Glu Pro Asp Leu Leu Arg Gln Asp Ile Val
    210                 215                 220

Lys Pro Val Val Gln Asp Val His Glu Thr Ile Val Pro Phe Arg Arg
225                 230                 235                 240

Ile Thr Gln Glu Leu Lys Pro Val Gln Glu Ser Val His Gln Ile Leu
                245                 250                 255

Pro Arg Gly Gln Glu Arg Gly Phe Tyr Gln Gln Gln Gln Gln Val Arg
            260                 265                 270
```

```
Val Ala Gln His Val Ala Ala Pro Ala Ala Val Ala Val Gln Pro Val
            275                 280                 285

Val Gln Ala Ala Pro Ala Ile Ser Ala Val Arg Val Ala Ala Ala Pro
    290                 295                 300

Ala Val Ala Tyr Ala Ala Pro Ala Val Ser Thr Val Ser Ala Ala Pro
305                 310                 315                 320

Ala Ala Ile Gly Val Ile Gly Val Gln Pro Val Ala Gly Tyr Ile Gly
                325                 330                 335

Tyr Gly Ala Gly Tyr Gly Thr Gly Gly Thr Gly Tyr Gly Val Ala
            340                 345                 350

Lys Tyr Gly Thr Gly Tyr Gly Leu Thr Ser Gly Leu Ile Gly Gly Gly
            355                 360                 365

Ser Tyr Gly Ser Ser Tyr Ser Val Gln Pro Ala Ser Tyr Gly Thr Gly
    370                 375                 380

Tyr Gly Tyr Thr Thr Tyr Ser Ser Asp Ala Tyr Pro Ile Arg Lys Lys
385                 390                 395                 400

<210> SEQ ID NO 85
<211> LENGTH: 654
<212> TYPE: PRT
<213> ORGANISM: Artificial sequence
<220> FEATURE:
<223> OTHER INFORMATION: tr^A088SAS1^A088SAS1_DERFA Der f 28
      allergen OS=Dermatophagoides farinae PE=2 SV=1

<400> SEQUENCE: 85

Met Pro Ser Lys Thr Leu Lys Ala Pro Ala Ile Gly Ile Asp Leu Gly
1               5                   10                  15

Thr Thr Tyr Ser Cys Val Gly Val Phe Gln Asn Gly Ser Val Glu Ile
            20                  25                  30

Ile Ala Asn Asp Gln Gly Asn Arg Thr Thr Pro Ser Tyr Val Ala Phe
        35                  40                  45

Asn Asp Thr Glu Arg Leu Ile Gly Asp Ala Ala Lys Asn Gln Val Ser
    50                  55                  60

Met Asn Pro Thr Asn Thr Ile Phe Asp Ala Lys Arg Leu Ile Gly Arg
65                  70                  75                  80

Arg Phe Asp Glu Ser Ser Val Lys Ser Asp Met Lys His Trp Pro Phe
                85                  90                  95

Lys Val Val Ser Glu Ser Gly Lys Pro Lys Leu Glu Val Glu Phe Lys
            100                 105                 110

Gly Glu Arg Lys Arg Phe Trp Pro Glu Glu Ile Ser Ala Met Val Leu
        115                 120                 125

Thr Lys Met Lys Glu Thr Ala Glu Ala Tyr Leu Gly Gln Lys Val Thr
    130                 135                 140

Asp Val Val Ile Thr Val Pro Ala Tyr Phe Asn Asp Ser Gln Arg Gln
145                 150                 155                 160

Ala Thr Lys Asp Ala Gly Val Ile Ala Gly Leu Asn Val Leu Arg Ile
                165                 170                 175

Ile Asn Glu Pro Thr Ala Ala Ala Ile Ala Tyr Gly Leu Asp Lys Lys
            180                 185                 190

Gly Gly Gly Glu Lys Asn Val Leu Ile Phe Asp Leu Gly Gly Gly Thr
        195                 200                 205

Phe Asp Val Ser Val Leu Thr Ile Asp Asn Gly Ile Phe Glu Val Lys
    210                 215                 220

Ser Thr Ala Gly Asp Thr His Leu Gly Gly Glu Asp Phe Asp Asn Arg
225                 230                 235                 240
```

```
Leu Val Asn His Phe Val Gln Glu Phe Lys Arg Lys Phe Gly Lys Asp
                245                 250                 255

Ile Met Ser Asn Lys Arg Ala Leu Arg Arg Leu Arg Thr Ser Cys Glu
                260                 265                 270

Arg Ala Lys Arg Thr Leu Ser Ser Ser Thr Gln Thr Ser Ile Glu Ile
                275                 280                 285

Asp Ser Leu His Glu Gly Ile Asp Phe Tyr Ser Thr Ile Thr Arg Ala
                290                 295                 300

Arg Phe Glu Glu Leu Cys Ser Asp Leu Phe Arg Ser Thr Leu Glu Pro
305                 310                 315                 320

Val Glu Lys Ala Leu Arg Asp Ala Lys Leu Asp Lys Ser Lys Ile Asp
                325                 330                 335

Glu Ile Val Leu Val Gly Gly Ser Thr Arg Ile Pro Lys Ile Gln Lys
                340                 345                 350

Leu Leu Ser Asp Phe Phe Asn Gly Lys Glu Leu Asn Lys Ser Ile Asn
                355                 360                 365

Pro Asp Glu Ala Val Ala Tyr Gly Ala Ala Val Gln Ala Ala Ile Leu
                370                 375                 380

Thr Gly Asp Asn Ser Asn Asn Val Lys Asp Leu Leu Leu Leu Asp Val
385                 390                 395                 400

Ala Pro Leu Ser Leu Gly Ile Glu Thr Ala Gly Gly Val Met Thr Thr
                405                 410                 415

Leu Ile Lys Arg Asn Thr Thr Ile Pro Thr Lys Gln Thr Gln Thr Phe
                420                 425                 430

Thr Thr Tyr Ala Asp Asn Gln Pro Ala Val Thr Ile Gln Val Tyr Glu
                435                 440                 445

Gly Glu Arg Ala Met Thr Lys Asp Asn Asn Arg Leu Gly Thr Phe Asp
                450                 455                 460

Leu Thr Gly Ile Pro Pro Ala Pro Arg Gly Val Pro Gln Ile Glu Val
465                 470                 475                 480

Thr Phe Asp Val Asp Ala Asn Gly Ile Leu Asn Val Ser Ala Val Asp
                485                 490                 495

Lys Ser Thr Gly Arg Gln Asn Lys Ile Thr Ile Thr Asn Asp Lys Gly
                500                 505                 510

Arg Leu Ser Lys Ala Asp Ile Glu Lys Met Val Gln Glu Ala Glu Gln
                515                 520                 525

Tyr Arg Glu Asp Asp Glu Arg Gln Arg Glu Arg Ile Ala Ala Lys Asn
                530                 535                 540

Gln Leu Glu Ala Tyr Ala Phe Gln Leu Lys Ser Thr Met Glu Glu Glu
545                 550                 555                 560

Ala Val Lys Ser Lys Leu Ser Glu Glu Asp Arg Lys Thr Val Leu Asn
                565                 570                 575

Lys Val Asp Glu Thr Leu Arg Trp Leu Asp Ser Asn Gln Leu Ala Asp
                580                 585                 590

Lys Glu Glu Phe Glu His Arg Gln Lys Glu Ile Glu Asn Ala Cys Arg
                595                 600                 605

Pro Ile Met Met Lys Ile Tyr Gln Gln Gln Gln Gln His His Pro
                610                 615                 620

Gly Ala Asn Gly Ser Cys Gly Ser Asn Ala Tyr Pro Gly Tyr Asn Gly
625                 630                 635                 640

Phe Lys Ser Asn Asn Asp Gly Pro Val Val Glu Glu Val Asn
                645                 650
```

<210> SEQ ID NO 86
<211> LENGTH: 279
<212> TYPE: PRT
<213> ORGANISM: Artificial sequence
<220> FEATURE:
<223> OTHER INFORMATION: tr■U5T1■U5T1_DERFA Der f 6 allergen
    OS=Dermatophagoides farinae PE=2 SV=1

<400> SEQUENCE: 86

```
Met Ile Lys Ile Phe Leu Val Thr Ile Leu Ile Val Ile Thr Val Thr
1               5                   10                  15

Val Asp Ala Arg Phe Pro Arg Ser Leu Gln Pro Lys Trp Ala Tyr Leu
            20                  25                  30

Asp Ser Asn Glu Phe Ser Arg Ser Lys Ile Gly Asp Ser Pro Ile Ala
        35                  40                  45

Gly Val Val Gly Gly Gln Asp Ala Asp Leu Ala Glu Ala Pro Phe Gln
    50                  55                  60

Ile Ser Leu Leu Lys Asp Tyr Leu Ile Met Lys Ser His Met Cys Gly
65                  70                  75                  80

Gly Ser Leu Ile Ser Glu Ser Thr Val Val Thr Ala Ala His Cys Thr
                85                  90                  95

Tyr Gly Gln Lys Ala Ser Ser Leu Ser Val Arg Tyr Gly Thr Asn Gln
            100                 105                 110

Arg Thr Ser Ser Tyr Gly Asp Leu Lys Val Lys Thr Ile Ile Gln
        115                 120                 125

His Glu Ser Tyr Asp Pro Asp Thr Ile Gln Asn Asp Ile Ser Leu Leu
    130                 135                 140

Ile Leu Ser Lys Pro Val Pro Ser Thr Asn Val Gln Met Ile Glu
145                 150                 155                 160

Ile Glu Thr Asp Asp Ile Val Asp Gly Asp Lys Val Thr Ile Tyr Gly
                165                 170                 175

Trp Gly Leu Thr Asp Gly Asn Gly Lys Asp Leu Pro Asp Lys Leu Gln
            180                 185                 190

Lys Gly Ser Met Thr Ile Val Gly Asn Asp Arg Cys Asn Glu Lys Trp
        195                 200                 205

Gly Ser Ile Asp Ala Ile His Pro Gly Met Ile Cys Ala Leu Asp Lys
    210                 215                 220

Thr Gln Ser Gly Cys Asn Gly Asp Ser Gly Gly Pro Leu Val Ser Ala
225                 230                 235                 240

Asn Arg Lys Leu Thr Gly Ile Val Ser Trp Gly Pro Ser Lys Cys Pro
                245                 250                 255

Pro Gly Glu Tyr Met Ser Val Phe Thr Arg Pro Lys Tyr Tyr Leu Asp
            260                 265                 270

Trp Ile Thr Lys Asn Ile Val
        275
```

<210> SEQ ID NO 87
<211> LENGTH: 150
<212> TYPE: PRT
<213> ORGANISM: Artificial sequence
<220> FEATURE:
<223> OTHER INFORMATION: trB4F3B4F3_DERPT LytFM
    OS=Dermatophagoides pteronyssinus GN=lytFM PE=4 SV=1

<400> SEQUENCE: 87

```
Met Lys Phe Phe Phe Thr Leu Ala Leu Phe Cys Thr Leu Ala Ile Ser
1               5                   10                  15
```

```
Gln Val Tyr Cys Asn Gly Ala Ala Ile Val Ser Ala Ala Arg Ser Gln
                20                  25                  30

Ile Gly Val Pro Tyr Ser Trp Gly Gly Gly Ile His Gly Lys Ser
        35                  40                  45

Arg Gly Ile Gly Glu Gly Ala Asn Thr Val Gly Phe Asp Cys Ser Gly
    50                  55                  60

Leu Ala Gln Tyr Ser Val Tyr Gln Gly Thr His Lys Val Leu Ala Arg
65                  70                  75                  80

Val Ala Ser Gly Gln Tyr Ser Asp Pro Lys Cys His His Val Ala Tyr
                85                  90                  95

Gly Ser His Gln Pro Gly Asp Leu Val Phe Phe Gly Asn Pro Ile His
            100                 105                 110

His Val Gly Ile Val Ser Ala His Gly Arg Met Ile Asn Ala Pro His
        115                 120                 125

Thr Gly Thr Asn Val Arg Glu Glu Asn Ile Trp Ser Asp His Ile Ala
    130                 135                 140

Asn Val Ala Arg Cys Trp
145                 150

<210> SEQ ID NO 88
<211> LENGTH: 175
<212> TYPE: PRT
<213> ORGANISM: Artificial sequence
<220> FEATURE:
<223> OTHER INFORMATION: tr_XXV2_XXV2_DERFA Der f 2 allergen
      OS=Dermatophagoides farinae PE=4 SV=1

<400> SEQUENCE: 88

Met Ile Ser Lys Ile Leu Cys Leu Ser Leu Leu Val Ala Ala Val Val
1               5                   10                  15

Ala Asp Gln Val Asp Val Lys Asp Cys Gly Lys Phe Val Cys Val Ile
                20                  25                  30

His Phe Phe Ser Phe His Leu Phe Asn Thr Lys His Asn Phe Leu Phe
            35                  40                  45

Leu Val Tyr Ile His Ile Ala Asn Asn Glu Ile Lys Lys Val Met Val
    50                  55                  60

Asp Gly Cys His Gly Ser Asp Pro Cys Ile Ile His Arg Gly Lys Pro
65                  70                  75                  80

Phe Thr Leu Glu Ala Leu Phe Asp Ala Asn Gln Asn Thr Lys Thr Ala
                85                  90                  95

Lys Ile Glu Ile Lys Ala Ser Leu Asp Gly Leu Glu Ile Asp Val Pro
            100                 105                 110

Gly Ile Asp Thr Asn Ala Cys His Phe Met Lys Cys Pro Leu Val Lys
        115                 120                 125

Gly Gln Gln Tyr Asp Ile Lys Tyr Thr Trp Asn Val Pro Lys Ile Ala
    130                 135                 140

Pro Lys Ser Glu Asn Val Val Val Thr Val Lys Leu Ile Gly Asp Asn
145                 150                 155                 160

Gly Val Leu Ala Cys Ala Ile Ala Thr His Gly Lys Ile Arg Asp
                165                 170                 175

<210> SEQ ID NO 89
<211> LENGTH: 493
<212> TYPE: PRT
<213> ORGANISM: Artificial sequence
<220> FEATURE:
<223> OTHER INFORMATION: iMAT-Cul o2 relates to a Cul o2 iMAT molecule
      [with n-terminal HEXA-HISTIDINE]:
```

<400> SEQUENCE: 89

| | | | | | | | | | | | | | | |
|---|---|---|---|---|---|---|---|---|---|---|---|---|---|---|
|Met|His|His|His|His|His|Tyr|Gly|Arg|Lys|Lys|Arg|Arg|Gln|Arg|
|1| | | |5| | | | |10| | | | |15|

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Phe Gln Gln Gln Gly Arg Leu
65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
        115                 120                 125

Gln His Leu Ile Gln Ala Glu Leu Pro Asp Ser Pro Leu Asn Ile Val
    130                 135                 140

Lys Glu Phe Asp Asp Gly Arg Asn Asn Asn Gln Asn Asp Phe
145                 150                 155                 160

Asn Phe Tyr Trp Asn Ile Pro Ser Phe Met Ser Ala Gln His Asn Ile
                165                 170                 175

Thr Phe Thr Asp Met Thr Ser Ser Tyr Asn Ile Val Gly Asn Lys Asp
            180                 185                 190

Asp Lys Trp Arg Gly Asp Lys Ile Val Ile Leu Tyr Asp Pro Gly Lys
        195                 200                 205

Phe Pro Ala Leu Leu Glu His Gln Gly Gln Leu Tyr Arg Arg Asn Gly
    210                 215                 220

Gly Val Pro Gln Glu Gly Asn Leu Gln Glu His Ile Asp Ile Leu Ala
225                 230                 235                 240

Glu His Ile Asn Lys Leu Ile Pro Asp Thr Gln Phe Ser Gly Ile Gly
                245                 250                 255

Val Ile Asp Phe Glu Ser Trp Arg Pro Ile Phe Arg Gln Asn Ser Gly
            260                 265                 270

Val Leu Gln Pro Tyr Lys Asp Leu Ser Tyr Lys Leu Val His Arg Asp
        275                 280                 285

His Lys Leu Trp Asn Arg Lys Arg Val Glu Ile Glu Ala Ala Arg Leu
    290                 295                 300

Phe Glu Ala Ala Gly Arg Thr Phe Val Glu Thr Ile Asn Val Ala
305                 310                 315                 320

Lys Ile Leu Arg Pro Lys Ala Lys Trp Gly Tyr Tyr Gly Phe Pro Tyr
                325                 330                 335

Ser Phe Asn Met Asn Gly Gly Ala Asn Met Asn Glu Asp Ser Pro Ala
            340                 345                 350

Asn Val Lys Glu Glu Asn Asp Gln Ile Lys Trp Leu Trp Asp Ile Val
        355                 360                 365

Asp Val Val Leu Pro Ser Val Tyr Leu Asn Asn Lys Ile Thr Ser Ala
    370                 375                 380

Gln Arg Val Gln Phe Val Arg Gly Arg Met Arg Glu Gly Tyr Arg Val
385                 390                 395                 400

Ala Lys Met Ser Lys Lys Ser Pro Lys Pro Pro Val Leu Ala Tyr Leu

```
                   405                 410                 415
Arg Tyr Val Tyr Thr Asp Thr Leu Lys Phe Leu Ser Asn Glu Asp Leu
            420                 425                 430

Lys Gln Ala Ile Lys Val Ser Lys Glu Gln Lys Ser Lys Gly Met Ile
            435                 440                 445

Phe Trp Gly Ser Ser Tyr Asp Val Lys Thr Lys Glu Gln Ser Ile Asp
    450                 455                 460

Phe Arg Lys Tyr Val Asp Asn Asn Leu Gly Pro Ile Val Leu Leu Ala
465                 470                 475                 480

Asn Asn Lys Ser Pro Lys Val Leu Thr Pro Asn Leu Ala
            485                 490

<210> SEQ ID NO 90
<211> LENGTH: 372
<212> TYPE: PRT
<213> ORGANISM: Artificial sequence
<220> FEATURE:
<223> OTHER INFORMATION: iMAT-Cul o3 relates to a Cul o3 iMAT molecule
      [with n-terminal HEXA-HISTIDINE]:

<400> SEQUENCE: 90

Met His His His His His His Tyr Gly Arg Lys Arg Arg Gln Arg
1               5                   10                  15

Arg Arg Met Glu Asp Gln Arg Asp Leu Ile Ser Asn His Glu Gln Val
            20                  25                  30

Pro Ile Leu Gly Gln Arg Pro Ala Ala Pro Glu Arg Lys Ser Ser Arg
        35                  40                  45

Gly Ala Leu Tyr Thr Gly Phe Ser Val Leu Val Ala Leu Leu Leu Ala
    50                  55                  60

Gly Gln Ala Thr Thr Ala Tyr Phe Leu Phe Gln Gln Gln Gly Arg Leu
65                  70                  75                  80

Asp Lys Leu Thr Val Thr Ala Gln Asn Leu Gln Leu Glu Lys Leu Arg
                85                  90                  95

Met Lys Leu Pro Lys Ser Ala Lys Pro Val Ser Lys Ile Arg Val Ala
            100                 105                 110

Thr Pro Met Leu Met Gln Ala Leu Pro Met Glu Gly Leu Ser His Gly
            115                 120                 125

Thr Asp Phe Ser Asp Arg Lys Leu Ser Arg Arg Gln Ile Glu Pro Asn
    130                 135                 140

Val Tyr Gln Asn Ile Pro His Ile Gly Ser Asn His Asp Gly Arg Asn
145                 150                 155                 160

Ser Pro Ala Ser Pro Ser Asp Ala Lys Ile Leu Pro Met Ser Thr Lys
                165                 170                 175

Arg Lys Asn Leu Ile Leu Arg Val His Asn Arg Leu Arg Asn Lys Val
            180                 185                 190

Ala Leu Gly Gln Leu Pro Gly Tyr Pro Lys Ala Val Arg Met Pro Ile
        195                 200                 205

Leu Arg Trp Asp Asp Glu Leu Ala Tyr Leu Ala Glu Leu Asn Val Lys
    210                 215                 220

Gln Ser Glu Met Lys His Asp Gln Ser Arg Asn Thr Asp Lys Phe Arg
225                 230                 235                 240

Tyr Ala Gly Gln Asn Leu Ala Tyr Ile Gly Gly Lys Glu Pro Asn
                245                 250                 255

Ala Val Arg Ile Lys Thr Leu Val Arg Ala Trp Phe Asp Glu Tyr Lys
            260                 265                 270
```

-continued

```
Asp Ala Asn Ser Ser Phe Ile Asp Lys Tyr Arg Ser His Pro Asn Gly
            275                 280                 285

Lys Ala Ile Gly His Phe Thr Ala Met Val Gln Asp Arg Thr Asp Thr
    290                 295                 300

Val Gly Ile Ala Ile Leu Arg His Thr Lys Asn Thr Tyr Phe Phe Leu
305                 310                 315                 320

Ala Ile Asn Tyr Ser Phe Thr Asn Met Val Lys Asp Lys Val Tyr Thr
                325                 330                 335

Arg Gly Ala Lys Ser Ser Ser Lys Ser Arg Thr Gly Ser Ser Pro Val
            340                 345                 350

Tyr Lys Gly Leu Ser Lys Pro His Glu Tyr Val Asn Pro Asp Pro Asp
            355                 360                 365

Glu Asp Leu Asp
    370

<210> SEQ ID NO 91
<211> LENGTH: 14
<212> TYPE: PRT
<213> ORGANISM: Artificial sequence
<220> FEATURE:
<223> OTHER INFORMATION: artificial peptide derived from SEQ ID NO: 10
      (Q86R84_AA 97-110) i.e.:

<400> SEQUENCE: 91

Gly Asn Ala Lys Ala Met Ile Ala Val Gly Gly Ser Thr Met
1               5                   10

<210> SEQ ID NO 92
<211> LENGTH: 14
<212> TYPE: PRT
<213> ORGANISM: Artificial sequence
<220> FEATURE:
<223> OTHER INFORMATION: artificial peptide derived from SEQ ID NO: 85
      (A0A088SAS1_AA 611-624)  i.e.:

<400> SEQUENCE: 92

Met Met Lys Ile Tyr Gln Gln Gln Gln Gln His His Pro
1               5                   10

<210> SEQ ID NO 93
<211> LENGTH: 14
<212> TYPE: PRT
<213> ORGANISM: Artificial sequence
<220> FEATURE:
<223> OTHER INFORMATION: artificial peptide derived from SEQ ID NO: 88
      (A7XXV2) AA 48-61) i.e.:

<400> SEQUENCE: 93

Phe Leu Val Tyr Ile His Ile Ala Asn Asn Glu Ile Lys Lys
1               5                   10

<210> SEQ ID NO 94
<211> LENGTH: 13
<212> TYPE: PRT
<213> ORGANISM: Artificial sequence
<220> FEATURE:
<223> OTHER INFORMATION: artificial peptide derived from SEQ ID NO: 86
      (B7U5T1_AA 166-178) i.e.:

<400> SEQUENCE: 94

Ile Val Asp Gly Asp Lys Val Thr Ile Tyr Gly Trp Gly
1               5                   10

<210> SEQ ID NO 95
```

```
<211> LENGTH: 14
<212> TYPE: PRT
<213> ORGANISM: Artificial sequence
<220> FEATURE:
<223> OTHER INFORMATION: artificial peptide derived from SEQ ID 87:
      (T2B4F3_AA 134-147) i.e.:

<400> SEQUENCE: 95

Arg Glu Glu Asn Ile Trp Ser Asp His Ile Ala Asn Val Ala
1               5                   10

<210> SEQ ID NO 96
<211> LENGTH: 14
<212> TYPE: PRT
<213> ORGANISM: Artificial sequence
<220> FEATURE:
<223> OTHER INFORMATION: artificial peptide derived from SEQ ID NO: 11
      (Q9U6R7_AA 469-482) i.e.:

<400> SEQUENCE: 96

Thr Pro Thr Thr Pro Thr Pro Ala Pro Thr Thr Ser Thr Pro
1               5                   10

<210> SEQ ID NO 97
<211> LENGTH: 223
<212> TYPE: PRT
<213> ORGANISM: Artificial sequence
<220> FEATURE:
<223> OTHER INFORMATION: artificial peptide derived from SEQ ID NO 7
      (Q58A71 Der f 1 allergen preproenzyme Dermatophagoides farinae
      (American house dust mite) AA 99-321) i.e.:

<400> SEQUENCE: 97

Thr Ser Ala Cys Arg Ile Asn Ser Val Asn Val Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Thr Ser Leu Asp Leu Ser Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln Gln Asn Gly Val Val Glu Glu Arg Ser Tyr Pro
                85                  90                  95

Tyr Val Ala Arg Glu Gln Gln Cys Arg Arg Pro Asn Ser Gln His Tyr
            100                 105                 110

Gly Ile Ser Asn Tyr Cys Gln Ile Tyr Pro Pro Asp Val Lys Gln Ile
        115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
            180                 185                 190

Trp Asp Thr Thr Trp Gly Asp Ser Gly Tyr Gly Tyr Phe Gln Ala Gly
        195                 200                 205

Asn Asn Leu Met Met Ile Glu Gln Tyr Pro Tyr Val Val Ile Met
    210                 215                 220
```

<210> SEQ ID NO 98
<211> LENGTH: 28
<212> TYPE: PRT
<213> ORGANISM: Artificial sequence
<220> FEATURE:
<223> OTHER INFORMATION: artificial peptide derived from SEQ ID NO 10
      (Q86R84 60 kDa allergen Der f 18p Dermatophagoides farinae
      (American house dust mite) AA 277-304) i.e.:

<400> SEQUENCE: 98

Phe Thr Gln Thr Asp Gly Phe Leu Ser Tyr Asn Glu Leu Cys Val Gln
1               5                   10                  15

Ile Gln Ala Glu Thr Asn Ala Phe Thr Ile Thr Arg
            20                  25

<210> SEQ ID NO 99
<211> LENGTH: 40
<212> TYPE: PRT
<213> ORGANISM: Artificial sequence
<220> FEATURE:
<223> OTHER INFORMATION: artificial peptide derived from SEQ ID NO 12
      (I7HDR2 Zen 1 protein Dermatophagoides farinae (American house
      dust mite) AA 181-220) i.e.:

<400> SEQUENCE: 99

Glu Pro Thr Thr Pro Thr Pro Glu Pro Thr Thr Lys Thr Pro Glu Pro
1               5                   10                  15

Thr Thr Lys Thr Pro Glu Pro Ser Thr Pro Thr Pro Glu Pro Thr Thr
            20                  25                  30

Lys Thr Pro Glu Pro Thr Thr Lys
        35                  40

<210> SEQ ID NO 100
<211> LENGTH: 70
<212> TYPE: PRT
<213> ORGANISM: Artificial sequence
<220> FEATURE:
<223> OTHER INFORMATION: artificial peptide derived from SEQ ID NO 9
      (A0A088SAW7 Der f 23 allergen Dermatophagoides farinae (American
      house dust mite) AA 22-91) i.e.:

<400> SEQUENCE: 100

Asp Ile Asp His Asp Asp Asp Pro Thr Thr Met Ile Asp Val Gln Thr
1               5                   10                  15

Thr Thr Val Gln Pro Ser Asp Glu Phe Glu Cys Pro Thr Arg Phe Gly
            20                  25                  30

Tyr Phe Ala Asp Pro Lys Asp Pro Cys Lys Phe Tyr Ile Cys Ser Asn
        35                  40                  45

Trp Glu Ala Ile His Lys Ser Cys Pro Gly Asn Thr Arg Trp Asn Glu
    50                  55                  60

Lys Glu Leu Thr Cys Thr
65                  70

<210> SEQ ID NO 101
<211> LENGTH: 27
<212> TYPE: PRT
<213> ORGANISM: Artificial sequence
<220> FEATURE:
<223> OTHER INFORMATION: artificial peptide derived from SEQ ID NO 11
      (Q9U6R7 98kDa HDM allergen (Der f 15 allergen) (Group 15 allergen
      Der f 15) Dermatophagoides farinae (American house dust mite) AA
      437-463) i.e.:

<400> SEQUENCE: 101

```
Ser Pro Thr Thr Pro Thr Thr Thr Pro Ser Pro Thr Thr Pro Thr Thr
1               5                   10                  15

Thr Pro Ser Pro Thr Thr Pro Thr Thr Thr Pro
            20              25
```

<210> SEQ ID NO 102
<211> LENGTH: 129
<212> TYPE: PRT
<213> ORGANISM: Artificial sequence
<220> FEATURE:
<223> OTHER INFORMATION: artificial peptide derived from SEQ ID NO 8
      (Q00855 Mite group 2 allergen Der f 2 (Allergen Der f II)
      (allergen Der f 2) Dermatophagoides farinae (American house dust
      mite) AA 18-146) i.e.:

<400> SEQUENCE: 102

```
Asp Gln Val Asp Val Lys Asp Cys Ala Asn Asn Glu Ile Lys Lys Val
1               5                   10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Cys Ala Ile Ala Thr His Gly Lys Ile Arg
        115                 120                 125

Asp
```